(12) United States Patent
Skolnick et al.

(10) Patent No.: US 12,290,596 B2
(45) Date of Patent: May 6, 2025

(54) COMPOSITIONS AND METHODS FOR THE TREATMENT OF OPIOID OVERDOSE

(71) Applicant: INDIVIOR INC., North Chesterfield, VA (US)

(72) Inventors: Phil Skolnick, Santa Monica, CA (US); Mark Ellison, Santa Monica, CA (US); Roger Crystal, Santa Monica, CA (US)

(73) Assignee: Indivior UK Limited, Hull (GB)

( * ) Notice: Subject to any disclaimer, the term of this patent is extended or adjusted under 35 U.S.C. 154(b) by 0 days.

(21) Appl. No.: 17/881,306

(22) Filed: Aug. 4, 2022

(65) Prior Publication Data

US 2023/0055547 A1 Feb. 23, 2023

Related U.S. Application Data

(60) Provisional application No. 63/229,300, filed on Aug. 4, 2021.

(51) Int. Cl.
| | | |
|---|---|---|
| *A61K 9/00* | (2006.01) | |
| *A61K 31/485* | (2006.01) | |
| *A61K 47/18* | (2017.01) | |
| *A61K 47/26* | (2006.01) | |
| *A61P 25/36* | (2006.01) | |

(52) U.S. Cl.
CPC .......... *A61K 9/0043* (2013.01); *A61K 31/485* (2013.01); *A61K 47/183* (2013.01); *A61K 47/186* (2013.01); *A61K 47/26* (2013.01); *A61P 25/36* (2018.01)

(58) Field of Classification Search
CPC ...... A61K 31/485; A61K 9/0043; A61P 25/36
See application file for complete search history.

(56) References Cited

U.S. PATENT DOCUMENTS

| | | | |
|---|---|---|---|
| 4,464,378 | A | 8/1984 | Hussain |
| 4,880,813 | A | 11/1989 | Frost |
| 4,882,335 | A | 11/1989 | Sinclair |
| 4,987,136 | A | 1/1991 | Kreek et al. |
| 5,069,895 | A | 12/1991 | Diamond et al. |
| 5,369,095 | A | 11/1994 | Kee et al. |
| 6,271,240 | B1 | 8/2001 | Simon |

(Continued)

FOREIGN PATENT DOCUMENTS

| | | |
|---|---|---|
| CA | 3028731 A1 | 12/2017 |
| CA | 3043028 A1 | 5/2018 |

(Continued)

OTHER PUBLICATIONS

Krieter P.A., et al. Comparison of the Pharmacokinetic Properties of Naloxone Following the Use of FDA-Approved Intranasal and Intramuscular Devices Versus a Common Improvised Nasal Naloxone Device. J Clin Pharmacol. Aug. 2019;59(8):1078-1084. doi: 10.1002/jcph.1401. (Year: 2019).*

(Continued)

*Primary Examiner* — Kortney L. Klinkel
*Assistant Examiner* — Richard Grant Peckham
(74) *Attorney, Agent, or Firm* — THE MARBURY LAW GROUP, PLLC

(57) ABSTRACT

Drug products adapted for nasal delivery, comprising a pre-primed device filled with a pharmaceutical composition comprising nalmefene are provided. Methods of treating opioid overdose with the drug products are also provided.

2 Claims, 31 Drawing Sheets

(56) References Cited

U.S. PATENT DOCUMENTS

| | | |
|---|---|---|
| 9,192,570 B2 | 11/2015 | Wyse et al. |
| 9,211,253 B2 | 12/2015 | Crystal et al. |
| 9,468,747 B2 | 10/2016 | Crystal et al. |
| 9,480,644 B2 | 11/2016 | Crystal et al. |
| 9,561,177 B2 | 2/2017 | Keegan et al. |
| 9,629,965 B2 | 4/2017 | Crystal et al. |
| 9,707,226 B2 | 7/2017 | Keegan et al. |
| 9,775,838 B2 | 10/2017 | Keegan et al. |
| 9,895,444 B2 | 2/2018 | Maggio |
| 10,085,937 B2 | 10/2018 | Keegan et al. |
| 11,458,091 B2 | 10/2022 | Crystal et al. |
| 2003/0153590 A1 | 8/2003 | Kurkela et al. |
| 2007/0212307 A1 | 9/2007 | Wermeling et al. |
| 2008/0090771 A1 | 4/2008 | Moncrief |
| 2009/0110735 A1 | 4/2009 | Maggio et al. |
| 2010/0256198 A1 | 10/2010 | Megiddo et al. |
| 2011/0038847 A1 | 2/2011 | Kawamura et al. |
| 2011/0065628 A1 | 2/2011 | Johnson et al. |
| 2012/0302592 A1 | 11/2012 | Johnson et al. |
| 2014/0057934 A1 | 2/2014 | Nutalapati |
| 2014/0107145 A1 | 4/2014 | Maggio |
| 2014/0171458 A1 | 6/2014 | Brown et al. |
| 2014/0249172 A1 | 9/2014 | Brown et al. |
| 2015/0174061 A1 | 6/2015 | Wyse et al. |
| 2015/0258019 A1 | 9/2015 | Crystal et al. |
| 2015/0258287 A1 | 9/2015 | Shahaf et al. |
| 2016/0008277 A1 | 1/2016 | Crystal et al. |
| 2016/0015895 A1 | 1/2016 | Blondino et al. |
| 2016/0166503 A1 | 6/2016 | Crystal et al. |
| 2017/0020862 A1 | 1/2017 | Brown et al. |
| 2017/0151230 A1 | 6/2017 | Keegan et al. |
| 2017/0304295 A1 | 10/2017 | Crystal et al. |
| 2018/0000942 A1* | 1/2018 | Cunningham ......... A61K 47/26 |
| 2018/0161320 A1 | 6/2018 | Wyse et al. |
| 2018/0169006 A1 | 6/2018 | Crystal et al. |
| 2019/0015323 A1 | 1/2019 | Keegan et al. |
| 2019/0209464 A1 | 7/2019 | Crystal et al. |
| 2019/0262263 A1 | 8/2019 | Crystal et al. |
| 2020/0030229 A1 | 1/2020 | Keegan et al. |
| 2020/0060967 A1* | 2/2020 | Crystal ................. A61K 47/18 |
| 2020/0390691 A1* | 12/2020 | Maggio ................ A61K 47/186 |
| 2021/0077382 A1 | 3/2021 | Crystal et al. |
| 2021/0093557 A1 | 4/2021 | Keegan et al. |
| 2021/0121573 A1 | 4/2021 | Maggio |
| 2021/0220346 A1 | 7/2021 | Crystal et al. |
| 2021/0275444 A1 | 9/2021 | Crystal et al. |
| 2021/0275519 A1 | 9/2021 | Crystal et al. |
| 2021/0401827 A1 | 12/2021 | Crystal et al. |
| 2022/0387306 A1 | 12/2022 | Crystal et al. |

FOREIGN PATENT DOCUMENTS

| | | |
|---|---|---|
| CA | 3044221 A1 | 5/2018 |
| CN | 1634062 A | 7/2005 |
| CN | 1305474 C | 3/2007 |
| CN | 103764119 A | 4/2014 |
| CN | 106361700 A | 2/2017 |
| CN | 109789122 A | 5/2019 |
| CN | 110139651 A | 8/2019 |
| CN | 113573696 A | 10/2021 |
| EP | 3538189 A1 | 9/2019 |
| EP | 3474842 A4 | 1/2020 |
| EP | 3541386 A4 | 5/2020 |
| JP | H04211011 A | 8/1992 |
| JP | 2011516425 A | 5/2011 |
| JP | 2013540805 A | 11/2013 |
| JP | 2014519525 A | 8/2014 |
| JP | 2019520361 A | 7/2019 |
| JP | 2019534315 A | 11/2019 |
| JP | 7312698 B2 | 11/2023 |
| KR | 20190055057 A | 5/2019 |
| MX | 2018015985 A | 9/2019 |
| RU | 2554814 C2 | 6/2015 |
| RU | 2019101810 A | 7/2020 |
| SG | 10202013034 | 2/2021 |
| WO | 2001010409 A1 | 2/2001 |
| WO | 2006025882 A2 | 3/2006 |
| WO | 2009128474 A1 | 10/2009 |
| WO | 2010075465 A1 | 7/2010 |
| WO | 2011014797 A1 | 2/2011 |
| WO | 2012054500 A2 | 4/2012 |
| WO | 2012056299 A1 | 5/2012 |
| WO | 2015054730 A1 | 4/2015 |
| WO | 2015095389 A1 | 6/2015 |
| WO | 2015136373 A1 | 9/2015 |
| WO | 2016007729 A1 | 1/2016 |
| WO | 2017223566 A1 | 12/2017 |
| WO | 2018089709 A1 | 5/2018 |
| WO | 2018093666 A1 | 5/2018 |
| WO | 2019222408 A1 | 11/2019 |
| WO | 2020097279 A1 | 5/2020 |
| WO | 2020132263 A1 | 6/2020 |

OTHER PUBLICATIONS

Berge SM, Bighley LD, Monkhouse DC. Pharmaceutical salts. J Pharm Sci. Jan. 1977;66(1): 1-19. doi: 10.1002/jps.2600660104. PMID: 833720. (Year: 1977).*
Ingman, K., Hagelberg, N., Aalto, S. et al. Prolonged Central μ-Opioid Receptor Occupancy after Single and Repeated Nalmefene Dosing. Neuropsychopharmacol 30, 2245-2253 (2005). https://doi.org/10.1038/sj.npp.1300790 (Year: 2005).*
Remifentanil 1 mg powder for concentrate for solution for injection or infusion: Summary of Product Characteristics. Health Products regulatory Authority. Apr. 16, 2019. pp. 1-19 (Year: 2019).*
Konieczko et al. British Journal of Anaesthesia (1988), 61, 318-323 (Year: 1988).*
Ireland's Health Products Regulatory Authority. Summary of Product Characteristics: Remifentanil 1 mg powder . . . , Health Products Regulatory Authority, Apr. 16, 2019, p. 1-19 (Year: 2019).*
Office Action for Russian Patent Application No. 2019118465/04(035468), dated Mar. 4, 2021.
English translation of Office Action for Russian Patent Application No. 2019118465/04(035468), dated Mar. 4, 2021.
Russian Search Report for Patent Application No. 2019118465/04(035468), dated Mar. 4, 2021.
English translation of Russian Search Report for Patent Application No. 2019118465/04(035468), dated Mar. 4, 2021.
Machine English translation of JP7312698, published on Jul. 21, 2023, (Provided by Google Patents).
Certificate of Patent for JP7312698 and Machine English translation of Certificate of Patent for JP7312698.
Crystal et al. "Pharmacokinetic Properties of an FDA-approved Intranasal Nalmefene Formulation for the Treatment of Opioid Overdose" Clin Pharmacol Drug Dev. Jul. 27, 2023, retrieved from the Internet: https://accp1.onlinelibrary.wiley.com/doi/10.1002/cpdd.1312, doi: 10.1002/cpdd.1312. Epub ahead of print. PMID: 37496452, 16 pages (with supplemental information attached).
"Understanding Fatal Overdoses to Inform Product Development & Public Health Interventions to Manage Overdose" Mar. 8, 2023, Reagan-Udall Foundation for the FDA, retrieved from the Internet: https://reaganudall.org/sites/default/files/2023-03/Understanding%20Fatal%20Overdoses_Slides_Day%201.pdf, 134 pages.
Mann et al. "Development of a Translational Model to Assess the Impact of Opioid Overdose and Naloxone Dosing on Respiratory Depression and Cardiac Arrest" Clin Pharmacol Ther. Nov. 2022;112(5):1020-1032, retrieved from the Internet: https://pubmed.ncbi.nlm.nih.gov/35766413/, doi: 10.1002/cpt.2696. Epub Jul. 22, 2022. PMID: 35766413, 13 pages.
OPVEE® (nalmefene) Nasal Spray Prescribing Information (May 2023).
FDA Orange Book: Approved Drug Products with Therapeutic Equivalence Evaluations, NDA 217470, OPVEE (nalmefene HCl) Eq. 2.7 mg base/spray (Approval Date: May 22, 2023).
Krieter et al. "Enhanced Intranasal Absorption of Naltrexone by Dodecyl Maltopyranoside: Implications for the Treatment of Opioid Overdose" 2019, The J. Clinical Pharmacology 59(7):947-957.

(56) References Cited

OTHER PUBLICATIONS

Krieter et al. "Fighting Fire with Fire: Development of Intranasal Nalmefene to Treat Synthetic Opioid Overdose" Nov. 2019, J. Pharmacology and Experimental Therapeutics 371:409-415.
Le et al. "Drug Bioavailability" Oct. 2020, Merck Manual Professional Version 2 Pages.
Machine English translation of CN1634062A published on Jul. 6, 2005, (Provided by Google Patents).
Maggio "Absorption Enhancing Excipients In Systemic Nasal Drug Delivery" Jun. 2014, (Receieved on Apr. 18, 2014), J. Excipients and Food Chemicals 5(2):100-112.
Maggio "Intravail: Highly Effective Intranasal Delivery of Peptide and Protein Drugs" Jul. 1, 2006, Expert Opinion on Drug Delivery, Informa Healthcare, GB 3(4):529-539, DOI: 10.1517/17425247.3. 4.529, ISSN 1742-5247, XP008152448.
Maggio et al. "High Efficiency Intranasal Drug Delivery Using Intravail Alkylsaccharide Absorption Enhancers" May 12, 2012, Drug Delivery and Translational Research, Germany 3(1): 16-25, DOI: 10.1007/s13346-012-0069-z, ISSN 2190-393X, XP055370902.
Marx et al. "Intranasal Drug Administration—An Attractive Delivery Route for Some Drugs" Jun. 2015, Chapter 13, Drug Discovery and Development—From Molecules to Medicine 24 Pages, Retrieved from the Internet: http://dx.doi.org/10.5772/59468.
Maxwell "Use of Naltrexone in the Treatment of Alcohol Use Disorders in Patients with Concomitant Major Mental Illness" 2000, J. Addictive Disease, 19(3):61-69.
Munjal et al. "A Randomized Trial Comparing the Pharmacokinetics, Safety, and Tolerability of DFN-02, an Intranasal Sumatriptan Spray Containing a Permeation Enhancer, with Intranasal and Subcutaneous Sumatriptan in Healthy Adults" 2016, Headache, 56, Retrieved from the internet: https://headachejournal.onlinelibrary.wiley.eom/doi/10.1111/head.12905 (Aug. 10, 2021), 4 Pages.
Naltrexone hydrochloride, Thermo Scientific Chemicals Catalog Description, CAS 16676-29-2.
Ngai et al. "Pharmacokinetics of Naloxone in Rats and in Man: Basis for Its Potency and Short Duration of Action" May 1976, Anesthesiology 44(5):398-401.
Niazi, "Handbook of Pharmaceutical Manufacturing Formulations: Compressed Solid Products" 2004, vol. Series 1-6, p. 24.
Office Action for Canadian Patent Application No. 3,028,731, mailed Jul. 26, 2023.
Olsen "Natural Rewards, Neuroplasticity, and Non-Drug Addictions" Dec. 2011, Neuropharmacology 61 (7):1109-1122.
Opiant Pharmaceuticals Incorporated "Opiant Receives FDA Fast Track Designation for OPNT0003, Nasal Nalmefene, for Treatment of Opioid Overdose" Nov. 4, 2021, retrieved from the internet: https://ir.opiant.com/news-releases/news-release-details/opiant-receives-fda-ast-track-designation-opnt003-nasal 04 Pages.
Osborn et al. "In Vivo Characterization of the Opioid Antagonist Nalmefene in Mice" 2010, Life Sciences 86:624-630.
Ozsoy et al. "Nasal Delivery of High Molecular Weight Drugs" Sep. 23, 2009, Molecules 14(9):3754-3779.
Rabinowicz et al. "Improvement of Intranasal Drug Delivery with Intravail Alkylsaccharide Excipient as a Mucosal Absorption Enhancer Aiding in the Treatment of Conditions of the Central Nervous System" 2021, Drugs in R&D 9 Pages.
Ray et al. "Naltrexone for the Treatment of Alcoholism: Clinical Findings, Mechanism of Action, and Pharmacogenetics" Mar. 2010, CNS & Neurological Disorders—Drug Targets 9(1): 13-22.
Russian Office Action for application No. 2021121189 dated May 30, 2023.
Scultz "Neuronal Reward and Decision Signals: From Theories to Data" Jul. 2015, Physiology Review 95:853-951.
Search History of PCT/US2019/060185.
Skolnick "Treatment of Overdose in the Synthetic Opioid Era" Oct. 9, 2021, Pharmacology & Therapeutics 13 Pages.
Sporer et al. "Out-of-hospital Treatment of Opioid Overdoses in an Urban Setting" Jul. 1996, Academic Emergency Medicine 3(7):660-667.
Taylor "Barda Backs Opiant Push to Develop Nasal Opioid Overdose Drug" Dec. 22, 2020, Fierce Pharma, retrieved from the internet: https://www.iercepharma.com/drug-delivery/barda-backs-opiant-push-to-develop=nasal-opioid-overdose-drug 03 Pages.
Thorat "Formulation and Product Development of Nasal Spray: an Overview" 2016, Scholars J. Applied Medical Sciences 4(8D):2976-2985.
Tomassoni et al. "Multiple Fentanyl Overdoses-New Haven, Connecticut, Jun. 23, 2016" Feb. 3, 2017, Morbidity and Mortality Weekly Report (MMWR) 66(4):107-111.
Tosymra "Full Prescribing Information, Patient Information and Instructions for Use" Jan. 2019, Dr. Reddys Laboratories Limited, 26 Pages.
Ujvary et al. "Dark Classics in Chemical Neuroscience: Etonitazene and Related Benzimidazoles" 2021, ACS Chemical Neuroscience 12(7):1072-1092.
Unterwald et al. "Repeated Cocaine Administration Upregulates Kappa and Mu, but Not Delta, Opioid Receptors" Aug. 15, 1994, Neuroreport 5:1613-1616, (Abstract only).
Valtoco "Prescribing Information" Revised in Feb. 2021, Neurelis, Incorporated 27 Pages.
Vidgren et al. "Nasal Delivery Systems and their Effect on Deposition and Absorption" Jan. 5, 1998, J. Advanced Drug Delivery Reviews 29: 157-177.
Volkow et al. "The Role of Science in Addressing the Opioid Crisis" Jul. 27, 2017, The New England J. Medicine 377:391-394.
Wentland et al. "Syntheses and Opioid Receptor Binding Properties of Carboxamido-Substituted Opioids" 2009, Bioorganic and Medicinal Chemistry Letters 19:203-208.
Wermeling "Review of Naloxone Safety for Opioid Overdose: Practical Considerations for New Technology and Expanded Public Access" Jan. 1, 2015, Therapeutic Advances in Drug Safety, 6(1):20-31, Retrieved from the Internet: https://journals.sagepub.com/doi/pdf/10.1177/2042098614564776 XP055935440, DOI: 10.1177/2042098614564776.
Yershov et al. "General Chemistry "Biophysical Chemistry, Chemistry of Biogenic Elements: Textbook for Universities, 4th Ed. 2003, p. 48-49 (in Russian).
Yong et al. "Nalmefene Reverses Carfentanyl-Induced Loss of Righting Reflex and Respiratory Depression in Rats" 2014, European J. Pharmacology 738:153-157.
Office Action for Australian Patent Application No. 2017360910, mailed Nov. 23, 2022.
Office Action for Chinese Patent Application No. 201780081719.4, mailed Jan. 5, 2023.
English translation of Office Action for Chinese Patent Application No. 201780081719.4, mailed Jan. 5, 2023.
English translation of CN1634062A, published on Jul. 6, 2005.
Office Action for Israeli Patent Application No. 26674, mailed Nov. 30, 2022.
English translation of Office Action for Israeli Patent Application No. 26674, mailed Nov. 30, 2022.
Office Action for Japanese Patent Application No. 2019-526565, mailed Mar. 1, 2023.
English translation of Office Action for Japanese Patent Application No. 2019-526565, mailed Mar. 1, 2023.
Decision to Grant Russian Patent Application No. 2019118465/04(035468), dated Feb. 1, 2022.
English translation of Decision to Grant Russian Patent Application No. 2019118465/04(035468), dated Feb. 1, 2022.
Office Action for Russian Patent Application No. 2019118465/04(035468), dated Jul. 29, 2021.
English translation of Office Action for Russian Patent Application No. 2019118465/04(035468), dated Jul. 29, 2021.
"Revex Package Insert—Nalmefene hydrochloride Injection" Jun. 21, 2007, Baxter Healthcare Corporation 11 Pages.
"U.S. Food & Drug Administration Fast Track" 2018, retrieved from the internet: https://www.fda.gov/patients/fast-track-breakthrough-therapy-accelerted-approval-priority-review/fast-track 2 Pages.
Ahmad et al. "Provisional Drug Overdose Death Counts" 2022, National Center for Health Statistics, retrieved from internet: https://www.cdc.gov/nchs/nvss/vsrr/drug-overdose-data.html 8 Pages.

(56) References Cited

OTHER PUBLICATIONS

Aungst "Absorption Enhancers: Applications and Advances" 2011, The American Association of Pharmaceutical Scientists Journal 14(1):10-18.
Bart et al. "Nalmefene Induces Elevation in Serum Prolactin in Normal Human Volunteers: Partial Kappa Opioid Agonist Activity?" 2005, Neuropsychopharmacology 30:2254-2262.
Berge et al., "Pharmaceutical Salts" Jan. 1977, Journal of Pharmaceutical Sciences, 66(1):1-19.
Burns et al. "DARK Classics in Chemical Neuroscience: Fentanyl" 2018, ACS Chemical Neuroscience 9:2428-2437.
Cassel et al. "[3H]Alvimopan Binding to the μ Opioid Receptor: Comparative Binding Kinetics of Opioid Antagonists" 2005, European J. Pharmacology 520:29-36.
Centers for Disease Control and Prevention "Understanding the Opioid Overdose Epidemic" 2021, Retrieved from the Internet : https://www.cdc.gov/opioids/basics/epideic.html 3 Pages.
Cerda et al. "Prescription Opioid Mortality Trends in New York City, 1990-2006: Examining the Emergence of an Epidemic" Sep. 1, 2013, Drug and Alcohol Dependence 132:53-62.
Clinical Trial "Pharmacokinetic Evaluation of Intranasal Nalmefene" 2021, ClinicalTrials.gov. Identifier: NCT04759768, 6 Pages.
Dezfulian et al. "Opioid-Associated Out-of-Hospital Cardiac Arrest Distinctive Clinical Features and Implications for Health Care and Public Responses" 2021, Circulation 143: e836-e870.
Dixon et al. "Nalmefene: Intravenous Safety and Kinetics of a New Opioid Antagonist" Jan. 1986, Clinical Pharmacology and Therapeutic 39(1):49-53.
Dowell et al. "Contribution of Opioid-involved Poisoning to the Change in Life Expectancy in the United States" Sep. 19, 2017, JAMA 318(11):1065-1067.
Edinoff et al. "Pharmacologic and Clinical Considerations of Nalmefene, a Long Duration Opioid Antagonist, in Opioid Overdose" Oct. 14, 2021, Psychiatry International 2:365-378.
European Search Report and Written Opinion for EP 17816377.0 received Jan. 8, 2020, 8 Pages.
European Search Report and Written Opinion for EP 17868907.1 received Mar. 25, 2020, 14 Pages.
European Search Report and Written Opinion for EP 17871739.3 received Apr. 30, 2020, 12 Pages.
European Search Report and Written Opinion for EP 19804071.9 received Mar. 23, 2022, 27 Pages.
European Search Report and Written Opinion for EP 19881497.2 received Jul. 5, 2022, 8 Pages.
European Search Report and Written Opinion for EP 19898164.9 received Oct. 17, 2022.
File History of U.S. Pat. No. 9,895,444, (access is obtained through the USTPO records).
File history of unpublished U.S. Appl. No. 16/551,524, filed Aug. 26, 2019 (access is obtained through the USPTO records).
File History of Unpublished U.S. Appl. No. 16/828,656, filed Mar. 24, 2020, (Access is Obtained through the USPTO Records).
File History of Unpublished U.S. Appl. No. 16/870,406, filed May 8, 2020, (Access is Obtained through the USPTO Records).
File History of Unpublished U.S. Appl. No. 17/122,671, filed Dec. 15, 2020, (Access is Obtained through the USPTO Records).
File History of Unpublished U.S. Appl. No. 17/506,973, filed Oct. 21, 2021, (Access is Obtained through the USPTO Records).
Frank et al. "Addressing the Fentanyl Threat to Public Health" Feb. 16, 2017, The New England J. Medicine 376 (7):605-607.
Fridericia "Die Systolendauer Im Elektrokardiogramm Bei Normalen Menschen and Bei Herzkranken" Jan.-Dec. 1920, Acta Medica Scandinavica, Stockholm 53:16 Pages, (Abstract).
Fu et al. "Common Knowledge Evidence" Oct. 31, 2008, Pharmaceutical Excipients, China Press of Traditional Chinese Medicine pp. 331 (with English translation).
Gennaro "Remington: The Science and Practice of Pharmacy 20th Ed." 2005, Lippincott Williams & Wilkins, Philadelphia, PA 4 Pages.
Gonzalez et al. "Naltrexone: A Review of its Pharmacodynamic and Pharmacokinetic Properties and Therapeutic Efficacy in the Management of Opioid Dependence" Mar. 1988, Drugs 35:192-213. (Abstract).
Illum "Nasal Drug Delivery-Recent Developments and Future Prospects" 2012, J. Controlled Release 161 (2):254-263.
International Preliminary Report on Patentability for PCT/US2017/039300 dated Jan. 3, 2019, 9 Pages.
International Preliminary Report on Patentability for PCT/US2017/060963 dated May 23, 2019, 07 Pages.
International Preliminary Report on Patentability for PCT/US2017/060964 dated May 31, 2019, 13 Pages.
International Preliminary Report on Patentability for PCT/US2019/032498 dated Nov. 26, 2020, 6 Pages.
International Preliminary Report on Patentability for PCT/US2019/060185 dated May 20, 2021, 6 Pages.
International Preliminary Report on Patentability for PCT/US2019/067513 dated Jul. 1, 2021, 9 Pages.
International Search Report and Written Opinion for PCT/US2017/039300 dated Nov. 8, 2017, 12 Pages.
International Search Report and Written Opinion for PCT/US2017/060963 dated Mar. 20, 2018, 10 Pages.
International Search Report and Written Opinion for PCT/US2017/060964 dated Feb. 22, 2018, 15 Pages.
International Search Report and Written Opinion for PCT/US2019/032498 dated Aug. 2, 2019, 8 Pages.
International Search Report and Written Opinion for PCT/US2019/060185 dated Jan. 31, 2020, 7 Pages.
International Search Report and Written Opinion for PCT/US2019/067513 dated Feb. 27, 2020, 11 Pages.
Johnson et al. "Addiction-Like Reward Dysfunction and Compulsive Eating in Obese Rats: Role for Dopamine D2 Receptors" May 2010, Nature Neuroscience 13(5):635-641.
Keller et al. "Intranasal Drug Delivery: Opportunities and Toxicologic Challenges During Drug Development" Jan. 25, 2021, Drug Delivery and Translation Research, retrieved from the internet: https://doi.org/10.1007/s13346-020-00891-5, 12:735-757.
Kelly et al. "The Opioid Receptor Pharmacology of GSK1521498 Compared to Other Ligands with Differential Effects on Impulsive Reward-related Behaviours" 2015, Psychopharmacology 232:305-314.
Kharkevich "Pharmacology Textbook" 10th Ed. 2010, p. 73 (Moscow) (in Russian).
Kiselev et al. "Fundamentals of Chemistry (part 1): Educational and methodical manual for students of medical and pediatric faculties of medical universities" 2017, Kazan (in Russian).
International Preliminary Report on Patentability for PCT/US2022/039463 dated Feb. 15, 2024, 9 pages.
Ahmad FB et al., Provisional Drug Overdose Death Counts, National Center For Health Statistics, 2024, https://www.cdc.gov/nchs/nvss/vsrr/drug-overdose-data.htm.
Irvine et al., Estimating naloxone need in the USA across fentanyl, heroin, and prescription opioid epidemics: a modelling study, Lancet Public Health 7(3): e210-e218 (2022).
FDA Approves Prescription Nasal Spray to Reverse Opioid Overdose, Press Release, FDA, May 22, 2023.
U.S. FDA, OPVEE Medical Officer, Cross-Discipline Team Leader, and Division Director Summary Review, 41 pages, May 22, 2023.
NARCAN Prescribing Information (2015), 18 pages.
David Strauss, Assessment of Intranasal Naloxone Repeat Dosing Strategies, U.S. FDA Slides, Mar. 8, 2023, 23 pages.
Van Lemmen et al., Opioid Overdose: Limitations in Naloxone Reversal of Respiratory Depression and Prevention of Cardiac Arrest, Anesthesiology, 139(3):342-353, Sep. 2023.
ANDA No. 212955, Orange Book: Approved Drug Products with Therapeutic Equivalence Evaluations, U.S. FDA.
Opiant Pharmaceuticals Announces Positive Topline Results from Head-to-Head Pharmacodynamic Study Comparing OPNT003, Nasal Nalmefene, to Nasal Naloxone, OPIANT Press Release, Apr. 27, 2022.
NPR, A new nasal spray to reverse fentanyl and other opioid overdoses gets FDA approval, May 22, 2023, 3 pages.

(56) References Cited

OTHER PUBLICATIONS

Sellers et al., Can Intranasal Nalmefene Reduce the Number of Opioid Overdose Deaths?, Clinical Pharmacology in Drug Development, Jan. 30, 2024, doi: 10.1002/cpdd.1381. Epub ahead of print. PMID: 38289185.

Skolnick P., Comment on: Can Intranasal Nalmefene Reduce the Number of Opioid Overdose Deaths?, Clinical Pharmacology in Drug Development, Jan. 1, 2024.

* cited by examiner

Mean Plasma Concentration-Time Profiles of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) on Linear Scale – PK Population Mean Plasma Concentration-Time Profiles of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) on Semi-Logarithmic Scale – PK Population Treatment A: T1: 3 mg IN nalmefene dose (one 0.1 mL spray of a 30 mg/mL solution in one nostril)
Treatment B: T2: 6 mg IN nalmefene dose (one 0.1 mL spray of a 30 mg/mL solution in each nostril)
Treatment C: T3: 6 mg IN nalmefene dose (two 0.1 mL sprays of a 30 mg/mL solution in one nostril)

Treatment A: T1: 3 mg IN nalmefene dose (one 0.1 mL spray of a 30 mg/mL solution in one nostril)
Treatment B: T2: 6 mg IN nalmefene dose (one 0.1 mL spray of a 30 mg/mL solution in each nostril)
Treatment C: T3: 6 mg IN nalmefene dose (two 0.1 mL sprays of a 30 mg/mL solution in one nostril)

MV=minute ventilation

OPNT003-OOD-001

50* healthy subjects
OPNT003, compared with nasal naloxone 4mg
*Evaluated for primary end point

- OPNT003 met the primary endpoint of non-inferiority, which was designed to assess whether nasal nalmefene performed as well or better than nasal naloxone
- Nasal nalmefene produced a mean increase in minute ventilation at five minutes that was almost double that produced by nasal naloxone

OPNT003-PK-001

69 healthy subjects
OPNT003, compared with intramuscular nalmefene injection, 1 mg

- Rapid absorption ($T_{max}$ 15 min)
- high plasma concentrations ($C_{max}$ 12.2 ng/ml) that surpassed intramuscular nalmefene
- long plasma half-life ($t_{1/2}$ ~ 11 h)

OPNT003-PK-002

23 healthy subjects
OPNT003 given as a single 3mg dose in one nostril, as a single dose in each nostril, and as two doses in one nostril

- Rapid absorption ($T_{max}$ 15 min) in all three study arms
- Dose proportional plasma concentrations to single dose whether administered as a single dose in each nostril or as two doses in a single nostril
- Confirmed long plasma half-life ($t_{1/2}$ ~ 11 h)
- Safe and well tolerated

FIG. 25

COMPOSITIONS AND METHODS FOR THE TREATMENT OF OPIOID OVERDOSE

This application claims priority from U.S. Prov. Appl. Ser. No. 63/229,300 filed on Aug. 4, 2021, which is incorporated herein by reference in its entirety to the extent permitted by law.

FIELD

The present invention relates to the field of treating opioid overdose, more particularly to pharmaceutical compositions comprising an opioid antagonist and methods of use thereof.

BACKGROUND

For almost 20 years, prescription opioid use and abuse has become more prevalent in the United States. In addition, the abuse of heroin and synthetic opioids such as fentanyl has increased dramatically since 2010. Consequently, the death rate due to opioid overdose has continued to rise dramatically. For example, it is estimated that there were almost 33,000 fatalities due to opioid overdose in 2015. Currently, naloxone injectable in initial doses ranging from 0.4 mg to 2 mg administered by intravenous (IV), intramuscular (IM), or subcutaneous (SC) routes is the accepted standard treatment for opioid overdose. These injections are most commonly administered by medical personnel in emergency departments and in ambulances. An intranasal (IN) formulation of naloxone was approved for the treatment of opioid overdose by the Food and Drug Administration (FDA) in 2015. Intranasal naloxone is easy to administer, and is quickly becoming the preferred route of administration for first responders who are either not trained or licensed to administer an injection. Moreover, the intranasal route of administration eliminates the potential for accidental transmission of infectious diseases (e.g., hepatitis C and HIV) to first response or medical personnel via needle-stick injury.

Nalmefene and naloxone are opioid antagonists that bind to the same brain opiate receptors as opioids. Both opioid antagonists bind to these receptors with high affinity, and compete by mass action with opioids (e.g., oxycodone, morphine, and heroin) for these receptor sites. By binding to these receptors in place of opioids, opioid antagonists like naloxone and nalmefene can reverse the pharmacological actions of opioids, including respiratory depression and somnolence.

Naloxone has a half-life of 1 to 2 hours, which results in a short duration of action. Opioid-induced central nervous system depression can reemerge if the patient has either overdosed with a long-acting opioid (e.g. methadone, carfentanil) and/or has a high level of opioids in their system and has not received additional doses of naloxone. This is particularly problematic if the patient has overdosed in a remote/rural area where emergency medical services could take an hour or more before arriving at the scene of an overdose.

Nalmefene—a 6-methylene analog of naltrexone—was approved by the US Food and Drug Administration (FDA) for the reversal of the effect of opioids, including respiratory depression, sedation, and hypotension. It has a reported half-life of between 8 hours and 10.8 hours after an intravenous (IV) dose. While IV administration of nalmefene is the recommended route, it can also be given by the intramuscular (IM) and subcutaneous (SC) route if venous access cannot be established. The relative bioavailability of nalmefene by the IM and SC routes is approximately 100%, but the maximum plasma concentration ($C_{max}$) occurs at 1.5±1.2 hours after SC injection. Nalmefene has a longer duration of action than naloxone when tested in healthy subjects who were given a continuous IV infusion of fentanyl. While equipotent on a milligram-per-milligram basis, the clearance of nalmefene was slower than naloxone, thus increasing its duration of action.

There are concerns about the risks to exposure of medical personnel to blood-borne pathogens through needle stick injuries. Further, non-medical personnel require training to administer injections. Nalmefene administered by the intranasal (IN) route, a needleless alternative, is much easier to use and could have a significant impact in reducing both morbidity and mortality from opioid overdose. Nalmefene could be particularly useful in cases where the overdose is due to an opioid with a long half-life. However, neither the half-life nor the time to peak effect ($T_{max}$) of IN nalmefene has been reported in the peer reviewed literature.

An IN administration of nalmefene has the potential to increase the time available for first responders to aid a person who has had an opioid overdose due to the longer half-life of nalmefene compared to naloxone.

Thus, there remains a need for durable, easy-to-use, needleless devices with storage-stable formulations that can enable untrained individuals to quickly deliver a therapeutically effective dose of a rapid-acting and long-lasting opioid antagonist to an opioid overdose patient. The therapeutically effective dose should be sufficient to obviate the need for the untrained individual to administer either a second dose of opioid antagonist or an alternative medical intervention to the patient, and to stabilize the patient until professional medical care becomes available. The devices described herein meet this and other needs.

SUMMARY

Provided herein are methods, compositions, and devices for the treatment of opioid overdose comprising administering a therapeutically effective amount of an intranasal formulation of the opioid antagonist nalmefene.

Accordingly, in one aspect, the invention provides methods of treating opioid overdose or a symptom thereof. The method includes nasally administering to a patient in need thereof a therapeutically effective amount of an opioid antagonist, such as nalmefene or pharmaceutically acceptable salts thereof, wherein the therapeutically effective amount is equivalent to about 1 mg to about 10 mg of nalmefene hydrochloride or a hydrate thereof.

Also provided are devices adapted for nasal delivery of a pharmaceutical composition to a patient, comprising a therapeutically effective amount of an opioid antagonist, such as nalmefene and pharmaceutically acceptable salts thereof, wherein the device is pre-primed, and wherein the therapeutically effective amount is equivalent to about 1 mg to about 10 mg of nalmefene hydrochloride or a hydrate thereof.

In some embodiments, the IN formulation is administered prior to exposure to an addictive substance or behavior. In some embodiments, the IN formulation is administered between about 1 and about 2 hours prior to exposure to an addictive substance or behavior. In some embodiments, the IN formulation is administered daily. In some embodiments, the IN formulation is administered twice daily. In some embodiments, the IN formulation is administered three times daily. In some embodiments, the IN formulation is administered four times daily. In some embodiments, the IN formulation is administered as needed by the subject throughout the day. In some embodiments, the IN formulation is administered once daily, followed by additional, subsequent administrations as needed by the subject throughout the day. In some embodiments, the IN formulation is administered contemporaneously with exposure to an addictive substance or behavior. In some embodiments, the IN formulation is administered following exposure to an addictive substance or behavior. In some embodiments, the IN formulation is administered between about 5 minutes and about 15 minutes before exposure to an addictive substance or behavior.

In some embodiments, the IN formulation comprises an aqueous solution. In some embodiments, the IN formulation comprises about 3 mg nalmefene or a salt thereof. In some embodiments, about 0.1 mL of said formulation is delivered to the subject. In some embodiments, the formulation comprises 30 mg/ml nalmefene or a salt thereof.

In some embodiments, the IN formulation is administered as a single administration to one nostril. In some embodiments, the IN formulation is administered as two administrations, one to each nostril. In some embodiments, the IN formulation is administered as four administrations, two to each nostril.

In some embodiments, the pharmaceutical composition comprising a therapeutically effective amount of nalmefene is administered in conjunction with an excipient. In some embodiments, the excipient is an absorption enhancer. In some embodiments, the absorption enhancer is an alkylsaccharide, such as dodecyl maltoside. In some embodiments, the absorption enhancer is an alkylglycoside.

In some embodiments, the pharmaceutical composition additionally comprises one or more excipients selected from sodium chloride, benzalkonium chloride, edetate disodium, and an acid. In some embodiments, the acid is sufficient to achieve a pH of about 3.5 to about 5.5.

In some embodiments, the therapeutically effective amount comprises about 1 to about 10 mg of nalmefene. In some embodiments, the therapeutically effective amount comprises about 1, about 2, about 3, about 4, about 5, about 6, about 7, about 8, about 9, about 10, about 11, about 12, about 13, about 14, or about 15 mg of nalmefene.

In some embodiments, the therapeutically effective amount of nalmefene is administered in 3 mg doses throughout the day as needed by the subject.

In some embodiments, the therapeutically effective amount of nalmefene is administered as a first 3 mg dose in the morning, and subsequent 3 mg doses as needed prior to exposure to an addictive substance or behavior. In some embodiments, the therapeutically effective amount of nalmefene is administered as a first 3 mg dose in the morning, and subsequent 3 mg doses as needed contemporaneously with exposure to an addictive substance or behavior. In some embodiments, the therapeutically effective amount of nalmefene is administered as a first 3 mg dose in the morning, and subsequent 3 mg doses as needed after prior to exposure to an addictive substance or behavior.

In certain embodiments, the nalmefene formulations of the present disclosure are stable (e.g., maintain at least about 80% potency) at room temperature for at least about 1 week, or 2 weeks, or 3 weeks, or 1 month, or 2 months, or 3 months, or 4 months, or 6 months, or 8 months, or 10 months, or 12 months, or 18 months, or 24 months.

Disclosed herein is a method of achieving a therapeutically effective plasma concentration of nalmefene to treat opioid overdose in a patient in need thereof. The method comprises the intranasal administration of a pharmaceutical formulation comprising between about 2 mg and about 16 mg nalmefene or a salt or hydrate thereof.

Also disclosed herein is an intranasal pharmaceutical formulation comprising nalmefene that upon its administration to one or more human subjects in need thereof achieves a $C_{max}$ of at least 4 ng/mL within about 40 minutes, or about 30 minutes, or about 20 minutes, or about 10 minutes, or about 5 minutes after administration.

In one embodiment, after the IN administration of a therapeutically effective amount of nalmefene to a human subject, the $T_{max}$ is between about 5 and 45 minutes, or between about 5 and 10 minutes, or between about 10 and 15 minutes, or between about 15 and 20 minutes, or between about 20 and 25 minutes, or between about 25 and 30 minutes, or between about 30 and 35 minutes, or between about 40 and 45 minutes. In some embodiments, the $T_{max}$ is between about 0.08 hours and about 1 hour.

In some embodiments, after the IN administration of a therapeutically effective amount of nalmefene to a human subject, the $T_{1/2}$ is between about 8.02 hours and about 15.4 hours.

In some embodiments, about 15 minutes after the IN administration of a therapeutically effective amount of nalmefene to a human subject, the plasma concentration of nalmefene is between about 3.83 to about 15.23 ng/mL. In some embodiments, about 30 minutes after the IN administration of a therapeutically effective amount of nalmefene to a human subject, the plasma concentration of nalmefene is between about 3.87 to about 8.63 ng/ml. in some embodiments, about 1 hour after the IN administration of a therapeutically effective amount of nalmefene to a human subject, the plasma concentration of nalmefene is between about 3.64 to about 5.64 ng/mL. In some embodiments, about 3 hours after the IN administration of a therapeutically effective amount of nalmefene to a human subject, the plasma concentration of nalmefene is between about 2.491 to about 3.85 ng/mL. In some embodiments, about 6 hours after the IN administration of a therapeutically effective amount of nalmefene to a human subject, the plasma concentration of nalmefene is between about 1.24 to about 2.14 ng/mL.

In one embodiment after the IN administration of a therapeutically effective amount of nalmefene to a human subject, the $C_{max}$ is between about 3 and 60 ng/mL, or between about 5 and 50 ng/mL, or between about 5 and 40 ng/mL, or between about 5 and 35 ng/ml, or between about 5 and 25 ng/mL, or between about 5 and 20 ng/mL, or between about 5 and 17 ng/ml, or between about 5 and 15 ng/mL, or between about 8 and 12 ng/mL. In some embodiments, the $C_{max}$ is between about 4.1 and about 30.4 ng/mL.

In one embodiment after the IN administration of a therapeutically effective amount of nalmefene to a human subject, the $AUC_{0-2.5min}$ is between about 0.007 and 0.15 h*ng/ml, or between about 0.01 and 0.1, or between about 0.05 and 0.08, or between about 0.02 and 0.05 h*ng/mL. In another embodiment, it is between about 0.000504 and about 0.155 h*ng/ml.

In one embodiment after the IN administration of a therapeutically effective amount of nalmefene to a human subject, the $AUC_{0-5min}$ is between about 0.02 and 0.5 h*ng/ml, or between about 0.05 and 0.25 h*ng/ml, or between about 0.125 and 0.5 h*ng/mL. In another embodiment, it is between about 0.00542 and 0.588 h*ng/mL.

In one embodiment after the IN administration of a therapeutically effective amount of nalmefene to a human subject, the $AUC_{0-10min}$ ranges between about 0.05 and 2 h*ng/ml, or between about 0.1 and 1.5 h*ng/ml, or between about 0.5 and 1 h*ng/mL, or between about 0.7 and 0.9 h*ng/mL. In another embodiment, it is between about 0.0815 to about 2.78 h*ng/mL.

In one embodiment after the IN administration of a therapeutically effective amount of nalmefene to a human subject, the $AUC_{0-15min}$ ranges between about 0.01 and 5 h*ng/mL, or between about 0.01 and 4 h*ng/mL, or between about 0.1 and 3 h*ng/mL, or between about 0.5 and 2 h*ng/ml, or between about 1 and 1.5 h*ng/mL. In another embodiment, it is between about 0.325 to about 5.03 h*ng/mL.

In one embodiment after the IN administration of a therapeutically effective amount of nalmefene to a human subject, the $AUC_{0-20min}$ ranges between about 0.01 and 3 h*ng/ml, or between about 0.01 and 2.5 h*ng/mL, or between about 0.1 and 2 h*ng/mL, or between about 0.5 and 1.5 h*ng/ml, or between about 0.8 and 1.25 h*ng/mL. In another embodiment, it is between about 0.350 to about 6.79 h*ng/mL.

In one embodiment after the IN administration of a therapeutically effective amount of nalmefene to a human subject, the $AUC_{0-30min}$ ranges between about 1 and 7 h*ng/ml, or between about 1.25 and 5 h*ng/mL, or between about 2.5 and 5.75 h*ng/ml, or between about 2.75 and 5.25 h*ng/ml, or between about 3 and 5 h*ng/mL, or between about 3.25 and 4.75 h*ng/ml, or between about 3.5 and 4.5 h*ng/mL, or between about 3.75 and 4.25 h*ng/mL. In another embodiment, it is between about 0.802 to about 9.16 h*ng/mL.

In one embodiment, after the IN administration of 3 mg nalmefene to a human subject, the $T_{max}$ is between about 5 and 30 minutes, or between about 10 and 25 minutes, or between about 15 and 20 minutes, or is about 5 minutes, or is about 10 minutes, or is about 15 minutes.

In another embodiment, after the IN administration of 3 mg nalmefene to a human subject, the $C_{max}$ is between about 3 and 25 ng/mL, or between about 10 and 20 ng/ml, or is about 12 ng/mL.

In one embodiment, after the IN administration of 3 mg nalmefene to a human subject, the $AUC_{0-2.5min}$ is between about 0.009 and 0.08 h*ng/mL, or between about 0.02 and 0.06 h*ng/ml, or between about 0.015 and 0.025 h*ng/mL, or is about 0.02 h*ng/mL.

In another embodiment, after the IN administration of 3 mg nalmefene to a human subject, the $AUC_{0-5min}$ is between about 0.01 and 0.3 h*ng/ml, or between about 0.05 and 0.2 h*ng/mL, or between about 0.05 and 0.15 h*ng/ml, or is about 0.125 h*ng/ml.

In another embodiment, after the IN administration of 3 mg nalmefene to a human subject, the $AUC_{0-10min}$ is between about 0.1 and 1.6 h*ng/ml, or between about 0.25 and 1.2 h*ng/ml, or between about 0.5 and 1 h*ng/mL, or is about 0.8 h*ng/mL.

In another embodiment, after the IN administration of 3 mg nalmefene to a human subject, the $AUC_{0-15min}$ ranges between about 0.5 and 3 h*ng/mL, or between about 1 and 2.5 h*ng/mL, or between about 1.2 and 2 h*ng/mL, or is about 1.6 h*ng/mL.

In another embodiment, after the IN administration of 3 mg nalmefene to a human subject, the $AUC_{0-20min}$ is between about 1 and 4 h*ng/mL, or between about 1.2 and 3 h*ng/ml, or between about 2 and 3 h*ng/mL, or is about 2.3 h*ng/ml.

In another embodiment, after the IN administration of 3 mg nalmefene to a human subject, the $AUC_{0-30min}$ is between about 1 and 5 h*ng/ml, or between about 1.5 and 4 h*ng/mL, or between about 2 and 3.75 h*ng/ml, or is about 0.35 h*ng/mL.

In certain embodiments, after the IN administration of 3 mg nalmefene to a plurality of human subjects, the $C_{max}$ geometric mean is between about 7 and 15 ng/ml, or between about 8 and 12 ng/ml, or is about 10 ng/mL.

In certain embodiments, after the IN administration of 3 mg nalmefene to a plurality of human subjects, the $AUC_{0-2.5min}$ geometric mean is between about 0.004 and 0.016 h*ng/ml, or between about 0.006 and 0.012 h*ng/mL, or is about 0.008 h*ng/mL. In other embodiments, after the IN administration of 3 mg nalmefene to a plurality of human subjects In another embodiment, after the IN administration of 3 mg nalmefene to a plurality of human subjects, the $AUC_{0-5min}$ geometric mean is between about 0.03 and 0.12 h*ng/ml, or between about 0.06 and 0.09 h*ng/ml, or is about 0.06 h*ng/mL.

In another embodiment, after the IN administration of 3 mg nalmefene to a plurality of human subjects, the $AUC_{0-10min}$ geometric mean is between about 0.25 and 0.75 h*ng/ml, or between 0.4 and 0.6 h*ng/ml, or about 0.5 h*ng/mL.

In another embodiment, after the IN administration of 3 mg nalmefene to a plurality of human subjects, the $AUC_{0-15min}$ geometric mean is between about 0.75 and 1.5 h*ng/mL, or between about 0.9 and 1.3 h*ng/mL, or is about 1.2 h*ng/mL.

In another embodiment, after the IN administration of 3 mg nalmefene to a plurality of human subjects, the $AUC_{0-20min}$ geometric mean is between about 1.25 and 2.25 h*ng/mL, or between about 1.50 and 2 h*ng/mL, or is about 1.9 h*ng/mL.

In another embodiment, after the IN administration of 3 mg nalmefene to a plurality of human subjects, the $AUC_{0-30min}$ geometric mean is between about 2 and 4 h*ng/ml, or between about 2.5 h*ng/ml and 3.50 h*ng/mL, or is about 3 h*ng/ml.

In another embodiment, after the IN administration of 3 mg nalmefene to a plurality of human subjects, the $AUC_{Last}$ geometric mean is between about 30 and 50 h*ng/ml, or between 35 and 45 h*ng/mL, or is about 40 h*ng/mL. In some embodiments, the $AUC_{Last}$ is between about 22.8 and about 58.3 h*ng/mL.

In another embodiment, after the IN administration of 3 mg nalmefene to a plurality of human subjects, the $AUC_{inf}$ geometric mean is between about 30 and 50 h*ng/mL, or between 35 and 45 h*ng/mL, or is about 40 h*ng/mL. In some embodiments, the $AUC_{inf}$ is between about 23.1 to about 60.9 h*ng/mL.

In another embodiment, after the IN administration of 3 mg nalmefene to a plurality of human subjects, the $AUC_{Extrap}$ is between about 1.12% to about 13.1%.

In another embodiment, after the IN administration of 3 mg nalmefene to a plurality of human subjects, the $K_{el}$ is between about 0.0281 to about 0.0864 (1/h).

Figure 5:
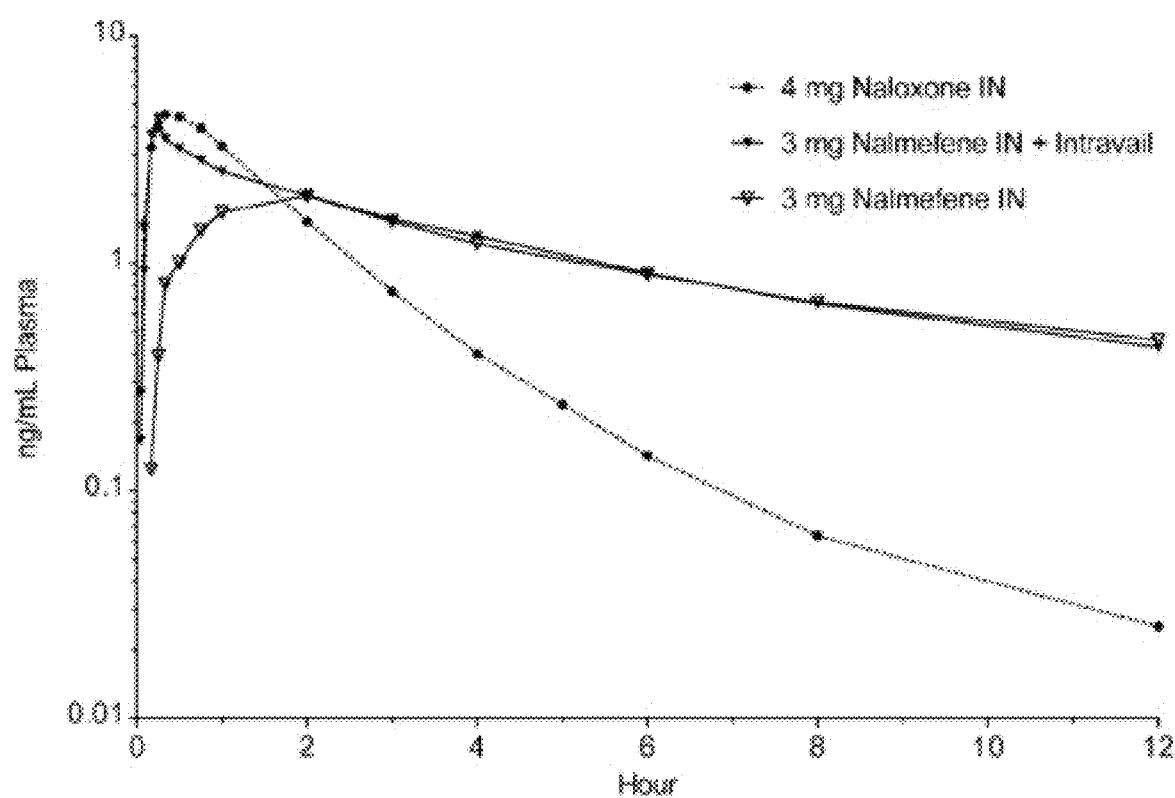

FIG. 5 is a semi-log graph showing the comparison of plasma concentrations of 4 mg naloxone IN (0.1 ml of 40 mg/ml solution) compared to 3 mg nalmefene (0.1 ml of 30 mg/ml solution) IN with and without 0.25% Intravail (dodecyl maltoside). These data are obtained from a previous study, in which the $T_{max}$ was 0.5 h (30 min).

Figure 6:
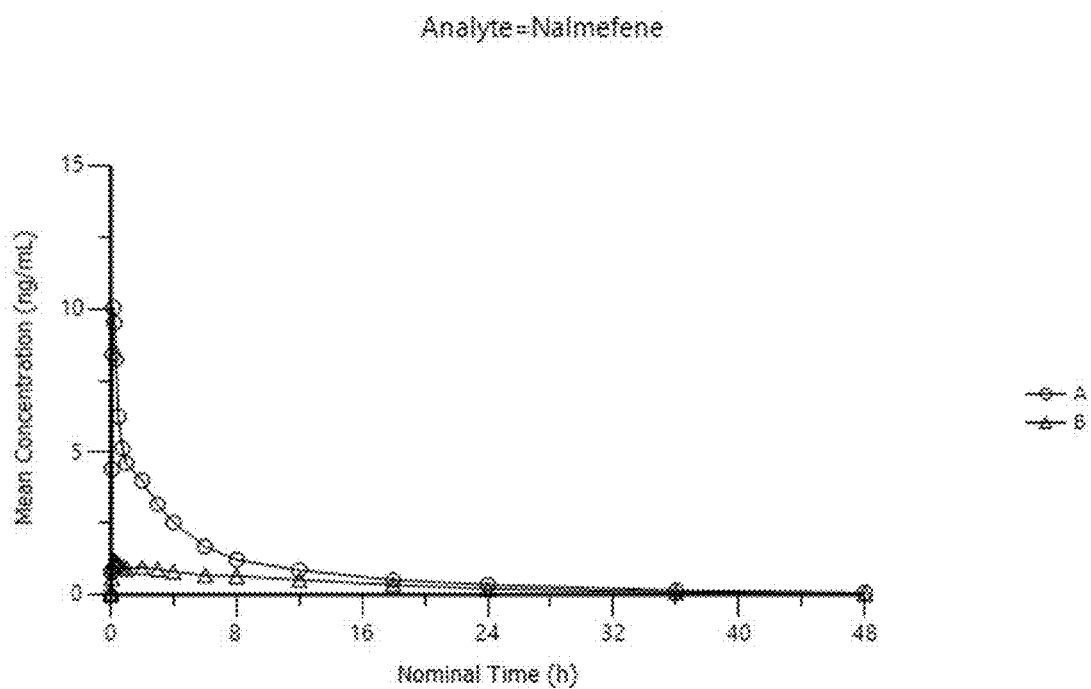

FIG. 6 is a line graph of the mean plasma concentration-time profiles of nalmefene after intranasal (IN) administration of 3.0 mg nalmefene hydrochloride (Treatment A) and intramuscular (IM) administration of 1.0 mg of nalmefene hydrochloride (Treatment B) on linear scale—PK population.

Figure 7:
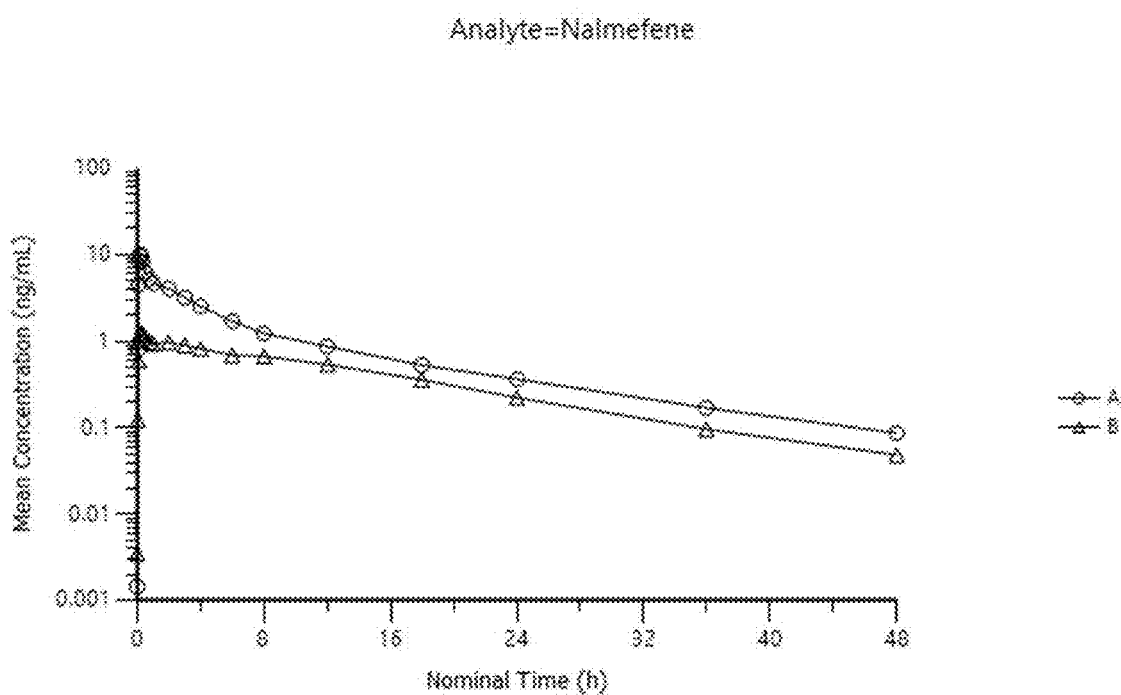

FIG. 7 is a semi-log graph of the mean plasma concentration-time profiles of nalmefene after intranasal (IN) administration of 3.0 mg nalmefene hydrochloride (Treatment A) and intramuscular (IM) administration of 1.0 mg of nalmefene hydrochloride (Treatment B).

Figure 8:
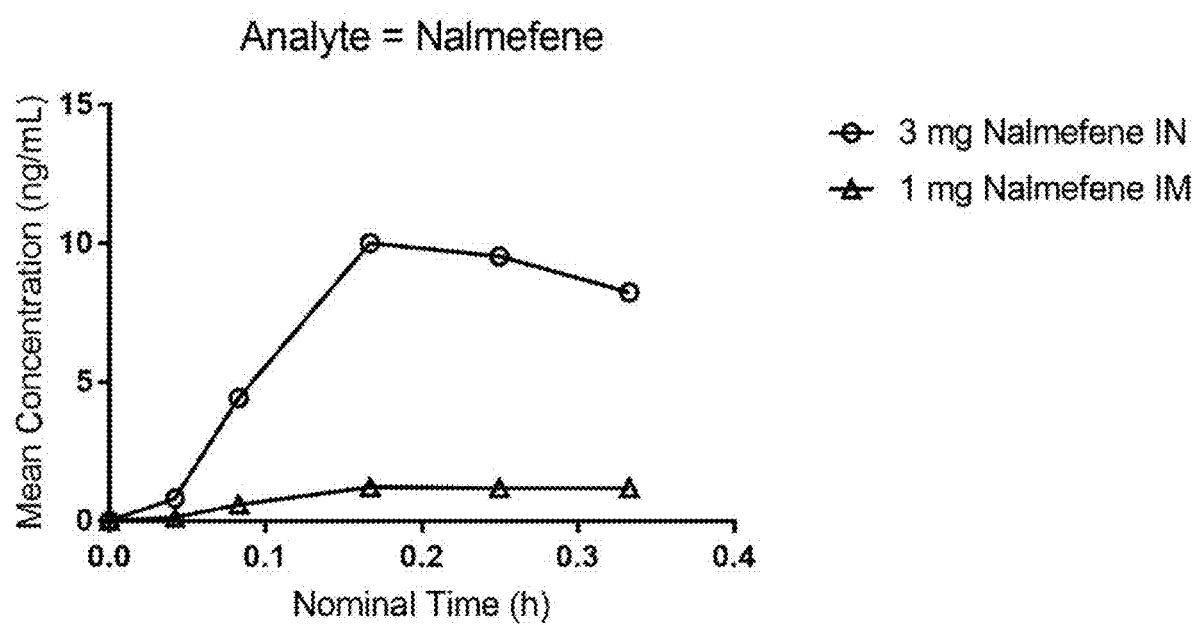

FIG. 8 is a line graph of the mean plasma concentration versus time of nalmefene after intranasal (IN) administration of 3.0 mg nalmefene hydrochloride (Treatment A) and intramuscular (IM) administration of 1.0 mg nalmefene hydrochloride (Treatment B).

Figure 9:
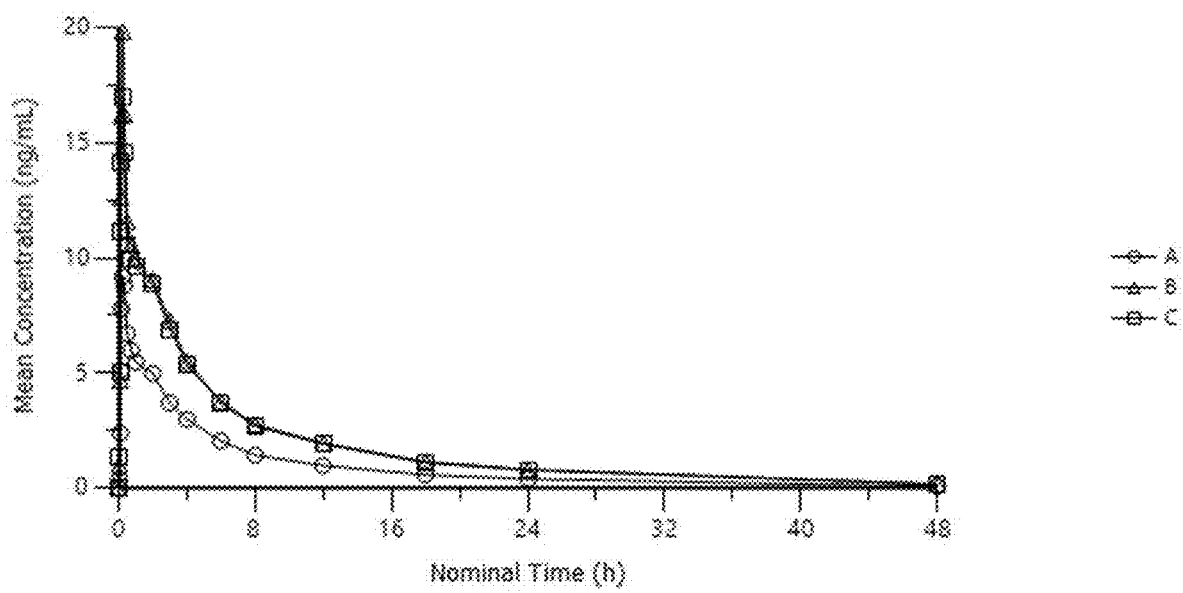

FIG. 9 is a line graph of nalmefene concentration-time data, mean profiles on a linear scale after intranasal (IN) administrations of 3 mg nalmefene hydrochloride in one nostril (Treatment A, T1), 3 mg nalmefene hydrochloride in each nostril (6 mg total dose, Treatment B, T2), and 6 mg nalmefene hydrochloride in one nostril (Treatment C, T3).

Figure 10:
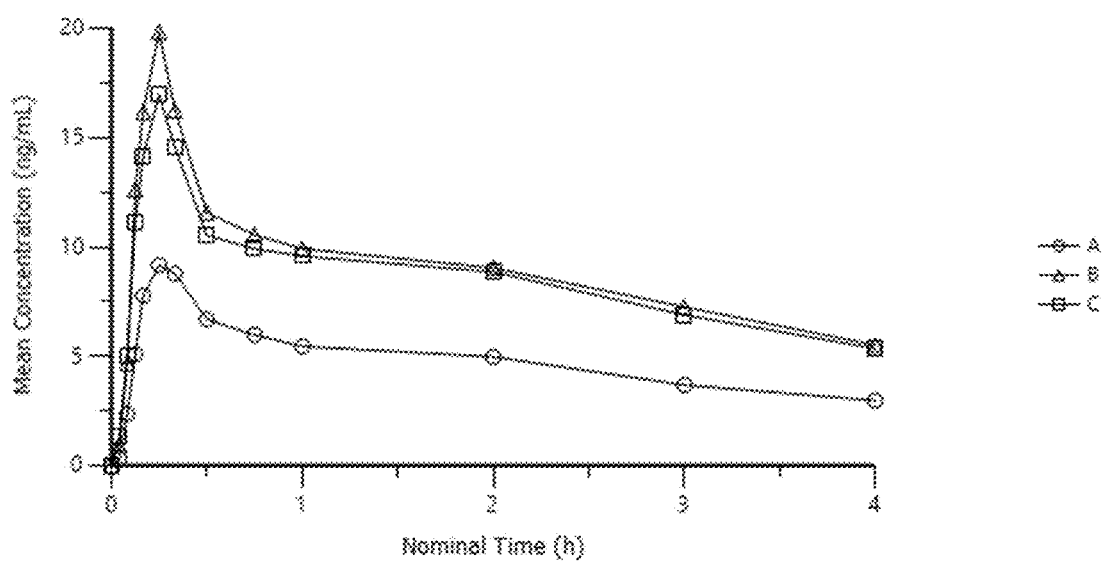

FIG. 10 is a line graph of nalmefene concentration-time data, mean profiles on a linear scale after intranasal (IN) administrations of 3 mg nalmefene hydrochloride in one nostril (Treatment A, T1), 3 mg nalmefene hydrochloride in each nostril (6 mg total dose, Treatment B, T2), and 6 mg nalmefene hydrochloride in one nostril (Treatment C, T3) (X-axis truncated to 4 h post dose).

Figure 11:
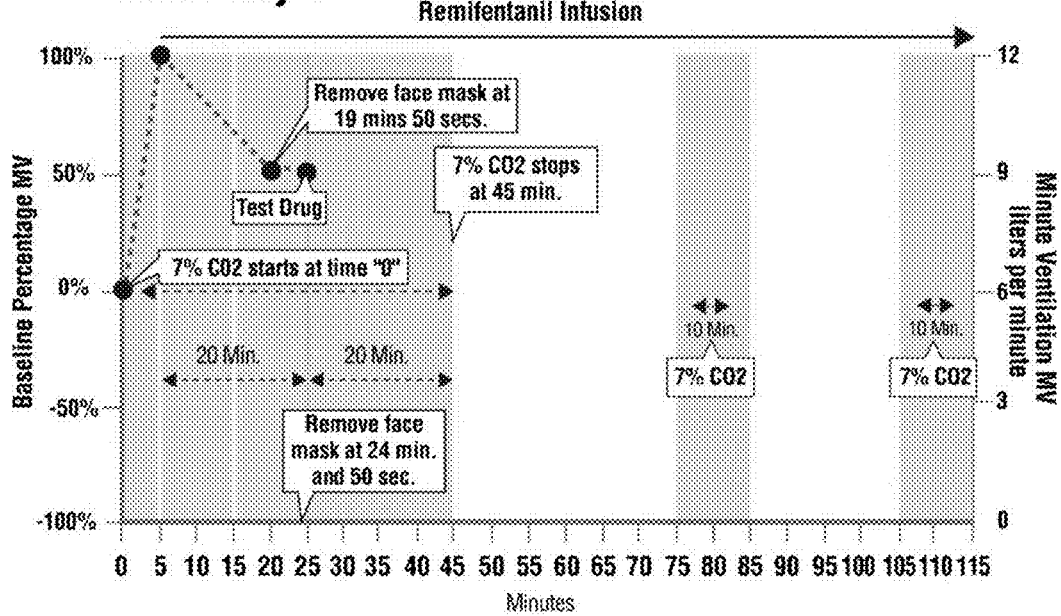
Figure 11:
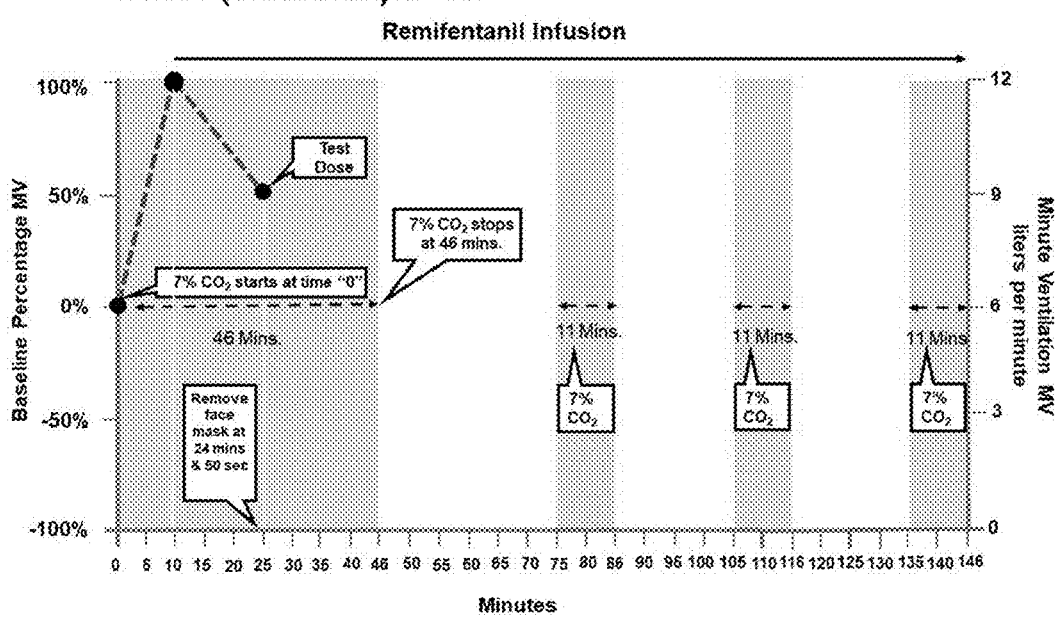

FIG. 11 illustrates the study design for single-center, open-label, 2-part study. Part 1 and the Part 1 extension was a pilot study to determine the relationship between remifentanil dose and suppression of $CO_2$-induced increases in minute ventilation in healthy volunteers with prior opioid exposure. Part 2 was a randomized, 2-period, 2-treatment, crossover study to evaluate the PD effects of IN nalmefene hydrochloride compared to IN naloxone hydrochloride to reverse remifentanil-induced suppression of $CO_2$-induced increases in minute ventilation, in healthy volunteers with prior opioid exposure.

Figure 12A:
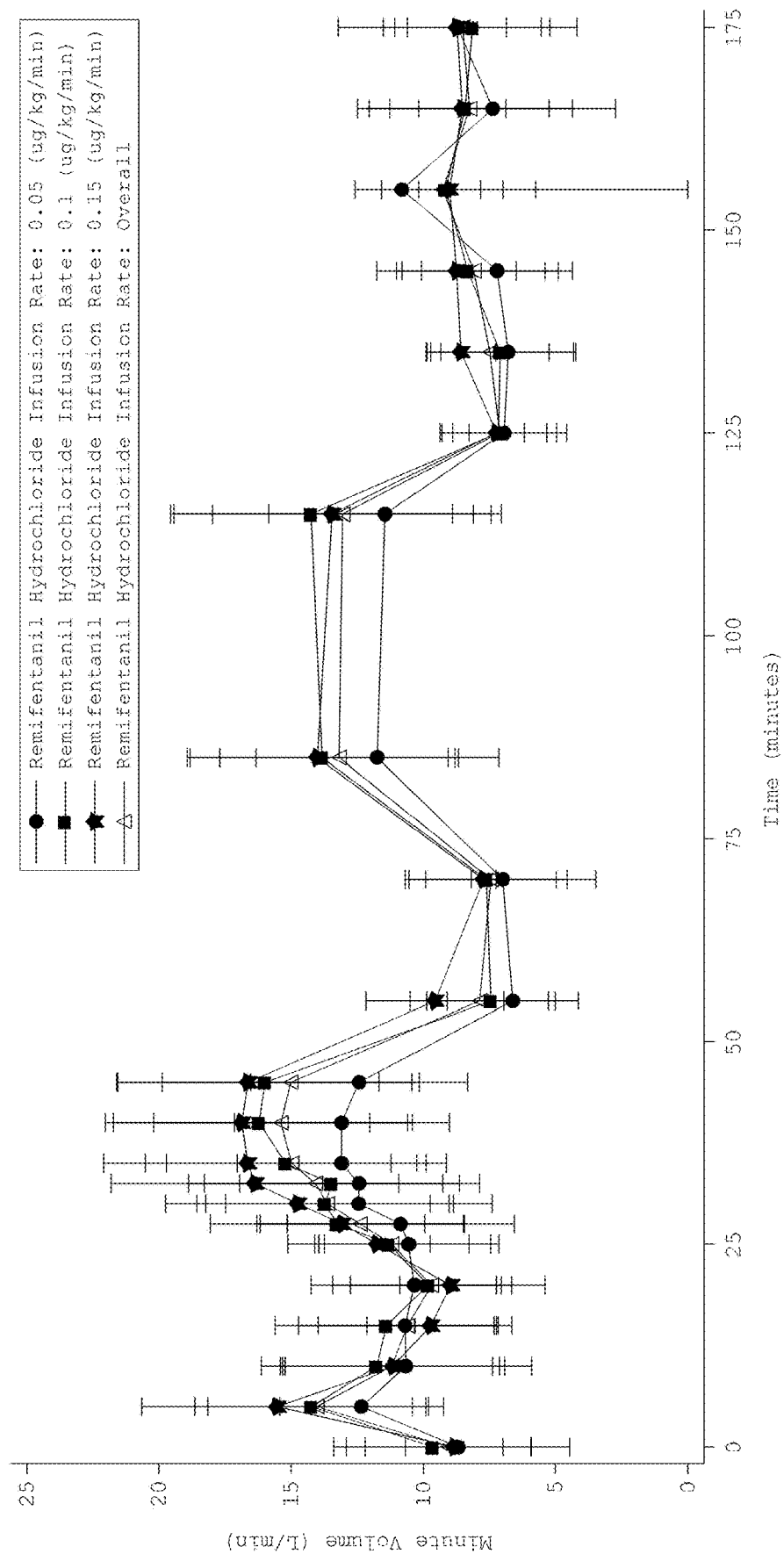
Figure 12B:
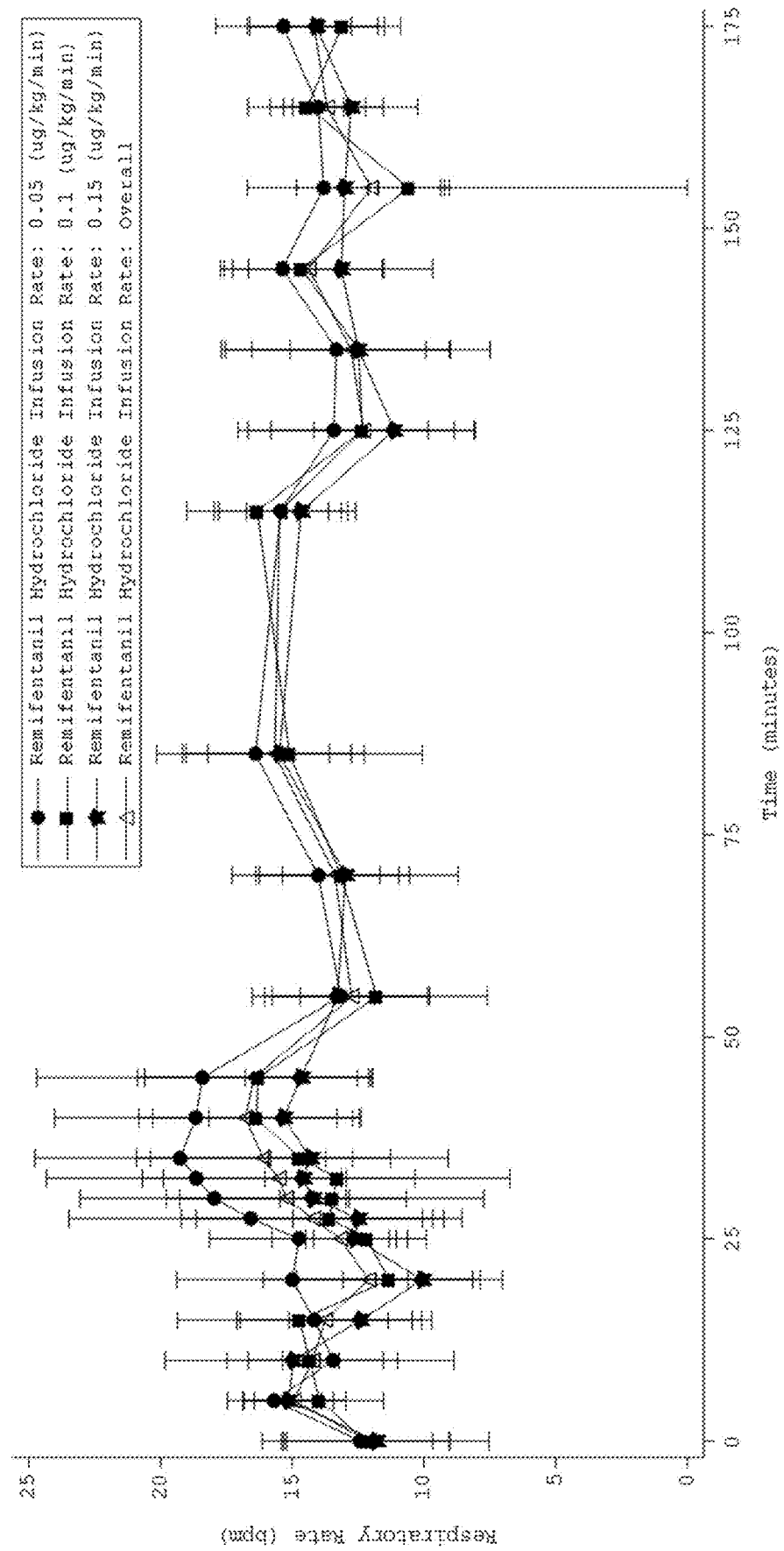
Figure 12C:
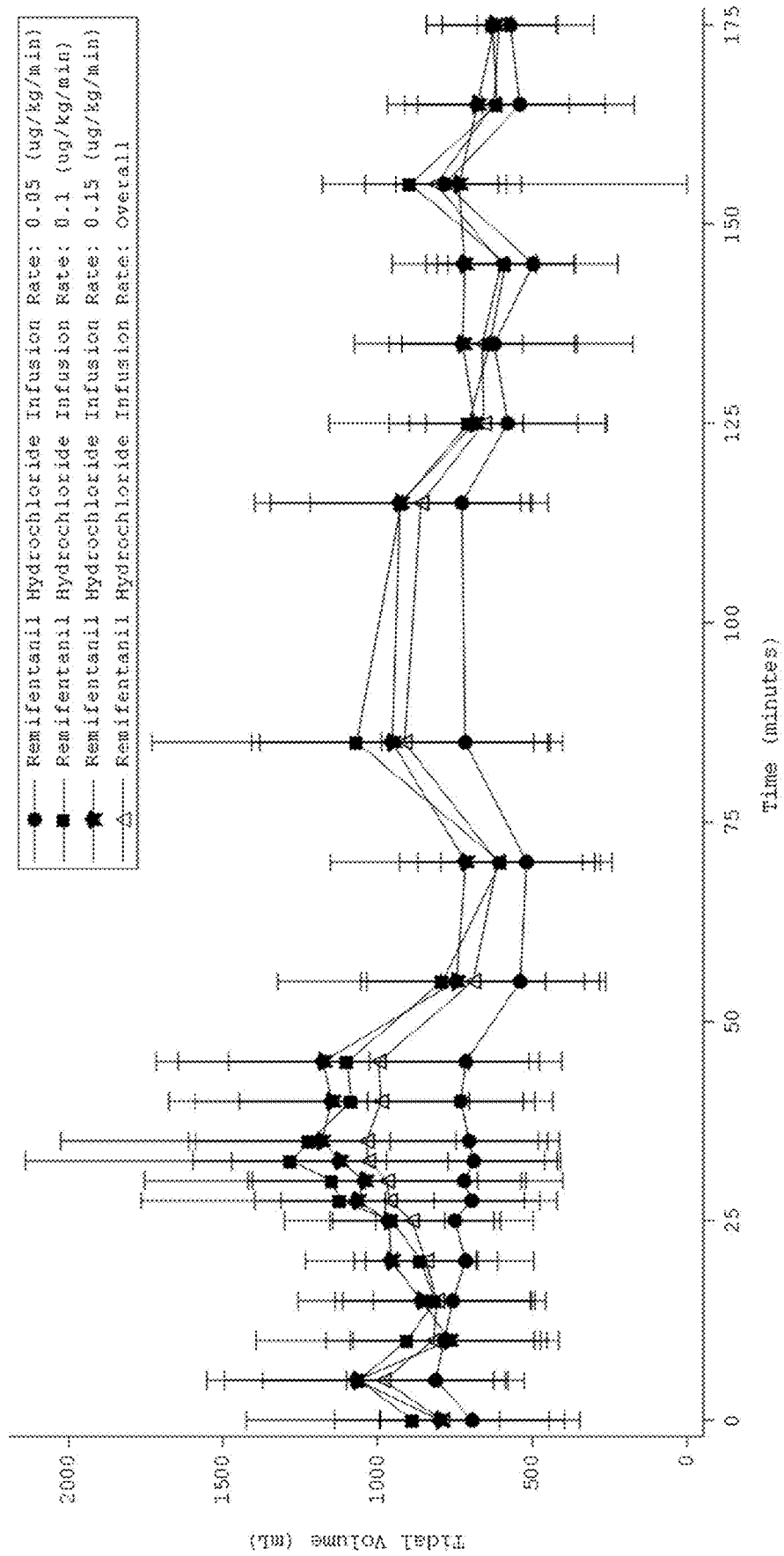

FIGS. 12A, 12B, and 12C are line graphs of mean (±SD) ExSpiron® Device PD measurement versus time—Part 1.

Figure 13:
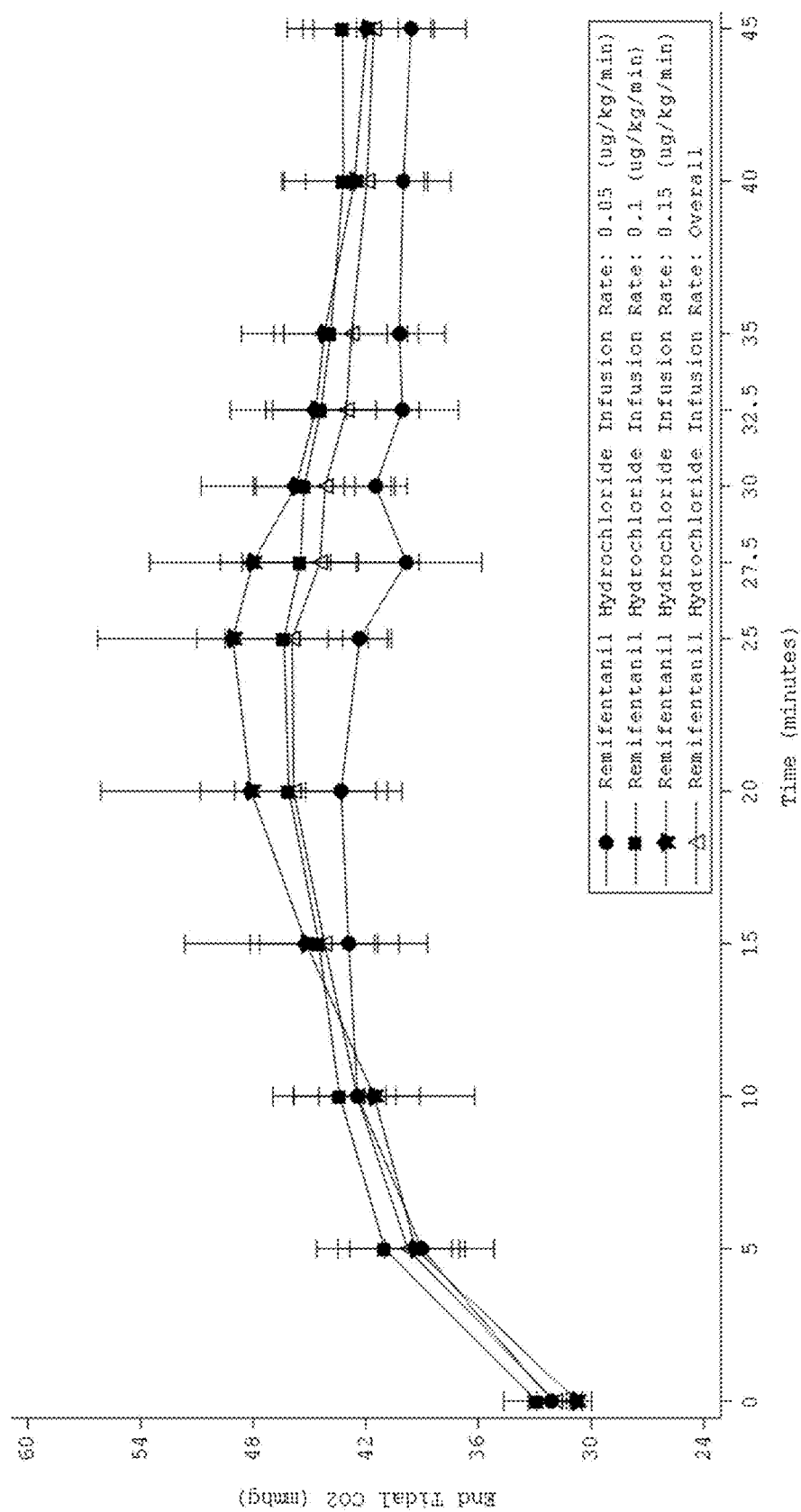

FIG. 13 is a line graph of mean (±SD) VRH $ET_{CO2}$ versus time-Part 1.

Figure 14A:
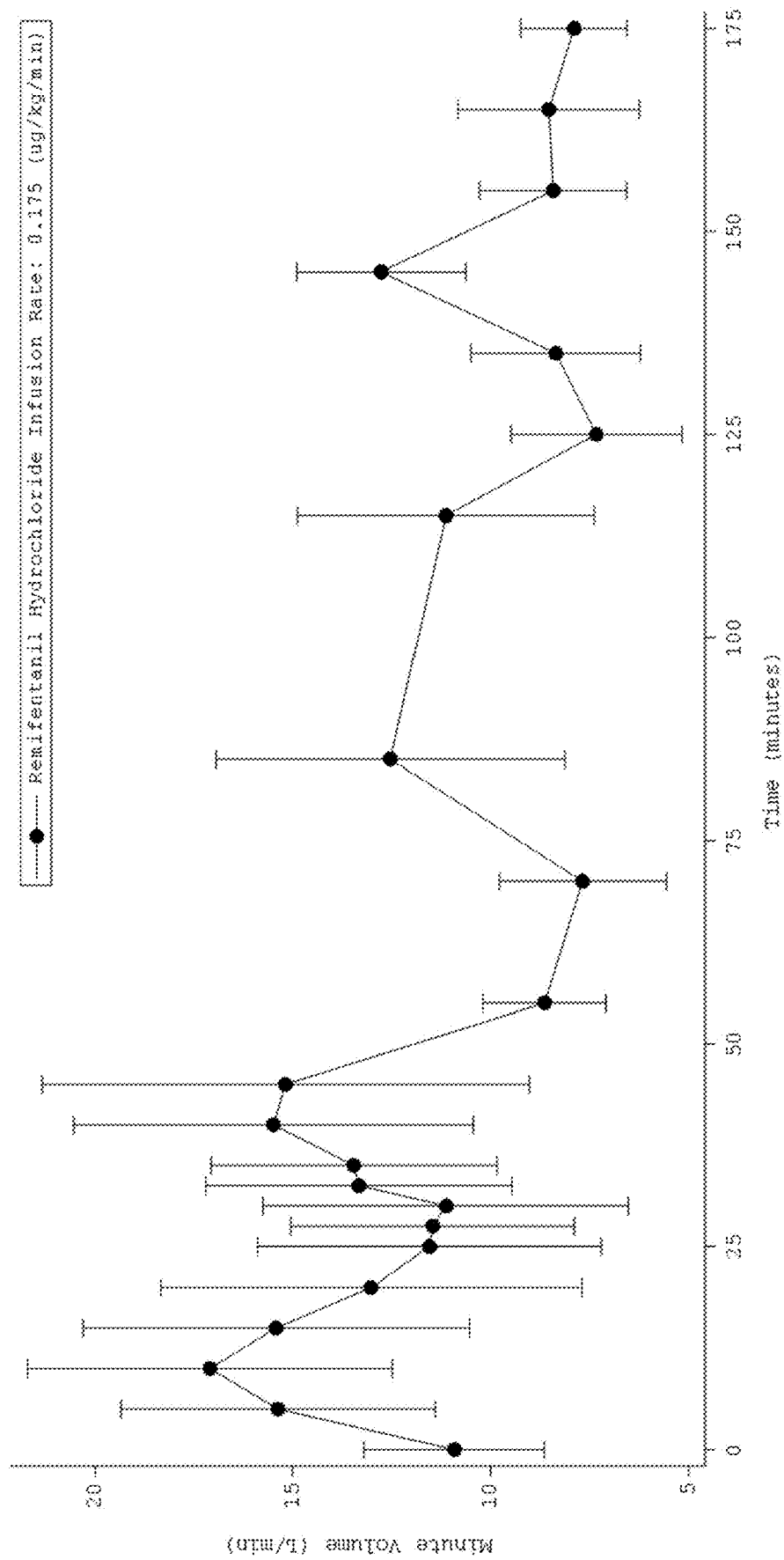
Figure 14B:
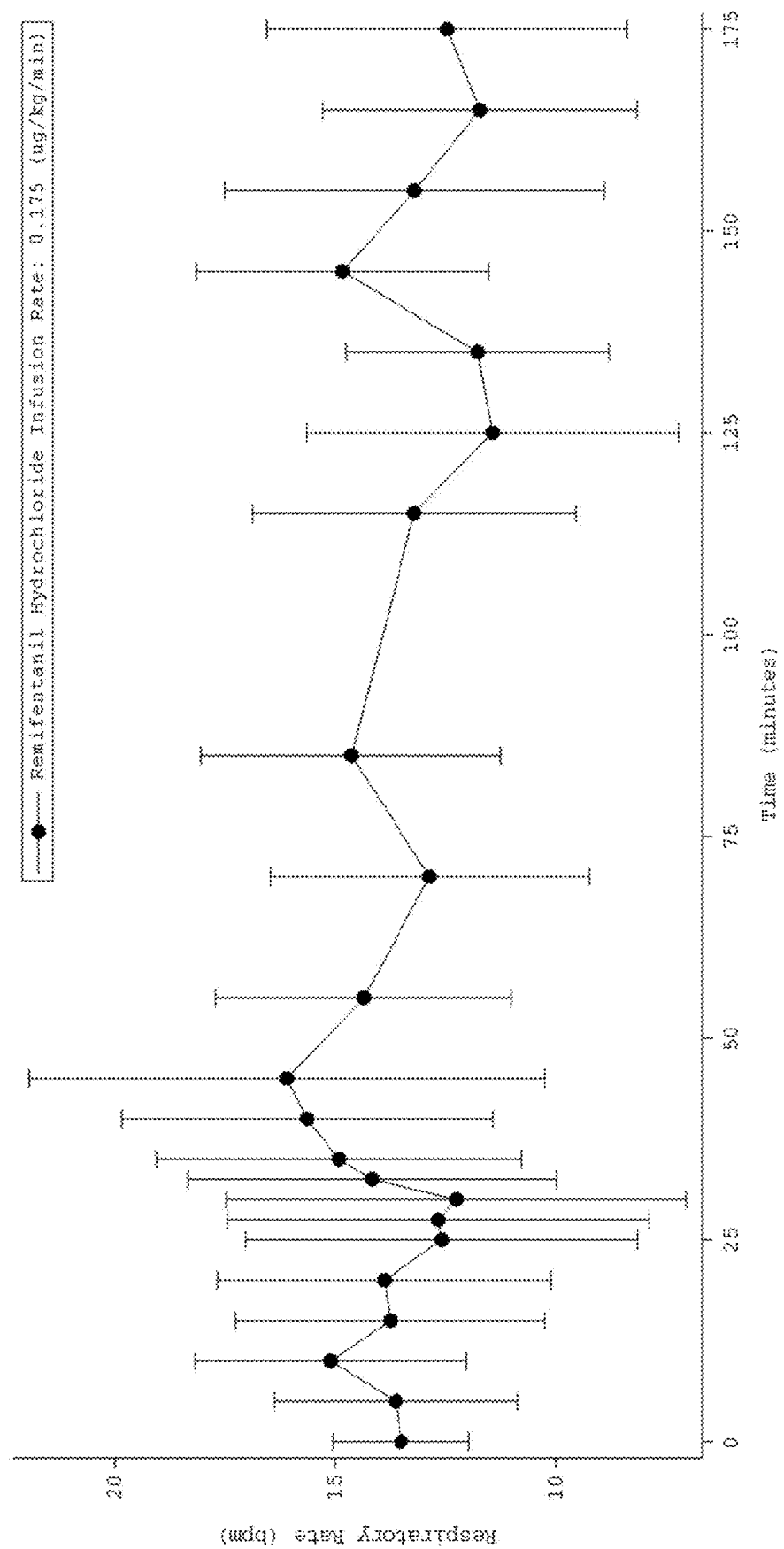
Figure 14C:
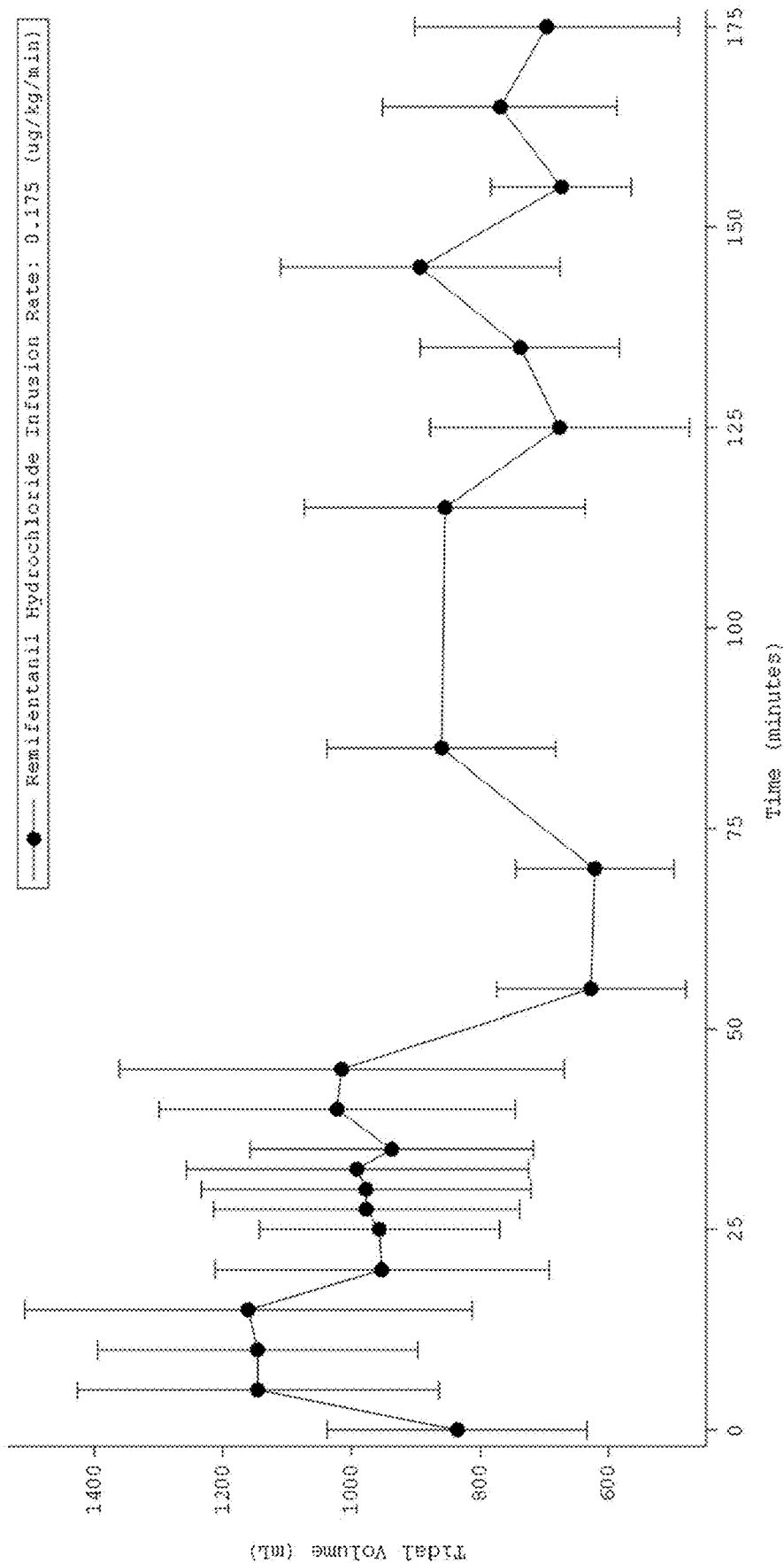

FIGS. 14A, 14B, and 14C are line graphs of mean (±SD) ExSpiron® Device PD measurement versus time—Part 1 Extension.

Figure 15:
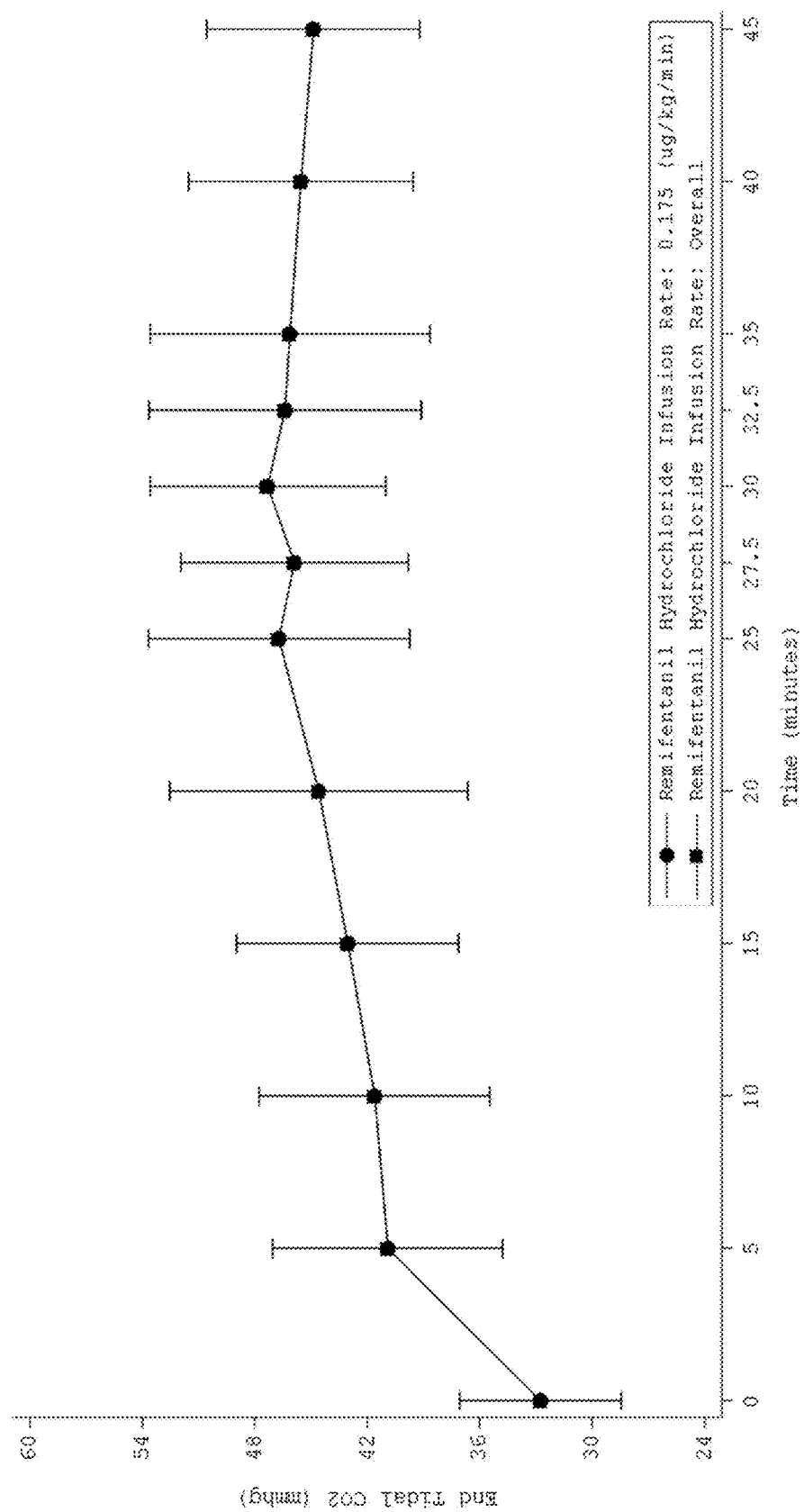
Figure 16A:
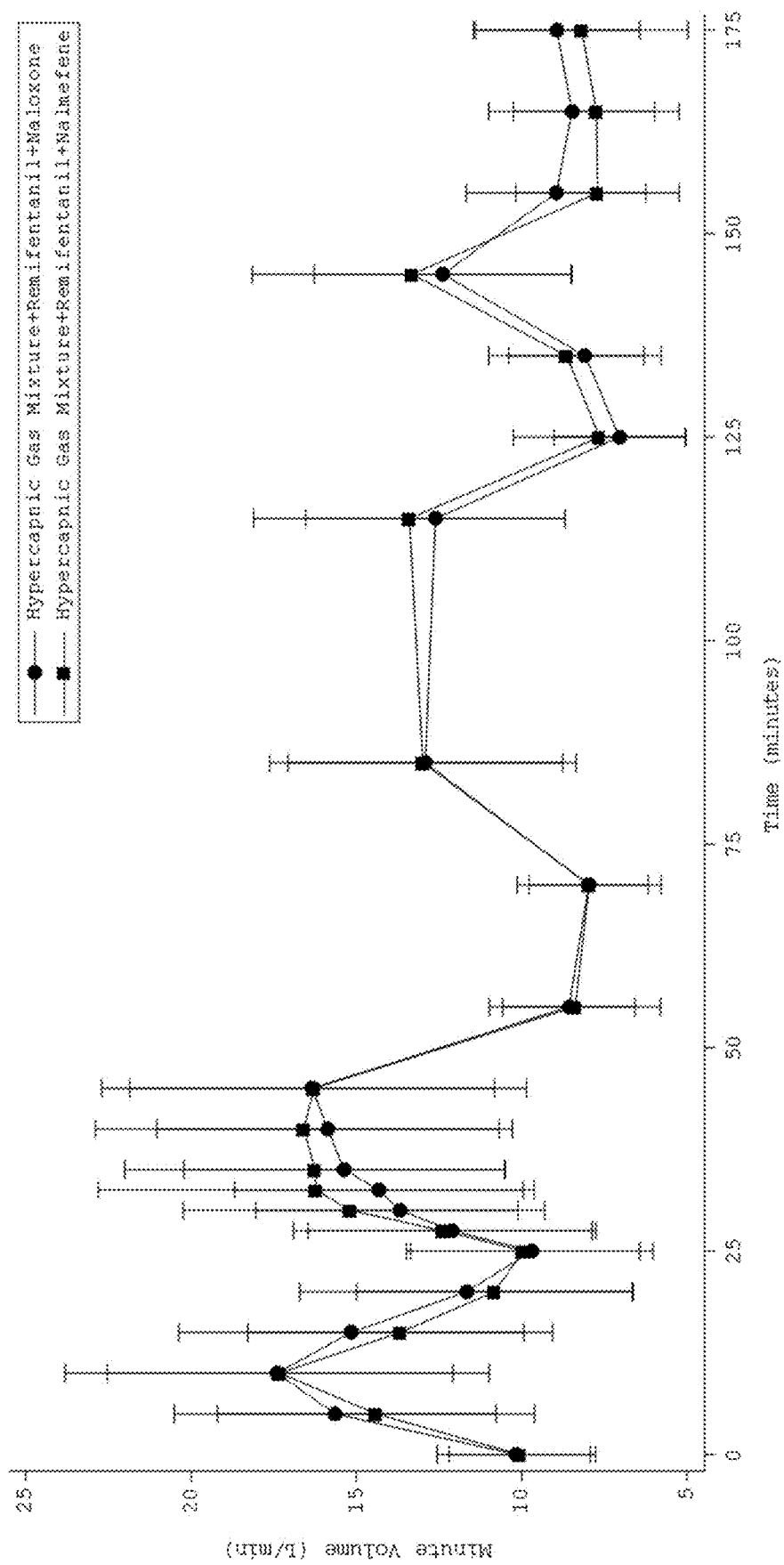
Figure 16B:
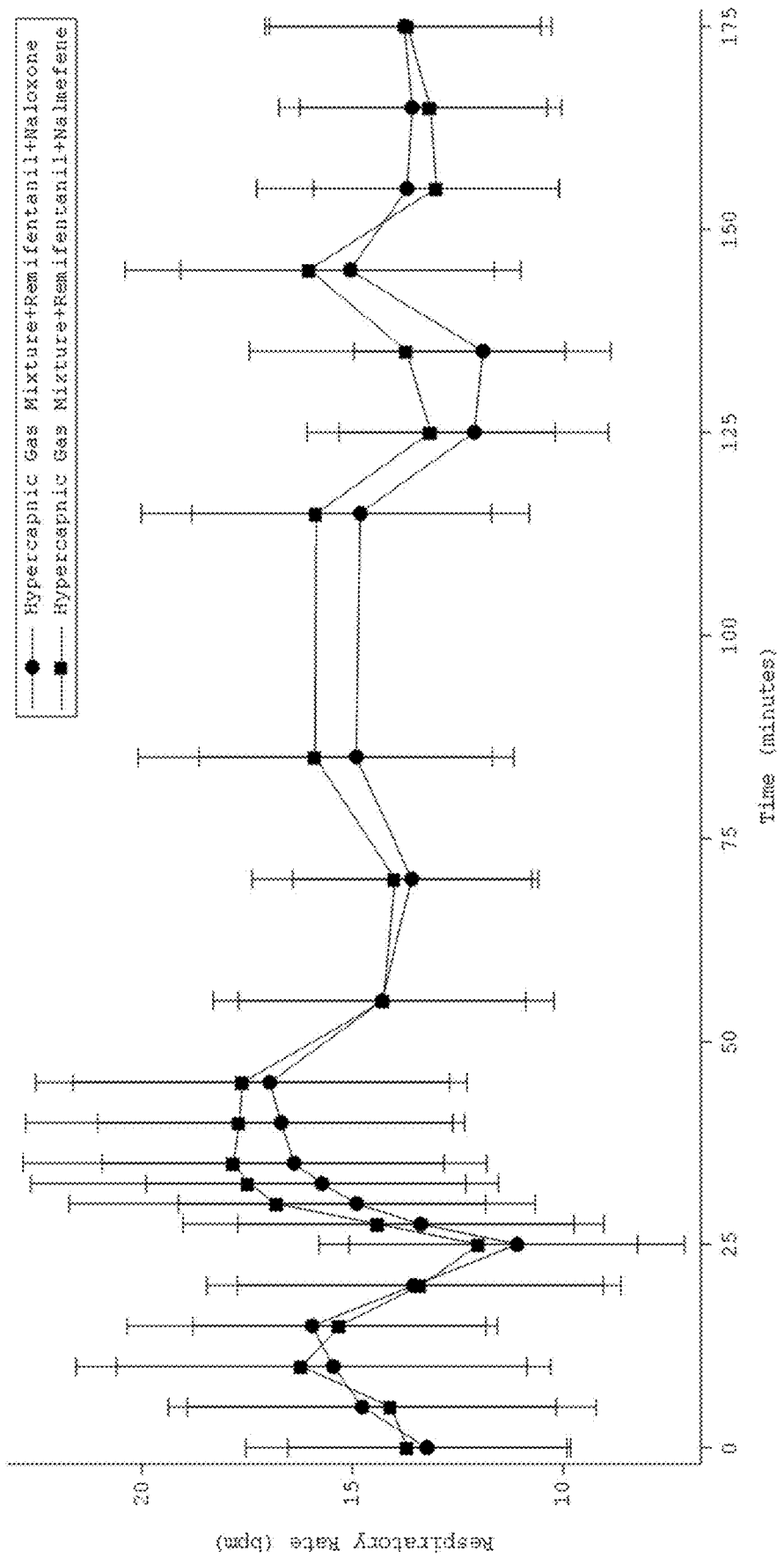
Figure 16C:
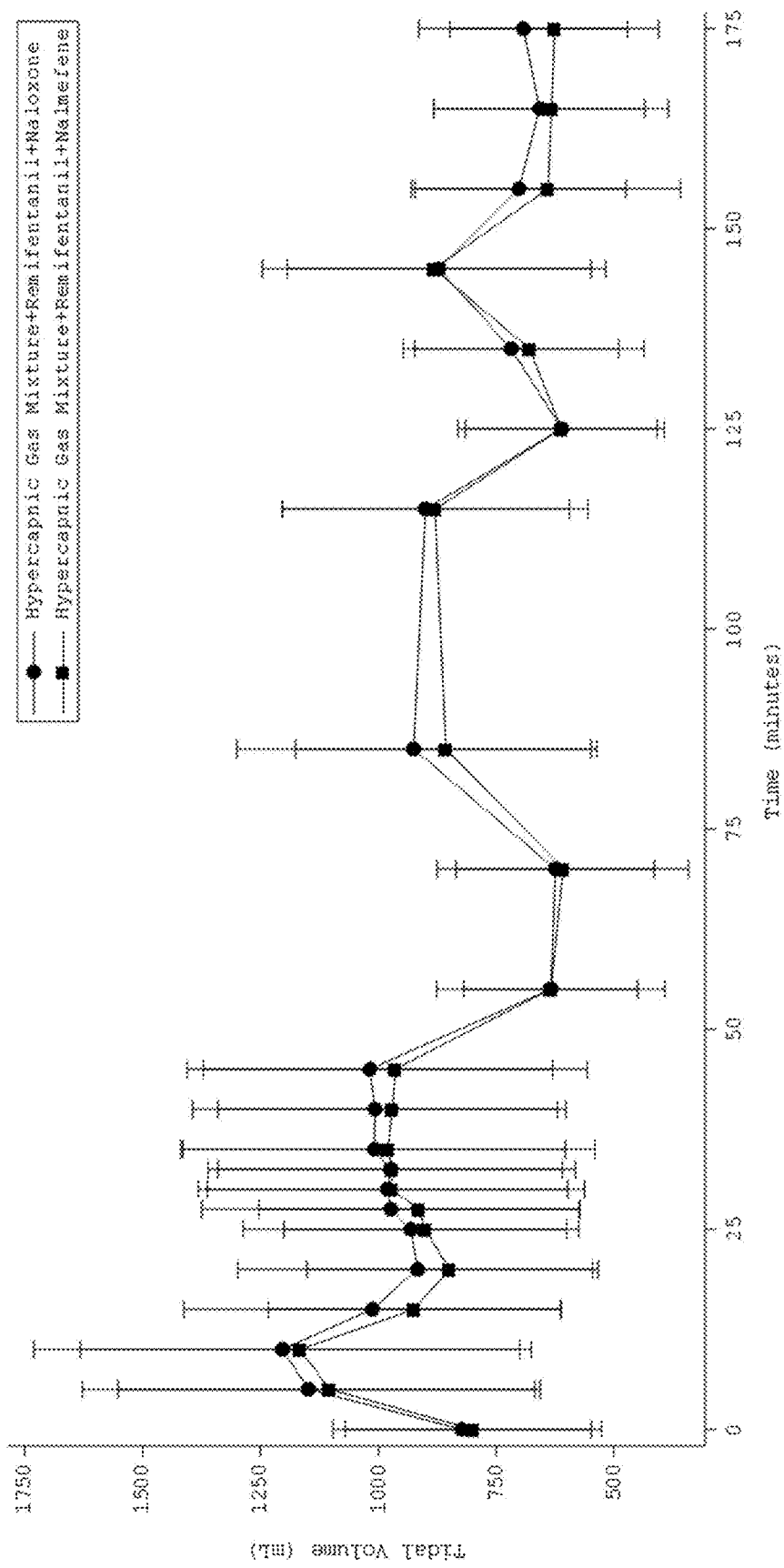

FIG. 15 is a line graph of mean (±SD) VRH $ET_{CO2}$ versus time—Part 1 Extension FIGS. 16A, 16B, and 16C are line graphs of mean (±SD) ExSpiron® Device PD measurement versus time—Part 2.

Figure 17:
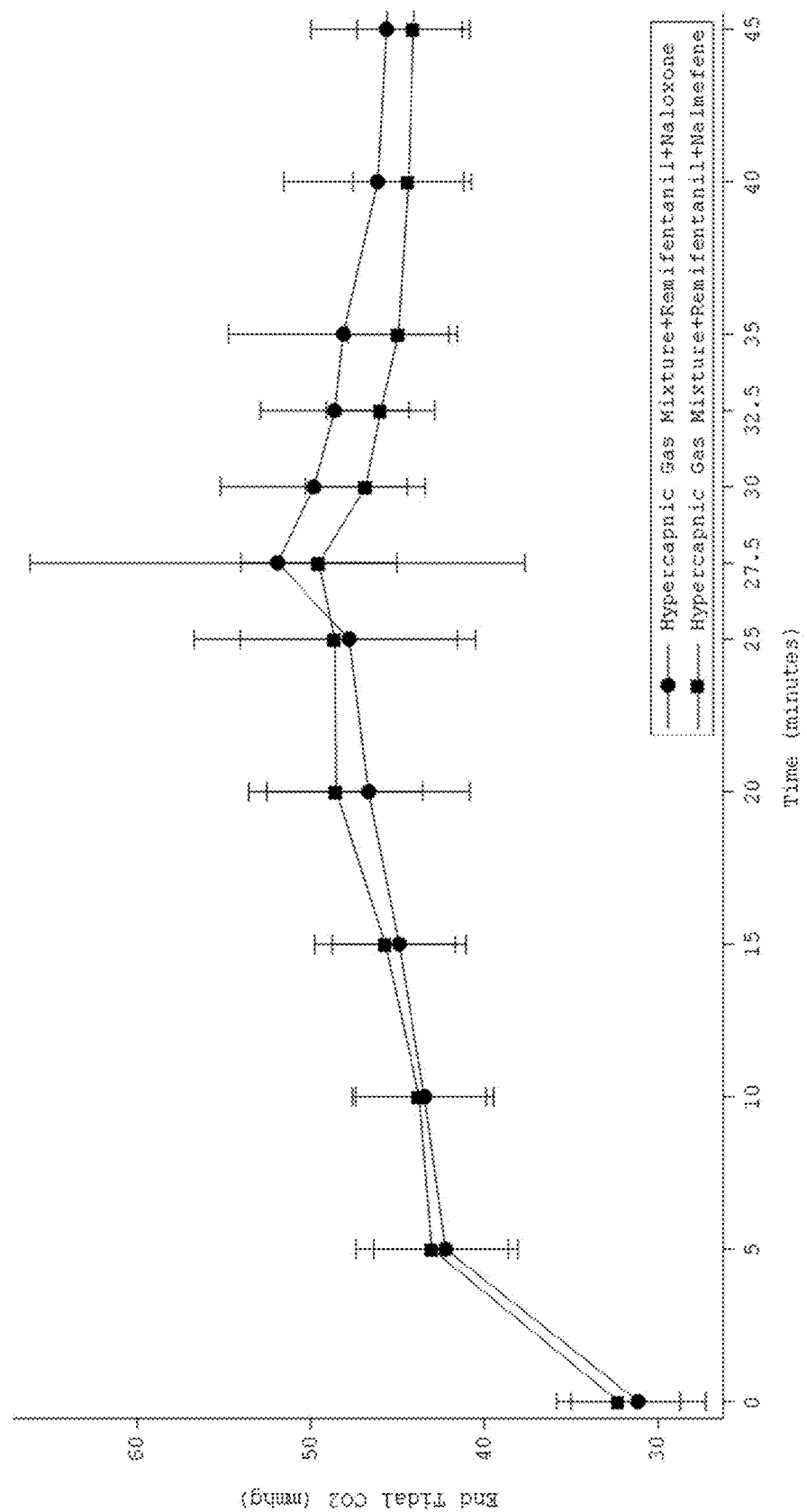

FIG. 17 is a line graph of mean (±SD) VRH $ET_{CO2}$ versus time—Part 2.

Figure 18:
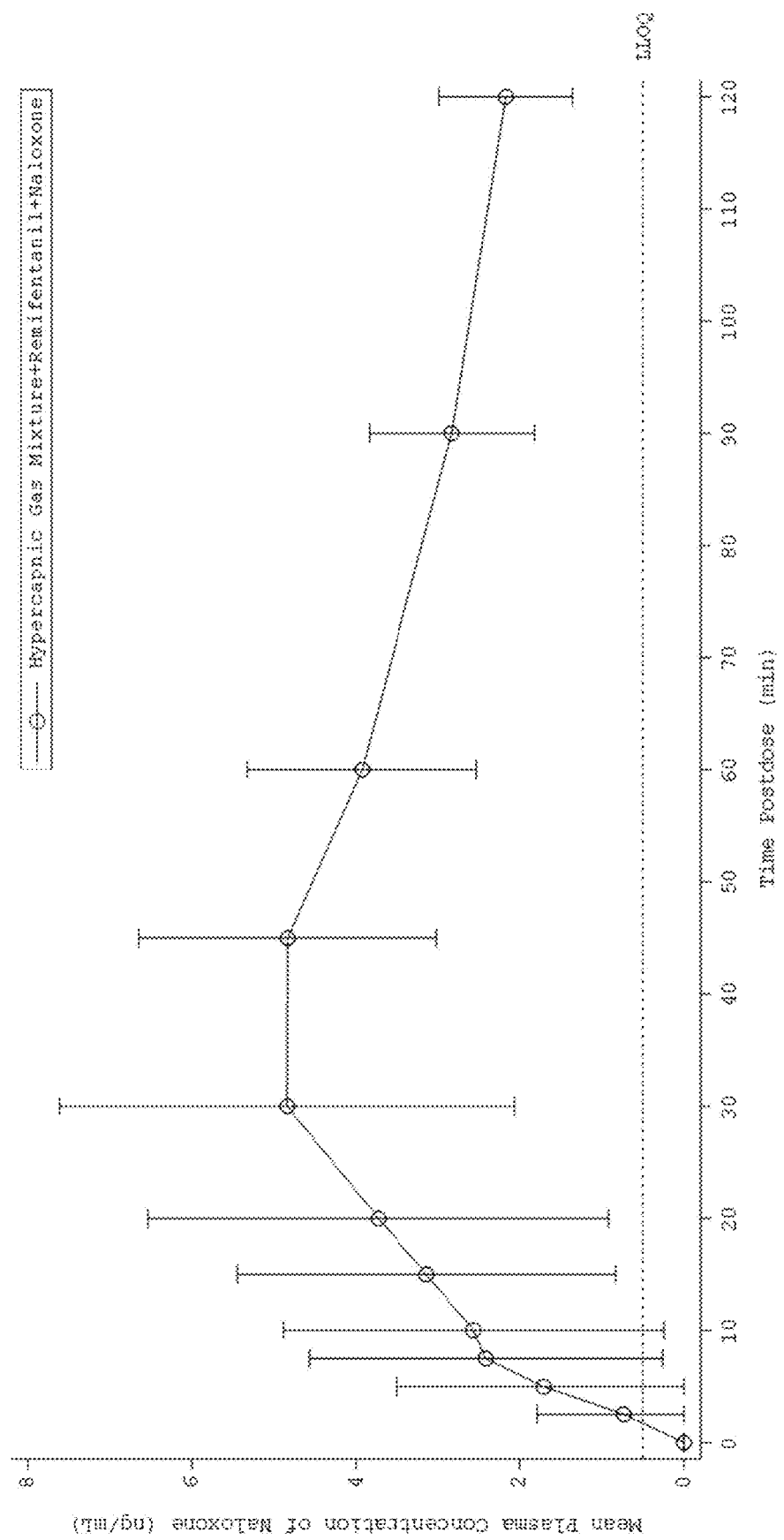

FIG. 18 is a line graph of mean (±SD) naloxone plasma concentrations versus time on a linear scale.

Figure 19:
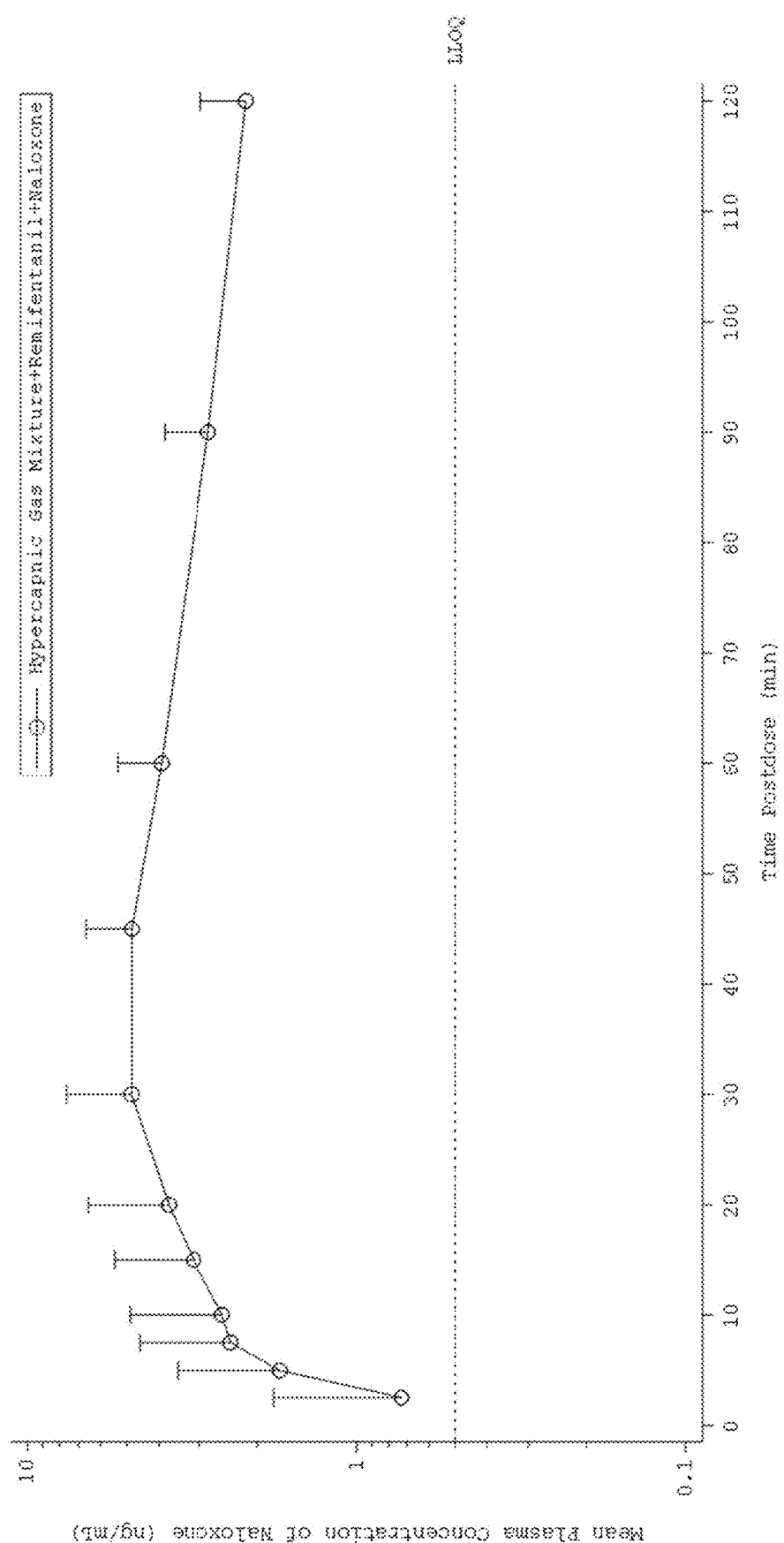

FIG. 19 is a line graph of mean (±SD) naloxone plasma concentrations versus time on a semi-log scale.

Figure 20:
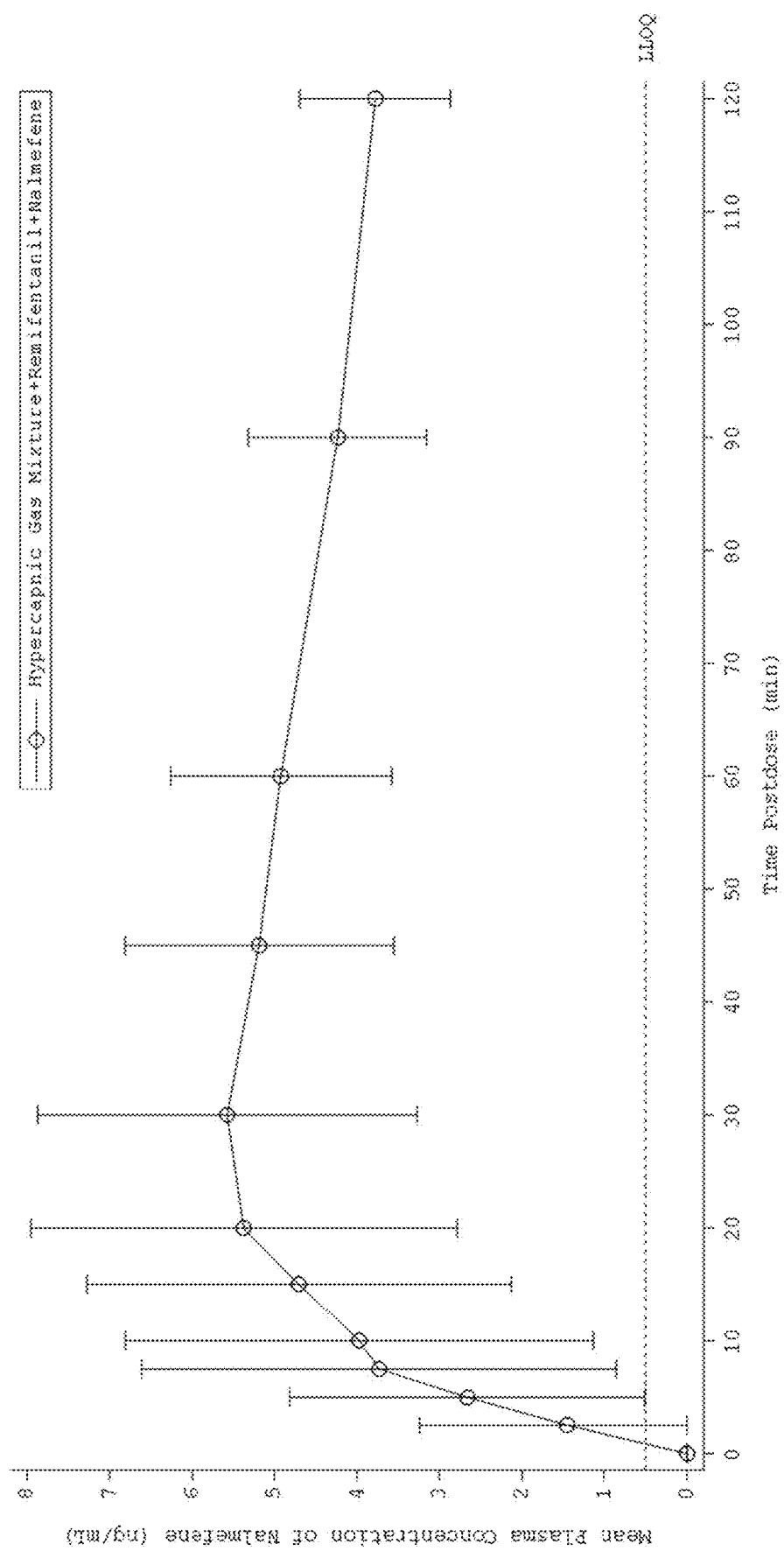

FIG. 20 is a line graph of mean (±SD) nalmefene plasma concentrations versus time on a linear scale.

Figure 21:
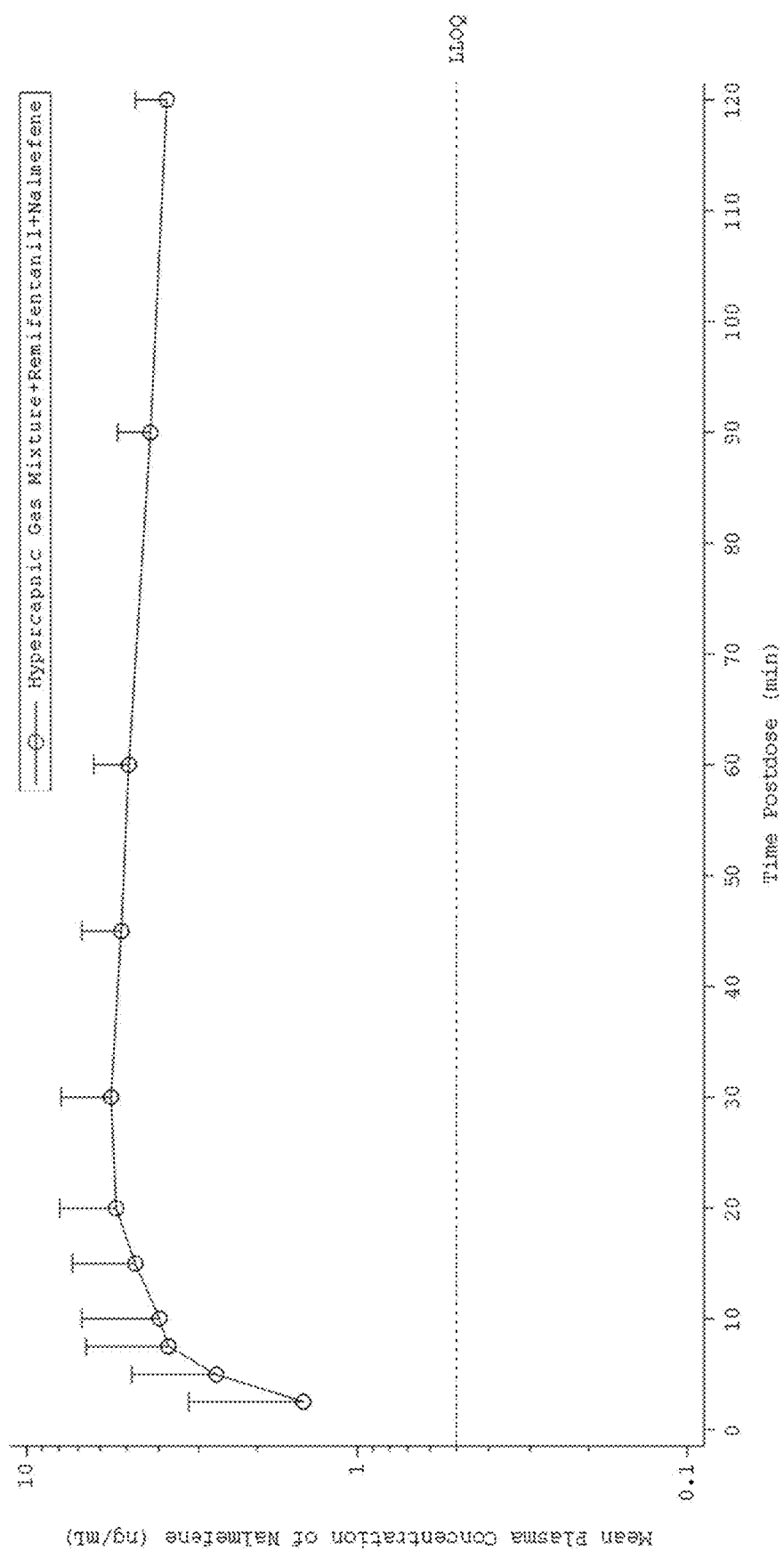

FIG. 21 is a line graph of mean (±SD) nalmefene plasma concentrations versus time on a semi-log scale.

Figure 22:
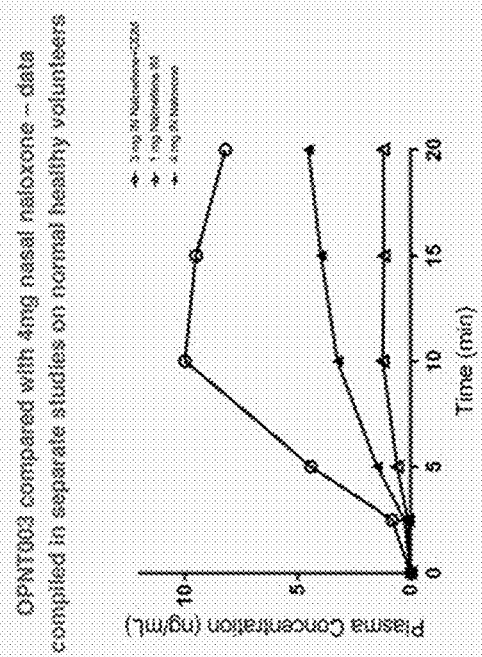
Figure 22:
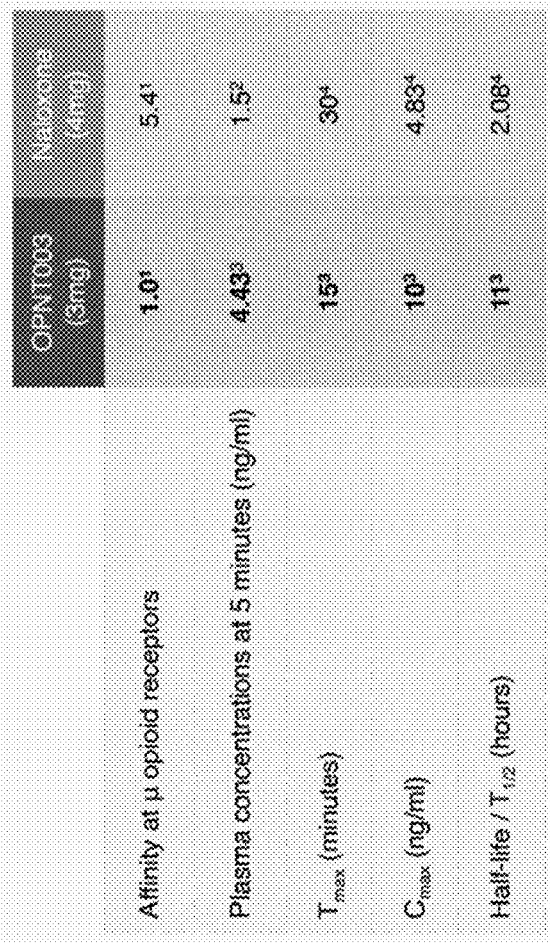

FIG. 22 shows a comparison of pharmacokinetic data between the nalmefene nasal spray (OPNT003) and the NARCAN nasal spray.

Figure 23:
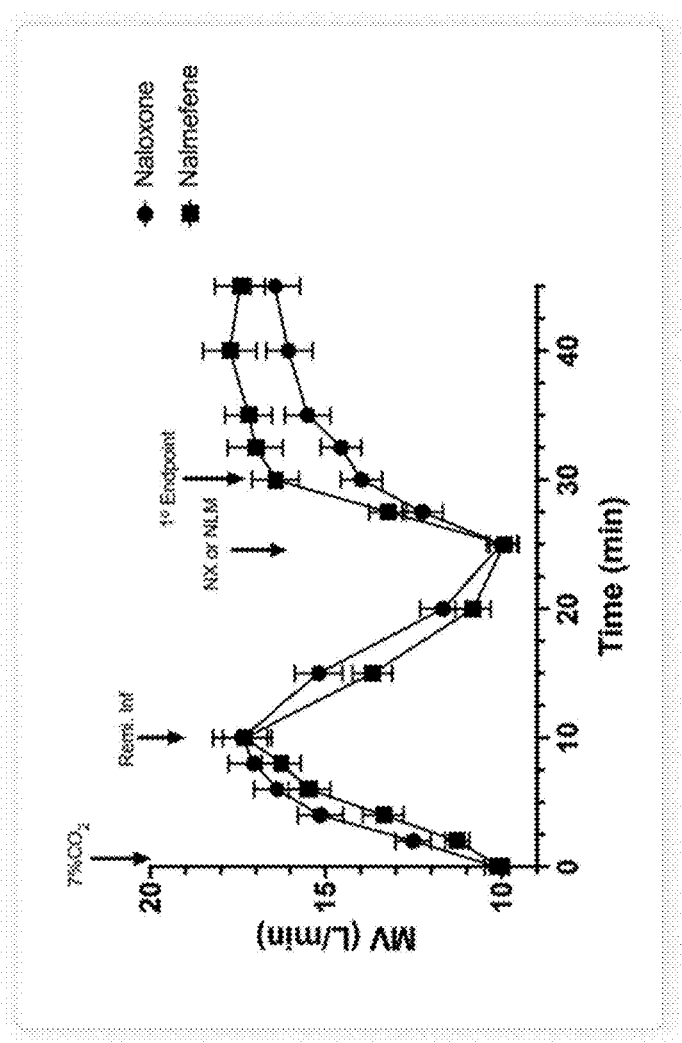

FIG. 23 illustrates the results of the non-inferiority study comparing nasal nalmefene and nasal naloxone in reversing the respiratory depression produced by remifentanil, using the change in minute ventilation, with a primary endpoint at 5 minutes.

Figures 24, 24A, 24B:
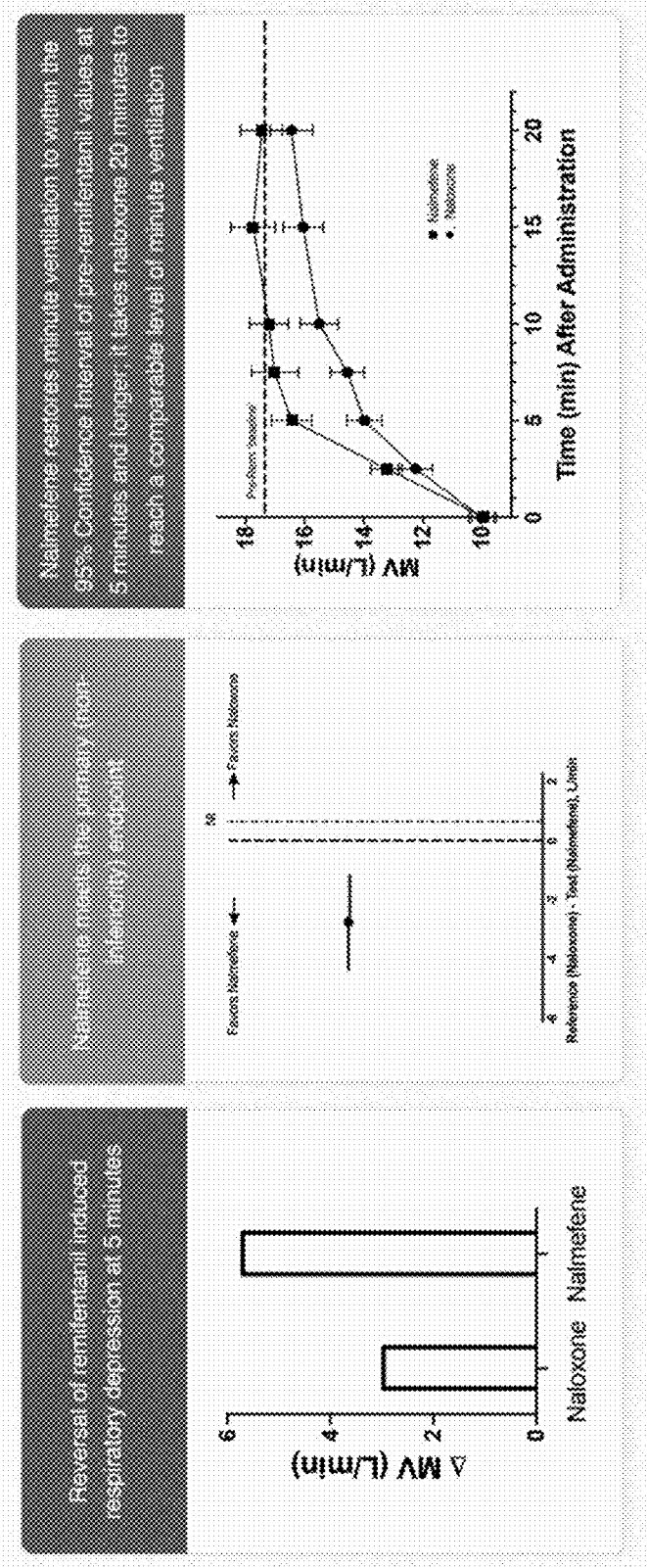

FIG. 24A shows the change in minute ventilation from the time nasal nalmefene or nasal naloxone is given until 5 minutes later. The increase in minute ventilation was 5.7 L/min for nasal nalmefene and 3.0 L/min for nasal naloxone, a difference that clearly favored nalmefene.

FIG. 24B represents the FDA criteria that were established to demonstrate non-inferiority. The filled circle represents the difference in MV between nasal nalmefene and nasal naloxone (the lines to either side of the filled circle represent the 95% confidence interval). The dotted line at "0" represents no difference in MV between the two treatments. The dotted line to the right of "0" is the point that was proposed by Opiant to represent non-inferiority between nasal nalmefene and nasal naloxone, where nasal nalmefene could be no more than 20% lower than nasal naloxone. This graph shows that the trial clearly met the primary endpoint.

FIG. 24C shows the first 20 minutes post dose of nasal nalmefene or nasal naloxone. By 5 minutes, treatment with nasal nalmefene results in MV returning to "pre-remifentanil" levels, while it takes 20 minutes for the MV of those treated with nasal naloxone to return to "pre-remifentanil" levels.

FIG. 25 illustrates an overview of the completed clinical studies.

DETAILED DESCRIPTION

A. Introduction

Disclosed herein are methods and compositions for the treatment of opioid overdose, comprising administering an intranasal formulation of an opioid antagonist. Also disclosed herein are methods and compositions for the treatment of opioid-receptor-mediated-diseases, disorders, addictions, symptoms, or conditions, comprising administering an intranasal formulation of an opioid antagonist alone or in combination with an absorption enhancer. For clarity and consistency, the following definitions will be used throughout this patent document.

Opioid receptors are G protein-coupled receptors (GPCRs) that are activated both by endogenous opioid peptides, by clinically important alkaloid analgesic drugs such as morphine, and by synthetic analgesics such as methadone and fentanyl. There are three principal types of opioid receptors: the δ-opioid receptor, the κ-opioid receptor, and the μ-opioid receptor. Opioids depress respiration, which is controlled principally through medullary respiratory centers with peripheral input from chemoreceptors and other sources. Opioids produce inhibition at the chemoreceptors via μ-opioid receptors and in the medulla via and δ-opioid receptors. While there are many neurotransmitters mediating the control of respiration, glutamate and γ-aminobutyric acid (GABA) are the major excitatory and inhibitory neurotransmitters, respectively. This explains the potential for interaction of opioids with benzodiazepines and alcohol: both benzodiazepines and alcohol facilitate the inhibitory effect of GABA at $GABA_A$ receptors, while alcohol also decreases the excitatory effect of glutamate at NMDA receptors. Oxycodone and other opioid analgesics (such as hydrocodone and fentanyl) as well as heroin and methadone are all implicated in fatal overdose.

In 2016, approximately 64,000 people died from drug overdoses. At least 14,400 of these deaths involved prescription opioid analgesics, almost 3,300 of these deaths involved methadone, 15,400 of these deaths involved heroin, and over 20,000 of these deaths were attributed to fentanyl and related synthetic opioids. Taken together, the number of opioid-related overdose deaths in 2016 far exceeded both the peak number of H.I.V. related deaths and the peak number of fatalities related to firearms.

Provided are devices adapted for nasal delivery of a pharmaceutical composition to a patient, comprising a therapeutically effective amount of the opioid antagonist nalmefene and pharmaceutically acceptable salts thereof, wherein the device is pre-primed, and wherein the therapeutically effective amount, is equivalent to about 1 mg to about 10 mg of nalmefene hydrochloride.

Also provided are methods of treating opioid overdose or a symptom thereof, comprising nasally administering, to a patient in need thereof, a therapeutically effective amount of the opioid antagonist nalmefene and pharmaceutically acceptable salts thereof, wherein the therapeutically effective amount is equivalent to about 1 mg to about 10 mg of nalmefene hydrochloride.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

B. Definitions

As used herein, the following terms have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a range. When no range, such as a margin of error or a standard deviation to a mean value given in a chart or table of data, is recited, the term "about" should be understood to mean the greater of the range which would encompass the recited value and the range which would be included by rounding up or down to that figure as well, considering significant figures, and the range which would encompass the recited value plus or minus 20%.

The term "absorption enhancer," as used herein, refers to a functional excipient included in formulations to improve the absorption of a pharmacologically active drug. This term usually refers to an agent whose function is to increase absorption by enhancing nasal mucous-membrane permeation, rather than increasing solubility. As such, such agents are sometimes called permeation enhancers. In particular, absorption enhancers described herein may improve paracellular transport (i.e., passage through intercellular spaces and tight junctions), transcellular transport (i.e., passive diffusion or active transport across cellular membranes), or transcytosis (i.e., cellular vesicular uptake). Ozsoy et al., Molecules 14:3754-79, 2009.

Examples of absorption enhancers include aprotinin, benzalkonium chloride, benzyl alcohol, capric acid, ceramides, cetylpyridinium chloride, chitosan, cyclodextrins, deoxycholic acid, decanoyl carnitine, dodecyl maltoside, EDTA, glycocholic acid, glycodeoxycholic acid, glycofurol, glycosylated sphingosines, glycyrrhetinic acids, 2-hydroxypropy-β-cyclodextrin, laureth-9, lauric acid, lauroyl carnitine, sodium lauryl sulfate, lysophosphatidylcholine, menthol, poloxamer 407 or F68, poly-L-arginine, polyoxyethylene-9-lauryl ether, polysorbate 80, propylene glycol, quillaia saponin, salicylic acid, sodium salt, β-sitosterol β-D-glucoside, sucrose cocoate, taurocholic acid, taurodeoxycholic acid, taurodihydrofusidic acid, and alkylsaccharides, including but not limited to dodecyl maltoside, dodecyl-β-D-maltoside, tetradecyl maltoside, tetradecyl-β-D-maltoside and sucrose dodecanoate. Alkylsaccharides (e.g., nonionic alkylsaccharide surfactants such as alkylglycosides and sucrose esters of fatty acids that consist of an aliphatic hydrocarbon chain coupled to a sugar moiety by a glycosidic or ester bond, respectively), cyclodextrins (cyclic oligosaccharides composed of six or more monosaccharide units with a central cavity, which form inclusion complexes with hydrophobic molecules and they have primarily been used to increase drug solubility and dissolution and to enhance low molecular weight drug absorption), chitosans (linear cationic polysaccharides produced from the deacetylation of chitin), and bile salts and their derivatives (such as sodium glycocholate, sodium taurocholate, and sodium taurodihydrofusidate) tend to be amongst the best-tolerated absorption enhancers. See, e.g., Aungst, AAPS Journal 14 (1): 10-8, 2011; and Maggio, J. Excipients and Food Chem. 5 (2): 100-12, 2014.

As used herein, the term "alkylsaccharide" refers to an absorption enhancer. As used herein, an alkylsaccharide refers to any sugar joined by a linkage to any hydrophobic alkyl, as is known in the art. Alkylsaccharides can include, but are not limited to: alkylsaccharides, such as octyl-, nonyl-, decyl-, undecyl-, dodecyl-, tridecyl-, tetradecyl-, pentadecyl-, hexadecyl-, heptadecyl-, and octadecyl-α- or β-D-maltoside, -glucoside or -sucroside; alkyl thiomaltosides, such as heptyl, octyl, dodecyl-, tridecyl-, and tetradecyl-β-D-thiomaltoside; alkyl thioglucosides, such as heptyl- or octyl 1-thio α- or β-D-glucopyranoside; alkyl thiosucroses; alkyl maltotriosides; long chain aliphatic carbonic acid amides of sucrose β-amino-alkyl ethers; derivatives of palatinose and isomaltamine linked by amide linkage to an alkyl chain; derivatives of isomaltamine linked by urea to an alkyl chain; long chain aliphatic carbonic acid ureides of sucrose β-amino-alkyl ethers; and long chain aliphatic carbonic acid amides of sucrose β-amino-alkyl ethers. The hydrophobic alkyl can be chosen of any desired size, depending on the hydrophobicity desired and the hydrophilicity of the saccharide moiety. For example, one preferred range of alkyl chains is from about 9 to about 24 carbon atoms. An even more preferred range is from about 9 to about 16 or about 14 carbon atoms. Similarly, some preferred saccharides include maltose, sucrose, and glucose linked by glycosidic linkage to an alkyl chain of 9, 10, 12, 13, 14, 16, 18, 20, 22, or 24 carbon atoms, e.g., nonyl-, decyl-, dodecyl- and tetradecyl sucroside, glucoside, and maltoside, etc.

As use herein, a "saccharide" is inclusive of monosaccharides, oligosaccharides or polysaccharides in straight chain or ring forms, or a combination thereof to form a saccharide chain. Oligosaccharides are saccharides having two or more monosaccharide residues. The saccharide can be chosen, for example, from any currently commercially available saccharide species or can be synthesized. Some examples of the many possible saccharides to use include glucose, maltose, maltotriose, maltotetraose, sucrose and trehalose. Preferable saccharides include maltose, sucrose and glucose.

The term "active ingredient" or "pharmaceutically active compound" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The term "actuation," as used herein, refers to operation of the device such that the pharmaceutical composition is delivered therefrom.

The term "agonist," as used herein, refers to a moiety that interacts with, and activates, a receptor and thereby initiates a physiological or pharmacological response characteristic of that receptor. The term "antagonist," as used herein, refers to a moiety that competitively binds to a receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist.

The term "antimicrobial preservative," as used herein, refers to a pharmaceutically acceptable excipient with antimicrobial properties which is added to a pharmaceutical composition to maintain microbiological stability.

The term "AUC," as used herein, refers to the area under the drug plasma concentration-time curve. The term "$AUC_{0-t}$," as used herein, refers to the area under the drug plasma concentration-time curve from t=0 to the last measurable concentration. The term "$AUC_{0-\infty}$" as used herein, refers to the area under the drug plasma concentration-time curve extrapolated to ∞. The term "$AUC_{0-t/D}$," as used herein, refers to the $AUC_{0-t}$, normalized to 0.4 mg IN nalmefene. The term "$AUC_{0-\infty/D}$," as used herein, refers to the $AUC_{0-\infty}$ normalized to 1.5 mg IM nalmefene.

The term "bioavailability (F)," as used herein, refers to the fraction of a dose of drug that is absorbed from its site of administration and reaches, in an unchanged form, the systemic circulation. The term "absolute bioavailability" is used when the fraction of absorbed drug is related to its IV bioavailability. It may be calculated using the following formula:

$$F = \frac{AUC_{extravascular}}{AUC_{intraverse}} \times \frac{DOSE_{intraverse}}{DOSE_{extravascular}}$$

The term "relative bioavailability ($F_{rel}$)" is used to compare two different extravascular routes of drug administration and it may be calculated using the following formula:

$$F_{rel} = \frac{AUC_{extravascular1}}{AUC_{extravascular2}} \times \frac{DOSE_{extravascular2}}{DOSE_{extravascular1}}$$

The term "bioequivalent," as used herein, refers to products or formulations which lack a significant difference in the rate and extent to which the active ingredient or active moiety in pharmaceutical equivalents or pharmaceutical alternatives become available at the site of drug action when administered at the same molar dose under similar conditions in an appropriately designed study.

The term "clearance (CL)," as used herein, refers to the rate at which a drug is eliminated divided by its plasma concentration, giving a volume of plasma from which drug is completely removed per unit of time. CL is equal to the elimination rate constant (2) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "$C_{max}$" as used herein, refers to the maximum observed plasma concentration. The term "$C_{maxD}$," as used herein, refers to $C_{max}$ normalized to 1.5 mg IM nalmefene.

The term "coefficient of variation (CV)," as used herein, refers to the ratio of the sample standard deviation to the sample mean. It is often expressed as a percentage.

The term "confidence interval," as used herein, refers to a range of values which will include the true average value of a parameter a specified percentage of the time.

The term "device," as used herein, refers to an apparatus capable of delivering a drug to patient in need thereof.

The term "delivery time," as used herein, refers to the amount of time that elapses between a determination made by a healthcare professional, or an untrained individual that an individual is in need of nasal delivery of an opioid antagonist and completion of the delivery.

The term "disease," as used herein, is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "elimination rate constant ($\lambda$)," as used herein, refers to the fractional rate of drug removal from the body. This rate is constant in first-order kinetics and is independent of drug concentration in the body. $\lambda$ is the slope of the plasma concentration-time line (on a logarithmic y scale). The term "$\lambda_z$," as used herein, refers to the terminal phase elimination rate constant, wherein the "terminal phase" of the drug plasma concentration-time curve is a straight line when plotted on a semi-logarithmic graph. The terminal phase is often called the "elimination phase" because the primary mechanism for decreasing drug concentration during the terminal phase is drug elimination from the body. The distinguishing characteristic of the terminal elimination phase is that the relative proportion of drug in the plasma and peripheral volumes of distribution remains constant. During this "terminal phase" drug returns from the rapid and slow distribution volumes to the plasma, and is permanently removed from the plasma by metabolism or renal excretion.

The term "equivalent," as used herein, refers to a weight of an opioid antagonist selected from nalmefene and pharmaceutically acceptable salts thereof that is equimolar to a specified weight of nalmefene hydrochloride.

The term "excipient," as used herein, refers to a natural or synthetic substance formulated alongside the active ingredient of a medication, included for long-term stabilization, bulking up solid formulations, or to confer a therapeutic enhancement on the active ingredient in the final dosage form, such as facilitating drug absorption, reducing viscosity, or enhancing solubility.

The term "filled," as used herein, refers to an association between a device and a pharmaceutical composition, for example, when a pharmaceutical composition described herein comprising a therapeutically effective amount of an opioid antagonist is present within a reservoir that forms a part of a device described herein.

The term "hydrate," as used herein, refers to an opioid antagonist described herein or a salt thereof that further includes a stoichiometric or non-stoichiometric amount of water bound by non-covalent intermolecular forces.

The term "in need of treatment" and the term "in need thereof" when referring to treatment are used interchangeably and refer to a judgment made by a caregiver (e.g. physician, nurse, nurse practitioner, that a patient will benefit from treatment. An individual "who is at risk for opioid overdose" includes an individual who illicitly uses opioids, on individual who accidentally ingests opioids, and an individual at risk for accidental misuse of opioids during medical opioid therapy.

As used herein, two embodiments are "mutually exclusive" when one is defined to be something which is different than the other. For example, an embodiment wherein the amount of nalmefene hydrochloride is specified to be 4 mg is mutually exclusive with an embodiment wherein the amount of nalmefene hydrochloride is specified to be 2 mg. However, an embodiment wherein the amount of nalmefene hydrochloride is specified to be 4 mg is not mutually exclusive with an embodiment in which less than about 10% of the pharmaceutical composition leaves the nasal cavity via drainage into the nasopharynx or externally.

The term "nalmefene," as used herein, refers to 17-cyclopropylmethyl-4,5α-epoxy-6-methylenemorphinan-3,14-diol, a compound of the following structure:

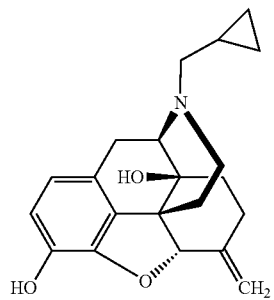

Nalmefene hydrochloride (CAS Reg. No. 5889564-0) has been marketed under the trade names Nalmetrene®, Cervene®, Revex®, Arthrene®, and Incystene®.

The term "naloxone," as used herein, refers to a compound of the following structure:

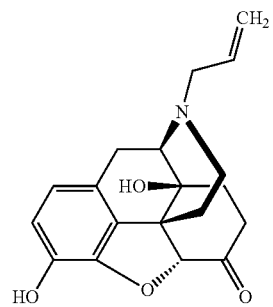

or a pharmaceutically acceptable salt, hydrate, or solvate thereof. The CAS registry number for naloxone is 465-65-6. Other names for naloxone include: 17-allyl-4,5a-epoxy-3,14-dihydroxymorphinan-6-one; (−)-17-allyl-4,5a-epoxy-3,14-dihydroxymorphinan-6-one; 4,5α-epoxy-3,14-dihydroxy-17-(2-propenyOmorphinan-6-one; and (−)-12-allyl-7,7a,8,9-tetrahydro-3,7a-dihydroxy-4aH-8,9c-iminoethanophenanthro[4,5-bcd]furan-5(6H)-one. Naloxone hydrochloride may be anhydrous (CAS Reg. No. 357-08-4) and also forms a dihydrate (CAS No. 51481-608). It has been sold under various brand names including Narcan®, Nalone®, Naloxone®, Naloxona®, Naloxonum®, Narcanti®, and Narcon®.

The term "naltrexone," as used herein, refers to a compound of the following structure:

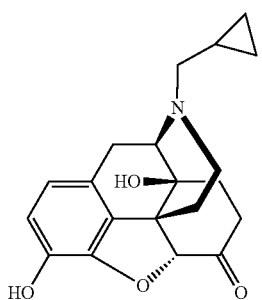

or a pharmaceutically acceptable salt, hydrate, or solvate thereof. The CAS registry number for naltrexone is 1659041-3. Other names for naltrexone include: 17-(cyclopropylmethyl)-4,5α-epoxy-3,14-dihydroxymorphinan-6-one; (5α)-17-(cyclopropylmethyl)-3,14-dihydroxy-4,5-epoxy-morphinan-6-one; and (1S,5R,13R,17S)-4-(cyclopropylmethyl)-10,17-dihydroxy-12-oxa-4-azapentacyclo[9.6.1.01,13.05,17.07,18]octadeca-7(18),8,10-trien-14-one. Naltrexone hydrochloride (CAS Reg. No. 16676-29-2) has been marketed under the trade names Antaxone®, Depade®, Nalorex®, Revia®, Trexan®, Vivitrex®, and Vivitrol®.

The term "methylnaltrexone," as used herein, refers to a pharmaceutically acceptable salt comprising the cation (5α)-17-(cyclopropylmethyl)-3,14-dihydroxy-17-methy 1-4,5-epoxymorphinanium-17-ium-6-one a compound of the following structure:

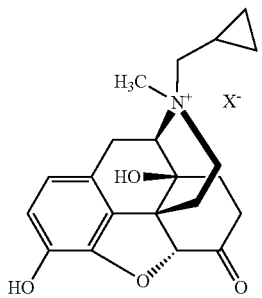

wherein X⁻ is a pharmaceutically acceptable anion. Methylnaltrexone bromide (CAS Reg. No. 75232-52-7) has been marketed under the trade name Relistor®.

The term "nostril," as used herein, is synonymous with "naris."

The term "opioid antagonist" includes naloxone, naltrexone, and nalmefene, and pharmaceutically acceptable salts thereof. In some embodiments, the opioid antagonist is nalmefene hydrochloride. In some embodiments, the opioid antagonist is nalmefene free base. In some embodiments, the nasally administering is accomplished using a device described herein.

The term "opioid overdose," as used herein, refers to an acute medical condition induced by excessive use of one or more opioids. Symptoms of opioid overdose include including respiratory depression (including postoperative opioid respiratory depression, acute lung injury, and aspiration pneumonia), central nervous system depression (which may include sedation, altered level consciousness, miotic (constricted) pupils), and cardiovascular depression (which may include hypoxemia and hypotension). Visible signs of opioid overdose or suspected opioid overdose include: unresponsiveness and/or loss of consciousness (won't respond to stimuli such as shouting, shaking, or rubbing knuckles on sternum); slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose and/or quantify, particularly by a lay person, as used herein, treatment of opioid overdose is meant to include treatment of suspected opioid overdose in opioid-intoxicated patients. Opioids that may induce overdose include, codeine, morphine, methadone, fentanyl, oxycodone HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol. In some embodiments, the opioid agonist is in an abuse-deterrent formulation. In some embodiments, the opioid agonist is in a tamper-resistant formulation. In some embodiments, the opioid agonist is selected from Acurox® Oxycodone DETERx®, Egalet hydrocodone, Egalet morphine, Egalet oxycodone, Exalgo®, Opana®, and Remoxy®.

The term "patient" refers to any subject (preferably human) afflicted with a condition likely to benefit from a treatment with a therapeutically effective amount of an opioid antagonist.

The term "pharmaceutical composition," as used herein, refers to a composition comprising at least one active ingredient; including but not limited to, salts, solvates and hydrates of the opioid antagonists described herein, whereby the composition is amenable to use for a specified, efficacious outcome in a mammal (for example, without limitation, a human). In some embodiments, the opioid antagonist is nalmefene.

The term "pharmaceutically acceptable," as used herein, refers to a component of a pharmaceutical composition that is compatible with the other ingredients of the formulation and not overly deleterious to the recipient thereof.

The term "pre-primed," as used herein, refers to a device, such as a nasal spray which can deliver a pharmaceutical composition to a patient in need thereof with the first actuation of the spray pump, i.e., without the need to prime the pump prior to dosing, such as by actuating the pump one or more times until a spray appears.

The term "prone," as used herein, refers to a patient who is lying face down.

As used herein, the term "protective packaging" refers to overwrap.

The term "receptor binding or occupancy" refers to a characterization of the kinetics between a radioactive drug and receptors or other binding sites throughout the body, and characterization of the radioactive drug binding affinity to these receptors.

The term "recovery position," as used herein, means a position of the human body in which a patient lies on his/her side, with a leg or knee out in front (e.g., to prevent rolling onto his/her stomach) and at least one hand supporting the head (e.g., to elevate the face to facilitate breathing and prevent inhalation of vomit).

The term "providing" in the context of providing a co-packaged drug product as disclosed herein to an individual includes co-packaging the drug product, prescribing the co-packaged drug product, and dispensing the co-packaged drug product. The providing may be done either directly to an individual (for example, to an individual for whom an opioid agonist prescription is appropriate, or who is otherwise at risk of opioid overdose) or to a second individual.

The term "solvate," as used herein, refers to an opioid antagonist described herein or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "sterile filling," as used herein, refers methods of manufacturing the devices and pharmaceutical compositions described herein, such that the use of preservatives is not required. Sterile drug products may be produced using aseptic processing or terminal sterilization. Terminal sterilization usually involves filling and sealing product containers under high-quality environmental conditions. In an aseptic process, the drug product, container, and closure are first subjected to sterilization methods separately, as appropriate, and then brought together.

The term "storage-stable," as used herein, refers to a pharmaceutical composition in which at least about 90% to 99.5% of the active ingredient remains in an undegraded state after storage of the pharmaceutical composition at specified temperature and humidity for a specified time, for example, for 12 months at 25° C. and 60% relative humidity.

The term "subject," as used herein, is intended to be synonymous with "patient," and refers to any mammal (preferably human) afflicted with a condition likely to benefit from a treatment with a therapeutically effective amount of the opioid antagonist nalmefene.

The term "substantially free of antimicrobial preservatives" is understood by one of ordinary skill in the art to described a pharmaceutical composition that comprises less than 1% w/w antimicrobial preservatives.

The term "supine," as used herein, refers to a patient who is lying face up.

The term "therapeutically effective amount" or "therapeutically effective dose," as used herein, refers to the amount or dose of active compound or pharmaceutical agent that elicits the biological or medicinal response in a tissue, system, or individual that is being sought by a researcher, healthcare provider or individual. A therapeutically effective amount may, but need not necessarily, eliminate one, more, or all symptoms of a disease, disorder, or condition being treated. A therapeutically effective amount may also prevent disease progression or the appearance of further symptoms.

The term "$t_{1/2}$" or "half-life," as used herein, refers to the amount of time required for half of a drug (for example, an opioid or an opioid antagonist) to be eliminated from the body or the time required for a drug concentration to decline by half.

The term "tonicity agent," as used herein, refers to a compound which modifies the osmolality of a formulation, for example, to render it isotonic. Tonicity agents include dextrose, lactose, sodium chloride, calcium chloride, magnesium chloride, sorbitol, sucrose, mannitol, trehalose, raffinose, polyethylene glycol, hydroxyethyl starch, glycine, glycerin, potassium chloride, lactated ringer's solution, combinations thereof; and the like.

The term "tomography," as used herein, refers to a process of imaging by sections. The images may be looked at individually, as a series of two-dimensional slices or together, as a computer-generated three-dimensional representation.

The term "$T_{max}$," as used herein, refers to the time from administration of the pharmaceutical compositions described herein to maximum drug plasma concentration.

The term "untrained individual" refers to an individual administering to patient an opioid antagonist using a device described herein, wherein the individual is not a healthcare professional and has received no training in the use of the device.

C. Opioid Antagonists

Provided are drug products adapted for nasal delivery of an opioid receptor antagonist. Opioid receptor antagonists are a well-recognized class of chemical agents. They have been described in detail in the scientific and patent literature. Opioid antagonists, such as nalmefene, are agents which specifically reverse the effects of opioid agonists but have no opioid agonist activity.

Nalmefene is commercially available as a hydrochloride salt and is a 6-methylene analog of naltrexone. Nalmefene hydrochloride (17-(cyclopropylmethyl)-4,5(-ep-oxy-6-methylenemorphinan-3,14-diol) is approved for opioid overdose reversal, and can be used to prevent euphorigenic effects in the treatment of patients addicted to opioids. It reverses the effects of opioids, including respiratory depression, sedation, and hypotension, but the patient does not develop tolerance or dependence to nalmefene.

Provided are pharmaceutical compositions, devices adapted for nasal delivery of a pharmaceutical composition to a patient, kits comprising the foregoing, and methods of using the same in treatment, each comprising a therapeutically effective amount of an opioid antagonist selected from nalmefene and pharmaceutically acceptable salts thereof, wherein the device is pre-primed, and wherein the therapeutically effective amount, is equivalent to about 1 mg to about 10 mg of nalmefene hydrochloride.

In some embodiments, the therapeutically effective amount is equivalent to about 0.5 mg to about 12 mg of nalmefene hydrochloride. In some embodiments, the therapeutically effective amount is equivalent to about 0.5 mg to about 10 mg of nalmefene hydrochloride. In some embodiments, the therapeutically effective amount is equivalent to about 1 mg to about 12 mg of nalmefene hydrochloride. In some embodiments, the therapeutically effective amount is equivalent to about 1 mg to about 10 mg of nalmefene hydrochloride. In some embodiments, the therapeutically effective amount is equivalent to about 1 mg to about 9 mg of nalmefene hydrochloride. In some embodiments, the therapeutically effective amount is equivalent to about 1 mg to about 8 mg of nalmefene hydrochloride. In some embodiments, the therapeutically effective amount is equivalent to about 1 mg to about 7 mg of nalmefene hydrochloride. In some embodiments, the therapeutically effective amount is equivalent to about 1 mg to about 6 mg of nalmefene hydrochloride. In some embodiments, the therapeutically effective amount is equivalent to about 1 mg to about 5 mg of nalmefene hydrochloride. In some embodiments, the therapeutically effective amount is equivalent to about 1 mg to about 4 mg of nalmefene hydrochloride. In some embodiments, the therapeutically effective amount is equivalent to about 1 mg to about 3 mg of nalmefene hydrochloride. In some embodiments, the therapeutically effective amount is equivalent to about 1 mg to about 2 mg of nalmefene hydrochloride. In some embodiments, the therapeutically effective amount is equivalent to about 1.5 mg to about 10 mg of nalmefene hydrochloride. In some embodiments, the therapeutically effective amount is equivalent to about 2 mg to about 10 mg of nalmefene hydrochloride. In some embodiments, the therapeutically effective amount is equivalent to about 3 mg to about 10 mg of nalmefene hydrochloride. In some embodiments, the therapeutically effective amount is equivalent to about 4 mg to about 10 mg of nalmefene hydrochloride. In some embodiments, the therapeutically effective amount is equivalent to about 5 mg to about 10 mg of nalmefene hydrochloride. In some embodiments, the therapeutically effective amount is equivalent to about 2 mg to about 8 mg of nalmefene hydrochloride. In some embodiments, the therapeutically effective amount is equivalent to about 2 mg to about 6 mg of nalmefene hydrochloride. In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride. In some embodiments, the therapeutically effective amount is equivalent to about 6 mg of nalmefene hydrochloride. In some embodiments, the therapeutically effective amount is equivalent to about 7 mg of nalmefene hydrochloride. In some embodiments, the therapeutically effective amount is equivalent to about 8 mg of nalmefene hydrochloride. In some embodiments, the therapeutically effective amount is equivalent to about 9 mg of nalmefene hydrochloride. In some embodiments, the therapeutically effective amount is equivalent to about 10 mg of nalmefene hydrochloride. In some embodiments, the therapeutically effective amount is equivalent to about 0.5, about 0.6, about 0.7, about 0.8, about 0.9, about 1, about 1.2, about 1.4, about 1.6, about 1.8, about 2 mg, about 2.2, about 2.4, about 2.6, about 2.8, about 3, about 3.2, about 3.4, about 3.6, about 3.8, or about 4 mg of nalmefene hydrochloride. In some embodiments, the therapeutically effective amount is equivalent to about 0.5 to about 1.0, about 0.5 to about 1.5, about 1.5 to about 2.0, about 1.5 to about 2.5, about 1.5 to about 3.0 mg, about 1.5 to about 3.5, or about 1.5 to about 4.0 mg of nalmefene hydrochloride. In some embodiments, the therapeutically effective amount is equivalent to less than 10 mg of nalmefene hydrochloride. In some embodiments, the therapeutically effective amount is equivalent to less than 5 mg of nalmefene hydrochloride.

In some embodiments, the therapeutically effective amount is equivalent to about 0.5 mg to about 12 mg of nalmefene free base. In some embodiments, the therapeutically effective amount is equivalent to about 0.5 mg to about 10 mg of nalmefene free base. In some embodiments, the therapeutically effective amount is equivalent to about 1 mg to about 12 mg of nalmefene free base. In some embodiments, the therapeutically effective amount is equivalent to about 1 mg to about 10 mg of nalmefene free base. In some embodiments, the therapeutically effective amount is equivalent to about 1 mg to about 9 mg of nalmefene free base. In some embodiments, the therapeutically effective amount is equivalent to about 1 mg to about 8 mg of nalmefene free base. In some embodiments, the therapeutically effective amount is equivalent to about 1 mg to about 7 mg of nalmefene free base. In some embodiments, the therapeutically effective amount is equivalent to about 1 mg to about 6 mg of nalmefene free base. In some embodiments, the therapeutically effective amount is equivalent to about 1 mg to about 5 mg of nalmefene free base. In some embodiments, the therapeutically effective amount is equivalent to about 1 mg to about 4 mg of nalmefene free base. In some embodiments, the therapeutically effective amount is equivalent to about 1 mg to about 3 mg of nalmefene free base. In some embodiments, the therapeutically effective amount is equivalent to about 1 mg to about 2 mg of nalmefene free base. In some embodiments, the therapeutically effective amount is equivalent to about 1.5 mg to about 10 mg of nalmefene free base. In some embodiments, the therapeutically effective amount is equivalent to about 2 mg to about 10 mg of nalmefene free base. In some embodiments, the therapeutically effective amount is equivalent to about 3 mg to about 10 mg of nalmefene free base. In some embodiments, the therapeutically effective amount is equivalent to about 4 mg to about 10 mg of nalmefene free base. In some embodiments, the therapeutically effective amount is equivalent to about 5 mg to about 10 mg of nalmefene free base. In some embodiments, the therapeutically effective amount is equivalent to about 2 mg to about 8 mg of nalmefene free base. In some embodiments, the therapeutically effective amount is equivalent to about 2 mg to about 6 mg of nalmefene free base. In some embodiments, the therapeutically effective amount is equivalent to about 1 mg of nalmefene free base. In some embodiments, the therapeutically effective amount is equivalent to about 1.5 mg of nalmefene free base. In some embodiments, the therapeutically effective amount is equivalent to about 2 mg of nalmefene free base. In some embodiments, the therapeutically effective amount is equivalent to about 2.5 mg of nalmefene free base. In some embodiments, the therapeutically effective amount is equivalent to about 2.7 mg of nalmefene free base. In some embodiments, the therapeutically effective amount is equivalent to about 3 mg of nalmefene free base. In some embodiments, the therapeutically effective amount is equivalent to about 3.5 mg of nalmefene free base. In some embodiments, the therapeutically effective amount is equivalent to about 4 mg of nalmefene free base. In some embodiments, the therapeutically effective amount is equivalent to about 4.5 mg of nalmefene free base. In some embodiments, the therapeutically effective amount is equivalent to about 5 mg of nalmefene free base. In some embodiments, the therapeutically effective amount is equivalent to about 6 mg of nalmefene free base. In some embodiments, the therapeutically effective amount is equivalent to about 7 mg of nalmefene free base. In some embodiments, the therapeutically effective amount is equivalent to about 8 mg of nalmefene free base. In some embodiments, the therapeutically effective amount is equivalent to about 9 mg of nalmefene free base. In some embodiments, the therapeutically effective amount is equivalent to about 10 mg of nalmefene free base. In some embodiments, the therapeutically effective amount is equivalent to about 0.5, about 0.6, about 0.7, about 0.8, about 0.9, about 1, about 1.2, about 1.4, about 1.6, about 1.8, about 2 mg, about 2.2, about 2.4, about 2.6, about 2.7, about 2.8, about 3, about 3.2, about 3.4, about 3.6, about 3.8, or about 4 mg of nalmefene free base. In some embodiments, the therapeutically effective amount is equivalent to about 0.5 to about 1.0, about 0.5 to about 1.5, about 1.5 to about 2.0, about 1.5 to about 2.5, about 2.7 to about 3.0 mg, about 1.5 to about 3.5, or about 1.5 to about 4.0 mg of nalmefene free base. In some embodiments, the therapeutically effective amount is equivalent to less than 10 mg of nalmefene free base. In some embodiments, the therapeutically effective amount is equivalent to less than 5 mg of nalmefene free base.

In some embodiments, the opioid antagonist is the only pharmaceutically active compound in pharmaceutical composition. In some embodiments, the opioid antagonist is nalmefene hydrochloride. In some embodiments, the opioid antagonist is anhydrous nalmefene hydrochloride.

Provided herein are methods of treatment employing nasal delivery of a pharmaceutical composition to a patient, comprising a therapeutically effective amount of the opioid antagonist nalmefene. In some embodiments, the therapeutically effective amount is equivalent to about 2 to about 16 mg of nalmefene. In some embodiments, the therapeutically effective amount is equivalent to about 2, about 3, about 4, about 5, about 6, about 7, about 8, about 9, about 10, about 11, about 12, about 13, about 14, about 15, or about 16 mg of nalmefene. In some embodiments, the therapeutically effective amount is equivalent to about 4 mg of nalmefene hydrochloride. In some embodiments, the opioid antagonist is nalmefene hydrochloride. In some embodiments, the opioid antagonist is anhydrous nalmefene hydrochloride. In some embodiments, the opioid antagonist is nalmefene hydrochloride dihydrate.

Accordingly, provided herein are pharmaceutical formulations for intranasal administration comprising nalmefene. In certain embodiments, the formulation is an aqueous solution. In certain embodiments, the formulation comprises, per dose, between about 25 and about 200 µL of the aqueous solution. In certain embodiments, the formulation comprises, per dose, between about 50 and about 200 µL of the aqueous solution. In certain embodiments, the formulation comprises, per dose, not more than about 140 µL. In certain embodiments, the formulation comprises, per dose, not more than about 100 µL. The formulation may comprise, per dose, about 25 µL, about 50 µL, about 75 µL, about 100 µL, about 125 µL, about 150 µL, about 175 µL, or about 200 µL of the aqueous solution.

In certain embodiments, the formulation comprises between about 1% (w/v) and about 16% (w/v) of the opioid antagonist nalmefene. In certain embodiments, the formulation comprises between about 2% (w/v) and about 12% (w/v) of nalmefene. In certain embodiments, the formulation comprises between about 2% (w/v) and about 10% (w/v) of nalmefene. In certain embodiments, the formulation comprises between about 2% (w/v) and about 8% (w/v) of nalmefene. In certain embodiments, the formulation comprises between about 2% (w/v) and about 4% (w/v) of nalmefene. In certain embodiments, the formulation comprises about 1% (w/v), about 2% (w/v), about 3% (w/v), about 4% (w/v), about 5% (w/v), about 6% (w/v), about 7% (w/v), or about 8% (w/v) of nalmefene. In certain embodiments, the formulation comprises about 1% (w/v) of nalmefene. In certain embodiments, the formulation comprises about 2% (w/v) of nalmefene. In certain embodiments, the formulation comprises about 4% (w/v) of nalmefene.

In certain embodiments, the formulation comprises between about 1 mg and about 16 mg of the opioid antagonist nalmefene. In certain embodiments, the formulation comprises between about 2 mg and about 12 mg of nalmefene. In certain embodiments, the formulation comprises between about 2 mg and about 10 mg of nalmefene. In certain embodiments, the formulation comprises between about 2 mg and about 8 mg of nalmefene. In certain embodiments, the formulation comprises between about 2 mg and about 4 mg of nalmefene. In certain embodiments, the formulation comprises about 1 mg, about 2 mg, about 3 mg, about 4 mg, about 5 mg, about 6 mg, about 7 mg, or about 8 mg of nalmefene. In certain embodiments, the formulation comprises about 1 mg of nalmefene. In certain embodiments, the formulation comprises about 2 mg of nalmefene. In certain embodiments, the formulation comprises about 4 mg of nalmefene.

In certain embodiments, provided herein are pharmaceutical formulations for intranasal administration comprising, in an aqueous solution of not more than about 140 µL: between about 2 mg and about 16 mg of nalmefene; and between about 0.2 mg and about 1.2 mg of an isotonicity agent.

In certain embodiments, provided herein are pharmaceutical formulations for intranasal administration comprising, in an aqueous solution of not more than about 140 µL: between about 2% (w/v) and about 16% (w/v) of nalmefene; and between about 0.2% (w/v) and about 1.2% (w/v) of an isotonicity agent.

In certain embodiments, the pharmaceutical formulation comprises: about 2 mg or about 4 mg nalmefene hydrochloride or a hydrate thereof; and between about 0.2 mg and about 1.2 mg of an isotonicity agent.

In certain embodiments, the pharmaceutical formulation comprises: about 2% (w/v) or about 4% (w/v) nalmefene hydrochloride or a hydrate thereof; and between about 0.2% (w/v) and about 1.2% (w/v) of an isotonicity agent.

In certain embodiments, the isotonicity agent is sodium chloride. In certain embodiments, the isotonicity agent is dextrose. In certain embodiments, the isotonicity agent is 5% (w/v) dextrose. In other embodiments, the isotonicity agent is glycerin. In other embodiments, the isotonicity agent is mannitol. In other embodiments, the isotonicity agent is potassium chloride. In other embodiments, the isotonicity agent is lactated ringer's solution.

In certain embodiments, the pharmaceutical formulation comprises: about 2 mg or about 4 mg nalmefene hydrochloride; and about 0.74 mg sodium chloride.

In certain embodiments, the pharmaceutical formulation comprises: about 4 mg nalmefene hydrochloride; and about 0.74 mg sodium chloride.

In certain embodiments, provided herein are pharmaceutical formulations above comprise an aqueous solution of not more than about 100 µL.

In certain embodiments, the pharmaceutical formulation comprises about 4 mg or about 4% (w/v) nalmefene hydrochloride or a hydrate thereof. In certain embodiments, the pharmaceutical formulation comprises about 2 mg or about 2% (w/v) nalmefene hydrochloride or a hydrate thereof. In certain embodiments, the nalmefene hydrochloride is provided as nalmefene hydrochloride dihydrate.

In certain embodiments, the pharmaceutical formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises between about 0.1% (w/v) to about 12.5% (w/v) of an absorption enhancer. In certain embodiments, the pharmaceutical formulation comprises between about 0.005% (w/v) to about 7.5% (w/v). In other embodiments, the pharmaceutical formulation comprises between about 1% (w/v) to about 5% (w/v) of an absorption enhancer. In certain embodiments, the pharmaceutical formulation comprises between about 0.01% (w/v) to about 7.5% (w/v) of an absorption enhancer. In certain embodiments, the pharmaceutical formulation comprises between about 0.005% (w/v) to about 1% (w/v) of an absorption enhancer. In certain embodiments, the pharmaceutical formulation comprises between about 0.01% (w/v) to about 0.75% (w/v) of an absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer. In certain embodiments, the absorption enhancer is an alkylsaccharide. In certain embodiments, the alkylsaccharide is chosen from dodecyl maltoside, tetradecyl maltoside (TDM) and sucrose dodecanoate.

In certain embodiments, the alkylsaccharide is Intravail® (dodecyl maltoside). Intravail® is the alkyl saccharide 1-O-n-dodecyl-β-D-maltopyranoside (alternately referred to as lauryl-β-D-maltopyranoside, dodecyl maltopyranoside, and DDM; C24H46O11). Alkylsaccharides are used in commercial food and personal care products and have been designated Generally Recognized as Safe (GRAS) substances for food applications. They are non-irritating enhancers of transmucosal absorption that are odorless, tasteless, non-toxic, non-mutagenic, and non-sensitizing in the Draize test up to a 25% concentration. Alkylsaccharides increase absorption by increasing paracellular permeability, as indicated by a decrease in transepithelial electrical resistance; they may also increase transcytosis. The effect is short-lived. Other alkylsaccharides include tetradecyl maltoside (TDM) and sucrose dodecanoate.

In certain embodiments, the pharmaceutical formulation comprises between about 0.005% to about 0.05% (w/v) of the absorption enhancer. In certain embodiments, the pharmaceutical formulation comprises between about 0.005% to about 0.015% (w/v) of the absorption enhancer. In certain embodiments, the pharmaceutical formulation comprises about 0.01% (w/v) of the absorption enhancer. In certain embodiments, the absorption enhancer is benzalkonium chloride.

In certain embodiments, an intranasal formulation comprises between about 0.05% and about 2.5% (w/v) Intravail®. In certain embodiments, an intranasal formulation comprises between about 0.1% and about 0.5% (w/v) Intravail®. In certain embodiments, an intranasal formulation comprises between about 0.15% and about 0.35% (w/v) Intravail®. In certain embodiments, an intranasal formulation comprises between about 0.15% and about 0.2% (w/v) Intravail®. In certain embodiments, an intranasal formulation comprises about 0.18% (w/v) Intravail®. In certain embodiments, an intranasal formulation comprises about 0.2% to about 0.3% (w/v) Intravail®. In certain embodiments, an intranasal formulation comprises about 0.25% (w/v) Intravail®.

When 0.18% Intravail® was added to an intranasal formulation of sumatriptan, the maximum plasma concentration increased almost four-fold in comparison to Imitrex nasal spray and $T_{max}$ was reduced from 1-2 hours to 8-10 minutes. Total exposure, as measured by the area under the concentration-time curve (AUC), increased 32%. An intranasal formulation of nalmefene has the potential to be used without the use of needles or an extended-release formulation. Inclusion of Intravail® may improve pharmacokinetic parameters in some applications.

In certain embodiments, the pharmaceutical formulation additionally comprises an isotonicity agent. The intra-nasal formulation may comprise between about 0.2% (w/v) and about 1.2% (w/v) isotonicity agent, such as about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), or about 1.2% (w/v). The intranasal formulation may comprise more than about 0.1% (w/v) isotonicity agent. The intranasal formulation may comprise less than about 1.2% (w/v) isotonicity agent.

In certain embodiments, provided herein are pharmaceutical formulations for intranasal administration comprising, in an aqueous solution of not more than about 140 μL: between about 2 mg and about 16 mg of nalmefene; about 0.05 mg to about 2.5 mg of an absorption enhancer; and between about 0.2 mg and about 1.2 mg of an isotonicity agent.

In certain embodiments, provided herein are pharmaceutical formulations for intranasal administration comprising, in an aqueous solution of not more than about 140 μL: between about 2% (w/v) and about 16% (w/v) of nalmefene; about 0.05% (w/v) to about 2.5% (w/v) of an absorption enhancer; and between about 0.2% (w/v) and about 1.2% (w/v) of an isotonicity agent.

In certain embodiments, the pharmaceutical formulation comprises: about 2 mg or about 4 mg nalmefene hydrochloride or a hydrate thereof; about 0.05 mg to about 2.5 mg of an absorption enhancer; and between about 0.2 mg and about 1.2 mg of an isotonicity agent.

In certain embodiments, the pharmaceutical formulation comprises: about 2% (w/v) or about 4% (w/v) nalmefene hydrochloride or a hydrate thereof; about 0.05% (w/v) to about 2.5% (w/v) of an absorption enhancer; and between about 0.2% (w/v) and about 1.2% (w/v) of an isotonicity agent.

In certain embodiments, provided herein are pharmaceutical formulations above comprise an aqueous solution of not more than about 100 μL.

In certain embodiments, provided herein are pharmaceutical formulations for intranasal administration comprising, in an aqueous solution of not more than about 140 μL: between about 2 mg and about 16 mg of nalmefene; about 0.005 mg to about 0.015 mg of an absorption enhancer; and between about 0.2 mg and about 1.2 mg of an isotonicity agent.

In certain embodiments, provided herein are pharmaceutical formulations for intranasal administration comprising, in an aqueous solution of not more than about 140 μL: between about 2% (w/v) and about 16% (w/v) of nalmefene; about 0.005% (w/v) to about 0.015% (w/v) of an absorption enhancer; and between about 0.2% (w/v) and about 1.2% (w/v) of an isotonicity agent.

In certain embodiments, the pharmaceutical formulation comprises: about 2 mg or about 4 mg nalmefene hydrochloride or a hydrate thereof; about 0.005 mg to about 0.015 mg of an absorption enhancer; and between about 0.2 mg and about 1.2 mg of an isotonicity agent.

In certain embodiments, the pharmaceutical formulation comprises: about 2 mg or about 4 mg nalmefene hydrochloride or a hydrate thereof; about 0.005 mg to about 0.015 mg of an absorption enhancer; and between about 0.2 mg and about 1.2 mg of an isotonicity agent.

In certain embodiments, provided herein are pharmaceutical formulations above comprise an aqueous solution of not more than about 100 μL.

In certain embodiments, the isotonicity agent is sodium chloride.

In certain embodiments, the absorption enhancer is Intravail® (dodecyl maltoside).

In certain embodiments, the pharmaceutical formulation comprises: about 2 mg or about 4 mg nalmefene hydrochloride; about 0.25 mg Intravail® (dodecyl maltoside); and about 0.74 mg sodium chloride.

In certain embodiments, the pharmaceutical formulation comprises: about 4 mg nalmefene hydrochloride; about 0.25 mg Intravail® (dodecyl maltoside); and about 0.74 mg sodium chloride.

In certain embodiments, the absorption enhancer is benzalkonium chloride.

In certain embodiments, the pharmaceutical formulation comprises: about 2 mg or about 4 mg nalmefene hydrochloride; about 0.01 mg benzalkonium chloride; and about 0.74 mg sodium chloride.

In certain embodiments, the pharmaceutical formulation comprises: about 4 mg nalmefene hydrochloride; about 0.01 mg benzalkonium chloride; and about 0.74 mg sodium chloride.

In certain embodiments, provided herein are pharmaceutical formulations above comprise an aqueous solution of not more than about 100 μL.

In certain embodiments, the pharmaceutical formulation comprises about 4 mg or about 4% (w/v) nalmefene hydrochloride or a hydrate thereof. In certain embodiments, the pharmaceutical formulation comprises about 2 mg or about 2% (w/v) nalmefene hydrochloride or a hydrate thereof. In certain embodiments, the nalmefene hydrochloride is provided as nalmefene hydrochloride dihydrate.

In certain embodiments, the pharmaceutical formulation additionally comprises a compound which is a preservative and/or surfactant.

In certain embodiments, the preservative and/or surfactant is chosen from benzalkonium chloride, methylparaben, sodium benzoate, benzoic acid, phenyl ethyl alcohol, and the like, and mixtures thereof surfactants such as Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, poly-oxyethylene (5) sorbitan monooleate, polyoxyethylene 20 sorbitan trioleate, polyoxyethylene 20 sorbitan monoisoste-arate, sorbitan monooleate, sorbitan monolaurate, sorbitan monopalmitate, sorbitan monostearate, sorbitan trilaurate, sorbitan trioleate, sorbitan tristearate, and the like, and mixtures thereof.

In certain embodiments, the pharmaceutical formulation comprises between about 0.005% (w/v) to about 2.5% (w/v) of a preservative. In certain embodiments, the pharmaceutical formulation comprises between about 0.02% (w/v) to about 1% (w/v) of a preservative. In certain embodiments, the pharmaceutical formulation comprises about 0.01% (w/v) to about 0.5% (w/v) of a preservative.

In certain embodiments, the pharmaceutical formulation additionally comprises a stabilizing agent.

In certain embodiments, the stabilizing agent is disodium edetate (EDTA). In certain embodiments, the stabilizing agent is trisodium edetate. In certain embodiments, the stabilizing agent is nitrilotriacetic acid (NTA). In certain embodiments, the stabilizing agent is tripolyphosphate (TPP). In certain embodiments, the stabilizing agent is hydroxyethylethylenediaminetriacetic acid (HEDTA). In certain embodiments, the stabilizing agent is diethylenetriaminepentaacetic acid (DTPA). In certain embodiments, the stabilizing agent is ethylenediaminetetraacetic acid.

In some embodiments the acid or base, is sufficient to achieve a pH of about 3.5-4.0. In some embodiments the acid or base, is sufficient to achieve a pH of about 3.5-4.5. In some embodiments the acid or base, is sufficient to achieve a pH of about 4.0-4.5. In some embodiments the acid or base, is sufficient to achieve a pH of about 3, about 3.5, about 4, about 4.5, about 5, about 5.5, about 6, or about 7.

In some embodiments, the preservative, absorption enhancer and/or a cationic surfactant is selected from benzalkonium chloride, cyclodextrins, an alkylsaccharide (e.g., a nonionic alkylsaccharide surfactant such as an alkylglycoside and a sucrose ester of fatty acids that consists of an aliphatic hydrocarbon chain coupled to a sugar moiety by a glycosidic or ester bond, respectively), fusidic acid derivatives, phosphatidylcholines, microspheres and liposomes, and bile salts. In a particular embodiment, the preservative, absorption enhancer and/or a cationic surfactant is benzalkonium chloride.

In some embodiments, the pharmaceutical composition further comprises one or more excipients selected from water, NaCl, benzalkonium chloride, sodium edetate, disodium edetate, and hydrochloric acid. In some embodiments, the pharmaceutical composition further comprises water, NaCl, benzalkonium chloride, disodium edetate, and hydrochloric acid.

In some embodiments, the pharmaceutical composition comprises benzalkonium chloride. The benzalkonium chloride can function as a preservative (even in low amounts), an absorption enhancer, and/or a cationic surfactant (typically at a higher amount for these latter two). Benzalkonium chloride is represented by the following structure:

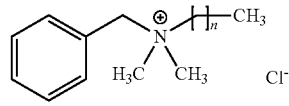

in which n is an integer, and a mixture of more than one thereof can be used. In some embodiments, n is 8, 10, 12, 14, 16, or 18, and in some embodiments, n is 10, 12, or 14. In some embodiments, the pharmaceutical composition comprises about 0.005% (w/v) to about 1% (w/v) benzalkonium chloride.

In its capacity as a surfactant, benzalkonium chloride can affect the surface tension of droplets from a delivered nasal spray plume, producing spherical or substantially spherical particles having a narrow droplet size distribution (DSD), as well as the viscosity of a liquid formulation.

In some embodiments, the absorption enhancer is benzalkonium chloride. The pharmaceutical composition may comprise about 0.01% (w/v) to about 1% (w/v) benzalkonium chloride. In some embodiments, the pharmaceutical composition comprises about 0.005% (w/v) to about 0.015% (w/v) benzalkonium chloride. In some embodiments, the pharmaceutical composition comprises about 0.01% (w/v) benzalkonium chloride.

In some embodiments, the absorption enhancer is an alkylsaccharide, for example, a nonionic alkylsaccharide surfactant such as an alkylglycoside and a sucrose ester of fatty acids that consists of an aliphatic hydrocarbon chain coupled to a sugar moiety by a glycosidic or ester bond, respectively. In some embodiments, the absorption enhancer is an alkylmaltoside (e.g., a tetradecyl maltoside (TDM), a dodecyl maltoside, etc.). In some embodiments, the absorption enhancer is sucrose dodecanoate. Alkylsaccharides are used in commercial food and personal care products and have been designated Generally Recognized as Safe (GRAS) substances for food applications. They are nonirritating enhancers of transmucosal absorption that are odorless, tasteless, non-toxic, non-mutagenic, and non-sensitizing in the Draize test up to a 25% concentration. Without being bound to any theory, it is believed that alkylsaccharides increase absorption by increasing paracellular permeability, as indicated by a decrease in transepithelial electrical resistance; they may also increase transcytosis. The effect may be short-lived.

In some embodiments, the absorption enhancer is Intravail®, the alkylsaccharide 1-O-n-dodecyl-β-D-maltopyranoside (alternately referred to as lauryl-β-D-maltopyranoside, dodecyl maltopyranoside, dodecyl maltoside, and DDM; C24H46O11). In certain embodiments, an intranasal formulation comprises about 0.01% (w/v) to about 2.5% (w/v) Intravail®. In certain embodiments, an intranasal formulation comprises about 0.1% (w/v) to about 0.5% (w/v) Intravail®. In certain embodiments, an intranasal formulation comprises about 0.15% (w/v) to about 0.35% (w/v) Intravail®. In certain embodiments, an intranasal formulation comprises about 0.15% (w/v) to about 0.2% (w/v) Intravail®. In certain embodiments, an intranasal formulation comprises about 0.18% (w/v) Intravail®. In certain embodiments, an intranasal formulation comprises about 0.2% (w/v) to about 0.3% (w/v) Intravail®. In certain embodiments, an intranasal formulation comprises about 0.25% (w/v) Intravail®

Also provided herein is a method of lowering opioid overdose risk in an individual at risk for opioid overdose, comprising providing to the individual at risk for opioid overdose a therapeutically effective amount of nalmefene hydrochloride or a hydrate thereof, wherein the nalmefene hydrochloride or hydrate thereof is contained in a pre-primed, bi-dose device adapted for nasal delivery of a pharmaceutical composition to a patient, wherein a first volume of the pharmaceutical composition is present in a first reservoir, and a second volume of the pharmaceutical composition is present in a second reservoir, and wherein the therapeutically effective amount of the opioid antagonist is delivered essentially by a first actuation of the drug delivery device from the first reservoir into a nostril of the patient and a second actuation of the drug delivery device from the second reservoir into a nostril of the patient; each reservoir comprising a pharmaceutical composition which is an aqueous solution of about 100 μL comprising:
  nalmefene hydrochloride or a hydrate thereof;
  between about 0.2 mg and about 1.2 mg of an isotonicity agent;
  benzalkonium chloride in an amount effective to function as an absorption enhancer and/or a cationic surfactant;
  of a stabilizing agent;
  and an amount of acid or base sufficient to achieve a pH of 3.5-5.5.

In certain embodiments, the absorption enhancer is selected from the group consisting of benzalkonium chloride, chitosan, cyclodextrins, deoxycholic acid, dodecyl maltoside, glycocholic acid, laureth-9, taurocholic acid, and taurodihydrofusidic acid. In certain embodiments, the absorption enhancer is Intravail®. In certain embodiments, the stabilizing agent is disodium edetate; and edetate disodium. In certain embodiments, the acid is hydrochloric acid.

In certain embodiments, the acid is pharmaceutical formulation comprises: about 2 mg or about 4 mg nalmefene hydrochloride or a hydrate thereof; about 0.74 mg sodium chloride; about 0.01 mg benzalkonium chloride; about 0.25 mg Intravail® (dodecyl maltoside); about 0.2 mg edetate disodium; and an amount of hydrochloric acid sufficient to achieve a pH of 3.5-5.5.

In certain embodiments, the pharmaceutical formulation comprises: about 2 mg or about 4 mg nalmefene hydrochloride or a hydrate thereof; about 0.74 mg sodium chloride; about 0.01 mg benzalkonium chloride; about 0.2 mg edetate disodium; and an amount of hydrochloric acid or the base sufficient to achieve a pH of 3.5-5.5.

In certain embodiments, the pharmaceutical formulation comprises: about 2 mg or about 4 mg nalmefene hydrochloride or a hydrate thereof; about 0.74 mg sodium chloride; about 0.25 mg Intravail® (dodecyl maltoside); about 0.2 mg edetate disodium; and an amount of hydrochloric acid sufficient to achieve a pH of 3.5-5.5.

In certain embodiments, the pharmaceutical formulation comprises about 4 mg nalmefene hydrochloride or a hydrate thereof. In certain embodiments, the pharmaceutical formulation comprises between about 2.5 mg and about 8 mg nalmefene hydrochloride or a hydrate thereof. In certain embodiments, the pharmaceutical formulation comprises about 2 mg nalmefene hydrochloride or a hydrate thereof. In certain embodiments, the pharmaceutical formulation comprises about 2.5 mg nalmefene hydrochloride or a hydrate thereof. In certain embodiments, the pharmaceutical formulation comprises about 4 mg nalmefene hydrochloride dihydrate.

Also provided herein are pharmaceutical formulations for intranasal administration comprising, in an aqueous solution of about 100 μL: about 4 mg nalmefene hydrochloride or a hydrate thereof between about 0.2 mg and about 1.2 mg of an isotonicity agent; between about 0.005 mg and about 0.015 mg of a compound which is a preservative and/or cationic surfactant; between about 0.00 and about 0.50 mg of a compound which is sodium hydroxide. an absorption enhancer; between about 0.1 mg and about 0.5 mg of a stabilizing agent; and an amount of an acid sufficient to achieve a pH of 3.5-5.5.

Also provided herein are pharmaceutical formulations for intranasal administration comprising, in an aqueous solution of about 100 μL: about 4 mg nalmefene hydrochloride or a hydrate thereof between about 0.2 mg and about 1.2 mg of an isotonicity agent; optionally, between about 0.005 mg and about 0.015 mg of a compound which is a preservative and/or cationic surfactant; between about 0.005 and about 0.50 mg of a compound which is an absorption enhancer; optionally, between about 0.1 mg and about 0.5 mg of a stabilizing agent; and an amount of an acid sufficient to achieve a pH of 3.5-5.5.

Also provided herein are pharmaceutical formulations for intranasal administration comprising, in an aqueous solution of about 100 μL: about 4 mg nalmefene hydrochloride or a hydrate thereof between about 0.2 mg and about 1.2 mg of an isotonicity agent; between about 0.005 mg and about 0.015 mg of a compound which is a preservative and/or cationic surfactant; between about 0.05 and about 0.50 mg of a compound which is an absorption enhancer; between about 0.1 mg and about 0.5 mg of a stabilizing agent; and an amount of an acid sufficient to achieve a pH of 3.5-5.5.

In certain embodiments, the pharmaceutical formulation comprises: about 4 mg nalmefene hydrochloride or a hydrate thereof; about 0.74 mg sodium chloride; about 0.01 mg benzalkonium chloride; about 0.18 mg Intravail® (dodecyl maltoside); about 0.2 mg edetate disodium; and an amount of hydrochloric acid sufficient to achieve a pH of 3.5-5.5.

Also provided herein are pharmaceutical formulations for intranasal administration comprising, in an aqueous solution of about 100 μL: about 2 mg nalmefene hydrochloride or a hydrate thereof, between about 0.2 mg and about 1.2 mg of an isotonicity agent; between about 0.005 mg and about 0.015 mg of a compound which is a preservative and/or cationic surfactant; between about 0.00 and about 0.50 mg of a compound which is an absorption enhancer; between about 0.1 mg and about 0.5 mg of a stabilizing agent; and an amount of an acid sufficient to achieve a pH of 3.5-5.5.

In certain embodiments, the pharmaceutical formulation comprises: about 2 mg nalmefene hydrochloride dihydrate; about 0.74 mg sodium chloride; about 0.01 mg benzalkonium chloride; about 0.18 mg Intravail® (dodecyl maltoside); about 0.2 mg edetate disodium; and an amount of hydrochloric acid sufficient to achieve a pH of 3.5-5.5.

In certain embodiments, the therapeutically effective amount comprises about 2 to about 16 mg of nalmefene. In certain embodiments, the pharmaceutical formulation comprises an amount equivalent to about 2, about 3, about 4, about 5, about 6, about 7, about 8, about 9, about 10, about 11, about 12, about 13, about 14, about 15, or about 16 mg of nalmefene hydrochloride. In certain embodiments, the pharmaceutical formulation comprises an amount equivalent to about 4 mg to about 8 mg of naloxone hydrochloride. In certain embodiments, the pharmaceutical formulation comprises an amount equivalent to about 16 mg of naloxone hydrochloride.

In certain embodiments, the pharmaceutical formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises between about 0.1% (w/v) to about 12.5% (w/v) of an absorption enhancer. In certain embodiments, the pharmaceutical formulation comprises between about 0.005% (w/v) to about 7.5% (w/v). In other embodiments, the pharmaceutical formulation comprises between about 1% (w/v) to about 5% (w/v) of an absorption enhancer. In certain embodiments, the pharmaceutical formulation comprises between about 0.01% (w/v) to about 7.5% (w/v) of an absorption enhancer. In certain embodiments, the pharmaceutical formulation comprises between about 0.005% (w/v) to about 1% (w/v) of an absorption enhancer. In certain embodiments, the pharmaceutical formulation comprises between about 0.01% (w/v) to about 0.75% (w/v) of an absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer. In certain embodiments, the absorption enhancer is an alkylsaccharide. In certain embodiments, the alkylsaccharide is chosen from dodecyl maltoside, tetradecyl maltoside (TDM) and sucrose dodecanoate.

D. Nasal Drug Delivery Devices and Kits

Also provided are nasal drug delivery devices comprising a pharmaceutical composition described herein. herein are pharmaceutical compositions in a device adapted for nasal delivery to a subject suffering from opioid overdose; or opioid-receptor-mediated-diseases, disorders, addictions, symptoms, or conditions, comprising administering an intranasal formulation of nalmefene. In some embodiments, the device is pre-primed. In some embodiments, the device can be primed before use. In some embodiments, the device can be actuated with one hand.

Nasal delivery is considered an attractive, safe, and easy-to-administer route for needle-free, systemic drug delivery, especially when rapid absorption and effect are desired. In addition, nasal delivery may help address issues related to poor bioavailability, slow absorption, drug degradation, and adverse events (AEs) in the gastrointestinal tract and avoids the first-pass metabolism in the liver.

Liquid nasal formulations are mainly aqueous solutions, but suspensions and emulsions can also be delivered. In traditional spray pump systems, antimicrobial preservatives are typically required to maintain microbiological stability in liquid formulations.

Some emergency medical service (EMS) programs have developed a system using existing technologies of an approved drug and an existing medical device to administer the opioid antagonist naloxone intranasally, albeit in a non-FDA approved manner. This has been accomplished by using the injectable formulation (1 mg/mL) and administering 1 mL per nostril via a marketed nasal atomizer/nebulizer device. The system combines an FDA-approved naloxone injection product (with a Luer fitted tip, no needles) with a marketed, medical device called the Mucosal Atomization Device (MADIM Nasal, Wolfe Tory Medical, Inc.). This initiative is consistent with the U.S. Needlestick Safety and Prevention Act (Public Law 106-430). The EMS programs recognize limitations of this system, one limitation being that it is not assembled and ready-to-use. Although this administration mode appears to be effective in reversing narcosis, the formulation is not concentrated for retention in the nasal cavity. The 1 mL delivery volume per nostril is larger than that generally utilized for intranasal drug administration. Therefore, there is loss of drug from the nasal cavity, due either to drainage into the nasopharynx or externally from the nasal cavity. The devices described herein are improved ready-to-use products specifically optimized, concentrated, and formulated for nasal delivery.

Metered spray pumps have dominated the nasal drug delivery market since they were introduced. The pumps typically deliver 100 μL, (25-200 μL) per spray, and they offer high reproducibility of the emitted dose and plume geometry in in vitro tests.

Metered spray pumps have dominated the nasal drug delivery market since they were introduced. The pumps typically deliver 100 μL (or other volumes in the range of 25-200 μL, and higher) per spray, and they offer high reproducibility of the emitted dose and plume geometry in in vitro tests.

Examples of standard metered spray pumps include those offered by Aptar Pharma, Inc., such as the multi-dose "classic technology platform" nasal spray devices. Such devices comprise a reservoir which holds multiple doses of the nasal spray formulation (e.g., 50, 100, 150, 200, 60, or 120 doses), a closure (e.g., screw, crimp, or snap-on), and an actuator which delivers anywhere from 45 to 1000 μL, (e.g. 50, 100, 140, 150, or 200 μL) of fluid per actuation to comprise a single dose. The actuator may be configured to count doses, deliver gel formulations, deliver in an upside-down configuration, etc.

In traditional spray pump systems, antimicrobial preservatives are typically required to maintain microbiological stability in liquid formulations. However, preservative-free systems are also available, e.g. the Advanced Preservative Free (APF) system from Aptar, which is vented, contains a filter membrane for air flow which prevents contamination, has a metal-free fluid path for oxidizing formulations, and can be used in any orientation. Additional nasal spray devices from Aptar and others are optimized with dispenser tips that prevent clogging (useful for high-viscosity and high-volatile formulations), actuators that do not need re-priming after long periods of disuse, etc.

The particle size and plume geometry can vary within certain limits and depend on the properties of the pump, the formulation, the orifice of the actuator, and the force applied. The droplet size distribution of a nasal spray is a critical parameter, since it significantly influences the in vivo deposition of the drug in the nasal cavity. The droplet size is influenced by the actuation parameters of the device and the formulation. The prevalent median droplet size should be between about 30 and about 100 µm. If the droplets are too large (>about 120 µm), deposition takes place mainly in the anterior parts of the nose, and if the droplets are too small (<about 10 µm), they can possibly be inhaled and reach the lungs, which should be avoided because of safety reasons. In its capacity as a surfactant, benzalkonium chloride can affect the surface tension of droplets from a delivered nasal spray plume, producing spherical or substantially spherical particles having a narrow droplet size distribution (DSD), as well as the viscosity of a liquid formulation.

Plume geometry, droplet size and DSD of the delivered plume subsequent to spraying may be measured under specified experimental and instrumental conditions by appropriate and validated and/or calibrated analytical procedures known in the art. These include photography, laser diffraction, and impaction systems (cascade impaction, NGI). Plume geometry, droplet size and DSD can affect pharmacokinetic outcomes such as $C_{max}$, $T_{max}$, and linear dose proportionality.

Droplet size distribution can be controlled in terms of ranges for the D10, D50, D90, span RD90-D10)/D501, and percentage of droplets less than 10 mm. In certain embodiments, the formulation will have a narrow DSD. In certain embodiments, the formulation will have a D (v,50) of 30-70 nm and a D (v, 90)<100 nm.

In certain embodiments, the percent of droplets less than 10 μm will be less than 10%. In certain embodiments, the percent of droplets less than 10 μm will be less than 5%. In certain embodiments, the percent of droplets less than 10 μm will be less than 2%. In certain embodiments, the percent of droplets less than 10 μm will be less than 1%.

In certain embodiments, the formulation when dispensed by actuation from the device will produce a uniform circular plume with an ovality ratio close to 1. Ovality ratio is calculated as the quotient of the maximum diameter ($D_{max}$) and the minimum diameter ($D_{min}$) of a spray pattern taken orthogonal to the direction of spray flow (e.g., from the "top"). In certain embodiments, the ovality ratio is less than ±2.0. In certain embodiments, the ovality ratio is less than ±1.5. In certain embodiments, the ovality ratio is less than ±1.3. In certain embodiments, the ovality ratio is less than ±1.2. In certain embodiments, the ovality ratio is less than ±1.1. In certain embodiments, the ovality ratio is about ±1.0.

The details and mechanical principles of particle generation for different types of nasal aerosol devices has been described. See, Vidgren and Kublik, Adv. Drug Deliv. Rev. 29:157-77, 1998. Traditional spray pumps replace the emitted liquid with air, and preservatives are therefore required to prevent contamination. However, driven by the studies suggesting possible negative effects of preservatives, pump manufacturers have developed different spray systems that avoid the need for preservatives. These systems use a collapsible bag, a movable piston, or a compressed gas to compensate for the emitted liquid volume (www.aptar.com and www.rexam.com). The solutions with a collapsible bag and a movable piston compensating for the emitted liquid volume offer the additional advantage that they can be emitted upside down, without the risk of sucking air into the dip tube and compromising the subsequent spray. This may be useful for some products where the patients are bedridden and where a head-down application is recommended. Another method used for avoiding preservatives is that the air that replaces the emitted liquid is filtered through an aseptic air filter. In addition, some systems have a ball valve at the tip to prevent contamination of the liquid inside the applicator tip (www.aptar.com). More recently, pumps have been designed with side-actuation and introduced for delivery of fluticasone furoate for the indication of seasonal and perennial allergic rhinitis. The pump was designed with a shorter tip to avoid contact with the sensitive mucosal surfaces. New designs to reduce the need for priming and re-priming, and pumps incorporating pressure point features to improve the dose reproducibility and dose counters and lock-out mechanisms for enhanced dose control and safety are available (www.rexam.com and www.aptar.com).

Traditional, simple metered-dose spray pumps require priming and some degree of overfill to maintain dose conformity for the labeled number of doses. They are well suited for drugs to be administered daily over a prolonged duration, but due to the priming procedure and limited control of dosing, unless a specialty device is selected, they are less suited for drugs with a narrow therapeutic window, particularly if they are not used often. For expensive drugs and vaccines intended for single administration or sporadic use and where tight control of the dose and formulation is of importance, single-dose or bi-dose spray devices are preferred (www.aptar.com). A simple variant of a single-dose spray device (MAD™) is offered by LMA (LMA, Salt Lake City, Utah, USA; www.lmana.com). A nosepiece with a spray tip is fitted to a standard syringe. The liquid drug to be delivered is first drawn into the syringe and then the spray tip is fitted onto the syringe. This device has been used in academic studies to deliver, for example, a topical steroid in patients with chronic rhinosinusitis and in a vaccine study. A pre-filled device based on the same principle for one or two doses (Accuspray™, Becton Dickinson Technologies, Research Triangle Park, N.C., USA; www.bdpharma.com) is used to deliver the influenza vaccine FluMist™ (www.flumist.com), approved for both adults and children in the US market. A similar device for two doses was marketed by a Swiss company for delivery of another influenza vaccine a decade ago.

Pre-primed single- and bi-dose devices are also available, and consist of a reservoir, a piston, and a swirl chamber (see, e.g., the UDS UnitDose™ and BDS BiDose™ devices from Aptar, formerly Pfeiffer). The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like Imitrex® (www.gsk.com) and Zomig® (www.az.com; Pfeiffer/Aptar single-dose device), the marketed influenza vaccine Flu-Mist (www.flumist.com; Becton Dickinson single-dose spray device), and the intranasal formulation of naloxone for opioid overdose rescue, Narcan Nasal® (narcan.com; Adapt Pharma) are delivered with this type of device.

In certain embodiments, the 90% confidence interval for dose delivered per actuation is ±about 2%. In certain embodiments, the 95% confidence interval for dose delivered per actuation is ±about 2.5%.

Historically, intranasal administration of drugs in large volume, such as from syringes adapted with mucosal atomizer devices, has encountered difficulty due to the tendency of some of the formulation to drip back out of the nostril or down the nasopharynx. Accordingly, in certain embodiments, upon nasal delivery of said pharmaceutical composition to said patient, less than about 20% of said pharmaceutical composition leaves the nasal cavity via drainage into the nasopharynx or externally. In certain embodiments, upon nasal delivery of said pharmaceutical composition to said patient, less than about 10% of said pharmaceutical composition leaves the nasal cavity via drainage into the nasopharynx or externally. In certain embodiments, upon nasal delivery of said pharmaceutical composition to said patient, less than about 5% of said pharmaceutical composition leaves the nasal cavity via drainage into the nasopharynx or externally.

Current container closure system designs for inhalation spray drug products include both pre-metered and device-metered presentations using mechanical or power assistance and/or energy from patient inspiration for production of the spray plume. Pre-metered presentations contain previously measured doses or a dose fraction in some type of units (e.g., single or multiple blisters or other cavities) that are subsequently inserted into the device during manufacture or by the patient before use. Typical device-metered units have a reservoir containing formulation sufficient for multiple doses that are delivered as metered sprays by the device itself when activated by the patient.

A new nasal drug delivery method, which can be adapted to any type of dispersion technology for both liquids and powders, is breath-powered Bi-Directional™ technology. This concept exploits natural functional aspects of the upper airways to offer a delivery method that may overcome many of the inherent limitations of traditional nasal devices. Breath-powered Bi-Directional™ devices consist of a mouthpiece and a sealing nosepiece with an optimized frusto-conical shape and comfortable surface that mechanically expands the first part of the nasal valve. The user slides a sealing nosepiece into one nostril until it forms a seal with the flexible soft tissue of the nostril opening, at which point, it mechanically expands the narrow slit-shaped part of the nasal triangular valve. The user then exhales through an attached mouthpiece. When exhaling into the mouthpiece against the resistance of the device, the soft palate (or velum) is automatically elevated by the positive oropharyngeal pressure, isolating the nasal cavity from the rest of the respiratory system. This mechanism enables release of liquid or powder particles into an air stream that enters one nostril, passes entirely around the nasal septum, and exits through the opposite nostril.

With sterile filling, the use of preservatives is not required in pre-primed devices, but overfill is required resulting in a waste fraction similar to the metered-dose, multi-dose sprays. To emit 100 μL a volume of 125 μL is filled in the device (Pfeiffer/Aptar single-dose device) used for the intranasal migraine medications ImitrexIM (sumatriptan) and Zomig™ (zolmitriptan) and about half of that for a bi-dose design. Sterile drug products may be produced using aseptic processing or terminal sterilization. Terminal sterilization usually involves filling and sealing product containers under high-quality environmental conditions. Products are filled and sealed in this type of environment to minimize the microbial and particulate content of the in-process product and to help ensure that the subsequent sterilization process is successful. In most cases, the product, container, and closure have low bioburden, but they are not sterile. The product in its final container is then subjected to a sterilization process such as heat or irradiation. In an aseptic process, the drug product, container, and closure are first subjected to sterilization methods separately, as appropriate, and then brought together. Because there is no process to sterilize the product in its final container, it is critical that containers be filled and sealed in an extremely high-quality environment. Aseptic processing involves more variables than terminal sterilization. Before aseptic assembly into a final product, the individual parts of the final product are generally subjected to various sterilization processes. For example, glass containers are subjected to dry heat; rubber closures are subjected to moist heat; and liquid dosage forms are subjected to filtration. Each of these manufacturing processes requires validation and control.

Devices recited herein may employ any of the pharmaceutical formulations, and are useful in all the methods disclosed herein.

Accordingly, provided herein are devices adapted for nasal delivery of a pharmaceutical composition to a patient, comprising a reservoir with a therapeutically effective amount of an opioid antagonist selected from nalmefene and pharmaceutically acceptable salts thereof, wherein the device is pre-primed. In some embodiments, the opioid antagonist is nalmefene hydrochloride. In some embodiments, the opioid antagonist is anhydrous nalmefene hydrochloride. In some embodiments, the therapeutically effective amount, is equivalent to any of the amounts of nalmefene hydrochloride provided above, for example, about 1 mg to about 10 mg of nalmefene hydrochloride.

In some embodiments, the relative bioavailability (comparing the dose-adjusted $AUC_{0-inf}$ after IN administration to that of the IM formulation) of nalmefene in a formulation as disclosed herein, will be about 40% to about 80%. In some embodiments, the relative bioavailability will be about 45% to about 75%. In some embodiments, the relative bioavailability will be about 50% to about 70%. In some embodiments, the relative bioavailability will be about 5% to about 65%. In some embodiments, the relative bioavailability will be about 60%.

In some embodiments, the pharmaceutical composition comprises about 1-10 mg nalmefene hydrochloride, or a hydrate thereof, formulated for intranasal administration, and produces a plasma concentration versus time curve having an area under the curve (AUC) that is about 60% of the AUC for 1.5 mg IM nalmefene. While Intravail® did not alter the AUC for IN nalmefene, the results with naltrexone were different. With naltrexone, the AUC increased significantly. This important difference could not be predicted based on structure of the opioid antagonists, or the function of these moieties as opioid antagonists.

In some embodiments, the patient is an opioid overdose patient or a suspected opioid overdose patient.

In some embodiments, the patient is in a lying, supine, or recovery position. In some embodiments, the patient is in a lying position. In some embodiments, the patient is in a supine position. In some embodiments, the patient is in a recovery position.

In some embodiments, the therapeutically effective amount of an opioid antagonist is delivered by an untrained individual.

In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride.

In some embodiments, the therapeutically effective amount is equivalent to about 1 mg of nalmefene free base. In some embodiments, the therapeutically effective amount is equivalent to about 1.5 mg of nalmefene free base. In some embodiments, the therapeutically effective amount is equivalent to about 2 mg of nalmefene free base. In some embodiments, the therapeutically effective amount is equivalent to about 2.5 mg of nalmefene free base. In some embodiments, the therapeutically effective amount is equivalent to about 2.7 mg of nalmefene free base. In some embodiments, the therapeutically effective amount is equivalent to about 3 mg of nalmefene free base. In some embodiments, the therapeutically effective amount is equivalent to about 3.5 mg of nalmefene free base. In some embodiments, the therapeutically effective amount is equivalent to about 4 mg of nalmefene free base. In some embodiments, the therapeutically effective amount is equivalent to about 4.5 mg of nalmefene free base. In some embodiments, the therapeutically effective amount is equivalent to about 5 mg of nalmefene free base.

In some embodiments, the opioid antagonist is the only pharmaceutically active compound in the pharmaceutical composition.

In some embodiments, the pharmaceutical composition comprises a solution of nalmefene hydrochloride, or a hydrate thereof.

In some embodiments, the volume of the pharmaceutical composition in the reservoir is not more than about 140 µL.

In some embodiments, about 100 µL of the pharmaceutical composition in the reservoir is delivered to the patient in one actuation.

In some embodiments, the pharmaceutical composition further comprises one or more excipients selected from water and NaCl.

In some embodiments, the pharmaceutical composition is substantially free of antimicrobial preservatives.

In some embodiments, the pharmaceutical composition further comprises a compound which acts as a preservative, absorption enhancer and/or a cationic surfactant; an isotonicity agent; a stabilizing agent; and an amount of acid or base or base sufficient to achieve a pH of about 3.5 to about 5.5. The use of absorption enhancers, such as alkylsaccharides, cyclodextrins, and chitosans may increase the rate at which nalmefene is absorbed. In general, absorption enhancers provide improved pharmacokinetic outcomes such as increased $C_{max}$, reduced $T_{max}$, and linear dose proportionality compared to both intramuscular formulations and intranasal formulations that do not contain an absorption enhancer. Without being bound to any theory, such absorption enhancers typically operate by affecting two primary mechanisms for nasal absorption: paracellular transport via opening of tight junctions between cells, and transcellular transport or transcytosis through cells via vesicle carriers.

For example, alkylsaccharides are used in commercial food and personal care products and have been designated Generally Recognized as Safe (GRAS) substances for food applications. They are non-irritating enhancers of transmucosal absorption that are odorless, tasteless, nontoxic, non-mutagenic, and non-sensitizing in the Draize test up to a 25% concentration. Alkylsaccharides increase absorption by increasing paracellular permeability, as indicated by a decrease in transepithelial electrical resistance; they may also increase transcytosis. The effect is short-lived.

When an alkylsaccharide is added to an intranasal formulation, the maximum plasma concentration can increase several-fold in comparison to Imitrex nasal spray, and the $T_{max}$ can be reduced from hours to minutes. Total exposure, as measured by the area under the concentration-time curve (AUC), can increase by about 30%. This increase in AUC of naltrexone could not be predicted by one of skill in the art, because structurally similar drugs, such as nalmefene, do not have increased AUC under these same conditions. An intranasal formulation of naltrexone has the potential to be used for treating AUD without the use of needles or an extended-release formulation.

Some absorption enhancing excipients can alter the paracellular and/or transcellular pathways, others can extend residence time in the nasal cavity or prevent metabolic changes. Without an absorption enhancer, the molecular-weight limit for nasal absorption is about 1 kDa, while administration of drugs in conjunction with absorption enhancers can enable the absorption of molecules from 1-30 kDa. Intranasal administration of most absorption enhancers, however, can cause nasal mucosa damage. Maggio, J. *Excipients and Food Chem.* 5 (2): 100-12, 2014. Examples of absorption enhancers include aprotinin, benzalkonium chloride, benzyl alcohol, capric acid, ceramides, cetylpyridinium chloride, chitosan, cyclodextrins, deoxycholic acid, decanoyl carnitine, EDTA, glycocholic acid, glycodeoxycholic acid, glycofurol, glycosylated sphingosines, glycyrrhetinic acids, 2-hydroxypropyl-β-cyclodextrin, laureth-9, lauric acid, lauroyl carnitine, lauryl sulfate, lysophosphatidylcholine, menthol, poloxamer 407, poloxamer F68, poly-L-arginine, polyoxyethylene-9-lauryl ether, polysorbate 80, propylene glycol, quillaia saponin, salicylic acid, β-sitosterol-β-D-glucoside, sucrose cocoate, taurocholic acid, taurodeoxycholic acid, taurodihydrofusidic acid, and alkylsaccharides, such as dodecyl maltoside, tetradecyl maltoside and sucrose dodecanoate.

The opioid antagonist naltrexone described herein can be formulated into pharmaceutical compositions using techniques well known to those in the art. Suitable pharmaceutically acceptable carriers, outside those mentioned herein, are known in the art.

The opioid antagonist nalmefene described herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. The acid addition salts may be obtained as the direct products of compound synthesis. In the alternative, the free base may be dissolved in a suitable solvent containing the appropriate acid and the salt isolated by evaporating the solvent or otherwise separating the salt and solvent. The opioid antagonist nalmefene described herein may form solvates with standard low molecular weight solvents using methods known to the skilled artisan.

Accordingly, provided herein is a drug product comprising a therapeutically effective amount of nalmefene hydrochloride, or a hydrate thereof, wherein the nalmefene hydrochloride, or hydrate thereof, is contained in a single-use, pre-primed device adapted for nasal delivery of a pharmaceutical composition to a patient by one actuation of the device into one nostril of the patient, and wherein the single-use, pre-primed device comprises a reservoir containing a pharmaceutical composition which is an aqueous solution of about 100 μL comprising: nalmefene hydrochloride or a hydrate thereof; benzalkonium chloride in an amount effective to function as an absorption enhancer and/or a cationic surfactant; an isotonicity agent; a stabilizing agent; and an amount of acid or base sufficient to achieve a pH of 3.5-5.5.

In some embodiments, the single-use, pre-primed device adapted for nasal delivery of a pharmaceutical composition to a patient comprises any of the amounts of nalmefene hydrochloride provided above, for example, between about 1 mg and about 10 mg of the nalmefene hydrochloride or a hydrate thereof.

In some embodiments, the single-use, pre-primed device adapted for nasal delivery of a pharmaceutical composition to a patient comprises the equivalent of about 1 mg of nalmefene hydrochloride. In some embodiments, the device comprises the equivalent of about 1.5 mg of nalmefene hydrochloride. In some embodiments, the device comprises the equivalent of about 2 mg of nalmefene hydrochloride. In some embodiments, the device comprises the equivalent of about 2.5 mg of nalmefene hydrochloride. In some embodiments, the device comprises the equivalent of about 3 mg of nalmefene hydrochloride. In some embodiments, the device comprises the equivalent of about 3.5 mg of nalmefene hydrochloride. In some embodiments, the device comprises the equivalent of about 4 mg of nalmefene hydrochloride. In some embodiments, the device comprises the equivalent of about 4.5 mg of nalmefene hydrochloride. In some embodiments, the device comprises the equivalent of about 5 mg of nalmefene hydrochloride.

In some embodiments, the single-use, pre-primed device adapted for nasal delivery of a pharmaceutical composition to a patient comprises the equivalent of about 1 mg of nalmefene free base. In some embodiments, the device comprises the equivalent of about 1.5 mg of nalmefene free base. In some embodiments, the device comprises the equivalent of about 2 mg of nalmefene free base. In some embodiments, the device comprises the equivalent of about 2.5 mg of nalmefene free base. In some embodiments, the device comprises the equivalent of about 2.7 mg of nalmefene free base. In some embodiments, the device comprises the equivalent of about 3 mg of nalmefene free base. In some embodiments, the device comprises the equivalent of about 3.5 mg of nalmefene free base. In some embodiments, the device comprises the equivalent of about 4 mg of nalmefene free base. In some embodiments, the device comprises the equivalent of about 4.5 mg of nalmefene free base. In some embodiments, the device comprises the equivalent of about 5 mg of nalmefene free base.

In certain embodiments, the pharmaceutical formulation additionally comprises an absorption enhancer. In certain embodiments, the pharmaceutical formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises between about 0.1% (w/v) to about 12.5% (w/v) of an absorption enhancer. In certain embodiments, the pharmaceutical formulation comprises between about 0.005% (w/v) to about 7.5% (w/v). In other embodiments, the pharmaceutical formulation comprises between about 1% (w/v) to about 5% (w/v) of an absorption enhancer. In certain embodiments, the pharmaceutical formulation comprises between about 0.01% (w/v) to about 7.5% (w/v) of an absorption enhancer. In certain embodiments, the pharmaceutical formulation comprises between about 0.005% (w/v) to about 1% (w/v) of an absorption enhancer. In certain embodiments, the pharmaceutical formulation comprises between about 0.01% (w/v) to about 0.75% (w/v) of an absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer. In certain embodiments, the absorption enhancer is an alkylsaccharide. In certain embodiments, the alkylsaccharide is chosen from dodecyl maltoside, tetradecyl maltoside (TDM) and sucrose dodecanoate.

In some embodiments, the aqueous solution comprises:
between about 1 mg and about 10 mg of the nalmefene hydrochloride or a hydrate thereof;
between about 0.005% (w/v) and about 1% (w/v) benzalkonium chloride;
between about 0.2 mg and about 1.2 mg of an isotonicity agent;
between about 0.1 mg and about 0.5 mg of a stabilizing agent; and
an amount of acid or base sufficient to achieve a pH of 3.5-5.5.

In some embodiments, the aqueous solution comprises:
between about 1 mg and about 10 mg of nalmefene hydrochloride or a hydrate thereof;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and 2.5 mg of an absorption enhancer; and
an amount of acid or base sufficient to achieve a pH of 3.5-5.5.

In some embodiments, the aqueous solution comprises:
between about 1 mg and about 10 mg of nalmefene free base;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and about 2.5 mg of an absorption enhancer; and an amount of acid or base sufficient to achieve a pH of 3.5-5.5.

In some embodiments, the aqueous solution comprises:
between about 1% (w/v) and about 10% (w/v) of nalmefene free base;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the aqueous solution comprises:
between about 1% (w/v) and about 10% (w/v) of nalmefene hydrochloride or a hydrate thereof;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the aqueous solution comprises:
about 2.7 mg of nalmefene free base;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the aqueous solution comprises:
about 3 mg of nalmefene hydrochloride;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the aqueous solution comprises:
about 3% (w/v) of nalmefene hydrochloride;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the aqueous solution comprises:
about 2.7% (w/v) of nalmefene free base;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the aqueous solution comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the aqueous solution comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the isotonicity agent is NaCl; the stabilizing agent is disodium edetate; the preservative is benzalkonium chloride and the acid is hydrochloric acid.

In some embodiments, the aqueous solution comprises:
about 3 mg nalmefene hydrochloride;
about 0.74 mg NaCl;
between about 0.005% (w/v) and about 1% (w/v) benzalkonium chloride;
about 0.2 mg disodium edetate; and
an amount of hydrochloric acid sufficient to achieve a pH of 3.5-5.5.

In some embodiments, the aqueous solution comprises:
about 1 mg to about 10 mg nalmefene hydrochloride;
about 0.74 mg NaCl;
between about 0.005% (w/v) and about 1% (w/v) benzalkonium chloride;
about 0.2 mg disodium edetate; and
an amount of hydrochloric acid sufficient to achieve a pH of 3.5-5.5.

Also provided herein is a drug product comprising a therapeutically effective amount of nalmefene hydrochloride or a hydrate thereof, wherein the nalmefene hydrochloride or hydrate thereof is contained in a pre-primed, bi-dose device adapted for nasal delivery of a pharmaceutical composition to a patient, wherein a first volume of the pharmaceutical composition is present in a first reservoir, and a second volume of the pharmaceutical composition is present in a second reservoir, and wherein the therapeutically effective amount of the opioid antagonist is delivered essentially by a first actuation of the drug delivery device from the first reservoir into a nostril of the patient and a second actuation of the drug delivery device from the second reservoir into a nostril of the patient; each reservoir comprising a pharmaceutical composition which is an aqueous solution of about 100 μL comprising:
nalmefene hydrochloride or a hydrate thereof;
an isotonicity agent;
benzalkonium chloride in an amount effective to function as an absorption enhancer and/or a cationic surfactant;
a stabilizing agent; and
an amount of acid or base sufficient to achieve a pH of 3.5-5.5.

In some embodiments, the pharmaceutical composition comprises:
between about 1 mg and about 10 mg of nalmefene hydrochloride or a hydrate thereof;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and 2.5 mg of an absorption enhancer; and
an amount of acid or base sufficient to achieve a pH of 3.5-5.5.

In some embodiments, the pharmaceutical composition comprises:
- between about 1 mg and about 10 mg of nalmefene free base;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and about 2.5 mg of an absorption enhancer; and
- an amount of acid or base sufficient to achieve a pH of 3.5-5.5.

In some embodiments, the pharmaceutical composition comprises:
- between about 1% (w/v) and about 10% (w/v) of nalmefene free base;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and
- an amount of acid or base sufficient to achieve a pH of 3.5-5.5.

In some embodiments, the pharmaceutical composition comprises:
- between about 1% (w/v) and about 10% (w/v) of nalmefene hydrochloride or a hydrate thereof;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and
- an amount of acid or base sufficient to achieve a pH of 3.5-5.5.

In some embodiments, the pharmaceutical composition comprises:
- about 2.7 mg of nalmefene free base;
- about 0.04 mg of a preservative;
- about 0.87 mg of an isotonicity agent;
- about 0.2 mg of a stabilizing agent;
- about 0.25 mg of an absorption enhancer; and
- an amount of acid or base sufficient to achieve a pH of 3.5-5.5.

In some embodiments, the pharmaceutical composition comprises:
- about 3 mg of nalmefene hydrochloride;
- about 0.04 mg of a preservative;
- about 0.87 mg of an isotonicity agent;
- about 0.2 mg of a stabilizing agent;
- about 0.25 mg of an absorption enhancer; and
- an amount of acid or base sufficient to achieve a pH of 3.5-5.5.

In some embodiments, the pharmaceutical composition comprises:
- about 3% (w/v) of nalmefene hydrochloride;
- about 0.04% (w/v) of benzalkonium chloride (50% solution);
- about 0.87% (w/v) of sodium chloride;
- about 0.2% (w/v) of disodium edetate;
- about 0.25% (w/v) of dodecyl maltoside; and
- an amount of acid or base sufficient to achieve a pH of 3.5-5.5.

In some embodiments, the pharmaceutical composition comprises:
- about 2.7% (w/v) of nalmefene free base;
- about 0.04% (w/v) of benzalkonium chloride (50% solution);
- about 0.87% (w/v) of sodium chloride;
- about 0.2% (w/v) of disodium edetate;
- about 0.25% (w/v) of dodecyl maltoside; and
- an amount of acid or base sufficient to achieve a pH of 3.5-5.5.

In some embodiments, the pharmaceutical composition comprises:
- about 3% (w/v) of nalmefene hydrochloride;
- about 0.02% (w/v) of benzalkonium chloride;
- about 0.87% (w/v) of sodium chloride;
- about 0.2% (w/v) of disodium edetate;
- about 0.25% (w/v) of dodecyl maltoside; and
- an amount of acid or base sufficient to achieve a pH of 3.5-5.5.

In some embodiments, the pharmaceutical composition comprises:
- about 2.7% (w/v) of nalmefene free base;
- about 0.02% (w/v) of benzalkonium chloride;
- about 0.87% (w/v) of sodium chloride;
- about 0.2% (w/v) of disodium edetate;
- about 0.25% (w/v) of dodecyl maltoside; and
- an amount of acid or base sufficient to achieve a pH of 3.5-5.5.

In some embodiments, each reservoir of the pre-primed, bi-dose device adapted for nasal delivery of a pharmaceutical composition to a patient comprises any of the amounts of nalmefene hydrochloride provided above, for example, between about 1 mg and about 10 mg of the nalmefene hydrochloride or a hydrate thereof.

In some embodiments, each reservoir of the pre-primed, bi-dose device adapted for nasal delivery of a pharmaceutical composition to a patient comprises the equivalent of about 1 mg of nalmefene hydrochloride. In some embodiments, each reservoir of the device comprises the equivalent of about 1.5 mg of nalmefene hydrochloride. In some embodiments, each reservoir of the device comprises the equivalent of about 2 mg of nalmefene hydrochloride. In some embodiments, each reservoir of the device comprises the equivalent of about 2.5 mg of nalmefene hydrochloride. In some embodiments, each reservoir of the device comprises the equivalent of about 3 mg of nalmefene hydrochloride. In some embodiments, each reservoir of the device comprises the equivalent of about 3.5 mg of nalmefene hydrochloride. In some embodiments, each reservoir of the device comprises the equivalent of about 4 mg of nalmefene hydrochloride. In some embodiments, each reservoir of the device comprises the equivalent of about 4.5 mg of nalmefene hydrochloride. In some embodiments, each reservoir of the device comprises the equivalent of about 5 mg of nalmefene hydrochloride.

In some embodiments, each reservoir of the pre-primed, bi-dose device adapted for nasal delivery of a pharmaceutical composition to a patient comprises the equivalent of about 1 mg of nalmefene free base. In some embodiments, each reservoir of the device comprises the equivalent of about 1.5 mg of nalmefene free base. In some embodiments, each reservoir of the device comprises the equivalent of about 2 mg of nalmefene free base. In some embodiments, each reservoir of the device comprises the equivalent of about 2.5 mg of nalmefene free base. In some embodiments, each reservoir of the device comprises the equivalent of about 2.7 mg of nalmefene free base. In some embodiments, each reservoir of the device comprises the equivalent of about 3 mg of nalmefene free base. In some embodiments, each reservoir of the device comprises the equivalent of about 3.5 mg of nalmefene free base. In some embodiments, each reservoir of the device comprises the equivalent of about 4 mg of nalmefene free base. In some embodiments, each reservoir of the device comprises the equivalent of about 4.5 mg of nalmefene free base. In some embodiments, each reservoir of the device comprises the equivalent of about 5 mg of nalmefene free base.

In some embodiments, the aqueous solution comprises:
between about 1 mg and about 10 mg of the nalmefene hydrochloride or a hydrate thereof;
between about 0.005% (w/v) and about 1% (w/v) benzalkonium chloride;
between about 0.2 mg and about 1.2 mg of an isotonicity agent;
between about 0.1 mg and about 0.5 mg of a stabilizing agent; and
an amount of acid or base sufficient to achieve a pH of 3.5-5.5.

In some embodiments:
the isotonicity agent is NaCl;
the stabilizing agent is disodium edetate; and
the acid is hydrochloric acid.

In some embodiments, the aqueous solution comprises:
about 1 mg or about 10 mg nalmefene hydrochloride;
between about 0.005% (w/v) and about 1% (w/v) benzalkonium chloride;
about 0.2 mg disodium edetate; and
an amount of hydrochloric acid sufficient to achieve a pH of 3.5-5.5.

In some embodiments, each reservoir comprises about 3 mg of the nalmefene hydrochloride.

Also provided herein is a method of lowering opioid overdose risk in an individual at risk for opioid overdose, comprising providing to the individual at risk for opioid overdose a therapeutically effective amount of nalmefene hydrochloride or a hydrate thereof, wherein the nalmefene hydrochloride or hydrate thereof is contained in a single-use, pre-primed device adapted for nasal delivery of a pharmaceutical composition to a patient by one actuation of the device into one nostril of the patient, and wherein the single-use, pre-primed device comprises a reservoir containing a pharmaceutical composition which is an aqueous solution of about 100 µL comprising:
nalmefene hydrochloride or a hydrate thereof;
an isotonicity agent;
benzalkonium chloride in an amount effective to function as an absorption enhancer and/or a cationic surfactant;
a stabilizing agent; and
an amount of acid or base sufficient to achieve a pH of 3.5-5.5.

In some embodiments, the pharmaceutical composition comprises:
between about 1 mg and about 10 mg of nalmefene hydrochloride or a hydrate thereof; between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and 2.5 mg of an absorption enhancer; and
an amount of acid or base sufficient to achieve a pH of 3.5-5.5.

In some embodiments, the pharmaceutical composition comprises:
between about 1 mg and about 10 mg of nalmefene free base;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and about 2.5 mg of an absorption enhancer; and
an amount of acid or base sufficient to achieve a pH of 3.5-5.5.

In some embodiments, the pharmaceutical composition comprises:
between about 1% (w/v) and about 10% (w/v) of nalmefene free base;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
between about 1% (w/v) and about 10% (w/v) of nalmefene hydrochloride or a hydrate thereof;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
about 2.7 mg of nalmefene free base;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3 mg of nalmefene hydrochloride;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3% (w/v) of nalmefene hydrochloride;
about 0.04% (w/v) of benzalkonium chloride (50% solution);
about 0.87% (w/v) of sodium chloride;

about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the single-use, pre-primed device adapted for nasal delivery of a pharmaceutical composition to a patient comprises any of the amounts of nalmefene hydrochloride provided above, for example, between about 1 mg and about 10 mg of the nalmefene hydrochloride or a hydrate thereof.

In some embodiments, the single-use, pre-primed device adapted for nasal delivery of a pharmaceutical composition to a patient comprises the equivalent of about 1 mg of nalmefene hydrochloride. In some embodiments, the device comprises the equivalent of about 1.5 mg of nalmefene hydrochloride. In some embodiments, the device comprises the equivalent of about 2 mg of nalmefene hydrochloride. In some embodiments, the device comprises the equivalent of about 2.5 mg of nalmefene hydrochloride. In some embodiments, the device comprises the equivalent of about 3 mg of nalmefene hydrochloride. In some embodiments, the device comprises the equivalent of about 3.5 mg of nalmefene hydrochloride. In some embodiments, the device comprises the equivalent of about 4 mg of nalmefene hydrochloride. In some embodiments, the device comprises the equivalent of about 4.5 mg of nalmefene hydrochloride. In some embodiments, the device comprises the equivalent of about 5 mg of nalmefene hydrochloride.

In some embodiments, the single-use, pre-primed device adapted for nasal delivery of a pharmaceutical composition to a patient comprises the equivalent of about 1 mg of nalmefene free base. In some embodiments, the device comprises the equivalent of about 1.5 mg of nalmefene free base. In some embodiments, the device comprises the equivalent of about 2 mg of nalmefene free base. In some embodiments, the device comprises the equivalent of about 2.5 mg of nalmefene free base. In some embodiments, the device comprises the equivalent of about 2.7 mg of nalmefene free base. In some embodiments, the device comprises the equivalent of about 3 mg of nalmefene free base. In some embodiments, the device comprises the equivalent of about 3.5 mg of nalmefene free base. In some embodiments, the device comprises the equivalent of about 4 mg of nalmefene free base. In some embodiments, the device comprises the equivalent of about 4.5 mg of nalmefene free base. In some embodiments, the device comprises the equivalent of about 5 mg of nalmefene free base.

In some embodiments, the aqueous solution comprises:
between about 1 mg and about 10 mg of the nalmefene hydrochloride or a hydrate thereof;
between about 0.005% (w/v) and about 1% (w/v) benzalkonium chloride;
between about 0.2 mg and about 1.2 mg of an isotonicity agent;
between about 0.1 mg and about 0.5 mg of a stabilizing agent; and
an amount of acid or base sufficient to achieve a pH of 3.5-5.5.

In some embodiments:
the isotonicity agent is NaCl;
the stabilizing agent is disodium edetate; and
the acid is hydrochloric acid.

In some embodiments, the aqueous solution comprises:
about 3 mg nalmefene hydrochloride;
about 0.74 mg NaCl;
between about 0.005% (w/v) and about 1% (w/v) benzalkonium chloride;
about 0.2 mg disodium edetate; and
an amount of hydrochloric acid sufficient to achieve a pH of 3.5-5.5.

In some embodiments, the aqueous solution comprises:
about 1 to about 10 mg nalmefene hydrochloride;
about 0.74 mg NaCl;
between about 0.005% (w/v) and about 1% (w/v) benzalkonium chloride;
about 0.2 mg disodium edetate; and
an amount of hydrochloric acid sufficient to achieve a pH of 3.5-5.5.

In some embodiments, the single-use, pre-primed device adapted for nasal delivery of a pharmaceutical composition to a patient comprises any of the amounts of nalmefene hydrochloride provided above, for example, between about 1 mg and about 10 mg of the nalmefene hydrochloride or a hydrate thereof.

In some embodiments, each reservoir of the pre-primed, bi-dose device adapted for nasal delivery of a pharmaceutical composition to a patient comprises the equivalent of about 1 mg of nalmefene hydrochloride. In some embodiments, each reservoir of the device comprises the equivalent of about 1.5 mg of nalmefene hydrochloride. In some embodiments, each reservoir of the device comprises the equivalent of about 2 mg of nalmefene hydrochloride. In some embodiments, each reservoir of the device comprises the equivalent of about 2.5 mg of nalmefene hydrochloride. In some embodiments, each reservoir of the device comprises the equivalent of about 3 mg of nalmefene hydrochloride. In some embodiments, each reservoir of the device comprises the equivalent of about 3.5 mg of nalmefene hydrochloride. In some embodiments, each reservoir of the device comprises the equivalent of about 4 mg of nalmefene hydrochloride. In some embodiments, each reservoir of the device comprises the equivalent of about 4.5 mg of nalmefene hydrochloride. In some embodiments, each reservoir of the device comprises the equivalent of about 5 mg of nalmefene hydrochloride.

In some embodiments, each reservoir of the pre-primed, bi-dose device adapted for nasal delivery of a pharmaceutical composition to a patient comprises the equivalent of about 1 mg of nalmefene free base. In some embodiments, each reservoir of the device comprises the equivalent of about 1.5 mg of nalmefene free base. In some embodiments, each reservoir of the device comprises the equivalent of about 2 mg of nalmefene free base. In some embodiments, each reservoir of the device comprises the equivalent of about 2.5 mg of nalmefene free base. In some embodiments, each reservoir of the device comprises the equivalent of about 2.7 mg of nalmefene free base. In some embodiments, each reservoir of the device comprises the equivalent of about 3 mg of nalmefene free base. In some embodiments, each reservoir of the device comprises the equivalent of about 3.5 mg of nalmefene free base. In some embodiments, each reservoir of the device comprises the equivalent of about 4 mg of nalmefene free base. In some embodiments, each reservoir of the device comprises the equivalent of about 4.5 mg of nalmefene free base. In some embodiments, each reservoir of the device comprises the equivalent of about 5 mg of nalmefene free base.

In some embodiments, the aqueous solution comprises:
between about 1 mg and about 10 mg of the nalmefene hydrochloride or a hydrate thereof;
between about 0.005% (w/v) and about 1% (w/v) benzalkonium chloride;
between about 0.2 mg and about 1.2 mg of an isotonicity agent;
between about 0.1 mg and about 0.5 mg of a stabilizing agent; and
an amount of acid or base sufficient to achieve a pH of 3.5-5.5.

In some embodiments the isotonicity agent is NaCl; the stabilizing agent is disodium edetate; and the acid is hydrochloric acid or the base is sodium hydroxide.

In some embodiments, each reservoir comprises:
about 1 mg or about 10 mg nalmefene hydrochloride;
about 0.74 mg NaCl;
between about 0.005% (w/v) and about 1% (w/v) benzalkonium chloride; and
about 0.2 mg disodium edetate.

In some embodiments, the pharmaceutical composition further comprises one or more excipients selected from water, NaCl, benzalkonium chloride, sodium edetate, disodium edetate, and hydrochloric acid.

In some embodiments, the pharmaceutical composition further comprises water, NaCl, benzalkonium chloride, disodium edetate, and hydrochloric acid.

In some embodiments, the pharmaceutical composition further comprises:
an isotonicity agent;
a preservative;
a stabilizing agent;
an amount of an acid or base sufficient to achieve a pH of 3.5-5.5; and
an amount of water sufficient to achieve a final volume of about 100 µL.

In some embodiments, the pharmaceutical composition comprises:
between about 0.2 mg and about 1.2 mg of an isotonicity agent;
between about 0.005 mg and about 0.015 mg of a compound which is a preservative, cationic surfactant, and/or absorption enhancer;
between about 0.1 mg and about 0.5 mg of a stabilizing agent;
an amount of an acid or base sufficient to achieve a pH of 3.5-5.5; and
an amount of water sufficient to achieve a final volume of about 100 µL.

In some embodiments,
the isotonicity agent is NaCl;
the compound which is a preservative, cationic surfactant, and/or absorption enhancer is benzalkonium chloride;
the stabilizing agent is disodium edetate; and
the acid is hydrochloric acid or the base is sodium hydroxide.

In some embodiments, the pharmaceutical composition comprises:
about 0.74 mg NaCl;
about 0.01 mg benzalkonium chloride;
about 0.2 mg disodium edetate;
an amount of hydrochloric acid or sodium hydroxide sufficient to achieve a pH of 3.5-5.5; and
an amount of water sufficient to achieve a final volume of about 100 µL.

In some embodiments, the pharmaceutical composition comprises:
between about 1 mg and about 10 mg of nalmefene hydrochloride or a hydrate thereof;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and 2.5 mg of an absorption enhancer; and
an amount of acid or base sufficient to achieve a pH of 3.5-5.5.

In some embodiments, the pharmaceutical composition comprises:
between about 1 mg and about 10 mg of nalmefene free base;
between about 0.005 mg and about 1 mg of a preservative;
between about 0.2 mg and about 1.2 mg of an isotonicity agent;
between about 0.1 mg and about 0.5 mg of a stabilizing agent;
between about 0.005 mg and about 2.5 mg of an absorption enhancer; and
an amount of acid or base sufficient to achieve a pH of 3.5-5.5.

In some embodiments, the pharmaceutical composition comprises:
between about 1% (w/v) and about 10% (w/v) of nalmefene free base;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
between about 1% (w/v) and about 10% (w/v) of nalmefene hydrochloride or a hydrate thereof;
between about 0.005% (w/v) and about 1% (w/v) of a preservative;

between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
about 2.7 mg of nalmefene free base;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3 mg of nalmefene hydrochloride;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3% (w/v) of nalmefene hydrochloride;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the device is filled with the pharmaceutical composition using sterile filling.

In some embodiments, the pharmaceutical composition is storage-stable for about twelve months at about 25° C. and about 60% relative humidity.

In some embodiments, the device is a single-dose device, wherein the pharmaceutical composition is present in one reservoir, and wherein the therapeutically effective amount of the opioid antagonist is delivered essentially by one actuation of the device into one nostril of the patient.

In some embodiments, about 100 µL of the pharmaceutical composition is delivered by the actuation.

In some embodiments, the device is actuatable with one hand.

In some embodiments, the delivery time is less than about 30 seconds. In some embodiments, the delivery time is less than about 25 seconds. In some embodiments, the delivery time is less than about 20 seconds. In some embodiments, the delivery time is less than about 15 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of the pharmaceutical composition to the patient, less than about 20% of the pharmaceutical composition leaves the nasal cavity via drainage into the nasopharynx or externally. In some embodiments, upon nasal delivery of the pharmaceutical composition to the patient, less than about 15% of the pharmaceutical composition leaves the nasal cavity via drainage into the nasopharynx or externally. In some embodiments, upon nasal delivery of the pharmaceutical composition to the patient, less than about 10% of the pharmaceutical composition leaves the nasal cavity via drainage into the nasopharynx or externally. In some embodiments, upon nasal delivery of the pharmaceutical composition to the patient, less than about 5% of the pharmaceutical composition leaves the nasal cavity via drainage into the nasopharynx or externally.

In some embodiments, the plasma concentration versus time curve of the opioid antagonist in the patient has a $T_{max}$ of less than 30 minutes. In some embodiments, the plasma concentration versus time curve of the opioid antagonist in the patient has a $T_{max}$ of less than 25 minutes. In some embodiments, the plasma concentration versus time curve of the opioid antagonist in the patient has a $T_{max}$ of less than 20 minutes. In some embodiments, the plasma concentration versus time curve of the opioid antagonist in the patient has a $T_{max}$ of less than 15 minutes. In some embodiments, the plasma concentration versus time curve of the opioid antagonist in the patient has a $T_{max}$ of less than 10 minutes. In some embodiments, the plasma concentration versus time curve of the opioid antagonist in the patient has a $T_{max}$ of less than 5 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, delivery of the therapeutically effective amount to the patient, provides occupancy at $T_{max}$ of the opioid antagonist at the opioid receptors in the respiratory control center of the patient of greater than about 90%. In some embodiments, delivery of the therapeutically effective amount to the patient, provides occupancy at $T_{max}$ of the opioid antagonist at the opioid receptors in the respiratory control center of the patient of greater than about 95%. In some embodiments, delivery of the therapeutically effective amount to the patient, provides occupancy at $T_{max}$ of the opioid antagonist at the opioid receptors in the respiratory control center of the patient of greater than about 99%.

In some embodiments, the patient is free from respiratory depression for at least about 1 hour following treatment comprising delivery of the therapeutically effective amount of the opioid antagonist. In some embodiments, the patient is free from respiratory depression for at least about 2 hours following treatment comprising delivery of the therapeutically effective amount of the opioid antagonist. In some embodiments, the patient is free from respiratory depression for at least about 3 hours following treatment comprising delivery of the therapeutically effective amount of the opioid antagonist. In some embodiments, the patient is free from respiratory depression for at least about 4 hours following treatment comprising delivery of the therapeutically effective amount of the opioid antagonist. In some embodiments, the patient is free from respiratory depression for at least about 6 hours following treatment comprising delivery of the therapeutically effective amount of the opioid antagonist. In some embodiments, the patient is free from respiratory depression for at least about 7 hours following treatment comprising delivery of the therapeutically effective amount of the opioid antagonist. In some embodiments, the patient is free from respiratory depression for at least about 8 hours following treatment comprising delivery of the therapeutically effective amount of the opioid antagonist. In some embodiments, the patient is free from respiratory depression for at least about 10 hours following treatment comprising delivery of the therapeutically effective amount of the opioid antagonist. In some embodiments, the patient is free from respiratory depression for at least about 12 hours following treatment comprising delivery of the therapeutically effective amount of the opioid antagonist. In some embodiments, the patient is free from respiratory depression for at least about 14 hours following treatment comprising delivery of the therapeutically effective amount of the opioid antagonist. In some embodiments, the patient is free from respiratory depression for at least about 16 hours following treatment comprising delivery of the therapeutically effective amount of the opioid antagonist. In some embodiments, the patient is free from respiratory depression for at least about 1 hour to at least about 15 hours following treatment comprising delivery of the therapeutically effective amount of the opioid antagonist. In some embodiments, the patient is free from respiratory depression for at least about 3 hours to at least about 15 hours following treatment comprising delivery of the therapeutically effective amount of the opioid antagonist. In some embodiments, the patient is free from respiratory depression for at least about 3 hours to at least about 12 hours following treatment comprising delivery of the therapeutically effective amount of the opioid antagonist. In some embodiments, the patient is free from respiratory depression for at least about 3 hours to at least about 10 hours following treatment comprising delivery of the therapeutically effective amount of the opioid antagonist. In some embodiments, the patient is free from respiratory depression for at least about 3 hours to at least about 8 hours following treatment comprising delivery of the therapeutically effective amount of the opioid antagonist.

Also provided herein is a single-use, pre-primed device adapted for nasal delivery of a pharmaceutical composition to a patient by one actuation of the device into one nostril of the patient, having a single reservoir comprising about 100 µL of a pharmaceutical composition which is an aqueous solution comprising:
- about 1 mg or about 10 mg nalmefene hydrochloride or a hydrate thereof;
- between about 0.2 mg and about 1.2 mg of an isotonicity agent;
- between about 0.005 mg and about 0.015 mg of a compound which acts as a preservative, cationic surfactant, and/or absorption enhancer;
- between about 0.1 mg and about 0.5 mg of a stabilizing agent;
- an amount of an acid or base sufficient to achieve a pH of 3.5-5.5.

In some embodiments, the device comprises any of the amounts of nalmefene hydrochloride provided above, for example, between about 1 mg and about 10 mg of the nalmefene hydrochloride or a hydrate thereof. In some embodiments, the device comprises about 3 mg nalmefene hydrochloride or a hydrate thereof.

In some embodiments,
- the isotonicity agent is NaCl;
- the compound which is a preservative, cationic surfactant, and/or absorption enhancer is benzalkonium chloride;
- the stabilizing agent is disodium edetate; and
- the acid is hydrochloric acid or the base is sodium hydroxide.

In some embodiments, the device comprises:
- about 1 mg or about 10 mg nalmefene hydrochloride;
- about 0.74 mg NaCl;
- about 0.01 mg benzalkonium chloride;
- about 0.2 mg disodium edetate; and
- an amount of hydrochloric acid or sodium hydroxide sufficient to achieve a pH of 3.5-5.5.

In some embodiments, the pharmaceutical composition comprises:
- between about 1 mg and about 10 mg of nalmefene hydrochloride or a hydrate thereof;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and 2.5 mg of an absorption enhancer; and
- an amount of acid or base sufficient to achieve a pH of 3.5-5.5.

In some embodiments, the pharmaceutical composition comprises:
- between about 1 mg and about 10 mg of nalmefene free base;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and about 2.5 mg of an absorption enhancer; and
- an amount of acid or base sufficient to achieve a pH of 3.5-5.5.

In some embodiments, the pharmaceutical composition comprises:
- between about 1% (w/v) and about 10% (w/v) of nalmefene free base;

between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
between about 1% (w/v) and about 10% (w/v) of nalmefene hydrochloride or a hydrate thereof;
between about 0.005% (w/v) and about 1% (w/v) of a preservative;
between about 0.2% (w/v) and about 1.2% (w/v) of an isotonicity agent;
between about 0.1% (w/v) and about 0.5% (w/v) of a stabilizing agent;
between about 0.005% (w/v) and about 2.5% (w/v) of an absorption enhancer; and
an amount of acid or base sufficient to achieve a pH of 3.5-5.5.

In some embodiments, the pharmaceutical composition comprises:
about 2.7 mg of nalmefene free base;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3 mg of nalmefene hydrochloride;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical composition comprises:
about 3% (w/v) of nalmefene hydrochloride;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical composition comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the device comprises about 1 mg nalmefene hydrochloride. In some embodiments, the device comprises about 1.5 mg nalmefene hydrochloride. In some embodiments, the device comprises about 2 mg nalmefene hydrochloride. In some embodiments, the device comprises about 2.5 mg nalmefene hydrochloride. In some embodiments, the device comprises about 3 mg nalmefene hydrochloride. In some embodiments, the device comprises about 3.5 mg nalmefene hydrochloride. In some embodiments, the device comprises about 4 mg nalmefene hydrochloride. In some embodiments, the device comprises about 4.5 mg nalmefene hydrochloride. In some embodiments, the device comprises about 5 mg nalmefene hydrochloride.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally, as provided above.

In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, the device is actuatable with one hand.

In some embodiments, the delivery time is less than about 30 seconds. In some embodiments, the delivery time is less than about 25 seconds. In some embodiments, the delivery time is less than about 20 seconds. In some embodiments, the delivery time is less than about 15 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally, as provided above.

In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, delivery of the therapeutically effective amount to the patient, provides occupancy at $T_{max}$ of the opioid antagonist at the opioid receptors in the respiratory control center of the patient of greater than about 90%, greater than about 95% or greater than about 99%, as provided above.

In some embodiments, the patient is free from respiratory depression for at least about 1 hour to at least about 8 hours following treatment comprising delivery of the therapeutically effective amount of the opioid antagonist, as provided above. In some embodiments, the patient is free from respiratory depression for at least about 3 hours to at least about 8 hours following treatment comprising delivery of the therapeutically effective amount of the opioid antagonist.

In some embodiments, said device is filled with said pharmaceutical composition using sterile filling.

In some embodiments, said pharmaceutical composition is storage-stable for about twelve months at about 25° C. and about 60% relative humidity.

In some embodiments, said opioid antagonist is the only pharmaceutically active compound in said pharmaceutical composition.

Also provided are devices as recited in any of the preceding embodiments for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension.

Also provided are devices as recited in any of the preceding embodiments for use in the reversal of respiratory depression induced by opioids.

In some embodiments, said respiratory depression is caused by the illicit use of opioids or by an accidental misuse of opioids during medical opioid therapy.

Also provided are devices as recited in any of the preceding embodiments for use in the complete or partial reversal of narcotic depression, including respiratory depression, induced by opioids selected from: natural and synthetic narcotics, propoxyphene, methadone, nalbuphine, pentazocine and butorphanol.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

In some embodiments, said device is a bi-dose device, wherein a first volume of said pharmaceutical composition is present in a first reservoir and a second volume of said pharmaceutical composition is present in a second reservoir, and wherein said therapeutically effective amount is delivered essentially by a first actuation of said device into a first nostril of said patient and a second actuation of said device into a second nostril of said patient.

In some embodiments, said first volume and said second volume combined is equal to not more than about 380 µL.

In some embodiments, about 100 µL of said first volume of said pharmaceutical composition is delivered by said first actuation.

In some embodiments, about 100 µL of said second volume of said pharmaceutical composition is delivered by said second actuation.

In some embodiments, said bi-dose device is actuatable with one hand.

In some embodiments, the delivery time is less than about 30 seconds. In some embodiments, the delivery time is less than about 25 seconds. In some embodiments, the delivery time is less than about 20 seconds. In some embodiments, the delivery time is less than about 15 seconds.

In some embodiments, the 90% confidence interval for dose delivered per actuation is ±about 2%. In some embodiments, the 95% confidence interval for dose delivered per actuation is =about 2.5%.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally. In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, delivery of the therapeutically effective amount to the patient, provides occupancy at $T_{max}$ of the opioid antagonist at the opioid receptors in the respiratory control center of the patient of greater than about 90%, greater than about 95% or greater than about 99%, as provided above.

In some embodiments, the patient is free from respiratory depression for at least about 1 hour to at least about 8 hours following treatment comprising delivery of the therapeutically effective amount of the opioid antagonist, as provided above. In some embodiments, the patient is free from respiratory depression for at least about 3 hours to at least about 8 hours following treatment comprising delivery of the therapeutically effective amount of the opioid antagonist.

E. Pharmaceutical Compositions

Also provided are pharmaceutical compositions comprising one or more opioid antagonist. In some embodiments, the pharmaceutical compositions comprise an opioid antagonist and a pharmaceutically acceptable carrier. The carrier(s) must be "acceptable" in the sense of being compatible with the other ingredients of the formulation and not overly deleterious to the recipient thereof. Some embodiments of the present disclosure include a method of producing a pharmaceutical composition comprising admixing at least one opioid antagonist and a pharmaceutically acceptable carrier. Pharmaceutical compositions are applied directly to the nasal cavity using the devices described herein. In the case of a spray, this may be achieved for example by means of a metering atomizing spray pump.

Liquid preparations include solutions, suspensions and emulsions, for example, water or water-propylene glycol solutions. Additional ingredients in liquid preparations may include: antimicrobial preservatives, such as benzalkonium chloride (which may also act as a cationic surfactant and/or a absorption enhancer), methylparaben, sodium benzoate, benzoic acid, phenyl ethyl alcohol, and the like, and mixtures thereof; surfactants such as Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, and the like, and mixtures thereof; a tonicity agent such as: dextrose, lactose, sodium chloride, calcium chloride, magnesium chloride, potassium chloride, sorbitol, sucrose, mannitol, trehalose, ramose, polyethylene glycol, hydroxyethyl starch, glycine, glycerin, lactated ringer's solution and the like, and mixtures thereof, and a suspending agent such as microcrystalline cellulose, carboxymethylcellulose sodium NF, polyacrylic acid, magnesium aluminum silicate, xanthan gum, and the like, and mixtures thereof.

The opioid antagonists described herein can be formulated into pharmaceutical compositions using techniques well known to those in the art.

The opioid antagonists described herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., Journal of Pharmaceutical Sciences, 66:1-19 (1977). The acid addition salts may be obtained as the direct products of compound synthesis. In the alternative, the free base may be dissolved in a suitable solvent containing the appropriate acid and the salt isolated by evaporating the solvent or otherwise separating the salt and solvent. The opioid antagonists described herein may form solvates with standard low molecular weight solvents using methods known to the skilled artisan.

Accordingly, provided herein are pharmaceutical formulations for intranasal administration comprising, in an aqueous solution of not more than about 140 μL:
- between about 1 mg and about 10 mg of an opioid antagonist;
- between about 0.2 mg and about 1.2 mg of an isotonicity agent;
- between about 0.005 mg and about 0.015 mg of a compound which is a preservative, cationic surfactant, and/or absorption enhancer;
- between about 0.1 mg and about 0.5 mg of a stabilizing agent;
- an amount of an acid or base sufficient to achieve a pH of 3.5-5.5.

In some embodiments, the pharmaceutical formulation comprises:
- between about 1 mg and about 10 mg of nalmefene hydrochloride or a hydrate thereof;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and 2.5 mg of an absorption enhancer; and
- an amount of acid or base sufficient to achieve a pH of 3.5-5.5.

In some embodiments, the pharmaceutical formulation comprises:
- between about 1 mg and about 10 mg of nalmefene free base;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and about 2.5 mg of an absorption enhancer; and
- an amount of acid or base sufficient to achieve a pH of 3.5-5.5.

In some embodiments, the pharmaceutical formulation comprises:
- between about 1% (w/v) and about 10% (w/v) of nalmefene free base;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and
- an amount of acid or base sufficient to achieve a pH of 3.5-5.5.

In some embodiments, the pharmaceutical formulation comprises:
- between about 1% (w/v) and about 10% (w/v) of nalmefene hydrochloride or a hydrate thereof;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and an amount of acid or base sufficient to achieve a pH of 3.5-5.5.

In some embodiments, the pharmaceutical formulation comprises:
about 2.7 mg of nalmefene free base;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical formulation comprises:
about 3 mg of nalmefene hydrochloride;
about 0.04 mg of a preservative;
about 0.87 mg of an isotonicity agent;
about 0.2 mg of a stabilizing agent;
about 0.25 mg of an absorption enhancer; and
an amount of acid or base sufficient to achieve a pH of 3.5-5.5.

In some embodiments, the pharmaceutical formulation comprises:
about 3% (w/v) of nalmefene hydrochloride;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical formulation comprises:
about 2.7% (w/v) of nalmefene free base;
about 0.04% (w/v) of benzalkonium chloride (50% solution);
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical formulation comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical formulation comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, said opioid antagonist is the only pharmaceutically active compound in said pharmaceutical composition.

In some embodiments, said opioid antagonist is nalmefene hydrochloride, or a hydrate thereof.

In some embodiments, said opioid antagonist is nalmefene hydrochloride.

The pharmaceutical formulation may comprise any of the amounts of nalmefene hydrochloride as provided above, for example, equivalent to about 1 mg to about 10 mg. In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride.

The pharmaceutical formulation may comprise any of the amounts of nalmefene free base as provided above, for example, equivalent to about 1 mg to about 10 mg. In some embodiments, the therapeutically effective amount is equivalent to about 1 mg of nalmefene free base. In some embodiments, the therapeutically effective amount is equivalent to about 1.5 mg of nalmefene free base. In some embodiments, the therapeutically effective amount is equivalent to about 2 mg of nalmefene free base. In some embodiments, the therapeutically effective amount is equivalent to about 2.5 mg of nalmefene free base. In some embodiments, the therapeutically effective amount is equivalent to about 2.7 mg of nalmefene free base. In some embodiments, the therapeutically effective amount is equivalent to about 3 mg of nalmefene free base. In some embodiments, the therapeutically effective amount is equivalent to about 3.5 mg of nalmefene free base. In some embodiments, the therapeutically effective amount is equivalent to about 4 mg of nalmefene free base. In some embodiments, the therapeutically effective amount is equivalent to about 4.5 mg of nalmefene free base. In some embodiments, the therapeutically effective amount is equivalent to about 5 mg of nalmefene free base.

In certain embodiments, the pharmaceutical formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises between about 0.1% (w/v) to about 12.5% (w/v) of an absorption enhancer. In certain embodiments, the pharmaceutical formulation comprises between about 0.005% (w/v) to about 7.5% (w/v). In other embodiments, the pharmaceutical formulation comprises between about 1% (w/v) to about 5% (w/v) of an absorption enhancer. In certain embodiments, the pharmaceutical formulation comprises between about 0.01% (w/v) to about 7.5% (w/v) of an absorption enhancer. In certain embodiments, the pharmaceutical formulation comprises between about 0.005% (w/v) to about 1% (w/v) of an absorption enhancer. In certain embodiments, the pharmaceutical formulation comprises between about 0.01% (w/v) to about 0.75% (w/v) of an absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer. In certain embodiments, the absorption enhancer is an alkylsaccharide. In certain embodiments, the alkylsaccharide is chosen from dodecyl maltoside, tetradecyl maltoside (TDM) and sucrose dodecanoate.

In some embodiments, the pharmaceutical composition is in an aqueous solution of about 100 μL.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally, as provided above.

In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, said device is actuatable with one hand.

In some embodiments, the delivery time is less than about 30 seconds. In some embodiments, the delivery time is less than about 25 seconds. In some embodiments, the delivery time is less than about 20 seconds. In some embodiments, the delivery time is less than about 15 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally, as provided above.

In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

In some embodiments, delivery of the therapeutically effective amount to the patient, provides occupancy at $T_{max}$ of the opioid antagonist at the opioid receptors in the respiratory control center of the patient of greater than about 90%, greater than about 95% or greater than about 99%, as provided above.

In some embodiments, the patient is free from respiratory depression for at least about 1 hour to at least about 8 hours following treatment comprising delivery of the therapeutically effective amount of the opioid antagonist, as provided above. In some embodiments, the patient is free from respiratory depression for at least about 3 hours to at least about 8 hours following treatment comprising delivery of the therapeutically effective amount of the opioid antagonist.

Also provided herein are pharmaceutical formulations for intranasal administration comprising, in an aqueous solution of not more than about 140 μL:
 about 1 mg or about 10 mg nalmefene hydrochloride or a hydrate thereof;
 between about 0.2 mg and about 1.2 mg of an isotonicity agent;
 between about 0.005 mg and about 0.015 mg of a compound which is a preservative, cationic surfactant, and/or absorption enhancer;
 between about 0.1 mg and about 0.5 mg of a stabilizing agent;
 an amount of hydrochloric acid or sodium hydroxide sufficient to achieve a pH of 3.5-5.5.

In some embodiments,
 the isotonicity agent is NaCl;
 the compound which is a preservative, cationic surfactant, and/or absorption enhancer is benzalkonium chloride;
 the stabilizing agent is disodium edetate; and
 the acid is hydrochloric acid or the base is sodium hydroxide.

In some embodiments, the pharmaceutical formulation comprises:
 about 2 mg or about 3 mg or about 4 mg nalmefene hydrochloride;
 about 0.74 mg NaCl;
 about 0.01 mg benzalkonium chloride;
 about 0.2 mg disodium edetate; and
 an amount of hydrochloric acid or sodium hydroxide sufficient to achieve a pH of 3.5-5.5.

In some embodiments, the pharmaceutical formulation comprises about 4 mg nalmefene hydrochloride or a hydrate thereof. In some embodiments, the pharmaceutical formulation comprises about 3 mg nalmefene hydrochloride or a hydrate thereof;

Also provided herein are pharmaceutical formulations for intranasal administration comprising, in an aqueous solution of about 100 μL:
 about 3 mg nalmefene hydrochloride or a hydrate thereof;
 between about 0.2 mg and about 1.2 mg of an isotonicity agent;
 between about 0.005 mg and about 0.015 mg of a compound which is a preservative, cationic surfactant, and/or absorption enhancer;
 between about 0.1 mg and about 0.5 mg of a stabilizing agent;
 an amount of an acid or base sufficient to achieve a pH of 3.5-5.5.

In some embodiments, the pharmaceutical formulation comprises:
- about 1 mg to about 10 mg nalmefene hydrochloride;
- about 0.74 mg NaCl;
- about 0.01 mg benzalkonium chloride;
- about 0.2 mg disodium edetate; and
- an amount of hydrochloric acid or sodium hydroxide sufficient to achieve a pH of 3.5-5.5.

Also provided herein are pharmaceutical formulations for intranasal administration comprising, in an aqueous solution of about 100 µL:
- about 3 mg nalmefene hydrochloride or a hydrate thereof;
- between about 0.2 mg and about 1.2 mg of an isotonicity agent;
- between about 0.005 mg and about 0.015 mg of a compound which is a preservative, cationic surfactant, and/or absorption enhancer;
- between about 0.1 mg and about 0.5 mg of a stabilizing agent;
- an amount of an acid or base sufficient to achieve a pH of 3.5-5.5.

In some embodiments, the pharmaceutical formulation comprises:
- about 3 mg nalmefene hydrochloride;
- about 0.74 mg NaCl;
- about 0.01 mg benzalkonium chloride;
- about 0.2 mg disodium edetate; and
- an amount of hydrochloric acid or sodium hydroxide sufficient to achieve a pH of 3.5-5.5.

Also provided herein are pharmaceutical formulations for intranasal administration comprising, in an aqueous solution of about 100 µL:
- about 1 to about 10 mg nalmefene hydrochloride or a hydrate thereof;
- between about 0.2 mg and about 1.2 mg of an isotonicity agent;
- between about 0.005 mg and about 0.015 mg of a compound which is a preservative, cationic surfactant, and/or absorption enhancer;
- between about 0.1 mg and about 0.5 mg of a stabilizing agent;
- an amount of an acid or base sufficient to achieve a pH of 3.5-5.5.

In some embodiments, the pharmaceutical formulation comprises:
- between about 1 mg and about 10 mg of nalmefene hydrochloride or a hydrate thereof;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and 2.5 mg of an absorption enhancer; and
- an amount of acid or base sufficient to achieve a pH of 3.5-5.5.

In some embodiments, the pharmaceutical formulation comprises:
- between about 1 mg and about 10 mg of nalmefene free base;
- between about 0.005 mg and about 1 mg of a preservative;
- between about 0.2 mg and about 1.2 mg of an isotonicity agent;
- between about 0.1 mg and about 0.5 mg of a stabilizing agent;
- between about 0.005 mg and about 2.5 mg of an absorption enhancer; and
- an amount of acid or base sufficient to achieve a pH of 3.5-5.5.

In some embodiments, the pharmaceutical formulation comprises:
- between about 1% (w/v) and about 10% (w/v) of nalmefene free base;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and
- an amount of acid or base sufficient to achieve a pH of 3.5-5.5.

In some embodiments, the pharmaceutical formulation comprises:
- between about 1% (w/v) and about 10% (w/v) of nalmefene hydrochloride or a hydrate thereof;
- between about 0.005% (w/v) and about 1% (w/v) of a preservative;
- between about 0.2% (w/v) and about 1.2% (w/v) of an isotonicity agent;
- between about 0.1% (w/v) and about 0.5% (w/v) of a stabilizing agent;
- between about 0.005% (w/v) and about 2.5% (w/v) of an absorption enhancer; and
- an amount of acid or base sufficient to achieve a pH of 3.5-5.5.

In some embodiments, the pharmaceutical formulation comprises:
- about 2.7 mg of nalmefene free base;
- about 0.04 mg of a preservative;
- about 0.87 mg of an isotonicity agent;
- about 0.2 mg of a stabilizing agent;
- about 0.25 mg of an absorption enhancer; and
- an amount of acid or base sufficient to achieve a pH of 3.5-5.5.

In some embodiments, the pharmaceutical formulation comprises:
- about 3 mg of nalmefene hydrochloride;
- about 0.04 mg of a preservative;
- about 0.87 mg of an isotonicity agent;
- about 0.2 mg of a stabilizing agent;
- about 0.25 mg of an absorption enhancer; and
- an amount of acid or base sufficient to achieve a pH of 3.5-5.5.

In some embodiments, the pharmaceutical formulation comprises:
- about 3% (w/v) of nalmefene hydrochloride;
- about 0.04% (w/v) of benzalkonium chloride (50% solution);
- about 0.87% (w/v) of sodium chloride;
- about 0.2% (w/v) of disodium edetate;
- about 0.25% (w/v) of dodecyl maltoside; and
- an amount of acid or base sufficient to achieve a pH of 3.5-5.5.

In some embodiments, the pharmaceutical formulation comprises:
- about 2.7% (w/v) of nalmefene free base;
- about 0.04% (w/v) of benzalkonium chloride (50% solution);
- about 0.87% (w/v) of sodium chloride;
- about 0.2% (w/v) of disodium edetate;
- about 0.25% (w/v) of dodecyl maltoside; and an amount of acid or base sufficient to achieve a pH of 3.5-5.5.

In some embodiments, the pharmaceutical formulation comprises:
about 3% (w/v) of nalmefene hydrochloride;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

In some embodiments, the pharmaceutical formulation comprises:
about 2.7% (w/v) of nalmefene free base;
about 0.02% (w/v) of benzalkonium chloride;
about 0.87% (w/v) of sodium chloride;
about 0.2% (w/v) of disodium edetate;
about 0.25% (w/v) of dodecyl maltoside; and
an amount of acid or base sufficient to achieve a pH of 3.5-5.5.

Provided are devices adapted for nasal delivery of a pharmaceutical composition to a patient, comprising a therapeutically effective amount of an opioid antagonist selected from nalmefene and pharmaceutically acceptable salts thereof, wherein the device is pre-primed, and wherein the therapeutically effective amount, is equivalent to about 1 mg to about 10 mg of nalmefene hydrochloride, as provided above. In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride.

In some embodiments, the therapeutically effective amount is equivalent to about 1 mg of nalmefene free base. In some embodiments, the therapeutically effective amount is equivalent to about 1.5 mg of nalmefene free base. In some embodiments, the therapeutically effective amount is equivalent to about 2 mg of nalmefene free base. In some embodiments, the therapeutically effective amount is equivalent to about 2.5 mg of nalmefene free base. In some embodiments, the therapeutically effective amount is equivalent to about 2.7 mg of nalmefene free base. In some embodiments, the therapeutically effective amount is equivalent to about 3 mg of nalmefene free base. In some embodiments, the therapeutically effective amount is equivalent to about 3.5 mg of nalmefene free base. In some embodiments, the therapeutically effective amount is equivalent to about 4 mg of nalmefene free base. In some embodiments, the therapeutically effective amount is equivalent to about 4.5 mg of nalmefene free base. In some embodiments, the therapeutically effective amount is equivalent to about 5 mg of nalmefene free base.

In some embodiments, the pharmaceutical composition comprises a solution prepared from nalmefene hydrochloride. In some embodiments, the pharmaceutical composition further comprises one or more excipients selected from water and NaCl. In some embodiments, the pharmaceutical composition is substantially free of antimicrobial preservatives. In some embodiments, the device is substantially free of benzalkonium chloride, methylparaben, sodium benzoate, benzoic acid, phenyl ethyl alcohol. In some embodiments, the device is filled with the pharmaceutical composition in a sterile environment. In some embodiments, the pharmaceutical composition is storage-stable for about twelve months at about 25° C. In some embodiments, the pharmaceutical composition comprises less than 0.1% w/w antimicrobial preservatives. In some embodiments, the pharmaceutical composition comprises 0.01% w/w or less antimicrobial preservatives. In some embodiments, the pharmaceutical composition comprises 0.01% w/w-0.001% w/w antimicrobial preservatives. In some embodiments, the pharmaceutical composition comprises less than 0.001% w/w antimicrobial preservatives.

Also provided are embodiments wherein any embodiment above may be combined with any one or more of these embodiments, provided the combination is not mutually exclusive.

Indications

Also provided are devices for use in treating opioid overdose and symptoms thereof and methods of using the devices. Nalmefene prevents or reverses the effects of opioids including respiratory depression, sedation and hypotension.

Accordingly, also provided herein are methods of treating opioid overdose or a symptom thereof, comprising nasally administering to a patient in need thereof a therapeutically effective amount of an opioid antagonist selected from nalmefene and pharmaceutically acceptable salts thereof, wherein said therapeutically effective amount is equivalent to about 1 mg to about 10 mg of nalmefene hydrochloride or a hydrate thereof. In some embodiments, the therapeutically effective amount of an opioid antagonist selected from nalmefene and pharmaceutically acceptable salts thereof is delivered in not more than about 140 µL of an aqueous carrier solution.

In some embodiments, also provided herein are methods of treating opioid overdose or a symptom thereof, comprising nasally administering to a patient in need thereof a therapeutically effective amount of an opioid antagonist selected from nalmefene and pharmaceutically acceptable salts thereof, wherein said therapeutically effective amount is equivalent to about 1 mg to about 10 mg of nalmefene hydrochloride or a hydrate thereof in not more than about 140 µL of an aqueous carrier solution. In some embodiments, the nalmefene is nalmefene free base.

In some embodiments are provided methods of treating opioid overdose, or a symptom thereof, comprising nasally administering with a spray device to a patient in need thereof a therapeutically effective amount of an opioid antagonist selected from nalmefene and pharmaceutically acceptable salts thereof, wherein the spray device is capable of spraying droplets having a median droplet size between about 30 and about 100 µm.

In some embodiments, the spray device can spray a formulation having a D (v,50) of 30-70 µm and a D (v,90) <100 µm.

In some embodiments, the spray device is capable of spraying in a manner that the percent of droplets less than 10 µm is less than 10%. In some embodiments, the percent of droplets less than 10 µm is less than 5%. In some embodiments, the percent of droplets less than 10 µm is less than 2%. In some embodiments, the percent of droplets less than 10 µm is less than 1%.

In some embodiments, the spray device can spray a uniform circular plume with an ovality ratio close to 1. Ovality ratio is calculated as the quotient of the maximum diameter ($D_{max}$) and the minimum diameter ($D_{min}$) of a spray pattern taken orthogonal to the direction of spray flow (e.g., from the "top"). In some embodiments, the ovality ratio is less than ±2.0. In some embodiments, the ovality ratio is less than ±1.5. In some embodiments, the ovality ratio is less than ±1.3. In some embodiments, the ovality ratio is less than ±1.2. In some embodiments, the ovality ratio is less than ±1.1. In some embodiments, the ovality ratio is about ±1.0.

In some embodiments, also provided herein are methods of treating opioid overdose or a symptom thereof, comprising nasally administering to a patient in need thereof a single dose of a therapeutically effective amount of an opioid antagonist selected from nalmefene and pharmaceutically acceptable salts thereof, wherein said therapeutically effective amount is equivalent to about 1 mg to about 10 mg of nalmefene hydrochloride or a hydrate thereof in not more than about 140 µL of an aqueous carrier solution.

In some embodiments, said opioid antagonist is the only pharmaceutically active compound in said pharmaceutical composition.

In some embodiments, said opioid antagonist is nalmefene hydrochloride.

In some embodiments, said pharmaceutical composition comprises a solution of nalmefene hydrochloride, or a hydrate thereof.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

In some embodiments, said therapeutically effective amount is equivalent to about 1 mg to about 10 mg of nalmefene hydrochloride, as provided above. In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride.

In some embodiments, said symptom is chosen from respiratory depression and central nervous system depression.

In some embodiments, said patient exhibits any of unresponsiveness to stimulus, unconsciousness, stopped breathing; erratic or stopped pulse, choking or gurgling sounds, blue or purple fingernails or lips, slack or limp muscle tone, contracted pupils, and vomiting.

In some embodiments, said patient is not breathing.

In some embodiments, said patient is in a lying, supine, or recovery position. In some embodiments, said patient is in a lying position.

In some embodiments, said patient is in a supine position.

In some embodiments, said patient is a recovery position.

In some embodiments, said therapeutically effective amount is equivalent to about 2 mg to about 10 mg of nalmefene hydrochloride.

In some embodiments, said therapeutically effective amount is equivalent to an amount chosen from about 1 mg nalmefene hydrochloride, about 1.5 mg nalmefene hydrochloride, about 2 mg of nalmefene hydrochloride, about 2.5 mg of nalmefene hydrochloride, about 3 mg nalmefene hydrochloride, about 3.5 mg nalmefene hydrochloride, about 4 mg nalmefene hydrochloride, about 4.5 mg nalmefene hydrochloride and about 5 mg nalmefene hydrochloride.

In some embodiments, said therapeutically effective amount is equivalent to about 2 mg of nalmefene hydrochloride.

In some embodiments, said therapeutically effective amount is equivalent to about 3 mg of nalmefene hydrochloride.

In some embodiments, said therapeutically effective amount is equivalent to about 4 mg of nalmefene hydrochloride.

In some embodiments, said opioid antagonist is the only pharmaceutically active compound in said pharmaceutical composition.

In some embodiments, said nasally administering is accomplished using a pre-primed device adapted for nasal delivery of a pharmaceutical composition.

In some embodiments, upon nasal delivery of the pharmaceutical composition to the patient, less than about 20%, less than about 15%, less than about 10%, or less than about 5%, of the pharmaceutical composition leaves the nasal cavity via drainage into the nasopharynx or externally, as provided above.

In some embodiments, the plasma concentration versus time curve of the opioid antagonist in the patient has a $T_{max}$ of less than 30 minutes, as provided above. In some embodiments, the plasma concentration versus time curve of the opioid antagonist in the patient has a $T_{max}$ of about 30 minutes. In some embodiments, the plasma concentration versus time curve of the opioid antagonist in the patient has a $T_{max}$ of about 25 minutes. In some embodiments, the plasma concentration versus time curve of the opioid antagonist in the patient has a $T_{max}$ of about 20 minutes. In some embodiments, the plasma concentration versus time curve of the opioid antagonist in the patient has a $T_{max}$ of about 15 minutes. In some embodiments, the plasma concentration versus time curve of the opioid antagonist in the patient has a $T_{max}$ of about 10 minutes. In some embodiments, the plasma concentration versus time curve of the opioid antagonist in the patient has a $T_{max}$ of about 5 minutes.

Also disclosed herein is an intranasal pharmaceutical formulation comprising nalmefene that upon its administration to one or more human subjects in need thereof achieves a $C_{max}$ of at least 4 ng/ml within about 40 minutes, or about 30 minutes, or about 20 minutes, or about 10 minutes, or about 5 minutes after administration.

In one embodiment, after the IN administration of a therapeutically effective amount of nalmefene to a human subject, the $T_{max}$ is between about 5 and 45 minutes, or between about 5 and 10 minutes, or between about 10 and 15 minutes, or between about 15 and 20 minutes, or between about 20 and 25 minutes, or between about 25 and 30 minutes, or between about 30 and 35 minutes, or between about 40 and 45 minutes. In some embodiments, the $T_{max}$ is between about 0.08 hours and about 1 hour.

In some embodiments, after the IN administration of a therapeutically effective amount of nalmefene to a human subject, the $T_{1/2}$ is between about 8.02 hours and about 15.4 hours.

In some embodiments, about 15 minutes after the IN administration of a therapeutically effective amount of nalmefene to a human subject, the plasma concentration of nalmefene is between about 3.83 to about 15.23 ng/mL. In some embodiments, about 30 minutes after the IN administration of a therapeutically effective amount of nalmefene to a human subject, the plasma concentration of nalmefene is between about 3.87 to about 8.63 ng/mL. in some embodiments, about 1 hour after the IN administration of a therapeutically effective amount of nalmefene to a human subject, the plasma concentration of nalmefene is between about 3.64 to about 5.64 ng/ml. In some embodiments, about 3 hours after the IN administration of a therapeutically effective amount of nalmefene to a human subject, the plasma concentration of nalmefene is between about 2.491 to about 3.85 ng/mL. In some embodiments, about 6 hours after the IN administration of a therapeutically effective amount of nalmefene to a human subject, the plasma concentration of nalmefene is between about 1.24 to about 2.14 ng/mL.

In one embodiment after the IN administration of a therapeutically effective amount of nalmefene to a human subject, the $C_{max}$ is between about 3 and 60 ng/mL, or between about 5 and 50 ng/ml, or between about 5 and 40 ng/mL, or between about 5 and 35 ng/ml, or between about 5 and 25 ng/mL, or between about 5 and 20 ng/ml, or between about 5 and 17 ng/ml, or between about 5 and 15 ng/ml, or between about 8 and 12 ng/mL. In some embodiments, the $C_{max}$ is between about 4.1 and about 30.4 ng/mL.

In one embodiment after the IN administration of a therapeutically effective amount of nalmefene to a human subject, the $AUC_{0-2.5min}$ is between about 0.007 and 0.15 h*ng/mL, or between about 0.01 and 0.1, or between about 0.05 and 0.08, or between about 0.02 and 0.05 h*ng/mL. In another embodiment, it is between about 0.000504 and about 0.155 h*ng/mL.

In one embodiment after the IN administration of a therapeutically effective amount of nalmefene to a human subject, the $AUC_{0-5min}$ is between about 0.02 and 0.5 h*ng/mL, or between about 0.05 and 0.25 h*ng/mL, or between about 0.125 and 0.5 h*ng/mL. In another embodiment, it is between about 0.00542 and 0.588 h*ng/mL.

In one embodiment after the IN administration of a therapeutically effective amount of nalmefene to a human subject, the $AUC_{0-10min}$ ranges between about 0.05 and 2 h*ng/ml, or between about 0.1 and 1.5 h*ng/ml, or between about 0.5 and 1 h*ng/ml, or between about 0.7 and 0.9 h*ng/mL. In another embodiment, it is between about 0.0815 to about 2.78 h*ng/mL.

In one embodiment after the IN administration of a therapeutically effective amount of nalmefene to a human subject, the $AUC_{0-15min}$ ranges between about 0.01 and 5 h*ng/ml, or between about 0.01 and 4 h*ng/mL, or between about 0.1 and 3 h*ng/mL, or between about 0.5 and 2 h*ng/mL, or between about 1 and 1.5 h*ng/mL. In another embodiment, it is between about 0.325 to about 5.03 h*ng/mL.

In one embodiment after the IN administration of a therapeutically effective amount of nalmefene to a human subject, the $AUC_{0-20min}$ ranges between about 0.01 and 3 h*ng/ml, or between about 0.01 and 2.5 h*ng/mL, or between about 0.1 and 2 h*ng/ml, or between about 0.5 and 1.5 h*ng/ml, or between about 0.8 and 1.25 h*ng/mL. In another embodiment, it is between about 0.350 to about 6.79 h*ng/mL.

In one embodiment after the IN administration of a therapeutically effective amount of nalmefene to a human subject, the $AUC_{0-30min}$ ranges between about 1 and 7 h*ng/ml, or between about 1.25 and 5 h*ng/mL, or between about 2.5 and 5.75 h*ng/mL, or between about 2.75 and 5.25 h*ng/mL, or between about 3 and 5 h*ng/mL, or between about 3.25 and 4.75 h*ng/ml, or between about 3.5 and 4.5 h*ng/mL, or between about 3.75 and 4.25 h*ng/mL. In another embodiment, it is between about 0.802 to about 9.16 h*ng/mL.

In one embodiment, after the IN administration of 3 mg nalmefene to a human subject, the $T_{max}$ is between about 5 and 30 minutes, or between about 10 and 25 minutes, or between about 15 and 20 minutes, or is about 5 minutes, or is about 10 minutes, or is about 15 minutes.

In another embodiment, after the IN administration of 3 mg nalmefene to a human subject, the $C_{max}$ is between about 3 and 25 ng/mL, or between about 10 and 20 ng/ml, or is about 12 ng/mL.

In one embodiment, after the IN administration of 3 mg nalmefene to a human subject, the $AUC_{0-2.5min}$ is between about 0.009 and 0.08 h*ng/ml, or between about 0.02 and 0.06 h*ng/mL, or between about 0.015 and 0.025 h*ng/mL, or is about 0.02 h*ng/mL.

In another embodiment, after the IN administration of 3 mg nalmefene to a human subject, the $AUC_{0-5min}$ is between about 0.01 and 0.3 h*ng/ml, or between about 0.05 and 0.2 h*ng/mL, or between about 0.05 and 0.15 h*ng/mL, or is about 0.125 h*ng/mL.

In another embodiment, after the IN administration of 3 mg nalmefene to a human subject, the $AUC_{0-10min}$ is between about 0.1 and 1.6 h*ng/mL, or between about 0.25 and 1.2 h*ng/ml, or between about 0.5 and 1 h*ng/mL, or is about 0.8 h*ng/mL.

In another embodiment, after the IN administration of 3 mg nalmefene to a human subject, the $AUC_{0-15min}$ ranges between about 0.5 and 3 h*ng/ml, or between about 1 and 2.5 h*ng/ml, or between about 1.2 and 2 h*ng/ml, or is about 1.6 h*ng/mL.

In another embodiment, after the IN administration of 3 mg nalmefene to a human subject, the $AUC_{0-20min}$ is between about 1 and 4 h*ng/ml, or between about 1.2 and 3 h*ng/ml, or between about 2 and 3 h*ng/ml, or is about 2.3 h*ng/ml.

In another embodiment, after the IN administration of 3 mg nalmefene to a human subject, the $AUC_{0-30min}$ is between about 1 and 5 h*ng/ml, or between about 1.5 and 4 h*ng/mL, or between about 2 and 3.75 h*ng/ml, or is about 0.35 h*ng/mL.

In certain embodiments, after the IN administration of 3 mg nalmefene to a plurality of human subjects, the $C_{max}$ geometric mean is between about 7 and 15 ng/ml, or between about 8 and 12 ng/ml, or is about 10 ng/mL.

In certain embodiments, after the IN administration of 3 mg nalmefene to a plurality of human subjects, the $AUC_{0-2.5min}$ geometric mean is between about 0.004 and 0.016 h*ng/ml, or between about 0.006 and 0.012 h*ng/mL, or is about 0.008 h*ng/mL. In other embodiments, after the IN administration of 3 mg nalmefene to a plurality of human subjects In another embodiment, after the IN administration of 3 mg nalmefene to a plurality of human subjects, the $AUC_{0-5min}$ geometric mean is between about 0.03 and 0.12 h*ng/ml, or between about 0.06 and 0.09 h*ng/ml, or is about 0.06 h*ng/ml.

In another embodiment, after the IN administration of 3 mg nalmefene to a plurality of human subjects, the $AUC_{0-10min}$ geometric mean is between about 0.25 and 0.75 h*ng/ml, or between 0.4 and 0.6 h*ng/ml, or about 0.5 h*ng/mL.

In another embodiment, after the IN administration of 3 mg nalmefene to a plurality of human subjects, the $AUC_{0-15min}$ geometric mean is between about 0.75 and 1.5 h*ng/ml, or between about 0.9 and 1.3 h*ng/ml, or is about 1.2 h*ng/mL.

In another embodiment, after the IN administration of 3 mg nalmefene to a plurality of human subjects, the $AUC_{0-20min}$ geometric mean is between about 1.25 and 2.25 h*ng/ml, or between about 1.50 and 2 h*ng/ml, or is about 1.9 h*ng/mL.

In another embodiment, after the IN administration of 3 mg nalmefene to a plurality of human subjects, the $AUC_{0-30min}$ geometric mean is between about 2 and 4 h*ng/ml, or between about 2.5 h*ng/ml and 3.50 h*ng/ml, or is about 3 h*ng/ml.

In another embodiment, after the IN administration of 3 mg nalmefene to a plurality of human subjects, the $AUC_{Last}$ geometric mean is between about 30 and 50 h*ng/mL, or between 35 and 45 h*ng/ml, or is about 40 h*ng/mL. In some embodiments, the $AUC_{Last}$ is between about 22.8 and about 58.3 h*ng/mL.

In another embodiment, after the IN administration of 3 mg nalmefene to a plurality of human subjects, the $AUC_{inf}$ geometric mean is between about 30 and 50 h*ng/ml, or between 35 and 45 h*ng/mL, or is about 40 h*ng/mL. In some embodiments, the $AUC_{inf}$ is between about 23.1 to about 60.9 h*ng/mL.

In another embodiment, after the IN administration of 3 mg nalmefene to a plurality of human subjects, the $AUC_{Extrap}$ is between about 1.12% to about 13.1%.

In another embodiment, after the IN administration of 3 mg nalmefene to a plurality of human subjects, the $K_{el}$ is between about 0.0281 to about 0.0864 (1/h).

In another embodiment, five minutes after the administration of about 3 mg of nalmefene hydrochloride, the increase in minute ventilation was about 5.7 L/min as compared to about 3.0 L/min for 4 mg of intranasally administered naloxone.

In some embodiments, the administration of about 3 mg of nalmefene hydrochloride restores minute ventilation to within the 95% Confidence Interval of pre-remifentanil values at about 5 minutes or longer as compared to about 4 mg of naloxone which restores minute ventilation to within the 95% Confidence Interval of pre-remifentanil values at about 20 minutes or longer.

In some embodiments, after the administration of about 3 mg of nalmefene hydrochloride, the VE $E_{max}$ is between about 3.8 L/min to about 14.8 L/min.

In some embodiments, the maximum $ET_{CO2}$ increase occurs about 2.5 minutes after nalmefene administration. In some embodiments, the maximum $ET_{CO2}$ increase occurs between about 1 minute to about 5 minutes after nalmefene administration In some embodiments, from administration of about 3 mg of nalmefene hydrochloride to about 20 minutes after, mean $ET_{CO2}$ decreases from about 48.6 to about 44.07 mm Hg.

In some embodiments, about 15 minutes after the administration of about 3 mg of nalmefene hydrochloride, the mean change in minute ventilation from nadir baseline was about 5 L/min to about 10 L/min. In certain embodiments, it is about 7.1 L/min. In some embodiments, the maximum minute ventilation value from nadir baseline occurs about 15 minutes after administration of about 3 mg of nalmefene hydrochloride. In some embodiments, the maximum minute ventilation value from nadir baseline occurs about 10 minutes after administration of about 3 mg of nalmefene hydrochloride. In some embodiments, the maximum minute ventilation value from nadir baseline occurs about 20 minutes after administration of about 3 mg of nalmefene hydrochloride.

In some embodiments, said opioid overdose symptom is selected from: respiratory depression, central nervous system depression, and cardiovascular depression.

In some embodiments, said opioid overdose symptom is respiratory depression induced by opioids.

In some embodiments, said respiratory depression is caused by the illicit use of opioids or by an accidental misuse of opioids during medical opioid therapy.

In some embodiments, said respiratory depression is induced by opioids selected from: natural and synthetic narcotics, propoxyphene, methadone, nalbuphine, pentazocine and butorphanol.

In some embodiments, said respiratory depression is induced by an opioid selected from codeine, morphine, methadone, fentanyl, oxycodone HCl, hydrocodone bitartrate, hydromorphone, oxymorphone, meperidine, propoxyphene, opium, heroin, tramadol, tapentadol.

In some embodiments, said respiratory depression is induced by a synthetic opioid. In some embodiments, said synthetic opioid is fentanyl or a derivative thereof.

In some embodiments, the patient is free from respiratory depression for at least about 1 hour to at least about 8 hours following treatment comprising delivery of the therapeutically effective amount of the opioid antagonist, as provided above. In some embodiments, the patient is free from respiratory depression for at least about 3 hours to at least about 8 hours following treatment comprising delivery of the therapeutically effective amount of the opioid antagonist.

Also provided are embodiments wherein any embodiment above may be combined with any one or more of these embodiments, provided the combination is not mutually exclusive.

Also provided are the devices, pharmaceutical compositions, kits, and methods of treatment described herein for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension. Also provided are the devices, pharmaceutical compositions, kits, and methods of treatment described herein for use in the reversal of respiratory depression induced by opioids. In some embodiments, the respiratory depression is caused by the illicit use of opioids or by an accidental misuse of opioids during medical opioid therapy.

Also provided are the devices, pharmaceutical compositions, kits, and methods of treatment described herein for use in the complete or partial reversal of narcotic depression, including respiratory depression, induced by opioids selected from: natural and synthetic narcotics, propoxyphene, methadone, nalbuphine, pentazocine and butorphanol. In some embodiments, narcotic depression, including respiratory depression, is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are devices, pharmaceutical formulations, and kits for, and methods of, treating opioid overdose or a symptom thereof, comprising nasally administering to a patient in need thereof a therapeutically effective amount of an opioid antagonist selected from nalmefene and pharmaceutically acceptable salts thereof, wherein the therapeutically effective amount is equivalent to about 1 mg to about 10 mg of nalmefene hydrochloride. In some embodiments, the patient is not breathing. Also provided are devices adapted for nasal delivery of a pharmaceutical composition to a patient, comprising a therapeutically effective amount of an opioid antagonist selected from nalmefene and pharmaceutically acceptable salts thereof, wherein the device is pre-primed, and wherein the therapeutically effective amount, is equivalent to about 1 mg to about 10 mg of nalmefene hydrochloride, as provided above.

In some embodiments, the therapeutically effective amount is equivalent to about 1 mg of nalmefene hydrochloride. In some embodiments, the therapeutically effective amount is equivalent to about 1.5 mg of nalmefene hydrochloride. In some embodiments, the therapeutically effective amount is equivalent to about 2 mg of nalmefene hydrochloride. In some embodiments, the therapeutically effective amount is equivalent to about 2.5 mg of nalmefene hydrochloride. In some embodiments, the therapeutically effective amount is equivalent to about 3 mg of nalmefene hydrochloride. In some embodiments, the therapeutically effective amount is equivalent to about 3.5 mg of nalmefene hydrochloride. In some embodiments, the therapeutically effective amount is equivalent to about 4 mg of nalmefene hydrochloride. In some embodiments, the therapeutically effective amount is equivalent to about 4.5 mg of nalmefene hydrochloride. In some embodiments, the therapeutically effective amount is equivalent to about 5 mg of nalmefene hydrochloride.

In some embodiments, the therapeutically effective amount is equivalent to about 1 mg of nalmefene free base. In some embodiments, the therapeutically effective amount is equivalent to about 1.5 mg of nalmefene free base. In some embodiments, the therapeutically effective amount is equivalent to about 2 mg of nalmefene free base. In some embodiments, the therapeutically effective amount is equivalent to about 2.5 mg of nalmefene free base. In some embodiments, the therapeutically effective amount is equivalent to about 2.7 mg of nalmefene free base. In some embodiments, the therapeutically effective amount is equivalent to about 3 mg of nalmefene free base. In some embodiments, the therapeutically effective amount is equivalent to about 3.5 mg of nalmefene free base. In some embodiments, the therapeutically effective amount is equivalent to about 4 mg of nalmefene free base. In some embodiments, the therapeutically effective amount is equivalent to about 4.5 mg of nalmefene free base. In some embodiments, the therapeutically effective amount is equivalent to about 5 mg of nalmefene free base.

In certain embodiments, the pharmaceutical formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises between about 0.1% (w/v) to about 12.5% (w/v) of an absorption enhancer. In certain embodiments, the pharmaceutical formulation comprises between about 0.005% (w/v) to about 7.5% (w/v). In other embodiments, the pharmaceutical formulation comprises between about 1% (w/v) to about 5% (w/v) of an absorption enhancer. In certain embodiments, the pharmaceutical formulation comprises between about 0.01% (w/v) to about 7.5% (w/v) of an absorption enhancer. In certain embodiments, the pharmaceutical formulation comprises between about 0.005% (w/v) to about 1% (w/v) of an absorption enhancer. In certain embodiments, the pharmaceutical formulation comprises between about 0.01% (w/v) to about 0.75% (w/v) of an absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer. In certain embodiments, the absorption enhancer is an alkylsaccharide. In certain embodiments, the alkylsaccharide is chosen from dodecyl maltoside, tetradecyl maltoside (TDM) and sucrose dodecanoate.

In some embodiments, the opioid antagonist is the only pharmaceutically active compound in pharmaceutical composition. In some embodiments, the opioid antagonist is nalmefene hydrochloride. In some embodiments, the opioid antagonist is anhydrous nalmefene hydrochloride. In some embodiments, the opioid antagonist is nalmefene free base. In some embodiments, the pharmaceutical composition comprises a solution of nalmefene hydrochloride. In some embodiments, the nasally administering is accomplished using a device described herein. In some embodiments, the opioid overdose symptom is selected from: respiratory depression, postoperative opioid respiratory depression, altered level consciousness, miotic pupils, cardiovascular depression, hypoxemia, acute lung injury, aspiration pneumonia, sedation, and hypotension. In some embodiments, the opioid overdose symptom is respiratory depression induced by opioids. In some embodiments, the respiratory depression is caused by the illicit use of opioids or by an accidental misuse of opioids during medical opioid therapy. In some embodiments, the respiratory depression is induced by opioids selected from: natural and synthetic narcotics, propoxyphene, methadone, nalbuphine, pentazocine and butorphanol. In some embodiments, the respiratory depression is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

In some embodiments, the respiratory depression is induced by opioids selected from: alpha-methylfentanyl, 3-methylthiofentanyl, acetyl-alpha-methylfentanyl, beta-hydroxy-3-methylfentanyl, alpha-methylthiofentanyl, thiofentanyl, beta-hydroxyfentanyl, para-fluorofentanyl, 3-methylfentanyl, acetyl fentanyl, butyryl fentanyl, beta-hydroxythiofentanyl, furanyl fentanyl, 4-fluoroisobutyryl fentanyl, acryl fentanyl, U-47700, and combinations thereof.

In some embodiments, the respiratory depression is induced by opium alkaloids (opiates: codeine, morphine), semisynthetic derivatives of the natural alkaloids (hydrocodone, hydromorphone, oxycodone, buprenorphine), synthetic opioids such as the anililopiperidines (fentanyl, alfentanil, sufentanil, remifentanil), diphenylpropylamine derivatives (propoxyphene, dextropropoxyphene, methadone, diphenoxylate, loperamide), or others (pentazocine, butorphanol, nalbuphine, levorphanol, tramadol).

Also provided are devices, kits, and pharmaceutical formulations for, and methods of, reversing the psychotomimetic and dysphoric effects of agonist-antagonists such as pentazocine, comprising nasally administering to a patient in need thereof a therapeutically effective amount of an opioid antagonist selected from nalmefene and pharmaceutically acceptable salts thereof, wherein the therapeutically effective amount is equivalent to about 1 mg to about 10 mg of nalmefene hydrochloride, as provided above.

Also provided are devices, kits, and pharmaceutical formulations for, and methods of, diagnosis of suspected acute opioid over-dosage, comprising nasally administering to a patient in need thereof a therapeutically effective amount of an opioid antagonist selected from nalmefene and pharmaceutically acceptable salts thereof, wherein the therapeutically effective amount is equivalent to about 1 mg to about 10 mg of nalmefene hydrochloride, as provided above. In some embodiments, the nalmefene is nalmefene free base.

Also provided are devices, kits, and pharmaceutical formulations for, and methods of, treating opioid addiction, comprising nasally administering to a patient in need thereof a therapeutically effective amount of an opioid antagonist selected from nalmefene and pharmaceutically acceptable salts thereof, wherein the therapeutically effective amount is equivalent to about 1 mg to about 10 mg of nalmefene hydrochloride, as provided above.

Also provided are devices, kits, and pharmaceutical formulations for, and methods of, treating septic shock, comprising nasally administering to a patient in need thereof a therapeutically effective amount of an opioid antagonist selected from nalmefene and pharmaceutically acceptable salts thereof, wherein the therapeutically effective amount is equivalent to about 1 mg to about 10 mg of nalmefene hydrochloride, as provided above.

Also provided are devices, kits, and pharmaceutical formulations for, and methods of, treating opioid overdose or a symptom thereof, reversing the psychotomimetic and dysphoric effects of agonist-antagonists such as pentazocine, diagnosing suspected acute opioid over-dosage, treating opioid addiction, or treating septic shock, comprising nasally administering to a patient in need thereof a therapeutically effective amount of an opioid antagonist, wherein the therapeutically effective amount is about 1 mg to about 10 mg, as provided above.

F. Other Embodiments

The detailed description set forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent or bioequivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

Also provided are embodiments wherein any embodiment above can be combined with any one or more of these embodiments, provided the combination is not mutually exclusive. Also provided herein are uses in the treatment of indications or one or more symptoms thereof as disclosed herein, and uses in the manufacture of medicaments for the treatment of indications or one or more symptoms thereof as disclosed herein, equivalent in scope to any embodiment disclosed above, or any combination thereof that is not mutually exclusive. The methods and uses may employ any of the devices disclosed herein, or any combination thereof that is not mutually exclusive, or any of the pharmaceutical formulations disclosed herein, or any combination thereof that is not mutually exclusive.

G. Examples

The following examples are included to demonstrate preferred embodiments of the disclosure. The following examples are presented only by way of illustration and to assist one of ordinary skill in using the disclosure. The examples are not intended in any way to otherwise limit the scope of the disclosure. Those of skill in the art should, in light of the present disclosure, appreciate that many changes can be made in the specific embodiments which are disclosed and still obtain a like or similar result without departing from the spirit and scope of the disclosure.

Example 1: Synopsis of Protocol for Phase 1 Pharmacokinetic Evaluation of Nalmefene Administered Intranasally to Healthy Volunteers The following is a synopsis of a single site study conducted at Vince & Associates Clinical Research, Overland Park, Kansas. The National Institute on Drug Abuse (NIDA) was the IND sponsor for this study. The drug used in this study was Nalmefene hydrochloride (nalmefene). The study was designed to have approximately 14 healthy volunteers enrolled and to have at least 10 subjects complete all study drug administrations and blood collections for PK assessments. If less than 10 subjects completed the study using the first cohort of 14, additional subjects were screened and enrolled until there were a total of at least 10 completers.

The objectives of the study were to compare the pharmacokinetics of nalmefene administered IN with, and without, an absorption enhancer compared to an IM injection as well as to determine the safety and tolerability of IN nalmefene, particularly with respect to nasal irritation (erythema, edema, and erosion).

The primary endpoint was to compare the pharmacokinetic parameters $C_{max}$, $T_{max}$, $AUC_{0-t}$ and $AUC_{0-inf}$ of nalmefene as 3 IN treatments to nalmefene 1M administration. The treatments were: 3 mg nalmefene IN; 3 mg nalmefene plus 0.25% (w/v) Intravail IN; 1.5 mg nalmefene IN; and 1.5 mg nalmefene 1M.

The study was designed to be an inpatient, double-blind (for IN administration), randomized, 4-period, 4-treatment, 6-sequence, crossover study involving 14 healthy volunteers. Subjects were assigned to one of the 6 sequences with at least 2 subjects in each sequence. Each subject received 4 treatments during the 4 dosing periods: IN dose of 3 mg nalmefene, IN dose of 3 mg nalmefene plus 0.25% (w/v) Intravail, IN dose of 1.5 mg nalmefene, and IM dose 1.5 mg nalmefene. If less than 10 subjects completed the study, additional subjects were screened and enrolled until there were a total of at least 10 completers. Subjects stayed in the inpatient facility for 17 days to complete the entire study and were discharged following completion of discharge procedures at the end of the last period. Subjects were called 3 to 5 days after discharge to inquire concerning adverse events (AEs) and concomitant medications since discharge.

After obtaining informed consent, subjects were screened for eligibility to participate in the study including medical history, physical examination, clinical chemistry, coagulation markers, hematology, infectious disease serology, urinalysis, urine drug and alcohol toxicology screen, vital signs and ECG. On the day after clinic admission, subjects were administered the IN-formulated drug in randomized order with 4 days between doses; the IM dose of nalmefene was administered during the fourth (last) treatment period.

Blood was collected for nalmefene PK prior to dosing and at 2.5, 5, 10, 15, 20, 30, 45 minutes and 1, 2, 3, 4, 6, 8, 12, 16, 24, 30, 36, 48, 60, and 72 hours after study drug administration. On days of study drug administration, a 12-lead ECG were performed approximately 1 hour prior to dosing and at approximately 1 and 8 hours post-dose. Vital signs were measured pre-dose and approximately 0.5, 1, 2, and 8 hours post-dose. On dosing days, the order of assessments was ECG, vital signs, then PK blood collection when scheduled at the same nominal times. The target time of the PK blood collection was considered the most critical and if the collection was more than ±1 minute from the scheduled time for the first 60 minutes of collections or more than ±5 minutes for the scheduled time points thereafter, this was considered a protocol deviation. ECG and vital signs were collected within the 15-minute period before the nominal time of blood collections. At screening, admission, discharge, and follow-up, ECG and vital signs were checked once per day. Vital signs were also checked approximately 24, 48, and 72 hours after study drug administration. Clinical laboratory measurements were repeated after the last PK blood draw prior to clinic discharge. AEs were assessed by spontaneous reports by subjects, by examination of the nasal mucosa, by measuring vital signs, ECG, and clinical laboratory parameters.

The criteria for inclusion and exclusion in this study as well as the protocol for safety assessment is provided in detail in the examples below.

The study drugs and design were as follows: cGMP nalmefene was obtained from Rusan Pharma Ltd. The study drug was supplied to the pharmacy at the study site. A detailed description for formulating the study drug was provided to the pharmacist. The 4 formulations were the following: a) 30 mg nalmefene HCl/mL water for injection (WFI); b) 30 mg nalmefene HCl/mL WFI plus 0.25% Intravail; c) 15 mg nalmefene HCl/mL WFI; d) 1.0 mg nalmefene/mL normal saline for injection.

The 3 IN formulations were given as one 0.1 mL spray into one nostril using an Aptar multi-dose nasal spray device with the subject in a reclining position. The subject was instructed to not breathe through the nose when the IN doses were administered. The IM formulation was given as 1.5 mL in the contralateral arm from where the blood samples were obtained.

For pharmacokinetics (PK) assessments, blood was collected in sodium heparin containing tubes prior to dosing and 2.5, 5, 10, 15, 20, 30, 45 minutes and 1, 2, 4, 6, 8, 12, 16, 24, 30, 36, 48, and 72 hours after study drugs administration. Plasma was stored at ≤−60° C. until assayed. Nalmefene plasma concentrations were determined by liquid chromatography with tandem mass spectrometry.

The analysis plan was as follows: $C_{max}$, $AUC_{0-t}$, $AUC_{0-inf}$, and $T_{max}$ of nalmefene were calculated. The relative IN bioavailability of nalmefene was determined by comparing the dose-adjusted $AUC_{0-inf}$ after IN administration to that of the IM formulation.

Within an analysis of variance (ANOVA) framework, comparisons of ln-transformed PK parameters (dose normalized $C_{max}$ and AUC) were performed using a mixed effects model where sequence, period, and treatment were the independent factors. The 90% confidence interval for the ratio of the geometric least squares means of $C_{max}$ and AUC was constructed for comparison of the three IN formulations to the IM formulation. These 90% confidence intervals were obtained by exponentiation of the 90% confidence intervals for the difference between the least squares means based upon an ln scale.

AEs were coded using the most recent version of the Medical Dictionary for Regulatory Activities (MedDRA) preferred terms and were grouped by system, organ, class (SOC) designation. The severity, frequency, and relationship of AEs to study drugs were presented by preferred term by SOC grouping. Separate summaries were provided for the 4 study periods: after the administration of each dose of study drug up until the time of the next dose of study drug or clinic discharge. Listings of each individual AE including start date, stop date, severity, relationship, outcome, and duration was provided. Vital signs, ECG, and clinical laboratory parameters were presented as summary statistics.

Example 2: Study Design

This was designed to be an inpatient, open-label, randomized (IN periods only), 4-period, 4-treatment, 6-sequence, crossover study involving 14 healthy volunteers. If less than 10 subjects completed the study, additional subjects were screened and enrolled until there were a total of at least 10 completers. Subjects were assigned to one of the 6 sequences and there were at least 2 subjects in each sequence. Each subject received 4 treatments during the 4 dosing periods:

Treatment A: 3 mg nalmefene IN dose (one 0.1 mL spray of a 30 mg/mL WFI in one nostril)

Treatment B: 3 mg nalmefene IN dose with 0.25% Intravail (one 0.1 mL spray of a 30 mg/mL WFI plus 0.25% Intravail in one nostril)

Treatment C: 1.5 mg nalmefene IN dose (one 0.1 mL spray of a solution of 15 mg/mL WFI in one nostril)

Treatment D: 1.5 mg nalmefene IM dose (1.5 mL of a 1.0 mg/mL normal saline for injection). This treatment was done in Period 4.

Subjects stayed in the inpatient facility for 17 days to complete the entire study and were released after Discharge Procedures were completed in Period 4. Subjects were called 3 to 5 days after discharge to inquire concerning AEs and concomitant medications since discharge.

After obtaining informed consent, subjects were screened for eligibility to participate in the study, including medical history, physical examination, height, weight, BMI, clinical chemistry, coagulation markers, hematology, infectious disease serology, urinalysis, urine toxicology screen, vital signs, and ECG. On the day after clinic admission, subjects were administered the study drugs in randomized order (IN only, Periods 1 to 3) with a 4-day washout period between doses until all 4 treatments have been administered. Blood was collected for PK analysis prior to dosing and at 2.5, 5, 10, 15, 20, 30, 45 minutes and 1, 2, 3, 4, 6, 8, 12, 16, 24, 30, 36, 48, 60, and 72 hours after study drugs administration. The IM formulation was administered in Period 4

On days of study drug administration, a 12-lead ECG was performed approximately 1 hour prior to dosing and 1 and 8 hours postdose. Vital signs were measured predose and approximately 0.5, 1, 2, and 8 hours postdose. On dosing days, the order of assessments was ECG, vital signs, then PK blood collection when scheduled at the same nominal times. The target time of the PK blood collection was considered the most critical and if the collection was more than ±1 minute from the scheduled time for the first 60 minutes of collections or more than ±5 minutes for the scheduled time points thereafter, this was considered a protocol deviation. ECG and vital signs were collected within the 15-minute period before the nominal time of blood collections. At screening, admission, discharge, and follow-up, ECG and vital signs were checked. Vital signs were also checked once a day after dosing. Clinical laboratory measurements were repeated after the last PK blood draw prior to clinic discharge. AEs were assessed by spontaneous reports by subjects, by examination of the nasal mucosa, by measuring vital signs, ECG, and clinical laboratory parameters.

Example 3: Subject Selection and Screening

Subjects were healthy volunteers who resided at the clinical site for a period of 17 days and fulfilled the following inclusion and exclusion criteria.
Inclusion Criteria:
Subjects were included if they fulfill the following inclusion criteria:
  Males and females 18 to 55 years of age, inclusive;
  Provided written informed consent;
  BMI ranging from 18 to 30 kg/m2, inclusive;
  Adequate venous access;
  No clinically significant concurrent medical conditions determined by medical history, physical examination, clinical laboratory examination, vital signs, and 12-lead ECG;
  Male subjects agreed to use an acceptable method of contraception with female partners as well as not to donate sperm throughout the study and for 90 days after the last study drug administration. Female subjects of childbearing potential agreed to use an acceptable method of birth control throughout the study and for 30 days after the last study drug administration. Oral contraceptives were prohibited;
  Agreed not to ingest alcohol, drinks containing xanthine >500 mg/day (e.g., Coca Cola®, coffee, tea, etc.), or grapefruit/grapefruit juice or participate in strenuous exercise 72 hours prior to admission through the last blood draw of the study.
Exclusion Criteria:
Subjects were excluded if they had any of the following criteria:
  Any IN conditions including abnormal nasal anatomy, nasal symptoms (i.e., blocked and/or runny nose, nasal polyps, etc.), or having a product sprayed into the nasal cavity prior to drug administration, or failed test for sense of smell;
  Been administered an investigational drug within 30 days prior to Day-1;
  Taken prescribed or over-the-counter medications, dietary supplements, herbal products, vitamins, or use of opioid analgesics for pain relief within 14 days of Day-1;
  Positive urine drug test for alcohol, opioids, cocaine, amphetamine, methamphetamine, benzodiazepines, THC, barbiturates, or methadone at screening or admission;
  Previous or current opioid, alcohol, or other drug dependence (excluding nicotine and caffeine), based on medical history;
  Subject consumed greater than 20 cigarettes per day on average, in the month prior to screening, or were unable to abstain from smoking (or use of any nicotine-containing substance) for at least one hour prior to and 2 hours after IN dosing;
  Systolic blood pressure (BP) less than 90 mmHg or greater than 140 mmHg;
  diastolic BP less than 55 mmHg or greater than 90 mmHg; respiratory rate less than 8 respirations per minute (rpm) or greater than 20 rpm;
  On standard 12-lead ECG, a QTcF interval >440 msec for males and >450 msec for females;
  Significant acute or chronic medical disease in the judgment of the investigator;
  A likely need for concomitant treatment medication during the study;
  Donated or received blood or underwent plasma or platelet apheresis within the 60 days prior to Day −1;
  Female who is pregnant, breast feeding, or plans to become pregnant during the study period or within 30 days after the last drug administration;
  Positive test for HBsAg, HCVAb, or HIVAb at screening;
  Current or recent (within 7 days prior to screening) upper respiratory tract infection;
  Abnormal liver function test (ALT, AST, total bilirubin)> 1.5 times upper limit of normal.

Example 4: Study Drugs

Study Drug Source and Description:
Nalmefene's systematic name is 17-cyclopropylmethyl-4,5α-epoxy-6-methylenemorphinan-3,14-diol. NIDA supplied cGMP-grade nalmefene HCl (manufactured by Rusan Pharma, Ltd.) to the pharmacy at the clinical site. The pharmacy prepared the nalmefene HCl solutions for IN administration at the strengths of 30 mg/mL with and without 0.25% Intravail and at 15 mg/mL using water for injection. The pharmacy also prepared the nalmefene HCl solution for IM administration at a strength of 1.0 mg/mL using sterile saline for injection, USP. The IM solution was tested for sterility, pyrogenicity, and other quality control tests before release for administration.

The pharmacy procured Aptar multi-dose nasal spray devices that deliver 0.1 mL intranasally.

An aliquot of each dosing solution was sent to Research Triangle Institute for the determination of nalmefene concentrations.

A detailed description for formulating the study drugs was provided by the pharmacist in a separate document.
Study Drug Administration:
Subjects were dosed with at least 5 minutes intervals between subjects.

Subjects were given each of the 3 IN formulations by administration into one nostril between 08:00 am and 10:00 am; the volume of each formulation was 0.1 mL. All 3 formulations were administered using a dosing device with the subject in a reclining position. The subjects remained reclined for approximately 1 hour post-dose. Subjects were instructed to hold breathing during administration of the nasal spray into the nose.

Each dosing device was weighed before and after dosing to determine the weight of the dose that was administered to each subject.

For the IM injection, 1.5 mL of the 1.0 mg/ml nalmefene solution was administered in the arm contralateral from the one used for blood collection. Subjects were given the IM formulation between 08:00 am and 10:00 am.

Study Drug Accountability:

The investigator maintained a log of all study drug administration to subjects throughout the trial. In addition, the study drugs were inventoried and audited against administration records. Inhaler devices were labeled with the subject ID and date and retained at the site until the clinical monitor completed accountability verification and the Sponsor notified the site how the devices were disposed.

Used/Unused Supplies:

At the end of the study, the unused study drugs were inventoried. If the study drug was lost or damaged, its disposition was documented. Unused study drugs were retained at the clinical site pending instructions by NIDA for disposition at the end of the study.

Example 5: Study Procedures

Subject Screening Assessments:

Screening of subjects to establish eligibility occurred initially before clinic entry and was completed at the time of clinic admission. Assessments performed during screening included collection of demographic information, medical history, a 12-lead ECG, physical examination, height, weight, BMI, nasal passage examination, sense of smell, and measurement of vital signs (heart rate, blood pressure, respiratory rate, temperature). The subjects were asked about alcohol and consumption of caffeine containing beverages or food (e.g., coffee, tea, chocolate, cola and drinks such as Red Bull®) and cigarette smoking to assure eligibility. Urine was collected for medical urinalysis and a urine toxicology screen. Blood was collected for hematology, chemistries, coagulation markers, a serum pregnancy test (if female), and viral serology (HIVAb, HBsAg, and HCVAb). Subjects were asked about prescription and over-the-counter medication, dietary supplements, herbal products, and vitamins use or recent use of opioid analgesics for pain relief in the 30 days prior to the start of screening. This information was updated throughout the screening process up to the time of clinic admission.

An eligibility checklist was provided and was reviewed at the completion of the outpatient screening assessments. If the subject remained eligible, he/she was scheduled to undergo clinic admission procedures and final eligibility assessments.

Up to 18 subjects (14 to be enrolled and 4 backups) underwent clinic admission procedures and were assessed for final eligibility on Study Day-1. Fourteen eligible subjects, including at least 6 females, were randomized.

Admission screening procedures occurred on Study Day-1. The following assessments were performed to determine eligibility: Update on medication use since the last visit; update of medical history (new diseases or conditions since last visit); physical examination and nasal passage examination; test for sense of smell; 12-lead ECG; vital signs [sitting (5 minutes) blood pressure, heart rate, respiration rate, and temperature] (may be repeated twice); chemistries, coagulation, hematology, serum pregnancy test, and urinalysis; urine drug and alcohol toxicology screen (both must be negative to be eligible); and review of eligibility checklist.

Subject Randomization:

If the subject still met eligibility criteria, he/she was randomized to the order of three IN doses (i) 3 mg IN nalmefene (one 0.1 mL spray of the 30 mg/mL formulation in one nostril); (ii) 3 mg IN nalmefene plus 0.25% Intravail (one 0.1 mL spray of the 30 mg/mL plus 0.25% Intravail formulation in one nostril); (iii) 1.5 mg nalmefene (one 0.1 mL spray of the 15 mg/mL formulation in one nostril).

Subjects were randomized to a sequence order of receipt of IN doses (Periods 1 to 3) after establishing eligibility and completing admission procedures. Subjects were assigned to each of the 6 possible sequences to ensure that at least 2 subjects were in each group. Periods 1 to 3 were the double-blind part of the study. The randomization schedule was provided by Technical Resources International, Inc. (Bethesda, Md,).

All subjects were administered 1.5 mg nalmefene IM (1.5 mL of a 1.0 mg/mL solution) in Period 4. The pharmacist was provided the randomization schedule to prepare the individual doses.

Study Drug Administration, PK Sample Collection, and Safety Monitoring:

The study drug was administered intranasally on Days 1, 5, and 9 as designated in the crossover randomization assignment; all subjects received the IM dose on Day 13. At approximately 1 hour prior to dosing, ECG, blood pressure, heart rate, sense of smell (Periods 1-3), and respiration rate was measured and the time was recorded. At approximately 1 and 8 hours after dosing, the ECG was repeated and the time was recorded. Vital signs including sitting (after 5 minutes) heart rate, blood pressure and respiration rate were measured pre-dose and approximately 0.5 (reclining position), 1, 2, and 8 hours after each administration.

The measurement at 0.5 hours post-dose was taken in the reclining position as the subject was to remain reclining for 1 hour post administration. A physician was present during the IN and IM dosing and for at least 5 minutes after administration. The nasal passage was examined at pre-dose, 5 minutes, 30 minutes, 1 hour, 4 hours, and 24 hours post-dose in Periods 1 to 3. Test for sense of smell was conducted at Screening, Day-1 (baseline); pre-dose and 4 hours post-dose during Periods 1 to 3; and prior to discharge to evaluate olfactory function. A clinical staff member observed the subject for at least 1 hour after dosing.

Blood was collected in 4-mL sodium heparin tubes for PK analysis prior to dosing and at 2.5, 5, 10, 15, 20, 30, 45 minutes and 1, 2, 3, 4, 6, 8, 12, 16, 24, 30, 36, 48, 60, and 72 hours after study drugs administration. On dosing days, the order of assessments was ECG, vital signs, then PK blood collection when scheduled at the same nominal times. The target time of the PK blood collection was considered the most critical. If the collection time was more than ±1 minute from the scheduled time for the first 60 minutes of collections or more than ±5 minutes for the scheduled time points thereafter, this was considered a protocol deviation. ECG and vital signs were collected within the 15-minute period before the nominal time of blood collections.

A total of 352 mL of blood in 88 samples were collected for PK analysis. Another 48 mL (males) to 63 mL (female) of blood was collected for clinical laboratory assessments during the trial. The estimated total volume of blood that was collected was 400 mL for males and 415 mL for females.

Dietary and Other Restrictions:

Subjects were required to abstain from nicotine and products containing caffeine or other xanthines (e.g., coffee, tea, chocolate, cola, and drinks such as Red Bull™) for at least 1 hour prior to and 2 hours after dosing. No alcohol consumption was permitted throughout the inpatient study period. Subjects were to abstain from smoking (or use of any nicotine-containing substance) for at least 1 hour prior to and 2 hours after dosing. Subjects fasted from midnight the day before dosing sessions until at least one hour after the study drugs were administered. Water was provided ad libitum. A standardized diet was provided for all meals for the duration of the inpatient portion of the study. Breakfast was provided approximately 1 hour after dosing, lunch approximately 4 hours after dosing, dinner approximately 10 hours after dosing, and a snack approximately 13 hours after dosing.

Study Drug Discontinuation:

Subjects were closely monitored while inpatient before and after drug administration. Vital signs, ECG measurements, and AE reports were used to determine the safety of nalmefene administrations and the appropriateness for administering the next dose. Vital signs needed to be within acceptable limits before nalmefene was administered.

On the 4 test days that the study drugs were administered, the following was the vital signs criteria that needed to be met before dosing (with subject sitting at least 5 minutes before obtaining measures): Systolic blood pressure: 140 mmHg or less and equal to or greater than 90 mmHg; Diastolic blood pressure: 90 mmHg or less and equal to or greater than 55 mmHg; Heart rate: 100 beats per minute (bpm) or less and equal to or greater than 40 bpm; Respiratory rate: 20 respirations per minute (rpm) or less and equal to or greater than 8 rpm. Vital signs could be repeated once. In addition, a clinically significant abnormal ECG at any time after clinic admission necessitated study drugs discontinuation.

Concomitant Medication Use:

Subjects were not permitted to take prescription or over-the-counter medications, oral contraceptives, herbal products, dietary supplements, or vitamins during the inpatient period; however, medical treatment was not denied in the judgment of the Investigator.

Clinic Discharge:

On the day of discharge from the clinic, whether at the end of the study or if a subject withdraws prematurely, the following assessments were conducted: Concomitant medications; AEs; Chemistry, coagulation markers, hematology, urinalysis, serum pregnancy test; Physical exam and nasal passage exam; Test for sense of smell; Urine drug and alcohol toxicology screen; ECG; Vital Signs.

If a subject completed all 4 periods, vital signs collected during Discharge Procedures substituted for those scheduled to be completed 72 hours post-dose after the fourth dose administration.

Subjects received a telephone call 3 to 5 days after clinic discharge to inquire as to whether they had any AEs or used any medications since discharge. If any clinically significant AEs were ongoing at the time of the phone call, they were followed until resolution or stabilized.

Volunteer Discontinuation:

Early Termination for an Individual Subject:

The criteria for terminating study participation for a single subject were: systolic blood pressure >180 mmHg, diastolic blood pressure >110 mmHg, respiratory rate <8 or >24 rpm confirmed by repeat; significant arrhythmia defined as >6 beats of supraventricular tachycardia or >3 beats of ventricular tachycardia; QTcF interval >500 msec; reported significant nausea or abdominal pain; reported significant chest pain or dyspnea; subject confusion, seizures or seizure like behavior, agitation or inability to cooperate; subject requested to leave the experiment or was unwilling or unable to cooperate in carrying out the assigned protocol procedures.

If stopping criteria were exceeded, subjects were closely observed and treated as necessary to assure return to their normal baseline state before being discharged from the clinic or transferred to another treatment facility. If more than 2 subjects showed a similar pattern of excessive cardiovascular or behavioral change or a pattern of change from baseline after drug administration not readily explainable by other factors, the study was halted.

Subject Discontinuation for Protocol Violations:

Subjects were excluded or discharged if their behavior was disruptive, noncompliant with study procedures, or otherwise inconsistent with remaining in the clinic.

Subject Withdrawal:

Any subject who wished to withdraw from the study on his/her own accord and for whatever reason was entitled to do so without obligation. The Investigator documented a subject's reason(s) for withdrawal from the study and indicated whether he/she thought this was related to study drugs. Any procedures/examinations planned for the subject on completion of the study were conducted as soon as possible following withdrawal. A subject was considered lost to follow-up if he/she did not respond to 2 telephone calls. Subjects who withdrew for medical reasons continued to be followed up by the Investigator or other physicians as appropriate.

Risks and Discomfort:

Most of the safety data regarding the use of nalmefene came from patients using opioid drugs, in which nalmefene may precipitate opioid withdrawal. All subjects were queried about opioid drug abuse and dependence and tested for opioid drug use (including methadone) prior to the start of the study to minimize the chances for withdrawal symptoms occurring during the study. Withdrawal is characterized by nausea, chills, myalgia, dysphoria, abdominal cramps, and joint pain. Common adverse reactions of nalmefene with an incidence greater than 1% are nausea, vomiting, tachycardia, hypertension, postoperative pain, fever, dizziness, headache, chills, hypotension, and vasodilation. Adverse events of nalmefene with an incidence less than 1% include bradycardia, arrhythmia, diarrhea, dry mouth, somnolence, depression, agitation, nervousness, tremor, confusion, withdrawal syndrome, myoclonus, pharyngitis, pruritus, and urinary retention. The incidence of adverse events was highest in patients who received more than the recommended 1.5 mg IM dose of nalmefene.

Example 6: Assessment Methods

Adverse Events:

Reports of AEs were elicited by a verbal probe (e.g., "How are you feeling?") administered starting after clinic admission. Any events spontaneously reported by the subject or observed by the investigative staff were also recorded. AEs were assessed for severity and relationship to the study drugs in accordance with the criteria described below.

Clinical Chemistries:

Clinical chemistries included total protein, albumin, blood urea nitrogen, creatinine, alkaline phosphatase, alanine aminotransferase, aspartate aminotransferase, total bilirubin, sodium, potassium, chloride, CO2, calcium, glucose, and total cholesterol. The laboratory performing these assessments were either directly regulated by CAP or CLIA or indirectly according to CLIA guidelines. The laboratory needed to provide a copy of current certification.

Coagulation Markers:

Coagulation markers including prothrombin time and activated partial thromboplastin time were performed. The laboratory performing these assessments were either directly regulated by CAP or CLIA or indirectly according to CLIA guidelines. The laboratory needed to provide a copy of current certification.

Demographics:

Age, gender, race/ethnicity, date of birth, and date and time of signing the informed consent were collected.

ECG:

Twelve-lead ECGs were performed according to standard procedures. Subjects were supine for at least 5 minutes prior to obtaining ECGs. The results were reviewed by the investigator or study physician for interpretation. The investigator could consult a board-certified cardiologist, if necessary. QT interval was corrected (QTcF) using the Fridericia formula (Fridericia L.S., *Acta Medica Scandinavica.* 1920; 53:469-586).

Eligibility Checklist:

An eligibility checklist that included the inclusion/exclusion criteria was used at the end of out-patient screening and reviewed on the day of clinic admission to assure eligibility to participate in the study.

Hematology:

A complete blood cell count including the following was performed: hemoglobin, hematocrit, red blood cells, total white blood cells; and automated differential and platelet count. The laboratory performing these assessments was either directly regulated by CAP or CLIA or indirectly according to CLIA guidelines. The laboratory needed to provide a copy of current certification.

Infectious Disease Serology:

Serology for HIVAb, HBsAg, and HCVAb was performed at screening. Only those subjects with negative tests for these viruses were eligible for enrollment into the study. The results of the HIVAB testing were retained by the study site under confidential restriction; information regarding this test result at no time become part of the study database.

Study Drug Administration Record:

Administration of the study drug was reported on a Study Drug Administration Record case report form (CRF) including the date and time of administration of study drug.

The dose, route, and time of administration was recorded. The nostril used for dose administration was recorded. If problems occurred, these were also recorded.

Medical History:

A medical history was taken on all potential study subjects to assure medical fitness including questions about current and past opioid use, abuse, and dependence and recent smoking history. Women were asked about their choice of method for birth control. Subjects were queried about recent alcohol and xanthine containing products consumption to assure eligibility.

Nalmefene Plasma Levels:

Blood was obtained via direct venipuncture or through an IV catheter in the forearm of the arm which was left in place through the collection period or longer, if possible. Four milliliters of blood were collected into a sodium heparin-containing Vacutainer® tube at each time point. Plasma nalmefene concentrations were determined using a sensitive and specific validated liquid chromatography-tandem mass spectrometry method at a bioanalytical laboratory.

Nasal Irritation Scoring:

Nasal irritation was evaluated by a trained observer at screening, baseline, within 2 hours before IN dosing and post-dose at 5, 30, and 60 minutes and 4 hours and 24 hours. If a PK sample corresponded to the nasal irritation assessment the nasal assessment was performed within 5 minutes after the PK sample was obtained.

Nasal Irritation Scale

0—Normal appearing mucosa, no bleeding
   1—Inflamed mucosa (erythema/edema), no bleeding
   2—Minor bleeding which stops within 1 minute
   3—Minor bleeding, taking 1-5 minutes to stop
   4—Substantial bleeding for 4-60 minutes, does not require medical intervention
   5—Ulcerated lesions, bleeding which requires medical intervention.

Test for Sense of Smell:

Test for sense of smell to evaluate olfactory function was performed using 'Sniffin' Sticks' at Screening and Admission (Day-1); pre-dose and 4 hours post-dose during Periods 1-3; and prior to discharge. 'Sniffin' Sticks' is a screening test using 12 different smells. Identification of 10 or more (out of 12 items) constitutes a normal smell test. To be eligible to participate in this study, subjects must identify 10 out of 12 smells correctly at Screening and Admission. A finding of a subject identifying less than 10 smells during study was reported as an adverse event (reduced sense of smell).

Physical Examination:

A physical exam of the oral cavity, head, eyes, ears, nose, neck, and throat, heart, lungs, abdomen, liver, extremities, skin, neurologic, lymph nodes, and psychiatric (mental status), and general appearance was performed by a physician during screening. Height and weight were recorded at screening. BMI was calculated to determine if the subject was eligible for the study. During screening and after each dose, the nasal passage was examined by a physician for evidence of irritation (erythema, edema, and erosion). The nasal passage examination was performed after blood sample collections when the timing of collection was the same.

Prior and Concomitant Medication Use:

Prescription and over-the-counter medications, herbal products, dietary supplements, and vitamins used in the 30 days prior to the start of screening and up to the day of clinic admission were recorded as prior medications. In addition, any medications taken by the subject, except study drugs, whether they were prescription or over-the-counter medications, herbal products, dietary supplements, and vitamins from the day of clinic admission until the last day of the study were considered concomitant medications. Oral contraceptives were not permitted. No concomitant medications were permitted except if the physician prescribed a medication to treat an AE or other concurrent illness. All medication used during the prior and concomitant medication use periods were recorded on the Prior and Concomitant Medications CRF.

Pregnancy Test:

An FDA-cleared qualitative serum pregnancy test that evaluates human β-chorionic gonadotropin was performed by the local clinical laboratory to test all female subjects.

Urinalysis:

A medical urinalysis for specific gravity, glucose, bilirubin, ketones, blood, pH, protein, nitrite, and leukocyte esterase was performed by the local clinical laboratory.

Vital Signs:

Vital signs to be collected included sitting (for at least 5 minutes) blood pressure, heart rate, and respiration rate before and after dosing with an exception for 30 minutes after IN administration, which was collected in the reclining position. Sitting (for at least 5 minutes) blood pressure, heart rate, respiration rate, and temperature were checked at all other times.

Urine Drug and Alcohol Toxicology Screen:

A urine toxicology screen for alcohol, opioids, cocaine, amphetamine, methamphetamine, benzodiazepines, barbiturates, THC, and methadone was performed by the local clinical laboratory.

Clinic Discharge/Final Subject Disposition:

The subject disposition CRF documented all data relevant to subject discharge from the clinic: reason for discharge (i.e., completion of inpatient portion of the study, or early termination from the study) and date of discharge.

Example 7: Regulatory and Reporting Requirements

Good Clinical Practices:

This study was conducted in accordance with the most current version of the International Conference on Harmonization Guidance Document E6(R1): Good Clinical Practices: Consolidated Guideline. An Operations Manual was provided to all investigational sites as a study quality assurance tool.

FDA Form 1572:

The Principal Investigator signed a Statement of Investigator (FDA Form 1572) prior to initiating this study. The Form 1572 was updated as needed.

IRB Approval:

Prior to initiating the study, the Principal Investigator obtained written approval from the IRB of record to conduct the study. If changes to the study protocol became necessary, protocol amendments were submitted in writing to the local IRB by the site Principal Investigator for IRB approval prior to implementation. In addition, NIDA and the local IRB approved all advertising materials used for subject recruitment and any educational materials given to the subject. Progress reports were submitted to the local IRB annually or at a frequency requested by the IRB.

Informed Consent:

All potential subjects for the study were given a current copy of the informed consent form to read and take home. All aspects of the study were explained in lay language. All study subjects were given a copy of the signed informed consent.

Drug Accountability:

Upon receipt, the investigator or designee was responsible for taking inventory of the study drugs. A record of this inventory was kept and usage was documented. Any unused or expired study drug was disposed according to directions provided by the Sponsor.

Outside Monitoring:

Medical Monitor:

A medical monitor was appointed for the study. The medical monitor was available for making recommendations to the investigator and the sponsor on the severity of any serious adverse events (SAEs), the relatedness to the study interventions, and for determining if the SAE should be reported to the FDA in a 7 or 15 day expedited report or an annual report. The medical monitor was also responsible for tracking and assessing trends in the AEs reported. If the medical monitor and investigator did not concur on SAE evaluations, both opinions were reported to the FDA.

Clinical Monitors:

All investigators allowed representatives of the Sponsor to periodically monitor, at mutually convenient times during and after the study, all case report forms (CRFs) and corresponding source documents for each subject. These monitoring visits provided the Sponsor with the opportunity to evaluate the progress of the study and to inform the Sponsor of potential problems. The monitors assured that submitted data were accurate and in agreement with source documentation; verified that the study drugs were properly stored and accounted for, verified that subjects' consent for study participation had been properly obtained and documented, confirmed that research subjects entered into the study met inclusion and exclusion criteria, and assured that all essential documentation required by GCP guidelines were appropriately filed.

Monitors conducted a study initiation visit prior to the start of the study. At this visit, they assured that proper study-related documentation existed, assisted in training investigators and other site personnel in study procedures and GCP guidelines, confirmed receipt of study supplies, and assured that acceptable facilities and staff were available to conduct the study.

Routine monitoring visits by NIDA's representatives were scheduled at appropriate intervals. At these visits, the monitors verified that study procedures were being conducted according to the protocol guidelines and reviewed AEs and SAEs and drug accountability. At the end of the study, they advise on storage of study records and disposal of unused study drugs according to directions provided by the Sponsor.

Adverse Events Reporting:

In accordance with FDA reporting requirements, all AEs occurring during the clinical trial were collected, documented, and reported by the Investigator or sub-investigators according to the procedure described below. The occurrence of AEs was assessed starting when the subject received the first dose of study drugs, then daily during the inpatient portion of the study until clinic release, and at the final follow-up telephone contact.

An AE is defined as any reaction, side effect, or untoward event that occurs during the clinical trial, whether the event is considered related to the study drug or clinically significant. For this study, events reported by the subject, as well as clinically significant abnormal findings on physical examination, vital signs, ECG, or laboratory evaluation were recorded on the AE CRF. A new illness, symptom, sign or clinically significant clinical laboratory abnormality or worsening of a pre-existing condition or abnormality was considered an AE. Stable chronic conditions, such as arthritis, which were present prior to clinical trial entry and did not worsen were not considered AEs.

All AEs, recorded during the inpatient portion of the study regardless of severity, were followed by study physicians until satisfactory resolution. AEs were required to be reported up to the date of final follow-up following hospital discharge. At the follow-up visit, AEs were recorded and followed; they were followed to resolution only if they were serious, or if the study physician assessed them to be clinically significant.

Serious Adverse Events:

Each adverse event or reaction was classified by a study physician as being serious or non-serious. Based on the seriousness of the adverse event or reaction, appropriate reporting procedures were followed. The Code of Federal Regulations Title 21 part 312.32 and International Conference on Harmonization (ICH) Guideline for Industry: Clinical Safety Data Management: Definitions and Standards for Expedited Reporting, ICH-E2A March 1995, as implemented by the U.S. Food and Drug Administration, defines a serious adverse event (SAE) or serious adverse drug experience as any untoward medical occurrence at any dose that: (i) results in death; (ii) is life-threatening; (NOTE: The term "life-threatening" in the definition of "serious" refers to an event in which the subject was at risk of death at the time of the event; it does not refer to an event which hypothetically might have caused death if it were more severe.); (iii) requires inpatient hospitalization or prolongation of existing hospitalization; (iv) results in persistent or significant disability/incapacity; or (v) is a congenital anomaly/birth defect.

In addition, important medical events that may not result in death, be life-threatening, or require hospitalization were considered a serious adverse drug reaction, when based on appropriate medical judgment that may jeopardize the subject and may require medical or surgical intervention to prevent one of the outcomes listed in the above definition.

An unexpected AE is one that is not described with respect to nature, severity, or frequency in the current product package insert.

Reporting of AEs and SAEs is described in below. There were serious consequences including ultimately, criminal and/or civil penalties for sponsors who failed to comply with FDA regulations governing the reporting of SAEs. The Investigator in this study had the responsibility of promptly reporting all SAEs to the designated Medical Monitor at NIDA in order that NIDA can comply with these regulations.

If a study subject withdrew from the study or if the Investigator decided to discontinue the subject from the study because of an SAE, the subject was required to have appropriate follow-up medical monitoring including, if necessary, hospitalization. Monitoring continued until the problem prompting hospitalization had resolved or stabilized with no further change expected or was discovered to be clearly unrelated to study medication or progresses to death.

Example 8: Analytical Plan

Study Endpoints:
The primary endpoints of the study were the pharmacokinetic parameters $C_{max}$, $T_{max}$, $AUC_{0-t}$, and $AUC_{0-inf}$ of nalmefene administered as 3 IN treatments and as the IM treatment: 3 mg nalmefene IN, 3 mg nalmefene plus 0.25% Intravail IN, 1.5 mg nalmefene IN, and 1.5 mg nalmefene IM.

The secondary endpoints of the study were to determine the secondary pharmacokinetic parameters and adverse events (AEs), vital signs (heart rate, sitting blood pressure, and respiration rate), electrocardiogram (ECG), clinical laboratory changes and nasal irritation (erythema, edema, and erosion) following administration of nalmefene,
Study Populations:
Safety Population:
The safety population included all subjects who receive at least one administration of the study drug.
PK Evaluable Population:
The evaluable population included all subjects who completed at least one treatment with sufficient sampling time points to derive meaningful PK parameters.
Sample Size:
This pilot study was designed to obtain information regarding the PK of IN nalmefene under the conditions of this study. The number of subjects was deemed appropriate for this type of study.

Descriptive Statistics:
Summaries of the demographics (N, age, weight, height, BMI, gender, race, and ethnicity) were provided. Demographics were also calculated for each gender (N, age, weight, height, BMI, race, and ethnicity).
PK Data Analyses:
Individual plasma concentrations over time were tabulated and summarized. The following summary statistics were presented: N, arithmetic mean, SD of the arithmetic mean, median, minimum and maximum. Plasma concentration versus time curves (individual and mean) was presented.

The pharmacokinetic parameters ($C_{max}$, $T_{max}$, $AUC_{0-t}$, $AUC_{0-\infty}$, $t_{1/2}$, $\lambda z$, and apparent clearance (CL/F) (Table 1) were calculated using noncompartmental methods with a PK software program (Phoenix WinNonlin version 6.3 or higher, Pharsight Corp, Mountain View, Calif.) or equivalent.

TABLE 1

PK Parameters of Nalmefene

| Parameter | Definition |
|---|---|
| $C_{max}$ | Maximum plasma concentration, observed by inspection of individual study participant plots of plasma concentration versus time. |
| $C_{max}$/Dose | $C_{max}$ adjusted for the nominal administered dose. |
| $T_{max}$ | Time of maximum observed concentration, obtained directly from the observed concentration versus time data. |
| $AUC_{0-t}$ | The area under the concentration-time curve from time 0 (pre-dose) to the time of last quantifiable concentration, calculated by the linear-up/log-down trapezoidal method. |
| $AUC_{0-t}$/Dose | $AUC_{0-t}$ adjusted for the nominal administered dose. |
| $AUC_{0-inf}$ | Area under the concentration-time curve from time 0 extrapolated to infinity, calculated as $AUC_{0t} + C_{last}/\lambda z$, where $C_{last}$ is the observed last quantifiable concentration. |
| $AUC_{0-inf}$/Dose | $AUC_{0-inf}$ adjusted for the nominal administered dose. |
| $AUC \%_{Extrap}$ | The percentage of $AUC_{0-inf}$ obtained by extrapolation, calculated as $[(AUC_{0-inf} - AUC_{0-t})/AUC_{0-inf}]*100$. |
| $\lambda z$ | $\lambda z$ is the terminal-phase elimination rate constant, estimated by linear regression of logarithmically-transformed concentration versus time data. |
| $t_{1/2}$ | The terminal phase half-life for drug concentrations in plasma is calculated as: $t_{1/2} = \ln(2)/\lambda z$. |
| CL/F | Apparent total body clearance is calculated as CL/F = Dose/$AUC_{0-inf}$. |
| Relative Bioavailability | Ratio of dose-adjusted $AUC_{inf}$ following IN administration relative to dose-adjusted $AUC_{inf}$ following IM administration. |

Individual PK parameters were tabulated and summarized. The following summary statistics were presented for PK parameters: N, arithmetic mean, SD of the arithmetic mean, geometric mean, SD of the geometric mean, median, minimum, and maximum. $T_{max}$ were presented as N, median, minimum, and maximum.
Statistical Analysis of PK Parameters:
Comparisons of $C_{max}$, $AUC_{0-t}$, and $AUC_{0-inf}$ administration of nalmefene were calculated. The relative bioavailability of nalmefene following the 3 IN administrations was determined by comparing the dose-adjusted $AUC_{0-inf}$ after IN administration to that of the IM formulation.

Within an ANOVA framework, comparisons of ln-transformed PK parameters ($C_{max}$ and AUC) were performed using a mixed effects model where sequence, period, and treatment were the independent factors. The 90% confidence interval for the ratio of the geometric least squares means of $C_{max}$ and AUC parameters was constructed for comparison of the three IN formulations to the IM formulation. These 90% confidence intervals were obtained by exponentiation of the 90% confidence intervals for the difference between the least squares means based upon an ln scale.

Safety Data Analyses:

Clinically significant values of systolic and diastolic blood pressure, heart rate, temperature, and respiration rate were presented. Clinically significant ECG changes were presented by dosing session.

Adverse Events:

AEs were coded using the most recent version of the Medical Dictionary of Regulatory Activities (MedDRA) preferred terms and were grouped by system, organ, class (SOC) designation. The severity, frequency, and relationship of AEs to study drugs were presented by preferred term by SOC grouping. Separate summaries were provided for 4 study periods: after each dose, up to the point of the next dose of clinic discharge. Listings of each individual AE including start date, stop date, severity, relationship, outcome, and duration were provided.

Clinical Laboratory Parameters:

Clinically significant concentrations of analytes were presented for each group by dosing session.

Missing Data:

Missing data were not to be imputed. The numbers of data points reflected in summary statistics were indicated by presenting the number of observations.

Example 9: Data Management and Case Report Forms

Data management activities and statistical analytical support were coordinated through the Data Management Center.

Data Collection:

Data were collected at the study sites on source documents, which were transcribed at the site into case report forms (CRFs). The CRFs were supplied by the Data Management Center. CRFs were to be completed on an ongoing basis during the study. The medical chart and the source documents were the source of verification of data. Completed CRFs were collected by clinical monitors after monitoring against the source documents on a regular basis throughout the trial. The Investigator was responsible for maintaining accurate, complete and up-to-date records for each subject. The Investigator was also responsible for maintaining any source documentation related to the study, including clinical laboratory data, ECG tracings, etc.

Case Report Form Completion:

Electronic CRFs (eCRF) were provided for each subject. The subject identifiers and actual date (and time, if applicable) of each assessment were entered in the eCRFs. The final, completed eCRF for each subject were signed and dated by the Investigator on the appropriate CRF page to signify that he/she had reviewed it and certified it to be complete and accurate.

Data Editing and Control:

Data received at the Data Management Center were reviewed, verified and edited prior to being entered into the main study database. If incomplete or inaccurate data were found, a data clarification request was forwarded to the clinical site for a response. The site resolved data inconsistencies and errors prior to returning data to the Data Management Center. All corrections and changes to the data were reviewed prior to being entered into the main study database. Data entry into the database utilized a single-data entry procedure with 100% quality control verification of all data entered into the database.

The Investigator agreed to routine data audits by Sponsor's appointed monitors to assure that data submitted on the appropriate forms agreed with source documents at the sites. They also verified that investigational agents had been properly stored and accounted for, subject informed consent for study participation had been obtained and documented in the subject's progress notes, all essential documents in accordance with GCP guidelines were on file, and sites were conducting the study according to the research protocol. Any inconsistencies were resolved, and any changes to the data forms were made using established Data Management Center procedures.

Data Processing:

A database was constructed from the eCRFs that captured each item of data from each CRF. The data were validated both manually and electronically. The database underwent 100% quality assurance audit before locking and release for statistical analysis.

All AE information was entered into the main study database from the AE CRF. AEs were coded using both the preferred term and system, organ, class designation using the most current version of MedDRA at the time of database closure.

Study Documentation and Records Retention:

Study documentation included all eCRFs, data correction forms, workbooks, source documents, monitoring logs and appointment schedules, sponsor and investigator correspondence and regulatory documents (e.g., signed protocol and amendments, IRB correspondence and approved consent form and signed informed consent form, statement of Investigator form, and clinical supplies receipt and distribution records).

Source documents included all original recordings of observations or notations of clinical activities and all reports and records necessary for the evaluation and reconstruction of the clinical research study. Accordingly, source documents included, but were not limited to, laboratory reports, ECG tracings, X-rays, radiologist reports, subject diaries, biopsy reports, ultrasound photographs, subject progress notes, hospital charts or pharmacy records and any other similar reports or records of any procedure performed in accordance with the protocol.

Whenever possible, the original recording of an observation was retained as the source document; however, a photocopy was acceptable if it was a clear, legible, and exact duplication of the original document.

Government agency regulations and directives required that the investigator retain all study documentation pertaining to the conduct of a clinical trial. These documents are to be kept for a minimum of 2 years after discontinuation of the IND or two years after the approval of an NDA.

Confidentiality:

Confidentiality of Data:

Attention was drawn to the regulations promulgated by the Food and Drug Administration (FDA) under the Freedom of Information Act providing, in part, that proprietary information furnished to clinical investigators and IRBs be kept confidential by the FDA only if maintained in confidence by the clinical investigator and IRB.

By signing this protocol, the Investigator affirmed to NIDA that information furnished to the investigator by NIDA will be maintained in confidence and such information will be divulged to the IRB, expert committee; affiliated institution; and employees only under an appropriate understanding of confidentiality with such board or committee, affiliated institution and employees.

Confidentiality of Subject Records:

To maintain subject confidentiality, all laboratory specimens, eCRFs, reports and other records were identified by a coded study subject number and alpha code only. Research and clinical records were stored in a locked cabinet. Only research staff, the NIDA monitoring contractor, and NIDA program officials had access to the records. Subject information was not released without written permission, except as necessary for monitoring by the FDA, the NIDA monitoring contractor, or NIDA personnel.

Example 10: Evaluation and Reporting Adverse Events and Serious Adverse Events

General Procedure:

AEs were recorded after the first dose of study drug was administered. AEs were reported on an AE CRF. The severity of the event following the guidance below was reported. The relatedness of the event to the study drug administration according to the guidance below was reported.

Severity of Events:

Mild: awareness of symptom, but easily tolerated; Moderate: discomfort enough to cause interference with usual activity; Severe: incapacitating with inability to work or do usual activity.

Relatedness of Events:

The study physician was responsible for defining, in his/her best judgment, the relationship of the AE/SAE to the study drug. The degree of certainty for which the AE/SAE was attributed to the study drug or alternative causes (e.g., natural history of the underlying disease, concomitant therapies, etc.) was determined by how well the experience was understood in terms of one or more of the following:

Exposure: is there evidence that the subject was exposed to the study drug?

Timing of the administration of study drug: did the AE/SAE follow in a reasonable temporal sequence from administration of the study drug?

Consistency with study drug safety profile: known pharmacology and toxicology of the study drug in animals and man; reaction of similar nature having been previously described with the study drug.

Alternative explanations for the adverse event such as concomitant medications, concurrent illness, non-medicinal therapies, diagnostic tests, procedures or other confounding findings.

Response to discontinuation of the study drug: terms and definitions to be used in assessing the study drug relationship to the AE/SAE were:

Unknown: this category was to be used only if the cause of the AE/SAE was not possible to determine;

Definitely Not Related: the subject did not receive study drug, the temporal sequence of the AE/SAE onset relative to administration of the study drug was not reasonable, or there was another obvious cause of the AE/SAE.

Unlikely Related: there was evidence of exposure to the study drug or there was another more likely cause of the AE/SAE.

Possibly Related: there was evidence of exposure to the study drug, the temporal sequence of the AE/SAE onset relative to administration of the study drug was reasonable, but the AE/SAE could have been due to another equally likely cause.

Probably Related: there was evidence of exposure to the study drug, the temporal sequence of the AE/SAE onset relative to administration of the study drug was reasonable, and the AE/SAE was more likely explained by the study drug than by any other cause.

Definitely Related: there was evidence of exposure to the study drug, the temporal sequence of the AE/SAE onset relative to administration of the study drug was reasonable, the AE/SAE was more likely explained by the study drug than by any other cause, and the AE/SAE showed a pattern consistent with previous knowledge of the study drug or study drug class.

Specific Instructions—Laboratory/ECG Adverse Event:

A laboratory or ECG AE is any clinically significant worsening in a test variable that occurs during the study, whether considered to be study drug related. For each such change, information requested on date of test, severity, likelihood of a relationship to study drug, change in study drug dosage due to the AE, and treatment required were provided.

All laboratory AEs were specified as an increased or decreased test result (e.g., "increased glucose," "decreased potassium") or as a term that implies an abnormality (e.g., hyperkalemia, azotemia, hypokalemia, or bradycardia). Any abnormal laboratory value that was considered not clinically significant was recorded as such on the clinical laboratory report CRF along with a comment providing justification for that determination.

Serious Adverse Event and Unexpected Adverse Event Reporting:

24-hour Reporting Requirements:

Any serious adverse event, including death due to any cause, which occurred to any subject from the time of admission through discharge whether related to the study drug, was reported within 24 hours to the NIDA Medical Monitor and the NIDA Project Officer via email.

Follow-Up of all Adverse Events/Serious Adverse Events:

All adverse medical events were followed until they were resolved, or until all attempts to determine the resolution of the AE/SAE were exhausted. This required an extended hospitalization period or a change in status from outpatient to inpatient. All treatments, outcomes and information regarding whether the subject was referred to their Primary Care Provider for additional follow-up was recorded in the source document. All serious and unexpected AEs occurring up to the final safety evaluation were reported. All follow-up Day 18-20 AEs were recorded and followed to resolution only if they were serious, or if the study physician assessed them to be clinically significant.

The investigator was required to provide the Medical Monitor and the IND Sponsor with all relevant follow-up information necessary to facilitate a thorough understanding of the event and judgment regarding the relationship to the study drug.

Reporting to the FDA:

The IND Sponsor was required to report SAEs to the FDA:

in 7 days if the SAE was unexpected (or, if expected, unusually serious or rarely seen), life-threatening or lethal, and at least possibly related to the study drug, with a follow-up written report in 8 days;

in 15 days if the SAE was unexpected (or, if expected, unusually serious or rarely seen), but not immediately life-threatening; and in an annual report in all other cases.

Example 11: Summary of PK Parameters

Table 2, below provides the mean (% CV) plasma concentrations of nalmefene following a single intranasal and intramuscular administration of nalmefene to healthy subjects. The coefficient of variability, expressed as a percent (% CV) is provided within parenthesis.

TABLE 2

Mean (% CV) Plasma Concentrations of Nalmefene Following a Single Intranasal and Intramuscular Administration of Nalmefene to Healthy Subjects

| Hour | 3 mg IN Mean | (SD) | 3 mg + 0.25% Intravail IN Mean | (SD) | 1.5 mg IN Mean | (SD) | 1.5 mg IM Mean | (SD) |
|---|---|---|---|---|---|---|---|---|
| 0.0 | 0.0 | (NC) | 0.0 | (NC) | 0.0 | (NC) | 0.0 | (NC) |
| 0.04 | 0.0 | (NC) | 0.167 | (183) | 0.0 | (NC) | 0.0 | (NC) |
| 0.08 | 0.0 | (NC) | 0.931 | (128) | 0.0 | (NC) | 0.457 | (120) |
| 0.17 | 0.124 | (171) | 3.69 | (94.7) | 0.0175 | (374) | 1.01 | (57.6) |
| 0.25 | 0.392 | (125) | 4.38 | (74.0) | 0.159 | (96.2) | 1.43 | (70.8) |
| 0.33 | 0.814 | (109) | 3.53 | (60.5) | 0.285 | (74.7) | 1.33 | (47.5) |
| 0.50 | 1.01 | (67.0) | 3.20 | (52.1) | 0.468 | (53.2) | 1.19 | (31.7) |
| 0.75 | 1.40 | (56.7) | 2.86 | (45.4) | 0.691 | (59.6) | 1.14 | (25.2) |
| 1.0 | 1.68 | (55.5) | 2.54 | (44.1) | 0.757 | (55.4) | 1.08 | (28.0) |
| 2.0 | 1.98 | (47.2) | 1.99 | (46.6) | 0.872 | (51.3) | 1.03 | (37.3) |
| 3.0 | 1.53 | (47.4) | 1.57 | (49.4) | 0.712 | (51.4) | 0.878 | (35.4) |
| 4.0 | 1.22 | (47.0) | 1.32 | (51.5) | 0.578 | (50.0) | 0.798 | (31.5) |
| 6.0 | 0.895 | (45.8) | 0.910 | (45.9) | 0.400 | (51.2) | 0.688 | (27.0) |
| 8.0 | 0.675 | (44.1) | 0.664 | (52.9) | 0.285 | (71.8) | 0.603 | (31.7) |
| 12.0 | 0.461 | (48.7) | 0.429 | (62.7) | 0.141 | (126) | 0.470 | (44.5) |
| 16.0 | 0.302 | (67.8) | 0.279 | (86.2) | 0.0799 | (170) | 0.298 | (74.2) |
| 24.0 | 0.125 | (126) | 0.118 | (149) | 0.0189 | (374) | 0.128 | (134) |
| 30.0 | 0.0559 | (201) | 0.0532 | (201) | 0.0 | (NC) | 0.0740 | (164) |
| 36.0 | 0.0151 | (374) | 0.0149 | (374) | 0.0 | (NC) | 0.0 | (NC) |
| 48.0 | 0.0 | (NC) | 0.0 | (NC) | 0.0 | (NC) | 0.0 | (NC) |
| 60.0 | 0.0 | (NC) | 0.0 | (NC) | 0.0 | (NC) | 0.0 | (NC) |
| 72.0 | 0.0 | (NC) | 0.0 | (NC) | 0.0 | (NC) | 0.0 | (NC) |

N = 10-14
lower limit of quantitation (LLOQ) = 0.2 ng/mL

Figure 1:
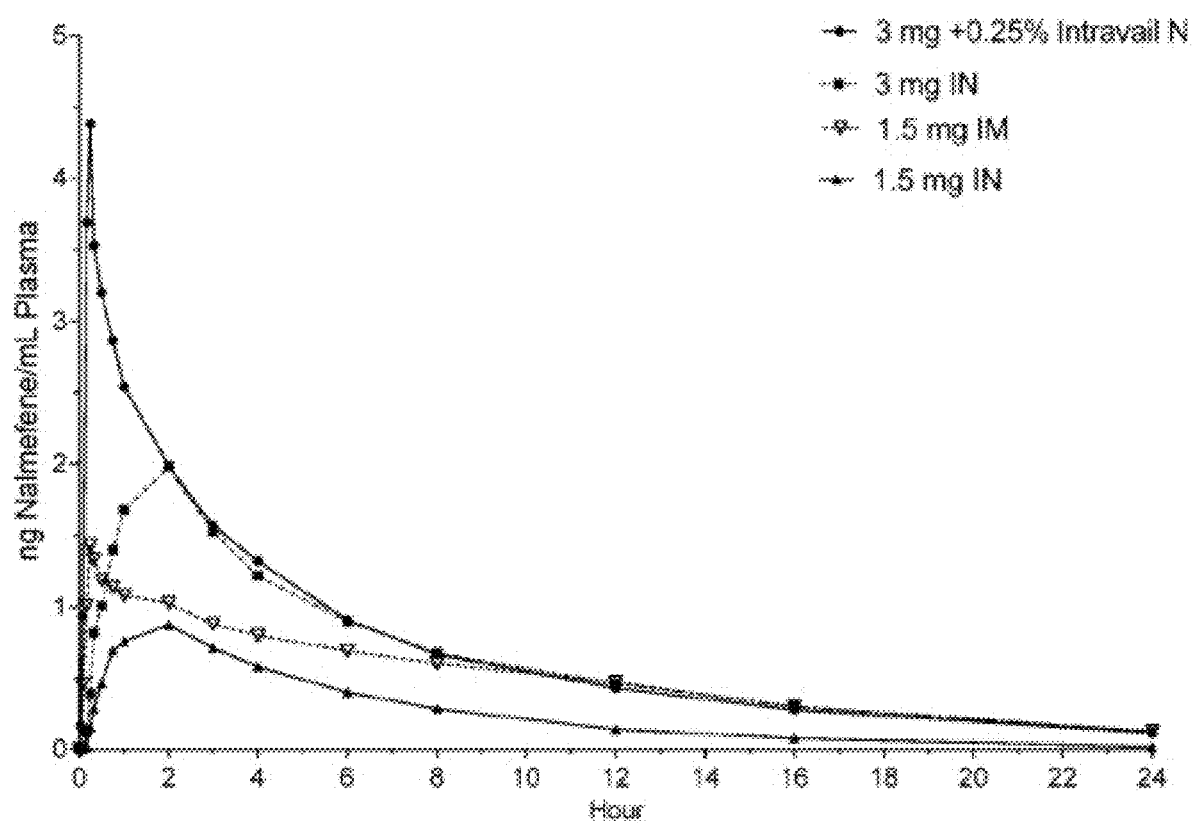
FIG. 1 is a linear plot showing the mean plasma concentrations of nalmefene following a single intramuscular injection and a comparison with IN administration with and without 0.25% Intravail® (dodecyl maltoside).
Figure 2:
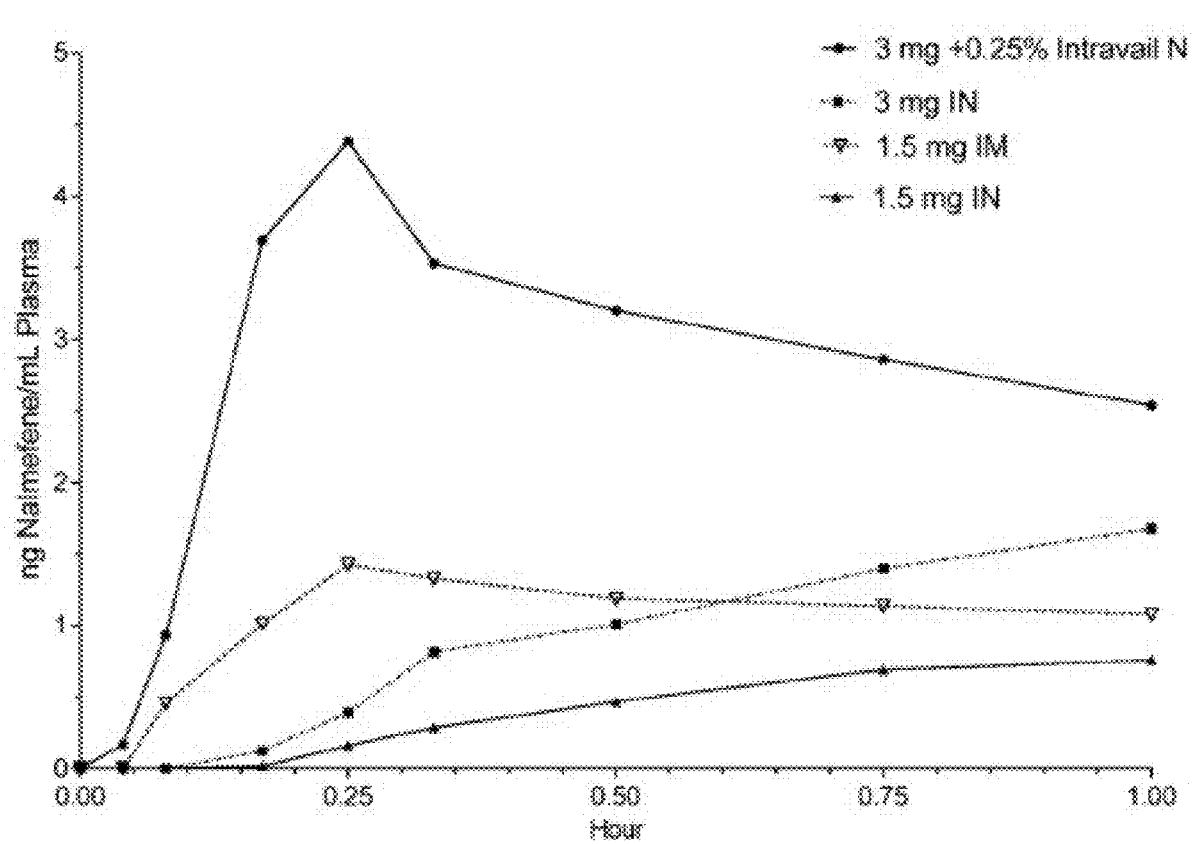
FIG. 2 is a linear plot of the data depicted in FIG. 1 from 0 to 1 hour.
Figure 3:
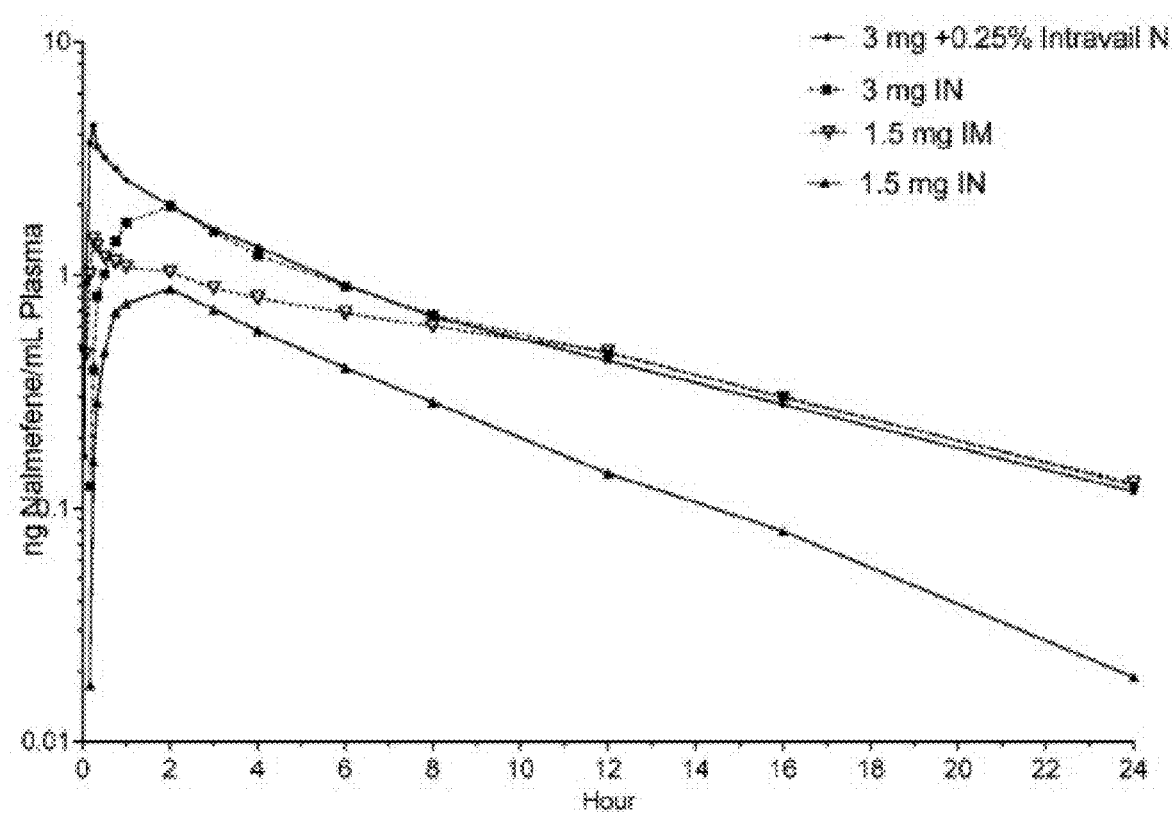
FIG. 3 is a semi-log plot of the data depicted in FIG. 1. These data are obtained from a previous study, in which the $T_{max}$ was 0.5 h (30 min).
Figure 4:
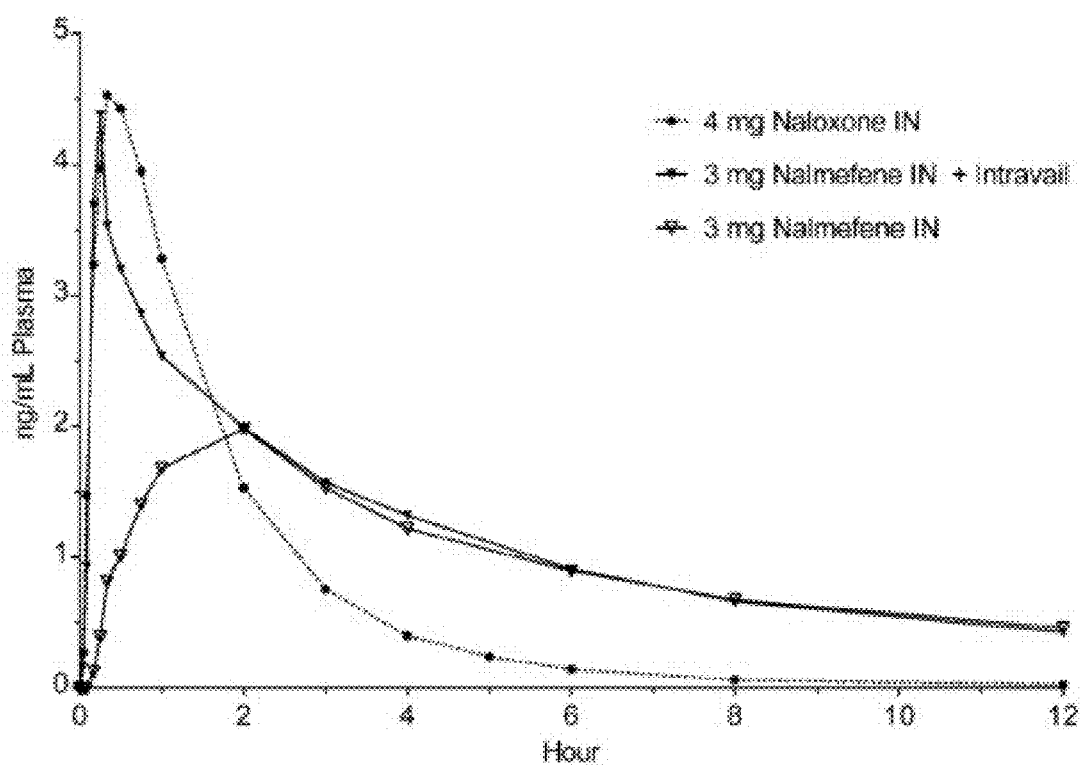
FIG. 4 is a graphical linear plot showing the comparison of plasma concentrations of 4 mg naloxone IN (0.1 ml of 40 mg/ml solution) compared to 3 mg nalmefene (0.1 ml of 30 mg/ml solution) IN with and without 0.25% Intravail (dodecyl maltoside). These data are obtained from a previous study, in which the $T_{max}$ was 0.5 h (30 min).

As can be seen from FIGS. 1 and 2 as well as Table 3, below, Intravail® (dodecyl maltoside) reduces the $T_{max}$ of IN nalmefene to make it even more rapid than an IM injection. Without Intravail®, the $T_{max}$ of 2 hours would make IN nalmefene unusable as a first-response (rescue) medication for overdose, but still suitable as a second or follow-up medication due to its long half-life ($T_{1/2}$). The dose-normalized $C_{max}$ is increased dramatically with Intravail® even when compared with IM administration (as seen in row 2). As seen from the data, Intravail® is a true absorption enhancer; it speeds up and enhances absorption, but does not alter the bioavailability of IN nalmefene (relative to IM); nor does it change the half-life.

It should be noted that while Intravail® did not alter the AUC for IN nalmefene, the results with naltrexone were different. With naltrexone, the AUC increased significantly (data not presented). This important difference could not be predicted based on structure of the opioid antagonists, or the function of these moieties as opioid antagonists.

TABLE 3

Mean Pharmacokinetics of Nalmefene Following a Single Intranasal and Intramuscular Administration of Nalmefene to Healthy Subjects

| Parameter (units) | 3 mg IN[a] Mean | (% CV) | 3 mg plus 0.25% Intravail[a] Mean | (% CV) | 1.5 mg IN[a] Mean | (% CV) | 1.5 mg IM[b] Mean | (% CV) |
|---|---|---|---|---|---|---|---|---|
| $C_{max}$ (ng/mL) | 2.19 | (42.8) | 4.94 | (57.2) | 0.969 | (45.9) | 1.67 | (50.6) |
| $C_{max}/D$ (ng/mL/mg) | 0.731 | (42.8) | 1.65 | (57.2) | 0.646 | (45.9) | 1.12 | (50.6) |
| $T_{max}$ (h)[e] | 2.00 | (0.33, 3.00) | 0.25 | (0.17, 1.00) | 2.00 | (1.00, 3.00) | 0.33 | (0.25, 8.00) |
| $AUC_{0-t}$ (ng h/mL) | 15.0 | (54.2) | 17.3 | (58.6) | 5.50 | (69.3) | 11.6 | (38.4) |
| $AUC_{0-inf}$ (ng h/mL) | 17.9 | (50.5) | 19.8 | (54.3) | 8.38 | (58.8) | 14.8 | (35.6) |
| $AUC_{0-inf}/D$ (ng h/mL/mg) | 5.97 | (50.5) | 6.62 | (54.3) | 5.59 | (58.8) | 9.86 | (35.6) |
| $AUC_{extrap}$ (%) | 17.9 | (30.7) | 14.6 | (41.7) | 30.6 | (29.8) | 22.6 | (45.3) |
| Lambda z (h$^{-1}$) | 0.101 | (35.9) | 0.117 | (41.5) | 0.131 | (46.3) | 0.094 | (35.5) |
| Half-life (h) | 7.84 | (38.2) | 6.78 | (35.6) | 6.74 | (54.7) | 8.45 | (42.7) |
| CL/F (L/h) | 225 | (66.3) | 209 | (63.7) | 233 | (47.9) | 115 | (36.8) |

[a]N = 14
[b]N = 13
[c]Median (minimum, maximum)

Formulations of Intranasal Naltrexone

The following tables set forth examples of formulations of nalmefene for intranasal administration for the treatments disclosed herein. Table 4 sets forth simple aqueous solution formulations such as those used in the experiment above, to be dispensed in increments of about 100 μL.

TABLE 4

| Ex. | Nalmdose HCl, dose (mg) | Absorption Enhancer | μL per dose | Conc., mg/mL |
|---|---|---|---|---|
| 1 | 1 | n/a | 100 | 10 |
| 2 | 1 | Intravail 0.25% | 100 | 10 |
| 3 | 2 | n/a | 100 | 20 |
| 4 | 2 | Intravail 0.25% | 100 | 20 |
| 5 | 3 | n/a | 100 | 30 |
| 6 | 3 | Intravail 0.25% | 100 | 30 |
| 7 | 4 | n/a | 100 | 40 |
| 8 | 4 | Intravail 0.25% | 100 | 40 |
| 9 | 5 | n/a | 100 | 50 |
| 10 | 5 | Intravail 0.25% | 100 | 50 |
| 11 | 6 | n/a | 100 | 60 |
| 12 | 6 | Intravail 0.25% | 100 | 60 |
| 13 | 7 | n/a | 100 | 70 |
| 14 | 7 | Intravail 0.25% | 100 | 70 |
| 15 | 8 | n/a | 100 | 80 |
| 16 | 8 | Intravail 0.25% | 100 | 80 |

Table 5 sets forth formulations for intranasal administration in 100 μL of an aqueous solution including excipients such as an isotonicity agent, a stabilizing agent, and/or a compound which acts as a preservative or surfactant. EDTA stands for disodium edetate and BZK stands for benzalkonium chloride.

TABLE 5

| Ex. | Nalmefene HCl | Absorption Enhancer | Isotonicity Agent | Stabilizing Agent | Preservative/ Surfactant |
|---|---|---|---|---|---|
| 17 | 3 mg | n/a | NaCl 0.74% | n/a | n/a |
| 18 | 3 mg | n/a | NaCl 0.74% | EDTA 0.2% | n/a |
| 19 | 3 mg | n/a | NaCl 0.74% | n/a | BZK 0.01% |
| 20 | 3 mg | n/a | NaCl 0.74% | EDTA 0.2% | BZK 0.01% |
| 21 | 3 mg | Intravail 0.25% | NaCl 0.74% | n/a | n/a |
| 21 | 3 mg | Intravail 0.25% | NaCl 0.74% | EDTA 0.2% | n/a |
| 22 | 3 mg | Intravail 0.25% | NaCl 0.74% | n/a | BZK 0.01% |
| 23 | 3 mg | Intravail 0.25% | NaCl 0.74% | EDTA 0.2% | BZK 0.01% |
| 24 | 3 mg | Intravail 0.18% | NaCl 0.74% | n/a | n/a |
| 25 | 3 mg | Intravail 0.18% | NaCl 0.74% | EDTA 0.2% | n/a |
| 26 | 3 mg | Intravail 0.18% | NaCl 0.74% | n/a | BZK 0.01% |
| 27 | 3 mg | Intravail 0.18% | NaCl 0.74% | EDTA 0.2% | BZK 0.01% |
| 28 | 3 mg | Benzalkonium chloride, 0.01% | NaCl 0.74% | n/a | n/a |
| 29 | 3 mg | Benzalkonium chloride, 0.01% | NaCl 0.74% | EDTA 0.2% | n/a |
| 30 | 3 mg | Benzalkonium chloride, 0.01% | NaCl 0.74% | n/a | BZK 0.01% |
| 31 | 3 mg | Benzalkonium chloride, 0.01% | NaCl 0.74% | EDTA 0.2% | BZK 0.01% |

Also provided are examples 1-31A which additionally contain an amount of hydrochloric acid sufficient to achieve a pH of 3.5-5.5. The acid should be pharmaceutically acceptable, for example, hydrochloric acid.

Although the present invention has been described with reference to specific details of certain embodiments thereof in the above examples, it will be understood that modifications and variations are encompassed within the spirit and scope of the invention.

Example 12: Two-Period, Two-Treatment, Randomized Crossover Study of the Pharmacokinetics of Nalmefene by Intranasal and Intramuscular Administration in Healthy Volunteers This study was conducted to determine the pharmacokinetics of nalmefene when given intranasally (IN) compared to a dose of nalmefene when given intramuscularly (IM). The purpose was to compare the blood levels of nalmefene when given IN to nalmefene when given IM, and to evaluate the safety and tolerability of nalmefene IN.

This was an open-label, randomized, 2-period, 2-treatment, 2-sequence, crossover study in 68 healthy volunteers. Subjects were assigned to each of the 2 possible sequences. Each subject received 2 treatments during the 2 dosing periods: An intranasal (IN) dose of 3 mg nalmefene hydrochloride and an intramuscular (IM) dose of 1.0 mg nalmefene hydrochloride, with a 4 day washout period between doses. Screening occurred up to 28 days before baseline admission, subjects then stayed in the inpatient facility for 7 days to complete the treatment phase of the study and were discharged following completion of the discharge procedures at the end of the last period. Subjects were called 3 to 5 days after discharge to inquire concerning adverse events (AEs) and concomitant medications since discharge.

The IN dosage form of nalmefene was formulated as follows.

| Component | mg/mL | Unit dose (100 microliter) |
|---|---|---|
| Nalmefene HCl[a] | 30.0 | 3.0 mg |
| Sodium chloride | 8.66 | 0.866 mg |
| Dodecyl maltoside | 2.5 | 0.25 mg |
| Di sodium edetate dihydrate | 2.0 | 0.2 mg |
| Benzalkonium chloride (50% solution) | 0.40 | 0.04 mg |
| Purified water | q.s. ad 1.0 mL | q.s. ad 100 microliter |

[a]Nalmefene HCl adjusted for potency and water content to account for the monohydrate.

One spray of the above IN formulation delivered 0.1 mL of 30 mg/mL nalmefene HCl, i.e., 3 mg nalmefene HCL in one nostril ("Treatment A (test)"). The IN nalmefene was delivered via a single-use spray device offered by Aptar Pharma, Inc. to deliver the 100 μL to the nasal cavity. Doses were administered with the subjects in a fully supine position. Each subject remained fully supine for approximately 1 hour (±15 minutes) post-dose. Subjects were instructed to hold their breath during administration of the nasal spray to the nose.

The specification for spray pattern used in the study was as follows:

Spray pattern at 3 cm
  Shape: ellipsoidal
  $D_{max}$ Mean: ≤37 mm
  Ovality: 1.0-3.0
Spray pattern at 6 cm
  Shape: ellipsoidal
  $D_{max}$ Mean: ≤95 mm
  Ovality: 1.0-3.0

The specification for droplet size distribution was as follows:

Droplet size distribution at 3 cm
  D10 Mean: 5-24 μm
  D50 Mean: 12-48 μm
  D90 Mean: 25-89 μm
  %<10 μm: NMT 10%
  Span mean: Not more than ("NMT") 2
Droplet size distribution at 6 cm
  D10 Mean: 8-30 μm
  D50 Mean: 15-53 μm
  D90 Mean: 24-92 μm
  <10 μm: NMT 10%
  Span mean: NMT 2

The prevalent median droplet size was between about 30 and about 100 μm. Plume geometry, droplet size and DSD of the delivered plume subsequent to spraying were measured under specified experimental and instrumental conditions by appropriate and validated and/or calibrated analytical procedures known in the art. These include photography, laser diffraction, and impaction systems (cascade impaction, NGI). In certain embodiments, the specification for the spray pattern is as follows: spray pattern at 3 cm, ellipsoidal, $D_{max}$ less than or equal to 37 mm, and ovality between 1.0 and 3.0. In another embodiment, the specification for the spray pattern is as follows: spray pattern at 3 cm, ellipsoidal, $D_{max}$ less than or equal to 95 mm, and ovality between 1.0 and 3.0.

Droplet size distribution can be controlled in terms of ranges for the D10, D50, D90, span RD90-D10)/D501, and percentage of droplets less than 10 mm. In certain embodiments, the formulation will have a narrow DSD. In certain embodiments, the formulation will have a D (v,50) of 30-70 nm and a D (v, 90)<100 nm.

The IN formulation when dispensed by actuation from the Aptar device produced a uniform circular plume with an ovality ratio close to 1. Ovality ratio is calculated as the quotient of the maximum diameter ($D_{max}$) and the minimum diameter ($D_{min}$) of a spray pattern taken orthogonal to the direction of spray flow (e.g., from the "top"). In certain cases, the ovality ratio was less than ±2.0, or less than ±1.5, or less than ±1.3, or less than ±1.2, or less than ±1.1. In other cases, the ovality ratio was about =1.0.

The IM dosage form of nalmefene comprised nalmefene hydrochloride dissolved in normal saline solution for injection with the pH adjusted to 3.9 using dilute HCl. This IM formulation is identical to that listed for REVEX® (nalmefene hydrochloride injection). The IM formulation administered in the study had a concentration of 1.108 mg/mL nalmefene HCl wherein 1.0 mL IM delivered 1.0 mg nalmefene. The 1.0 mL was administered IM in the gluteal muscle ("Treatment B (reference)").

The primary outcome measures of the study were as follows:

1. Maximum plasma concentration (Cmax) (Time Frame: 48 hours)—Maximum concentration of plasma nalmefene comparing IN to IM.
2. Time to maximum plasma concentration (Tmax) (Time Frame: 48 hours)—Time to maximum concentration of plasma nalmefene comparing IN to IM.
3. Area under the curve (AUC) (Time Frame: 48 hours)—Area under the curve of plasma nalmefene comparing IN to IM.
4. Half-life (t½) (Time Frame: 48 hours)—Half-life of plasma nalmefene comparing IN to IM.

Patients eligible for the study were as follows:

Inclusion Criteria:
  Male or female aged 18 to 55 years inclusive
  BMI ranging from 18 to 30 kg/m2, inclusive
  Adequate venous access
  Subjects must be non-smokers
  Patients ineligible for the study were as follows:
  History of clinically significant disease
  Significant trauma injury, major surgery, open biopsy within 30 days prior to screening
  Following an abnormal diet 4 weeks prior to screening
  Use of over the counter medications, dietary supplements, herbal products, vitamins or opioid analgesics 14 days before intervention
  Use of enzyme altering drugs 30 days before intervention
  Use of nasal products 28 days before intervention and throughout the study
  Previous or current opioid, alcohol, or other drug dependence
  Donated or received blood 30 days before intervention
  Women who are pregnant or breastfeeding at screening
  Women of childbearing potential unless surgically sterile or use effective contraception
  Current or recent upper respiratory tract infection
  Allergic to nalmefene The results of the study revealed that nasal nalmefene achieved significantly higher plasma concentrations compared to an intramuscular injection (p<0.0001). The time for nasal nalmefene to achieve maximum plasma concentrations ($T_{max}$) was approximately 15 minutes. The plasma half-life of nasal nalmefene was approximately 11 hours. This is significantly longer than intranasal naloxone, currently the only FDA-approved treatment for opioid overdose, which has a half-life of approximately 2 hours.

As shown in FIGS. 6 and 7, IN nalmefene achieved high serum concentrations (about 10 ng/ml) quickly after administration, and such concentrations were significantly higher than IM nalmefene. Additional data are provided in the tables below.

As shown in FIG. 8, the mean concentration (ng/mL) of 3 mg nalmefene IN is significantly higher than the 1 mg nalmefene IM at the corresponding time points.

TABLE 6

Table 6 Descriptive Statistics for Plasma Concentration-Time Data of Nalmefene after Intranasal (IN) Administration of 3.0 mg of Nalmefene Hydrochloride (Treatment A) and Intramuscular (IM) Administration of 1.0 mg of Nalmefene Hydrochloride (Treatment B) - PK Population

| Treatment | Time (h) | n | Mean (ng/mL) | SD (ng/mL) | CV % | Min (ng/mL) | Median (ng/mL) | Max (ng/mL) |
|---|---|---|---|---|---|---|---|---|
| A | 0.00 | 66 | 0.00146 | 0.0104 | 710 | 0.00 | 0.00 | 0.0833 |
|   | 0.0420 | 61 | 0.818 | 1.31 | 159 | 0.0105 | 0.213 | 5.89 |
|   | 0.0830 | 64 | 4.43 | 4.83 | 109 | 0.198 | 1.76 | 17.7 |
|   | 0.125 | 64 | 8.41 | 7.04 | 83.7 | 0.821 | 6.20 | 27.1 |
|   | 0.167 | 66 | 10.0 | 7.47 | 74.4 | 1.19 | 7.92 | 30.4 |
|   | 0.250 | 65 | 9.53 | 5.70 | 59.9 | 1.57 | 8.11 | 24.8 |
|   | 0.333 | 66 | 8.23 | 4.03 | 48.9 | 2.14 | 7.53 | 19.7 |
|   | 0.500 | 66 | 6.25 | 2.38 | 38.1 | 0.549 | 5.86 | 12.9 |
|   | 0.750 | 66 | 5.16 | 1.31 | 25.4 | 2.39 | 4.89 | 7.93 |
|   | 1.00 | 66 | 4.64 | 0.998 | 21.5 | 2.30 | 4.68 | 6.67 |
|   | 2.00 | 66 | 4.03 | 0.779 | 19.4 | 2.01 | 3.99 | 5.99 |
|   | 3.00 | 66 | 3.17 | 0.679 | 21.4 | 1.55 | 3.13 | 5.39 |
|   | 4.00 | 66 | 2.52 | 0.570 | 22.6 | 1.18 | 2.49 | 4.09 |
|   | 6.00 | 66 | 1.69 | 0.452 | 26.7 | 0.627 | 1.65 | 2.99 |
|   | 8.00 | 66 | 1.23 | 0.333 | 27.1 | 0.547 | 1.18 | 2.40 |
|   | 12.0 | 66 | 0.870 | 0.208 | 23.9 | 0.445 | 0.832 | 1.59 |
|   | 18.0 | 66 | 0.529 | 0.139 | 26.2 | 0.245 | 0.518 | 0.881 |
|   | 24.0 | 66 | 0.366 | 0.114 | 31.1 | 0.168 | 0.341 | 0.770 |
|   | 36.0 | 66 | 0.171 | 0.0626 | 36.7 | 0.0534 | 0.165 | 0.319 |
|   | 48.0 | 66 | 0.0875 | 0.0380 | 43.4 | 0.0276 | 0.0843 | 0.194 |
| B | 0.00 | 68 | 0.00352 | 0.00712 | 202 | 0.00 | 0.00 | 0.0281 |
|   | 0.0420 | 64 | 0.123 | 0.157 | 128 | 0.00 | 0.0721 | 0.905 |
|   | 0.0830 | 64 | 0.599 | 0.852 | 142 | 0.0344 | 0.298 | 5.22 |
|   | 0.125 | 66 | 1.01 | 1.15 | 114 | 0.0739 | 0.630 | 5.67 |
|   | 0.167 | 68 | 1.23 | 1.18 | 96.4 | 0.124 | 0.835 | 6.43 |
|   | 0.250 | 67 | 1.19 | 0.874 | 73.7 | 0.200 | 0.851 | 3.75 |
|   | 0.333 | 68 | 1.20 | 0.694 | 58.1 | 0.244 | 0.984 | 2.91 |
|   | 0.500 | 67 | 1.11 | 0.715 | 64.7 | 0.317 | 0.945 | 4.95 |
|   | 0.750 | 68 | 0.990 | 0.431 | 43.5 | 0.350 | 0.879 | 2.17 |
|   | 1.00 | 68 | 0.931 | 0.366 | 39.3 | 0.415 | 0.829 | 1.88 |
|   | 2.00 | 68 | 0.972 | 0.397 | 40.9 | 0.482 | 0.858 | 1.93 |
|   | 3.00 | 68 | 0.896 | 0.361 | 40.3 | 0.441 | 0.818 | 1.69 |
|   | 4.00 | 68 | 0.824 | 0.320 | 38.8 | 0.346 | 0.770 | 1.47 |
|   | 6.00 | 68 | 0.688 | 0.229 | 33.3 | 0.302 | 0.673 | 1.24 |
|   | 8.00 | 68 | 0.670 | 0.240 | 35.9 | 0.244 | 0.629 | 1.47 |
|   | 12.0 | 68 | 0.538 | 0.153 | 28.4 | 0.283 | 0.516 | 0.898 |
|   | 18.0 | 68 | 0.360 | 0.129 | 36.0 | 0.162 | 0.341 | 0.721 |
|   | 24.0 | 68 | 0.223 | 0.0777 | 34.8 | 0.103 | 0.203 | 0.449 |
|   | 36.0 | 68 | 0.0968 | 0.0468 | 48.3 | 0.0304 | 0.0915 | 0.326 |
|   | 48.0 | 68 | 0.0491 | 0.0236 | 48.1 | 0.0159 | 0.0436 | 0.132 |

Treatment A = 3.0 mg nalmefene hydrochloride IN dose (one 0.1 mL spray of a 30 mg/mL solution in one nostril)
Treatment B = 1.0 mg nalmefene IM dose (1.0 mL of 1.108 mg/mL nalmefene hydrochloride solution as a single dose in the gluteal muscle)
Note:
Plasma samples analyzed using a bioanalytical method with a validated range 0.0100 to 10.0 ng/mL; concentrations below limit of quantification set to zero (0.00 ng/mL) in the data summarization

TABLE 7

Table 7: Plasma PK Parameters of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $T_{max}$ (h) | $C_{max}$ (ng/mL) | $AUC_{last}$ (h*ng/mL) | $AUC_{inf}$ (h*ng/mL) | $AUC_{Extrap}$ (%) | $K_{el}$ (1/h) | $T_{1/2}$ (h) | CL/F (L/h) | $V_z$/F (L) | $T_{last}$ (h) | $C_{last}$ (ng/mL) |
|---|---|---|---|---|---|---|---|---|---|---|---|---|---|---|
| A | 904 | 1 | AB | 0.333 | 10.5 | 40.5 | 41.6 | 2.48 | 0.0708 | 9.79 | 72.2 | 1020 | 48.0 | 0.0731 |
|   | 905 | 2 | BA | 0.333 | 4.11 | 33.6 | 35.7 | 5.85 | 0.0541 | 12.8 | 84.0 | 1550 | 48.0 | 0.113 |
|   | 906 | 2 | BA | 0.250 | 8.62 | 34.3 | 35.3 | 2.80 | 0.0664 | 10.4 | 84.9 | 1280 | 48.0 | 0.0657 |
|   | 907 | 1 | AB | 0.500 | 2.77 | 23.2 | 24.1 | 3.70 | 0.0591 | 11.7 | 124 | 2110 | 48.0 | 0.0528 |
|   | 913 | 1 | AB | 0.167 | 18.4 | 41.6 | 42.8 | 2.80 | 0.0627 | 11.1 | 70.0 | 1120 | 48.0 | 0.0751 |
|   | 914 | 2 | BA | 0.250 | 23.2 | 53.4 | 54.7 | 2.37 | 0.0614 | 11.3 | 54.9 | 893 | 48.1 | 0.0795 |
|   | 917 | 1 | AB | 0.333 | 8.42 | 45.8 | 52.7 | 13.1 | 0.0281 | 24.7 | 57.0 | 2030 | 48.0 | 0.194 |
|   | 918 | 2 | BA | 0.167 | 15.3 | 43.6 | 44.5 | 1.87 | 0.0786 | 8.82 | 67.5 | 859 | 48.1 | 0.0654 |
|   | 921 | 1 | AB | 0.167 | 15.5 | 23.3 | 23.7 | 1.81 | 0.0752 | 9.22 | 127 | 1690 | 48.0 | 0.0322 |
|   | 922 | 1 | AB | 0.500 | 8.30 | 37.8 | 38.7 | 2.40 | 0.0637 | 10.9 | 77.5 | 1220 | 48.0 | 0.0591 |
|   | 925 | 2 | BA | 0.183 | 19.6 | 39.7 | 41.2 | 3.81 | 0.0566 | 12.3 | 72.7 | 1290 | 48.0 | 0.0888 |
|   | 929 | 2 | BA | 0.333 | 11.8 | 43.1 | 43.8 | 1.60 | 0.0798 | 8.69 | 68.5 | 859 | 48.0 | 0.0559 |
|   | 931 | 1 | AB | 1.00 | 5.00 | 37.4 | 39.5 | 5.37 | 0.0466 | 14.9 | 75.9 | 1630 | 48.0 | 0.0988 |
|   | 932 | 2 | BA | 0.250 | 19.2 | 46.3 | 48.0 | 3.64 | 0.0570 | 12.2 | 62.5 | 1100 | 48.0 | 0.0995 |

TABLE 7-continued

Table 7: Plasma PK Parameters of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $T_{max}$ (h) | $C_{max}$ (ng/mL) | $AUC_{last}$ (h*ng/mL) | $AUC_{inf}$ (h*ng/mL) | $AUC_{Extrap}$ (%) | $K_{el}$ (1/h) | $T_{1/2}$ (h) | CL/F (L/h) | $V_z$/F (L) | $T_{last}$ (h) | $C_{last}$ (ng/mL) |
|---|---|---|---|---|---|---|---|---|---|---|---|---|---|---|
| | 933 | 2 | BA | 0.233 | 11.2 | 45.1 | 47.3 | 4.70 | 0.0517 | 13.4 | 63.4 | 1230 | 48.2 | 0.115 |
| | 938 | 1 | AB | 0.333 | 5.54 | 35.3 | 36.7 | 3.84 | 0.0582 | 11.9 | 81.7 | 1400 | 48.0 | 0.0822 |
| | 940 | 1 | AB | 0.250 | 11.0 | 45.3 | 46.8 | 3.14 | 0.0649 | 10.7 | 64.2 | 989 | 48.1 | 0.0952 |
| | 944 | 2 | BA | 0.250 | 24.8 | 45.0 | 46.0 | 2.08 | 0.0695 | 9.97 | 65.3 | 939 | 48.3 | 0.0664 |
| | 945 | 2 | BA | 0.167 | 22.8 | 47.4 | 49.6 | 4.43 | 0.0482 | 14.4 | 60.5 | 1250 | 48.0 | 0.106 |
| | 948 | 1 | AB | 0.167 | 30.4 | 48.2 | 50.6 | 4.79 | 0.0504 | 13.8 | 59.3 | 1180 | 48.0 | 0.122 |
| | 949 | 2 | BA | 0.167 | 15.9 | 47.6 | 50.3 | 5.44 | 0.0512 | 13.5 | 59.7 | 1170 | 48.0 | 0.140 |
| | 950 | 1 | AB | 0.333 | 11.1 | 46.9 | 48.2 | 2.82 | 0.0658 | 10.5 | 62.2 | 946 | 48.0 | 0.0895 |
| | 954 | 1 | AB | 0.167 | 13.1 | 47.6 | 51.6 | 7.83 | 0.0455 | 15.2 | 58.1 | 1280 | 48.0 | 0.184 |
| | 956 | 1 | AB | 0.167 | 10.3 | 35.9 | 36.5 | 1.72 | 0.0789 | 8.78 | 82.2 | 1040 | 48.0 | 0.0496 |
| | 959 | 1 | AB | 0.0833 | 8.54 | 35.8 | 36.7 | 2.51 | 0.0722 | 9.60 | 81.8 | 1130 | 48.0 | 0.0665 |
| | 960 | 2 | BA | 0.117 | 16.5 | 31.5 | 32.4 | 2.86 | 0.0642 | 10.8 | 92.5 | 1440 | 48.0 | 0.0596 |
| | 962 | 2 | BA | 0.250 | 16.8 | 39.8 | 40.3 | 1.19 | 0.0864 | 8.02 | 74.5 | 862 | 48.0 | 0.0413 |
| | 966 | 1 | AB | 0.117 | 17.9 | 43.7 | 45.8 | 4.50 | 0.0563 | 12.3 | 65.5 | 1160 | 48.0 | 0.116 |
| | 967 | 2 | BA | 0.500 | 6.66 | 58.3 | 60.9 | 4.38 | 0.0614 | 11.3 | 49.2 | 802 | 48.0 | 0.164 |
| | 968 | 1 | AB | 0.133 | 14.4 | 28.0 | 28.6 | 2.23 | 0.0707 | 9.80 | 105 | 1480 | 48.0 | 0.0452 |
| | 970 | 2 | BA | 0.250 | 5.29 | 45.4 | 47.0 | 3.29 | 0.0643 | 10.8 | 63.9 | 994 | 48.0 | 0.0993 |
| | 972 | 2 | BA | 0.250 | 6.62 | 48.4 | 50.2 | 3.62 | 0.0661 | 10.5 | 59.8 | 904 | 48.0 | 0.120 |
| | 976 | 2 | BA | 0.250 | 23.4 | 48.1 | 48.7 | 1.12 | 0.0837 | 8.28 | 61.7 | 737 | 48.0 | 0.0457 |
| | 977 | 1 | AB | 0.267 | 12.0 | 34.0 | 35.0 | 2.81 | 0.0615 | 11.3 | 85.7 | 1390 | 48.0 | 0.0605 |
| | 983 | 1 | AB | 0.250 | 12.3 | 35.8 | 38.5 | 7.02 | 0.0451 | 15.4 | 77.8 | 1730 | 48.0 | 0.122 |
| | 986 | 1 | AB | 0.133 | 9.20 | 38.7 | 39.4 | 1.84 | 0.0742 | 9.34 | 76.2 | 1030 | 48.0 | 0.0539 |
| | 987 | 2 | BA | 0.333 | 8.52 | 33.1 | 34.1 | 2.81 | 0.0600 | 11.6 | 88.1 | 1470 | 48.0 | 0.0574 |
| | 989 | 2 | BA | 0.250 | 7.73 | 32.5 | 33.3 | 2.54 | 0.0651 | 10.6 | 90.0 | 1380 | 48.0 | 0.0551 |
| | 992 | 1 | AB | 0.500 | 5.10 | 41.2 | 43.3 | 4.87 | 0.0593 | 11.7 | 69.3 | 1170 | 48.0 | 0.125 |
| | 995 | 2 | BA | 0.500 | 4.44 | 40.2 | 41.8 | 3.89 | 0.0548 | 12.6 | 71.8 | 1310 | 48.0 | 0.0891 |
| | 997 | 1 | AB | 0.167 | 8.99 | 22.5 | 23.2 | 3.10 | 0.0630 | 11.0 | 129 | 2050 | 48.0 | 0.0453 |
| | 998 | 2 | BA | 0.167 | 9.36 | 42.8 | 44.4 | 3.72 | 0.0635 | 10.9 | 67.5 | 1060 | 48.0 | 0.105 |
| | 999 | 1 | AB | 0.117 | 7.66 | 29.2 | 30.0 | 2.50 | 0.0692 | 10.0 | 100 | 1450 | 48.0 | 0.0520 |
| | 1001 | 2 | BA | 0.167 | 13.5 | 47.0 | 49.6 | 5.25 | 0.0595 | 11.6 | 60.4 | 1020 | 48.0 | 0.155 |
| | 1002 | 1 | AB | 0.250 | 9.23 | 37.4 | 39.1 | 4.25 | 0.0567 | 12.2 | 76.7 | 1350 | 48.0 | 0.0943 |
| | 1004 | 1 | AB | 0.250 | 19.5 | 39.5 | 40.0 | 1.41 | 0.0762 | 9.09 | 75.0 | 983 | 48.0 | 0.0429 |
| | 1005 | 1 | AB | 1.00 | 5.19 | 42.8 | 45.2 | 5.35 | 0.0538 | 12.9 | 66.4 | 1230 | 48.0 | 0.130 |
| | 1008 | 2 | BA | 0.167 | 21.5 | 38.3 | 39.2 | 2.25 | 0.0661 | 10.5 | 76.5 | 1160 | 48.0 | 0.0582 |
| | 1012 | 2 | BA | 0.333 | 12.6 | 48.0 | 50.2 | 4.35 | 0.0637 | 10.9 | 59.7 | 938 | 48.0 | 0.139 |
| | 1015 | 1 | AB | 0.167 | 24.4 | 38.5 | 39.3 | 1.86 | 0.0746 | 9.29 | 76.4 | 1020 | 48.0 | 0.0545 |
| | 1016 | 2 | BA | 0.750 | 4.17 | 22.8 | 23.1 | 1.57 | 0.0758 | 9.14 | 130 | 1710 | 48.2 | 0.0276 |
| | 1017 | 1 | AB | 0.333 | 7.40 | 38.2 | 40.1 | 4.65 | 0.0542 | 12.8 | 74.8 | 1380 | 48.0 | 0.101 |
| | 1018 | 2 | BA | 0.250 | 16.3 | 50.3 | 52.2 | 3.68 | 0.0624 | 11.1 | 57.5 | 921 | 48.0 | 0.120 |
| | 1020 | 1 | AB | 0.350 | 9.66 | 54.1 | 56.6 | 4.38 | 0.0573 | 12.1 | 53.0 | 925 | 48.0 | 0.142 |
| | 1031 | 1 | AB | 0.500 | 4.10 | 39.3 | 42.0 | 6.42 | 0.0508 | 13.6 | 71.5 | 1410 | 48.0 | 0.137 |
| | 1032 | 2 | BA | 0.167 | 9.62 | 30.9 | 31.7 | 2.66 | 0.0659 | 10.5 | 94.6 | 1440 | 48.0 | 0.0557 |
| | 1033 | 1 | AB | 0.167 | 14.0 | 36.4 | 37.4 | 2.91 | 0.0544 | 12.7 | 80.1 | 1470 | 48.0 | 0.0593 |
| | 1034 | 2 | BA | 0.750 | 6.76 | 56.6 | 58.0 | 2.33 | 0.0665 | 10.4 | 51.7 | 779 | 48.0 | 0.0897 |
| | 1035 | 1 | AB | 0.250 | 5.75 | 34.1 | 36.4 | 6.36 | 0.0553 | 12.5 | 82.4 | 1490 | 48.0 | 0.128 |
| | 1037 | 2 | BA | 2.00 | 4.47 | 31.7 | 32.3 | 1.75 | 0.0779 | 8.90 | 92.9 | 1190 | 48.0 | 0.0440 |
| | 1039 | 1 | AB | 0.167 | 26.8 | 40.5 | 41.4 | 2.19 | 0.0657 | 10.5 | 72.5 | 1100 | 48.0 | 0.0597 |
| | 1040 | 2 | BA | 0.167 | 19.8 | 41.9 | 42.8 | 2.08 | 0.0718 | 9.65 | 70.1 | 976 | 48.1 | 0.0639 |
| | 1041 | 2 | BA | 0.167 | 5.44 | 32.9 | 34.8 | 5.33 | 0.0555 | 12.5 | 86.2 | 1550 | 48.0 | 0.103 |
| | 1044 | 1 | AB | 0.500 | 4.76 | 31.1 | 31.6 | 1.73 | 0.0736 | 9.41 | 94.9 | 1290 | 48.0 | 0.0403 |
| | 1045 | 1 | AB | 0.350 | 5.48 | 49.6 | 51.3 | 3.44 | 0.0650 | 10.7 | 58.4 | 898 | 48.0 | 0.115 |
| | 1048 | 2 | BA | 0.167 | 23.3 | 40.8 | 42.2 | 3.33 | 0.0616 | 11.3 | 71.2 | 1160 | 48.0 | 0.0864 |
| | | | n | 66 | 66 | 66 | 66 | 66 | 66 | 66 | 66 | 66 | 66 | 66 |
| | | | Mean | 0.318 | 12.2 | 40.0 | 41.5 | 3.56 | 0.0629 | 11.4 | 75.7 | 1230 | 48.0 | 0.0875 |
| | | | SD | 0.281 | 6.71 | 7.95 | 8.45 | 1.91 | 0.0104 | 2.37 | 18.0 | 305 | 0.0459 | 0.0380 |
| | | | CV % | 88.4 | 55.2 | 19.9 | 20.3 | 53.8 | 16.5 | 20.8 | 23.8 | 24.9 | 0.0957 | 43.4 |
| | | | Geo. Mean | 0.260 | 10.4 | 39.2 | 40.6 | 3.16 | 0.0620 | 11.2 | 73.9 | 1190 | 48.0 | 0.0796 |
| | | | Geo. CV % | 63.1 | 62.6 | 21.5 | 22.0 | 50.9 | 18.0 | 18.0 | 22.0 | 24.3 | 0.0955 | 46.6 |
| | | | Min | 0.0833 | 2.77 | 22.5 | 23.1 | 1.12 | 0.0281 | 8.02 | 49.2 | 737 | 48.0 | 0.0276 |
| | | | Median | 0.250 | 10.4 | 40.0 | 41.5 | 3.12 | 0.0633 | 11.0 | 72.3 | 1170 | 48.0 | 0.0843 |
| | | | Max | 2.00 | 30.4 | 58.3 | 60.9 | 13.1 | 0.0864 | 24.7 | 130 | 2110 | 48.3 | 0.194 |
| B | 904 | 2 | AB | 18.0 | 0.721 | 16.9 | 17.9 | 5.66 | 0.0743 | 9.32 | 55.8 | 751 | 48.0 | 0.0754 |
| | 905 | 1 | BA | 8.00 | 0.652 | 13.1 | 13.8 | 5.23 | 0.0586 | 11.8 | 72.3 | 1230 | 48.0 | 0.0424 |
| | 906 | 1 | BA | 0.517 | 1.21 | 13.2 | 13.6 | 3.33 | 0.0738 | 9.39 | 73.5 | 996 | 48.0 | 0.0334 |
| | 907 | 2 | AB | 1.00 | 0.858 | 13.9 | 14.3 | 3.12 | 0.0699 | 9.91 | 69.9 | 999 | 48.0 | 0.0312 |
| | 909 | 1 | BA | 0.250 | 1.31 | 12.8 | 13.0 | 1.55 | 0.0797 | 8.70 | 77.1 | 968 | 48.0 | 0.0160 |
| | 913 | 2 | AB | 0.333 | 1.87 | 16.1 | 16.7 | 3.38 | 0.0776 | 8.93 | 59.9 | 772 | 48.0 | 0.0438 |
| | 914 | 1 | BA | 0.167 | 6.43 | 18.8 | 19.4 | 2.73 | 0.0604 | 11.5 | 51.7 | 855 | 48.0 | 0.0319 |
| | 917 | 2 | AB | 2.00 | 0.925 | 19.0 | 20.1 | 5.64 | 0.0587 | 11.8 | 49.6 | 846 | 48.0 | 0.0666 |
| | 918 | 1 | BA | 2.00 | 1.53 | 15.4 | 15.7 | 1.95 | 0.0781 | 8.88 | 63.6 | 814 | 48.0 | 0.0240 |
| | 921 | 2 | AB | 0.117 | 0.847 | 10.5 | 10.9 | 3.39 | 0.0788 | 8.79 | 91.8 | 1160 | 48.0 | 0.0291 |

TABLE 7-continued

Table 7: Plasma PK Parameters of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $T_{max}$ (h) | $C_{max}$ (ng/mL) | $AUC_{last}$ (h*ng/mL) | $AUC_{inf}$ (h*ng/mL) | $AUC_{Extrap}$ (%) | $K_{el}$ (1/h) | $T_{1/2}$ (h) | CL/F (L/h) | $V_z/F$ (L) | $T_{last}$ (h) | $C_{last}$ (ng/mL) |
|---|---|---|---|---|---|---|---|---|---|---|---|---|---|---|
| | 922 | 2 | AB | 0.250 | 0.922 | 15.7 | 16.5 | 4.87 | 0.0640 | 10.8 | 60.4 | 945 | 48.0 | 0.0515 |
| | 925 | 1 | BA | 0.117 | 3.71 | 16.8 | 17.5 | 4.16 | 0.0602 | 11.5 | 57.1 | 949 | 48.0 | 0.0438 |
| | 929 | 1 | BA | 0.167 | 1.64 | 14.1 | 14.7 | 4.06 | 0.0673 | 10.3 | 68.0 | 1010 | 48.0 | 0.0402 |
| | 931 | 2 | AB | 0.500 | 4.95 | 15.7 | 16.6 | 5.43 | 0.0649 | 10.7 | 60.1 | 926 | 48.0 | 0.0587 |
| | 932 | 1 | BA | 6.00 | 1.15 | 17.2 | 17.8 | 3.66 | 0.0650 | 10.7 | 56.1 | 862 | 48.0 | 0.0424 |
| | 933 | 1 | BA | 0.750 | 1.88 | 16.3 | 17.0 | 4.14 | 0.0534 | 13.0 | 58.9 | 1100 | 48.0 | 0.0375 |
| | 938 | 2 | AB | 18.0 | 0.601 | 14.5 | 15.4 | 5.41 | 0.0712 | 9.73 | 65.1 | 914 | 48.0 | 0.0592 |
| | 940 | 2 | AB | 8.00 | 1.47 | 19.1 | 20.1 | 5.09 | 0.0609 | 11.4 | 49.7 | 816 | 48.0 | 0.0623 |
| | 944 | 1 | BA | 0.167 | 5.12 | 22.0 | 22.3 | 1.40 | 0.0803 | 8.63 | 44.8 | 557 | 48.0 | 0.0251 |
| | 945 | 1 | BA | 0.167 | 3.41 | 17.9 | 18.5 | 3.48 | 0.0739 | 9.38 | 54.0 | 731 | 48.0 | 0.0476 |
| | 948 | 2 | AB | 0.250 | 1.74 | 20.2 | 21.9 | 8.03 | 0.0527 | 13.1 | 45.6 | 865 | 48.0 | 0.0928 |
| | 949 | 1 | BA | 0.167 | 2.23 | 19.7 | 21.8 | 9.66 | 0.0628 | 11.0 | 46.0 | 731 | 48.0 | 0.132 |
| | 950 | 2 | AB | 4.00 | 0.991 | 18.2 | 18.8 | 3.08 | 0.0728 | 9.52 | 53.3 | 732 | 48.0 | 0.0420 |
| | 954 | 2 | AB | 12.0 | 0.873 | 18.6 | 20.7 | 10.2 | 0.0473 | 14.7 | 48.3 | 1020 | 48.0 | 0.100 |
| | 956 | 2 | AB | 0.117 | 2.37 | 14.7 | 14.9 | 1.28 | 0.0835 | 8.30 | 67.3 | 806 | 48.0 | 0.0159 |
| | 959 | 2 | AB | 0.250 | 1.23 | 15.9 | 16.5 | 3.58 | 0.0780 | 8.88 | 60.6 | 777 | 48.0 | 0.0461 |
| | 960 | 1 | BA | 0.250 | 1.57 | 12.4 | 13.3 | 6.53 | 0.0528 | 13.1 | 75.2 | 1420 | 48.0 | 0.0459 |
| | 962 | 1 | BA | 0.250 | 1.60 | 17.1 | 17.6 | 3.02 | 0.0844 | 8.22 | 56.8 | 673 | 48.0 | 0.0449 |
| | 966 | 2 | AB | 0.167 | 1.60 | 16.8 | 17.6 | 4.55 | 0.0702 | 9.88 | 56.9 | 811 | 48.0 | 0.0561 |
| | 967 | 1 | BA | 3.00 | 1.54 | 24.2 | 25.0 | 3.16 | 0.0694 | 9.99 | 40.0 | 577 | 48.0 | 0.0548 |
| | 968 | 2 | AB | 0.750 | 0.965 | 12.1 | 12.4 | 2.41 | 0.0796 | 8.70 | 80.6 | 1010 | 48.0 | 0.0238 |
| | 970 | 1 | BA | 3.00 | 1.44 | 19.4 | 20.0 | 3.10 | 0.0750 | 9.24 | 50.0 | 667 | 48.0 | 0.0465 |
| | 972 | 1 | BA | 3.00 | 1.47 | 20.8 | 21.5 | 3.05 | 0.0690 | 10.0 | 46.6 | 675 | 48.0 | 0.0452 |
| | 976 | 1 | BA | 0.117 | 5.23 | 16.9 | 17.1 | 1.13 | 0.0888 | 7.81 | 58.6 | 660 | 48.0 | 0.0172 |
| | 977 | 2 | AB | 0.250 | 1.18 | 13.6 | 14.2 | 4.60 | 0.0625 | 11.1 | 70.4 | 1130 | 48.0 | 0.0409 |
| | 983 | 2 | AB | 2.00 | 1.07 | 15.6 | 17.2 | 9.37 | 0.0440 | 15.8 | 58.1 | 1320 | 48.0 | 0.0709 |
| | 986 | 2 | AB | 0.333 | 1.03 | 14.5 | 15.3 | 4.83 | 0.0589 | 11.8 | 65.4 | 1110 | 48.0 | 0.0435 |
| | 987 | 1 | BA | 0.250 | 3.14 | 12.4 | 13.0 | 4.76 | 0.0519 | 13.3 | 76.7 | 1480 | 48.0 | 0.0322 |
| | 989 | 1 | BA | 0.750 | 0.910 | 15.2 | 15.7 | 3.06 | 0.0798 | 8.69 | 63.7 | 798 | 48.0 | 0.0383 |
| | 992 | 2 | AB | 2.00 | 1.38 | 16.1 | 17.2 | 6.02 | 0.0536 | 12.9 | 58.3 | 1090 | 48.0 | 0.0553 |
| | 995 | 1 | BA | 0.167 | 0.683 | 17.7 | 18.6 | 5.11 | 0.0724 | 9.58 | 53.7 | 742 | 48.0 | 0.0689 |
| | 997 | 2 | AB | 0.500 | 0.753 | 10.5 | 11.0 | 4.24 | 0.0703 | 9.85 | 91.2 | 1300 | 48.0 | 0.0327 |
| | 998 | 1 | BA | 12.0 | 0.790 | 17.9 | 18.8 | 4.46 | 0.0696 | 9.96 | 53.3 | 766 | 48.0 | 0.0582 |
| | 999 | 2 | AB | 0.333 | 1.97 | 14.4 | 15.0 | 3.50 | 0.0702 | 9.87 | 66.8 | 951 | 48.0 | 0.0368 |
| | 1001 | 1 | BA | 0.167 | 1.56 | 19.2 | 20.3 | 5.54 | 0.0625 | 11.1 | 49.3 | 789 | 48.0 | 0.0702 |
| | 1002 | 2 | AB | 0.250 | 2.95 | 14.8 | 15.3 | 3.07 | 0.0729 | 9.50 | 65.5 | 899 | 48.0 | 0.0342 |
| | 1003 | 1 | BA | 2.00 | 1.08 | 12.7 | 13.3 | 4.48 | 0.0591 | 11.7 | 74.9 | 1270 | 48.0 | 0.0354 |
| | 1004 | 2 | AB | 0.117 | 3.65 | 15.1 | 15.4 | 1.65 | 0.0794 | 8.73 | 65.0 | 820 | 48.0 | 0.0201 |
| | 1005 | 2 | AB | 0.383 | 1.34 | 20.7 | 21.7 | 4.70 | 0.0680 | 10.2 | 46.0 | 677 | 48.0 | 0.0694 |
| | 1008 | 1 | BA | 0.167 | 1.53 | 14.0 | 14.5 | 3.45 | 0.0755 | 9.18 | 69.1 | 914 | 48.0 | 0.0377 |
| | 1012 | 1 | BA | 0.267 | 1.78 | 21.0 | 22.7 | 7.20 | 0.0584 | 11.9 | 44.1 | 756 | 48.0 | 0.0953 |
| | 1015 | 2 | AB | 0.333 | 1.70 | 15.1 | 15.5 | 2.94 | 0.0844 | 8.21 | 64.4 | 762 | 48.0 | 0.0386 |
| | 1016 | 1 | BA | 1.98 | 0.539 | 11.1 | 11.5 | 2.91 | 0.0730 | 9.50 | 87.3 | 1200 | 48.0 | 0.0243 |
| | 1017 | 2 | AB | 2.08 | 1.77 | 18.3 | 18.9 | 3.35 | 0.0673 | 10.3 | 52.8 | 784 | 48.2 | 0.0427 |
| | 1018 | 1 | BA | 0.167 | 1.55 | 18.0 | 18.9 | 4.87 | 0.0657 | 10.5 | 53.0 | 806 | 48.0 | 0.0604 |
| | 1020 | 2 | AB | 0.250 | 3.15 | 22.1 | 23.5 | 5.87 | 0.0546 | 12.7 | 42.5 | 779 | 48.0 | 0.0753 |
| | 1031 | 2 | AB | 2.00 | 1.51 | 17.8 | 19.7 | 9.43 | 0.0495 | 14.0 | 50.9 | 1030 | 48.0 | 0.0918 |
| | 1032 | 1 | BA | 0.333 | 1.16 | 16.1 | 18.6 | 13.3 | 0.0394 | 17.6 | 53.9 | 1370 | 48.0 | 0.0974 |
| | 1033 | 2 | AB | 0.167 | 1.27 | 13.8 | 14.3 | 3.12 | 0.0741 | 9.35 | 70.0 | 945 | 48.0 | 0.0330 |
| | 1034 | 1 | BA | 0.167 | 1.95 | 20.0 | 20.5 | 2.18 | 0.0703 | 9.86 | 48.8 | 694 | 48.0 | 0.0314 |
| | 1035 | 2 | AB | 0.500 | 1.01 | 15.3 | 17.2 | 10.9 | 0.0512 | 13.5 | 58.2 | 1140 | 48.0 | 0.0959 |
| | 1037 | 1 | BA | 1.00 | 1.70 | 14.4 | 14.7 | 1.53 | 0.0762 | 9.09 | 68.2 | 895 | 48.0 | 0.0171 |
| | 1039 | 2 | AB | 0.500 | 2.53 | 14.9 | 15.1 | 1.82 | 0.0968 | 7.16 | 66.1 | 683 | 48.0 | 0.0266 |
| | 1040 | 1 | BA | 0.167 | 2.08 | 15.7 | 16.2 | 3.13 | 0.0656 | 10.6 | 61.6 | 939 | 48.0 | 0.0333 |
| | 1041 | 1 | BA | 1.00 | 0.610 | 12.6 | 13.6 | 7.35 | 0.0567 | 12.2 | 73.5 | 1300 | 48.0 | 0.0567 |
| | 1044 | 2 | AB | 0.750 | 1.07 | 14.2 | 14.6 | 2.52 | 0.0792 | 8.75 | 68.6 | 866 | 48.0 | 0.0291 |
| | 1045 | 2 | AB | 2.00 | 1.57 | 19.0 | 19.6 | 3.01 | 0.0741 | 9.35 | 51.0 | 688 | 48.0 | 0.0437 |
| | 1048 | 1 | BA | 0.167 | 2.46 | 15.8 | 17.1 | 7.33 | 0.0585 | 11.8 | 58.5 | 1000 | 48.0 | 0.0732 |
| | | | n | 68 | 68 | 68 | 68 | 68 | 68 | 68 | 68 | 68 | 68 | 68 |
| | | | Mean | 1.90 | 1.77 | 16.3 | 17.0 | 4.50 | 0.0677 | 10.6 | 60.7 | 916 | 48.0 | 0.0491 |
| | | | SD | 3.75 | 1.18 | 2.91 | 3.13 | 2.45 | 0.0112 | 1.95 | 11.5 | 211 | 0.0226 | 0.0236 |
| | | | CV % | 197 | 66.7 | 17.9 | 18.4 | 54.5 | 16.6 | 18.5 | 18.9 | 23.0 | 0.0471 | 48.1 |
| | | | Geo. Mean | 0.603 | 1.50 | 16.0 | 16.8 | 3.94 | 0.0667 | 10.4 | 59.6 | 894 | 48.0 | 0.0440 |
| | | | Geo. CV % | 249 | 59.4 | 18.2 | 18.7 | 56.4 | 17.5 | 17.5 | 18.7 | 22.5 | 0.0470 | 49.9 |
| | | | Min | 0.117 | 0.539 | 10.5 | 10.9 | 1.13 | 0.0394 | 7.16 | 40.0 | 557 | 48.0 | 0.0159 |
| | | | Median | 0.333 | 1.52 | 15.9 | 17.0 | 3.86 | 0.0695 | 9.98 | 58.7 | 865 | 48.0 | 0.0436 |
| | | | Max | 18.0 | 6.43 | 24.2 | 25.0 | 13.3 | 0.0968 | 17.6 | 91.8 | 1480 | 48.2 | 0.132 |

TABLE 8

Table 8: Plasma PK Partial AUCs of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $AUC_{0\text{-}2.5\ min}$ (h*ng/mL) | $AUC_{0\text{-}5\ min}$ (h*ng/mL) | $AUC_{0\text{-}10\ min}$ (h*ng/mL) | $AUC_{0\text{-}15\ min}$ (h*ng/mL) | $AUC_{0\text{-}20\ min}$ (h*ng/mL) | $AUC_{0\text{-}30\ min}$ (h*ng/mL) |
|---|---|---|---|---|---|---|---|---|---|
| A | 904 | 1 | AB | 0.00263 | 0.0143 | 0.188 | 0.771 | 1.59 | 2.92 |
|  | 905 | 2 | BA | 0.0107 | 0.0417 | 0.239 | 0.552 | 0.869 | 1.52 |
|  | 906 | 2 | BA | 0.0193 | 0.0753 | 0.372 | 0.990 | 1.66 | 2.66 |
|  | 907 | 1 | AB | 0.00145 | 0.0163 | 0.150 | 0.325 | 0.517 | 0.969 |
|  | 913 | 1 | AB | 0.0666 | 0.333 | 1.66 | 2.70 | 3.31 | 4.63 |
|  | 914 | 2 | BA | 0.0103 | 0.142 | 1.10 | 2.61 | 4.40 | 6.76 |
|  | 917 | 1 | AB | 0.00256 | 0.0220 | 0.196 | 0.644 | 1.30 | 2.62 |
|  | 918 | 2 | BA | 0.0235 | 0.160 | 1.24 | 2.42 | 3.30 | 4.41 |
|  | 921 | 1 | AB | 0.155 | 0.566 | 1.79 | 2.87 | 3.58 | 4.49 |
|  | 922 | 1 | AB | 0.000932 | 0.0115 | 0.110 | 0.449 | 1.04 | 2.40 |
|  | 925 | 2 | BA | 0.0661 | 0.419 | 1.77 | 3.22 | 4.35 | 6.20 |
|  | 929 | 2 | BA | 0.0189 | 0.161 | 0.992 | 1.88 | 2.81 | 4.73 |
|  | 931 | 1 | AB | 0.00529 | 0.0260 | 0.261 | 0.651 | 1.01 | 1.40 |
|  | 932 | 2 | BA | 0.0104 | 0.126 | 1.20 | 2.68 | 3.89 | 5.33 |
|  | 933 | 2 | BA | 0.00481 | 0.0188 | 0.376 | 1.18 | 1.82 | 2.99 |
|  | 938 | 1 | AB | 0.000945 | 0.00853 | 0.109 | 0.342 | 0.720 | 1.60 |
|  | 940 | 1 | AB | 0.00574 | 0.0255 | 0.208 | 0.838 | 1.68 | 3.18 |
|  | 944 | 2 | BA | 0.0129 | 0.138 | 1.75 | 3.79 | 5.61 | 8.17 |
|  | 945 | 2 | BA | 0.0149 | 0.0606 | 1.16 | 2.87 | 4.18 | 5.87 |
|  | 948 | 1 | AB | 0.0988 | 0.582 | 2.78 | 5.03 | 6.79 | 9.16 |
|  | 949 | 2 | BA | 0.00300 | 0.169 | 1.26 | 2.57 | 3.59 | 5.06 |
|  | 950 | 1 | AB | 0.000504 | 0.00853 | 0.409 | 1.09 | 1.89 | 3.44 |
|  | 954 | 1 | AB | 0.0134 | 0.0677 | 0.907 | 1.75 | 2.40 | 3.59 |
|  | 956 | 1 | AB | 0.0157 | 0.190 | 0.954 | 1.73 | 2.48 | 3.81 |
|  | 959 | 1 | AB | 0.0332 | 0.256 | 0.886 | 1.49 | 2.13 | 3.20 |
|  | 960 | 2 | BA | 0.0535 | 0.324 | 1.52 | 2.56 | 3.42 | 4.61 |
|  | 962 | 2 | BA | 0.00444 | 0.0555 | 0.772 | 1.95 | 3.01 | 4.30 |
|  | 966 | 1 | AB | 0.0326 | 0.278 | 1.67 | 2.99 | 4.14 | 5.96 |
|  | 967 | 2 | BA | 0.00825 | 0.0566 | 0.333 | 0.726 | 1.18 | 2.19 |
|  | 968 | 1 | AB | 0.0635 | 0.346 | 1.42 | 2.37 | 3.12 | 4.12 |
|  | 970 | 2 | BA | 0.00323 | 0.0201 | 0.192 | 0.556 | 0.921 | 1.57 |
|  | 972 | 2 | BA | 0.000864 | 0.0146 | 0.307 | 0.724 | 1.19 | 1.97 |
|  | 976 | 2 | BA | 0.0167 | 0.218 | 1.62 | 3.51 | 5.23 | 7.82 |
|  | 977 | 1 | AB | 0.0497 | 0.194 | 0.728 | 1.45 | 2.39 | 3.98 |
|  | 983 | 1 | AB | 0.00185 | 0.0175 | 0.233 | 0.923 | 1.71 | 2.61 |
|  | 986 | 1 | AB | 0.00541 | 0.0538 | 0.695 | 1.17 | 1.76 | 2.88 |
|  | 987 | 2 | BA | 0.00174 | 0.0155 | 0.121 | 0.384 | 0.935 | 2.11 |
|  | 989 | 2 | BA | 0.00357 | 0.0306 | 0.227 | 0.692 | 1.20 | 1.83 |
|  | 992 | 1 | AB | 0.00290 | 0.0179 | 0.132 | 0.414 | 0.770 | 1.52 |
|  | 995 | 2 | BA | 0.00254 | 0.0136 | 0.127 | 0.370 | 0.691 | 1.41 |
|  | 997 | 1 | AB | 0.00450 | 0.0345 | 0.540 | 1.26 | 1.87 | 2.69 |
|  | 998 | 2 | BA | 0.00728 | 0.102 | 0.663 | 1.34 | 1.91 | 2.94 |
|  | 999 | 1 | AB | 0.0165 | 0.189 | 0.819 | 1.43 | 1.93 | 2.62 |
|  | 1001 | 2 | BA | 0.00589 | 0.129 | 1.13 | 2.17 | 2.87 | 3.72 |
|  | 1002 | 1 | AB | 0.00156 | 0.0226 | 0.347 | 1.00 | 1.64 | 2.65 |
|  | 1004 | 1 | AB | 0.00254 | 0.161 | 1.45 | 3.01 | 4.32 | 6.13 |
|  | 1005 | 1 | AB | 0.00919 | 0.0530 | 0.338 | 0.700 | 1.07 | 1.79 |
|  | 1008 | 2 | BA | 0.0384 | 0.404 | 2.05 | 3.65 | 4.95 | 6.85 |
|  | 1012 | 2 | BA | 0.00478 | 0.0430 | 0.367 | 0.878 | 1.67 | 3.13 |
|  | 1015 | 1 | AB | 0.0656 | 0.408 | 2.22 | 3.69 | 4.42 | 5.74 |
|  | 1016 | 2 | BA | 0.00174 | 0.0112 | 0.0815 | 0.196 | 0.350 | 0.802 |
|  | 1017 | 1 | AB | 0.00495 | 0.0193 | 0.203 | 0.548 | 1.02 | 2.11 |
|  | 1018 | 2 | BA | 0.00549 | 0.0669 | 0.786 | 1.99 | 3.00 | 4.25 |
|  | 1020 | 1 | AB | 0.0173 | 0.0839 | 0.513 | 1.16 | 1.84 | 3.10 |
|  | 1031 | 1 | AB | 0.00979 | 0.0382 | 0.155 | 0.354 | 0.643 | 1.32 |
|  | 1032 | 2 | BA | 0.00435 | 0.0633 | 0.672 | 1.21 | 1.54 | 2.31 |
|  | 1033 | 1 | AB | 0.000780 | 0.00542 | 0.534 | 1.59 | 2.44 | 3.91 |
|  | 1034 | 2 | BA | 0.00425 | 0.0325 | 0.214 | 0.500 | 0.885 | 1.94 |
|  | 1035 | 1 | AB | 0.00389 | 0.0243 | 0.294 | 0.762 | 1.23 | 2.05 |
|  | 1037 | 2 | BA | 0.00288 | 0.00951 | 0.172 | 0.439 | 0.722 | 1.39 |
|  | 1039 | 1 | AB | 0.00268 | 0.0188 | 1.48 | 3.15 | 4.34 | 6.21 |
|  | 1040 | 2 | BA | 0.126 | 0.588 | 2.08 | 3.46 | 4.41 | 5.79 |
|  | 1041 | 2 | BA | 0.00447 | 0.0410 | 0.372 | 0.793 | 1.17 | 1.88 |
|  | 1044 | 1 | AB | 0.00676 | 0.0264 | 0.126 | 0.329 | 0.633 | 1.39 |
|  | 1045 | 1 | AB | 0.00175 | 0.0151 | 0.207 | 0.560 | 0.990 | 1.84 |
|  | 1048 | 2 | BA | 0.0740 | 0.395 | 1.97 | 3.21 | 4.08 | 5.92 |
|  |  |  | n | 66 | 66 | 66 | 66 | 66 | 66 |
|  |  |  | Mean | 0.0193 | 0.125 | 0.787 | 1.60 | 2.34 | 3.55 |
|  |  |  | SD | 0.0305 | 0.152 | 0.666 | 1.15 | 1.49 | 1.93 |
|  |  |  | CV % | 158 | 121 | 84.6 | 71.8 | 63.5 | 54.2 |
|  |  |  | Geo. Mean | 0.00763 | 0.0599 | 0.523 | 1.20 | 1.89 | 3.07 |
|  |  |  | Geo. CV % | 233 | 201 | 124 | 94.2 | 77.2 | 60.4 |

TABLE 8-continued

Table 8: Plasma PK Partial AUCs of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $AUC_{0-2.5\,min}$ (h*ng/mL) | $AUC_{0-5\,min}$ (h*ng/mL) | $AUC_{0-10\,min}$ (h*ng/mL) | $AUC_{0-15\,min}$ (h*ng/mL) | $AUC_{0-20\,min}$ (h*ng/mL) | $AUC_{0-30\,min}$ (h*ng/mL) |
|---|---|---|---|---|---|---|---|---|---|
| | | | Min | 0.000504 | 0.00542 | 0.0815 | 0.196 | 0.350 | 0.802 |
| | | | Median | 0.00561 | 0.0546 | 0.537 | 1.19 | 1.85 | 3.04 |
| | | | Max | 0.155 | 0.588 | 2.78 | 5.03 | 6.79 | 9.16 |
| B | 904 | 2 | AB | 0.000410 | 0.00174 | 0.0100 | 0.0259 | 0.0493 | 0.114 |
| | 905 | 1 | BA | 2.58E−05 | 0.000849 | 0.00819 | 0.0243 | 0.0471 | 0.102 |
| | 906 | 1 | BA | 4.33E−05 | 0.00142 | 0.0198 | 0.0639 | 0.122 | 0.279 |
| | 907 | 2 | AB | 0.00135 | 0.00631 | 0.0377 | 0.0789 | 0.126 | 0.249 |
| | 909 | 1 | BA | 0.00290 | 0.0113 | 0.0588 | 0.152 | 0.243 | 0.393 |
| | 913 | 2 | AB | 0.000944 | 0.0135 | 0.0920 | 0.206 | 0.358 | 0.584 |
| | 914 | 1 | BA | 0.0125 | 0.143 | 0.631 | 1.05 | 1.33 | 1.77 |
| | 917 | 2 | AB | 0.00116 | 0.00545 | 0.0323 | 0.0755 | 0.126 | 0.233 |
| | 918 | 1 | BA | 0.000911 | 0.00540 | 0.0563 | 0.126 | 0.210 | 0.424 |
| | 921 | 2 | AB | 0.00396 | 0.0252 | 0.0901 | 0.147 | 0.211 | 0.331 |
| | 922 | 2 | AB | 0.000247 | 0.00235 | 0.0241 | 0.0805 | 0.152 | 0.275 |
| | 925 | 1 | BA | 0.0149 | 0.0659 | 0.342 | 0.605 | 0.825 | 1.20 |
| | 929 | 1 | BA | 0.000953 | 0.0124 | 0.121 | 0.216 | 0.296 | 0.495 |
| | 931 | 2 | AB | 0.00114 | 0.00499 | 0.0388 | 0.0898 | 0.140 | 0.599 |
| | 932 | 1 | BA | 0.00131 | 0.00679 | 0.0437 | 0.0920 | 0.144 | 0.256 |
| | 933 | 1 | BA | 0.00288 | 0.0165 | 0.0885 | 0.175 | 0.267 | 0.496 |
| | 938 | 2 | AB | 0.000344 | 0.00241 | 0.0143 | 0.0357 | 0.0660 | 0.134 |
| | 940 | 2 | AB | 0.00163 | 0.00651 | 0.0309 | 0.0663 | 0.113 | 0.226 |
| | 944 | 1 | BA | 0.0127 | 0.0833 | 0.420 | 0.760 | 1.01 | 1.48 |
| | 945 | 1 | BA | 0.000693 | 0.0193 | 0.233 | 0.499 | 0.725 | 1.06 |
| | 948 | 2 | AB | 0.00620 | 0.0342 | 0.145 | 0.280 | 0.403 | 0.597 |
| | 949 | 1 | BA | 0.000403 | 0.00489 | 0.0956 | 0.227 | 0.313 | 0.517 |
| | 950 | 2 | AB | 0.000715 | 0.00442 | 0.0236 | 0.0574 | 0.0983 | 0.180 |
| | 954 | 2 | AB | 0.00201 | 0.00797 | 0.0410 | 0.0751 | 0.108 | 0.177 |
| | 956 | 2 | AB | 0.00348 | 0.0323 | 0.205 | 0.391 | 0.582 | 0.944 |
| | 959 | 2 | AB | 0.000725 | 0.00542 | 0.0554 | 0.135 | 0.224 | 0.348 |
| | 960 | 1 | BA | 0.00835 | 0.0409 | 0.160 | 0.286 | 0.405 | 0.612 |
| | 962 | 1 | BA | 0.00260 | 0.0201 | 0.101 | 0.220 | 0.348 | 0.536 |
| | 966 | 2 | AB | 0.00120 | 0.0105 | 0.105 | 0.222 | 0.316 | 0.467 |
| | 967 | 1 | BA | 0.00211 | 0.0118 | 0.0686 | 0.143 | 0.222 | 0.396 |
| | 968 | 2 | AB | 0.000586 | 0.00663 | 0.0620 | 0.132 | 0.197 | 0.343 |
| | 970 | 1 | BA | 0.000598 | 0.00636 | 0.0455 | 0.106 | 0.179 | 0.361 |
| | 972 | 1 | BA | 0.00698 | 0.0256 | 0.108 | 0.206 | 0.308 | 0.510 |
| | 976 | 1 | BA | 0.0249 | 0.124 | 0.505 | 0.827 | 1.09 | 1.52 |
| | 977 | 2 | AB | 0.00210 | 0.00973 | 0.0577 | 0.144 | 0.240 | 0.410 |
| | 983 | 2 | AB | 0.00333 | 0.0133 | 0.0530 | 0.0956 | 0.142 | 0.249 |
| | 986 | 2 | AB | 0.00376 | 0.0167 | 0.0860 | 0.160 | 0.243 | 0.394 |
| | 987 | 1 | BA | 0.00160 | 0.00761 | 0.0803 | 0.276 | 0.514 | 0.826 |
| | 989 | 1 | BA | 0.00169 | 0.00661 | 0.0268 | 0.0672 | 0.128 | 0.257 |
| | 992 | 2 | AB | 0.00181 | 0.00875 | 0.0476 | 0.101 | 0.171 | 0.357 |
| | 995 | 1 | BA | 0.00109 | 0.00458 | 0.0366 | 0.0851 | 0.131 | 0.240 |
| | 997 | 2 | AB | 0.000249 | 0.00150 | 0.0135 | 0.0453 | 0.0980 | 0.221 |
| | 998 | 1 | BA | 0.000810 | 0.00487 | 0.0424 | 0.0842 | 0.137 | 0.236 |
| | 999 | 2 | AB | 0.00280 | 0.0293 | 0.156 | 0.298 | 0.442 | 0.708 |
| | 1001 | 1 | BA | 0.00234 | 0.00913 | 0.0857 | 0.189 | 0.263 | 0.378 |
| | 1002 | 2 | AB | 0.00353 | 0.0111 | 0.0941 | 0.310 | 0.543 | 0.871 |
| | 1003 | 1 | BA | 0.00142 | 0.00547 | 0.0268 | 0.0705 | 0.133 | 0.275 |
| | 1004 | 2 | AB | 0.00203 | 0.0224 | 0.276 | 0.494 | 0.639 | 0.926 |
| | 1005 | 2 | AB | 0.00414 | 0.0135 | 0.0550 | 0.117 | 0.200 | 0.405 |
| | 1008 | 1 | BA | 0.00393 | 0.0181 | 0.0958 | 0.188 | 0.250 | 0.388 |
| | 1012 | 1 | BA | 0.00302 | 0.0114 | 0.0463 | 0.134 | 0.270 | 0.487 |
| | 1015 | 2 | AB | 0.00748 | 0.0389 | 0.154 | 0.274 | 0.400 | 0.618 |
| | 1016 | 1 | BA | 0.000340 | 0.00143 | 0.00831 | 0.0218 | 0.0402 | 0.0845 |
| | 1017 | 2 | AB | 0.00300 | 0.0108 | 0.0419 | 0.0921 | 0.161 | 0.329 |
| | 1018 | 1 | BA | 0.00125 | 0.00910 | 0.103 | 0.192 | 0.242 | 0.352 |
| | 1020 | 2 | AB | 0.00182 | 0.0123 | 0.0993 | 0.292 | 0.523 | 0.881 |
| | 1031 | 2 | AB | 0.00210 | 0.00887 | 0.0589 | 0.146 | 0.232 | 0.390 |
| | 1032 | 1 | BA | 0.000339 | 0.00209 | 0.0186 | 0.0429 | 0.101 | 0.255 |
| | 1033 | 2 | AB | 0.00136 | 0.0179 | 0.0961 | 0.189 | 0.256 | 0.358 |
| | 1034 | 1 | BA | 0.00373 | 0.0277 | 0.158 | 0.314 | 0.461 | 0.738 |
| | 1035 | 2 | AB | 0.00120 | 0.00429 | 0.0321 | 0.0848 | 0.143 | 0.296 |
| | 1037 | 1 | BA | 0.00345 | 0.0113 | 0.0383 | 0.0891 | 0.158 | 0.329 |
| | 1039 | 2 | AB | 0.00226 | 0.00900 | 0.0494 | 0.145 | 0.308 | 0.717 |
| | 1040 | 1 | BA | 0.0103 | 0.0400 | 0.165 | 0.308 | 0.430 | 0.638 |
| | 1041 | 1 | BA | 0.00100 | 0.00518 | 0.0270 | 0.0616 | 0.102 | 0.192 |
| | 1044 | 2 | AB | 0.000981 | 0.00573 | 0.0323 | 0.0768 | 0.137 | 0.279 |
| | 1045 | 2 | AB | 0.00195 | 0.00780 | 0.0415 | 0.100 | 0.178 | 0.370 |

TABLE 8-continued

Table 8: Plasma PK Partial AUCs of Nalmefene after Intranasal (IN) Administration of 3.0 mg Nalmefene Hydrochloride (Treatment A) and Intramuscular (IM) Administration of 1.0 mg of Nalmefene Hydrochloride (Treatment B) - PK Population

| Treatment | Subject | Period | Sequence | $AUC_{0-2.5\ min}$ (h*ng/mL) | $AUC_{0-5\ min}$ (h*ng/mL) | $AUC_{0-10\ min}$ (h*ng/mL) | $AUC_{0-15\ min}$ (h*ng/mL) | $AUC_{0-20\ min}$ (h*ng/mL) | $AUC_{0-30\ min}$ (h*ng/mL) |
|---|---|---|---|---|---|---|---|---|---|
| | 1048 | 1 | BA | 0.0105 | 0.0543 | 0.244 | 0.420 | 0.550 | 0.741 |
| | | | n | 68 | 68 | 68 | 68 | 68 | 68 |
| | | | Mean | 0.00315 | 0.0181 | 0.0994 | 0.200 | 0.299 | 0.491 |
| | | | SD | 0.00416 | 0.0254 | 0.114 | 0.192 | 0.249 | 0.337 |
| | | | CV % | 132 | 140 | 114 | 96.0 | 83.3 | 68.6 |
| | | | Geo. Mean | 0.00168 | 0.0102 | 0.0639 | 0.142 | 0.228 | 0.405 |
| | | | Geo. CV % | 186 | 142 | 118 | 98.6 | 84.5 | 69.2 |
| | | | Min | 0.0000258 | 0.000849 | 0.00819 | 0.0218 | 0.0402 | 0.0845 |
| | | | Median | 0.00182 | 0.00943 | 0.0583 | 0.143 | 0.228 | 0.389 |
| | | | Max | 0.0249 | 0.143 | 0.631 | 1.05 | 1.33 | 1.77 |

Treatment A = 3.0 mg nalmefene hydrochloride IN dose (one 0.1 mL spray of a 30 mg/mL solution in one nostril)
Treatment B = 1.0 mg nalmefene IM dose (1.0 mL of 1.108 mg/mL nalmefene hydrochloride solution as a single dose in the gluteal muscle)

TABLE 9

Table 9: Statistical Analysis of the Natural Log-Transformed Systemic Exposure of Nalmefene Comparing 3.0 mg Nalmefene hydrochloride (IN) (Treatment A, Test) to 1.0 mg of Nalmefene Hydrochloride (IM) (Treatment B, Reference) - PK Population

| Dependent Variable | LSMean[a] Test | LSMean[a] Ref | GeoMean[b] Test | GeoMean[b] Ref | Diff[c] | SE[d] | Ratio (%)[e] (Test/Ref) | 90% CI[f] Lower | 90% CI[f] Upper | p-value[g] | Power | ANOVA CV % |
|---|---|---|---|---|---|---|---|---|---|---|---|---|
| $C_{max}$ | 2.33 | 0.409 | 10.3 | 1.50 | 1.93 | 0.0712 | 685.98 | 609.14 | 772.51 | <0.0001 | 0.9262 | 42.64 |
| $AUC_{0-2.5\ min}$ | −4.870 | −6.390 | 0.008 | 0.002 | 1.52 | 0.192 | 456.58 | 331.53 | 628.80 | <0.0001 | 0.3106 | 153.66 |
| $AUC_{0-5\ min}$ | −2.820 | −4.590 | 0.060 | 0.010 | 1.77 | 0.146 | 584.17 | 458.02 | 745.06 | <0.0001 | 0.4464 | 100.73 |
| $AUC_{0-10\ min}$ | −0.665 | −2.750 | 0.514 | 0.064 | 2.08 | 0.0979 | 803.98 | 682.79 | 946.68 | <0.0001 | 0.7282 | 60.96 |
| $AUC_{0-15\ min}$ | 0.174 | −1.950 | 1.19 | 0.142 | 2.12 | 0.0864 | 837.01 | 724.57 | 966.91 | <0.0001 | 0.8176 | 52.85 |
| $AUC_{0-20\ min}$ | 0.628 | −1.480 | 1.87 | 0.228 | 2.11 | 0.0765 | 821.20 | 722.79 | 933.00 | <0.0001 | 0.8919 | 46.12 |
| $AUC_{0-30\ min}$ | 1.11 | −0.905 | 3.04 | 0.405 | 2.02 | 0.0681 | 752.66 | 671.80 | 843.27 | <0.0001 | 0.9436 | 40.65 |
| $AUC_{Last}$ | 3.66 | 2.77 | 38.9 | 16.0 | 0.889 | 0.0130 | 243.15 | 237.91 | 248.50 | <0.0001 | 1.0000 | 7.50 |
| $AUC_{inf}$ | 3.70 | 2.82 | 40.3 | 16.8 | 0.878 | 0.0138 | 240.61 | 235.14 | 246.21 | <0.0001 | 1.0000 | 7.92 |

Treatment A = 3.0 mg nalmefene hydrochloride IN dose (one 0.1 mL spray of a 30 mg/mL solution in one nostril)
Treatment B = 1.0 mg nalmefene IM dose (1.0 mL of 1.108 mg/mL nalmefene hydrochloride solution as a single dose in the gluteal muscle)
[a] = Least Squares Mean based on natural log-transformed data for the Treatment A (Test) and Treatment B (Ref)
[b] = Geometric Mean based on Least Squares Mean
[c] = Difference = LS Mean (Test) − LS Mean (Ref)
[d] = SE = Standard error of the difference
[e] = Ratio(%) = Geometric Mean (Test)/Geometric Mean (Ref)
[f] = 90% Confidence Interval
[g] = p-value for the difference between treatments; Significant difference defined a priori as $p < 0.05$ Based on the data above, the following observations were made:

As shown in FIG. 8, the mean plasma concentration of IN nalmefene is significantly higher than IM during the first 20 minutes after administration, a period which is important in treating an overdose victim to maximize the potential for a successful rescue.

The $C_{max}$ of IN nalmefene was higher than previously reported. This could be due to a number of factors, including:

1. The final formulation differs than the formulation used in Krieter et. al., *Fighting Fire with Fire: Development of Intranasal Nalmefene to Treat Synthetic Opioid Overdose*, J. Pharmacol. Exp. Ther. 371:409-415 (November 2019);
2. The use of a different delivery device; or
3. A combination of the two aforementioned factors.

As a result of factors 1 and 2 above, the $AUC_{0-2.5min}$ and $AUC_{0-20min}$ were also higher than previously reported, attaining high plasma concentrations quickly, thus favoring a successful rescue medication.

Example 13: An Open-Label, Three-Period, Three-Treatment, Six-Sequence, Randomized Crossover Study of the Pharmacokinetics of Intranasal Nalmefene in Healthy Volunteers Using Three Dosing Regimens Objectives: The primary objective was to compare the pharmacokinetics (PK) of nalmefene following three different dosing regimens of 30 mg/mL nalmefene hydrochloride IN spray:
  T1: 3 mg, one 0.1 mL spray in one nostril.
  T2: 6 mg, one 0.1 mL spray in each nostril.
  T3: 6 mg, two 0.1 mL sprays in one nostril.
The secondary objective was to evaluate the safety and tolerability of IN nalmefene in healthy volunteers.

Study Methodology: This was an open-label, randomized, 6-sequence, 3-treatment, 3-period crossover pilot study in which 24 healthy subjects received 3 separate administrations of IN nalmefene hydrochloride. Subjects were randomly assigned to 1 of 6 sequences (4 subjects per sequence). Each subject received one of the 3 treatments in each of the 3 treatment periods:

The IN dosage form of nalmefene was formulated as follows.

| Component | mg/mL | Unit dose (100 microliter) |
|---|---|---|
| Nalmefene HCl[a] | 30.0 | 3.0 mg |
| Sodium chloride | 8.66 | 0.866 mg |
| Dodecyl maltoside | 2.5 | 0.25 mg |
| Di sodium edetate dihydrate | 2.0 | 0.2 mg |
| Benzalkonium chloride (50% solution) | 0.40 | 0.04 mg |
| Purified water | q.s. ad 1.0 mL | q.s. ad 100 microliter |

[a]Nalmefene HCl adjusted for potency and water content to account for the monohydrate.

Treatment 1 (T1): 3 mg (one 0.1 mL spray of 30 mg/mL nalmefene hydrochloride in one nostril).

Treatment 2 (T2): 6 mg (one 0.1 mL sprays of 30 mg/mL nalmefene hydrochloride in each nostril).

Treatment 3 (T3): 6 mg (two 0.1 mL sprays of 30 mg/mL nalmefene hydrochloride in one nostril).

Each drug administration was separated by a washout period of 6 days. Subjects stayed in the inpatient facility for 15 nights to complete the entire study and were discharged on the second day after the last dose. Subjects were called 3 to 5 days after discharge to inquire concerning adverse events (AEs) and concomitant medications since discharge.

Diagnosis and Criteria for Inclusion: Volunteers were healthy, nonsmoking, adult male or female subjects, 18 to 55 years of age inclusive, with BMI ranging from 18 to 30 kg/m2 inclusive. Female subjects were not pregnant or breastfeeding.

Duration of Treatment: Three treatments were administered with a six day washout period between doses.

Criteria for Evaluation:

Pharmacokinetics (PK): The following PK parameters were calculated for nalmefene: maximum plasma concentration ($C_{max}$), time to maximum plasma concentration ($T_{max}$), area under the curve to the final time with a concentration equal to or greater than the lower limit of quantitation [AUC (0-t)], to infinity [AUC (inf)] and during the first 30 minutes [$AUC_{0-2.5mins}$, $AUC_{0-5mins}$, $AUC_{0-7.5mins}$, $AUC_{0-10mins}$, $AUC_{0-15mins}$, $AUC_{0-20mins}$, and $AUC_{0-30mins}$], percentage of $AUC_{inf}$ based on extrapolation ($AUC_{extrap\%}$), elimination rate constant ($\lambda_z$), half-life ($t_{1/2}$), clearance (CL/F), and volume of distribution ($V_z$/F). Dose-normalized $C_{max}$ and AUCs ($C_{max}$ and AUCs divided by nominal dose) were also calculated.

Safety: The Investigator evaluated safety using the following assessments: reported or observed AEs, clinical laboratory evaluations, vital sign measurements, physical examinations, ECGs (including telemetry), nasal irritation determined from nasal passage examinations, and NRS to determine acute nasal pain.

Efficacy: No efficacy evaluations were performed in this study.

Statistical Methods:

Analysis Populations

Safety Population: The safety population included all subjects who received at least one administration of the study drugs.

PK Analysis Population for Test 2 versus Test 1 Comparison (B vs. A): The PK analysis population for Test 2 versus Test 1 comparison included all subjects who had evaluable PK data on the Test 2 period and on the Test 1 period and did not deviate from the protocol in a way that affected the evaluation of the PK endpoints.

PK Analysis Population for Test 3 versus Test 1 Comparison (C vs. A): The PK analysis population for Test 3 versus Test 1 comparison included all subjects who had evaluable PK data on the Test 3 period and on the Test 1 period and did not deviate from the protocol in a way that affected the evaluation of the PK endpoints.

PK Analysis Population for Test 2 versus Test 3 Comparison (B vs. C): The PK analysis population for Test 2 versus Test 3 comparison will include all subjects who have evaluable PK data on the Test 2 period and on the Test 3 period and did not deviate from the protocol in a way that affected the evaluation of the PK endpoints.

PK Analysis

Concentration-time data for nalmefene were analyzed using noncompartmental methods in Phoenix™ WinNonlin® (Version 8.1, Certara, L.P.) in conjunction with the internet-accessible implementation of Pharsight® Knowledgebase Server™ (PKSO; Version 4.0.4, Certara, L.P.).

During the PK analysis, concentrations below the limit of quantitation (BLQ) up to the time of the first quantifiable concentration were treated as zero. Embedded (values between 2 quantifiable concentrations) and terminal BLQ concentrations were treated as missing. PK analysis was based on actual elapsed sample times, relative to time of dose.

Statistical Analysis:

The dose-normalized PK parameters Cmax, AUCinf, AUC0-2.5 mins, AUC0 5 mins, AUC0-7.5 mins, AUC0 10 mins, AUC0 15 mins, AUC0-20 mins and AUC0-30 mins for nalmefene were compared between the treatments using an analysis of variance (ANOVA) model with treatment, period, sequence, and subject within sequence as the factors using the natural logarithms (ln) of the dose-normalized parameters. The following comparisons were made:

6 mg IN (2×3 mg in one nostril; T3, Treatment C) vs. 3 mg IN (in one nostril; T1, Treatment A)

6 mg IN (3 mg in each nostril; T2, Treatment B) vs. 3 mg IN (in one nostril; T1, Treatment A)

6 mg IN (3 mg in each nostril; T2, Treatment B) vs. 6 mg IN (2×3 mg in one nostril; T3, Treatment C)

Confidence intervals (CI) (90%) were constructed for the geometric mean ratios, using the log-transformed data and the two one-sided t tests procedure. The point estimates and confidence limits were exponentiated back to the original scale. Comparability between the nalmefene intranasal 2 sprays and nalmefene intranasal 1 spray was assessed from the geometric mean ratios and 90% CIs. All three treatments were included in the same ANOVA model with separate contrasts defined for each comparison.

Pharmacokinetic Results: The PK Analysis Population included all subjects who had evaluable PK data for both periods for at least one comparison (B vs. A; C vs. A; and B vs. C). PK data from 24 subjects (n=23 in Treatment A, T1; n=23 in Treatment B, T2; and n=24 in Treatment C, T3) were included in the PK analysis; 23 subjects were included in the statistical analyses. Subject 202 withdrew consent from the study prior to Period 2 dosing. Data for Subject 202 were included in the PK analysis for Treatment C (T3, Period 1) and were excluded from statistical analysis.

Mean nalmefene concentration-time profiles are shown on linear scales in FIG. 9 (full profile) and FIG. 10 (x axis truncated to 4 h post dose). Plasma concentrations (ng/ml) of nalmefene following T1, T2, and T3 treatments are shown in Tables 10, 11, and 12, respectively. Summary PK parameters are shown in Table 13 (PK parameters) and Table 14 (dose-normalized PK parameters). ANOVA results are shown in Table 15 (Treatment C, T3 vs. Treatment A, T1), Table 16 (Treatment B, T2 vs. Treatment A, T1), and Table 17 (Treatment B, T2 vs. Treatment C, T3).

TABLE 10

Plasma Concentrations (ng/mL) of Nalmefene Following T1 Treatment
(3 mg nalmefene HCl IN dose, one 0.1 mL spray in one nostril)

| Subject | Time | | | | | | | | | | |
|---|---|---|---|---|---|---|---|---|---|---|---|
| | 0.00 | 0.0416 | 0.0833 | 0.125 | 0.166 | 0.250 | 0.333 | 0.500 | 0.750 | 1.00 | 2.00 |
| 901 | 0.00 | 0.222 | 1.01 | 2.75 | 6.47 | 10.2 | 8.68 | 8.76 | 6.30 | 5.74 | 3.88 |
| 906 | 0.00 | 0.509 | 12.3 | 16.9 | 17.8 | 8.78 | 8.88 | 6.57 | 5.46 | 3.80 | 4.64 |
| 907 | 0.00 | 0.331 | 1.15 | 3.94 | 5.21 | 7.36 | 7.57 | 7.17 | 6.62 | 5.61 | 5.49 |
| 912 | 0.00 | 0.456 | 1.29 | 3.40 | 6.94 | 8.79 | 7.77 | 6.28 | 3.46 | 3.82 | 4.52 |
| 913 | 0.00 | 0.766 | 0.986 | 3.22 | 5.61 | 10.3 | 8.03 | 3.34 | 3.81 | 3.38 | 3.35 |
| 916 | 0.00 | 0.0738 | 0.702 | 1.32 | 2.00 | 2.71 | 3.33 | 2.77 | 3.35 | 3.40 | 3.69 |
| 917 | 0.00 | 0.133 | 0.486 | 4.44 | 13.0 | 15.6 | 14.8 | 7.79 | 6.50 | 5.99 | 6.79 |
| 919 | 0.00 | 0.234 | 1.52 | 3.39 | 6.08 | 7.11 | 8.09 | 8.11 | 6.20 | 5.05 | 4.59 |
| 921 | 0.00 | 0.00 | 3.59 | 0.642 | 1.09 | 1.88 | 1.97 | 1.43 | 2.52 | 3.20 | 3.61 |
| 922 | 0.00 | 0.713 | . | . | 2.96 | 3.75 | 3.87 | 7.01 | 7.28 | 7.24 | 5.85 |
| 923 | 0.00 | 0.575 | 1.24 | 2.95 | 4.22 | 8.00 | 5.58 | 6.00 | 5.84 | 7.86 | 5.38 |
| 924 | 0.00 | 0.654 | 1.28 | 3.23 | 5.69 | 5.24 | 6.36 | 5.11 | 4.59 | 4.41 | 4.18 |
| 927 | 0.00 | 0.0978 | 0.530 | 1.30 | 2.60 | 6.27 | 8.05 | 4.64 | 4.65 | 5.11 | 6.17 |
| 930 | 0.00 | 0.534 | 1.39 | 4.10 | 5.51 | 8.04 | 9.28 | 10.4 | 10.7 | 8.34 | 6.92 |
| 932 | 0.00 | 0.145 | 2.73 | 3.89 | 7.10 | 6.78 | 4.75 | 5.61 | 4.53 | 4.13 | 3.28 |
| 933 | 0.00 | 0.313 | 1.23 | 2.15 | 7.31 | 13.7 | 8.68 | 4.96 | 5.79 | 5.66 | 6.06 |
| 936 | 0.00 | 0.00 | 0.319 | 5.14 | 9.19 | 15.3 | 9.02 | 7.43 | 5.92 | 4.61 | 3.65 |
| 937 | 0.00 | 0.490 | 8.41 | 11.1 | 14.6 | 22.1 | 19.9 | 9.12 | 10.9 | 6.93 | 6.35 |
| 938 | 0.00 | 0.392 | 4.68 | 14.6 | 20.4 | 15.0 | 20.2 | 15.1 | 7.93 | 5.58 | 4.62 |
| 940 | 0.00 | 0.569 | 3.21 | 5.70 | . | 7.53 | . | 10.9 | 9.87 | 9.54 | 7.64 |
| 945 | 0.00 | 0.161 | 0.860 | 6.98 | 11.7 | 10.7 | 12.4 | 6.19 | 5.85 | 4.75 | 3.69 |
| 946 | 0.00 | . | 2.06 | 8.19 | 11.9 | 8.35 | 12.1 | 7.40 | 5.89 | 7.94 | 6.45 |
| 948 | 0.00 | 0.404 | 1.39 | 2.85 | 3.82 | 7.52 | 4.10 | 1.99 | 3.73 | 3.67 | 3.91 |
| n | 23 | 22 | 22 | 22 | 22 | 23 | 22 | 23 | 23 | 23 | 23 |
| Mean | 0.00 | 0.353 | 2.38 | 5.10 | 7.78 | 9.17 | 8.79 | 6.70 | 5.99 | 5.47 | 4.99 |
| SD | 0.00 | 0.232 | 2.86 | 4.19 | 5.12 | 4.65 | 4.75 | 3.05 | 2.23 | 1.78 | 1.31 |
| CV % | NC | 65.7 | 120 | 82.2 | 65.8 | 50.7 | 54.0 | 45.6 | 37.2 | 32.5 | 26.4 |
| Min | 0.00 | 0.00 | 0.319 | 0.642 | 1.09 | 1.88 | 1.97 | 1.43 | 2.52 | 3.20 | 3.28 |
| Median | 0.00 | 0.362 | 1.29 | 3.65 | 6.28 | 8.04 | 8.07 | 6.57 | 5.85 | 5.11 | 4.62 |
| Max | 0.00 | 0.766 | 12.3 | 16.9 | 20.4 | 22.1 | 20.2 | 15.1 | 10.9 | 9.54 | 7.64 |

| Subject | Time | | | | | | | |
|---|---|---|---|---|---|---|---|---|
| | 3.00 | 4.00 | 6.00 | 8.00 | 12.0 | 18.0 | 24.0 | 48.0 |
| 901 | 3.51 | 2.78 | 1.76 | 1.26 | 0.805 | 0.397 | 0.278 | 0.00 |
| 906 | 3.32 | 2.51 | 1.97 | 1.34 | 1.13 | 0.581 | 0.484 | 0.165 |
| 907 | 3.61 | 2.75 | 1.76 | 1.58 | 0.999 | 0.581 | 0.403 | 0.0647 |
| 912 | 3.75 | 3.37 | 2.41 | 1.71 | 1.20 | 0.839 | 0.785 | 0.184 |
| 913 | 3.01 | 2.20 | 1.52 | 1.00 | 0.755 | 0.450 | 0.326 | 0.127 |
| 916 | 2.99 | 2.26 | 1.54 | 1.06 | 0.821 | 0.549 | 0.261 | 0.00 |
| 917 | 2.47 | 2.46 | 1.46 | 1.34 | 0.782 | 0.370 | 0.276 | 0.0705 |
| 919 | 4.31 | 3.71 | 2.56 | 1.62 | 1.06 | 0.583 | 0.387 | 0.0803 |
| 921 | 2.70 | 2.56 | 1.65 | 1.20 | 0.846 | 0.583 | 0.320 | 0.0630 |
| 922 | 4.53 | 3.09 | 2.17 | 1.27 | 0.912 | 0.405 | 0.343 | 0.0961 |
| 923 | 4.79 | 3.51 | 1.97 | 1.25 | 1.05 | 0.649 | 0.452 | 0.132 |
| 924 | 2.95 | 2.62 | 2.07 | 1.31 | 0.863 | 0.445 | 0.301 | 0.0697 |
| 927 | 4.61 | 3.39 | 2.35 | 1.66 | 0.985 | 0.650 | 0.411 | 0.0936 |
| 930 | 5.75 | 4.86 | 2.85 | 2.03 | 1.27 | 0.784 | 0.497 | 0.0880 |
| 932 | 2.16 | 1.97 | 1.43 | 1.00 | 0.887 | 0.500 | 0.334 | 0.0925 |
| 933 | 4.27 | 3.46 | 2.26 | 1.59 | 0.789 | 0.671 | 0.413 | 0.0695 |
| 936 | 2.87 | 2.54 | 1.87 | 1.22 | 1.05 | 0.629 | 0.370 | 0.0852 |
| 937 | 4.48 | 3.41 | 2.37 | 1.33 | 0.848 | 0.490 | 0.366 | 0.117 |
| 938 | 2.94 | 2.90 | 2.45 | 1.64 | 1.16 | 0.724 | 0.600 | 0.153 |
| 940 | 6.01 | 4.34 | 3.01 | 2.19 | 1.29 | 0.813 | 0.598 | 0.0874 |
| 945 | 2.34 | 2.15 | 1.32 | 1.05 | 0.727 | 0.526 | 0.303 | 0.0713 |
| 946 | 4.68 | 3.53 | 2.51 | 1.97 | 1.51 | 0.851 | 0.603 | 0.163 |
| 948 | 3.15 | 2.39 | 2.15 | 1.51 | 1.07 | 0.529 | 0.366 | 0.0940 |
| n | 23 | 23 | 23 | 23 | 23 | 23 | 23 | 23 |
| Mean | 3.70 | 2.99 | 2.06 | 1.44 | 0.992 | 0.591 | 0.412 | 0.0942 |
| SD | 1.06 | 0.724 | 0.465 | 0.328 | 0.202 | 0.141 | 0.131 | 0.0460 |
| CV % | 28.5 | 24.2 | 22.6 | 22.8 | 20.3 | 23.9 | 31.7 | 48.8 |
| Min | 2.16 | 1.97 | 1.32 | 1.00 | 0.727 | 0.370 | 0.261 | 0.00 |
| Median | 3.51 | 2.78 | 2.07 | 1.34 | 0.985 | 0.581 | 0.370 | 0.0880 |
| Max | 6.01 | 4.86 | 3.01 | 2.19 | 1.51 | 0.851 | 0.785 | 0.184 |

TABLE 11

Plasma Concentrations (ng/mL) of Nalmefene Following T2 Treatment
(6 mg nalmefene HCl IN dose, one 0.1 mL spray in each nostril).

| | | | | Time | | | | | |
|---|---|---|---|---|---|---|---|---|---|
| Subject | 0.00 | 0.0416 | 0.0833 | 0.125 | 0.166 | 0.250 | 0.333 | 0.500 | 0.750 | 1.00 |
| 901 | 0.00 | 1.37 | 10.0 | . | 18.4 | 29.4 | 24.7 | 13.5 | 10.1 | 8.45 |
| 906 | 0.00 | 0.164 | 6.38 | 29.0 | 36.7 | 34.5 | 13.9 | 10.4 | 9.29 | 8.75 |
| 907 | 0.00 | 1.74 | 1.40 | 6.05 | 4.79 | 11.8 | 10.9 | 9.00 | 8.55 | 9.43 |
| 912 | 0.00 | 3.96 | 8.00 | 9.47 | 17.3 | 19.6 | 19.7 | 15.9 | 16.9 | 8.50 |
| 913 | 0.00 | 0.140 | 0.564 | 3.53 | 6.48 | 9.81 | 11.5 | 10.5 | 8.65 | 6.46 |
| 916 | 0.00 | 0.189 | 1.55 | 2.82 | 7.16 | 10.1 | 11.1 | 6.22 | 7.63 | 11.8 |
| 917 | 0.00 | 0.0610 | 0.871 | 4.92 | 30.5 | 35.9 | 25.9 | 21.3 | 14.7 | 8.93 |
| 919 | 0.00 | 0.597 | 1.92 | 2.79 | 4.64 | 6.08 | 8.26 | 6.51 | 7.34 | 8.81 |
| 921 | 0.00 | 0.194 | 2.02 | 3.59 | 5.59 | 9.95 | 6.18 | 6.38 | 7.47 | 7.93 |
| 922 | 0.00 | 1.33 | 5.86 | 6.88 | 9.52 | 10.4 | 11.7 | 12.0 | 10.9 | 12.0 |
| 923 | 0.00 | 0.817 | 4.60 | 7.60 | 9.68 | 12.5 | 10.6 | 12.4 | 11.3 | 11.5 |
| 924 | 0.00 | 0.839 | 3.02 | 8.84 | 19.1 | 28.8 | 23.0 | 6.69 | 10.3 | 7.49 |
| 927 | 0.00 | 0.311 | 0.973 | 2.39 | 3.68 | 14.3 | 8.73 | 11.0 | 8.95 | 10.1 |
| 930 | 0.00 | 1.00 | 12.7 | 29.8 | 33.8 | 23.8 | 32.3 | 15.0 | 12.2 | 12.6 |
| 932 | 0.00 | . | 5.88 | 6.81 | 7.80 | 11.5 | 10.9 | 8.83 | 9.26 | 8.86 |
| 933 | 0.00 | 0.784 | 2.63 | 27.2 | 24.0 | 23.1 | 15.3 | 10.8 | 8.74 | 10.3 |
| 936 | 0.00 | 0.0781 | 1.92 | 8.01 | 27.2 | 30.9 | 17.6 | 10.3 | 10.2 | 6.33 |
| 937 | 0.00 | 4.17 | 18.1 | 36.2 | 44.7 | 42.8 | 32.4 | 21.6 | 17.8 | 14.3 |
| 938 | 0.00 | 1.34 | 3.04 | 9.95 | 12.8 | 19.4 | 20.4 | 10.7 | 7.13 | 6.73 |
| 940 | 0.00 | 0.405 | 6.67 | 5.02 | 8.89 | . | 14.5 | 14.1 | . | 16.6 |
| 945 | 0.00 | 0.138 | 1.15 | 3.41 | 6.87 | . | 12.3 | 10.3 | 11.8 | 11.2 |
| 946 | 0.00 | . | . | 60.1 | 28.2 | 24.7 | 24.0 | 16.6 | 17.2 | 14.7 |
| 948 | 0.00 | . | 4.07 | 3.52 | 3.95 | 6.74 | 7.60 | 6.21 | 5.86 | 6.54 |
| n | 23 | 20 | 22 | 22 | 23 | 21 | 23 | 23 | 22 | 23 |
| Mean | 0.00 | 0.981 | 4.70 | 12.6 | 16.2 | 19.8 | 16.2 | 11.6 | 10.6 | 9.93 |
| SD | 0.00 | 1.17 | 4.39 | 14.7 | 12.2 | 10.7 | 7.69 | 4.36 | 3.37 | 2.79 |
| CV % | NC | 119 | 93.4 | 116 | 75.3 | 54.2 | 47.3 | 37.6 | 31.9 | 28.1 |
| Min | 0.00 | 0.0610 | 0.564 | 2.39 | 3.68 | 6.08 | 6.18 | 6.21 | 5.86 | 6.33 |
| Median | 0.00 | 0.691 | 3.03 | 6.85 | 9.68 | 19.4 | 13.9 | 10.7 | 9.70 | 8.93 |
| Max | 0.00 | 4.17 | 18.1 | 60.1 | 44.7 | 42.8 | 32.4 | 21.6 | 17.8 | 16.6 |

| | | | | Time | | | | | |
|---|---|---|---|---|---|---|---|---|---|
| Subject | 2.00 | 3.00 | 4.00 | 6.00 | 8.00 | 12.0 | 18.0 | 24.0 | 48.0 |
| 901 | 7.44 | 6.29 | 5.07 | 3.45 | 2.08 | 1.30 | 0.714 | 0.447 | 0.0855 |
| 906 | 8.22 | 6.80 | 4.35 | 3.44 | 2.00 | 1.92 | 1.24 | 0.659 | 0.241 |
| 907 | 10.3 | 8.41 | 6.86 | 4.10 | 3.40 | 2.73 | 1.47 | 0.999 | 0.164 |
| 912 | 9.64 | 8.39 | 7.56 | 5.54 | 4.13 | 2.95 | 1.39 | 1.33 | 0.417 |
| 913 | 6.88 | 7.18 | 5.78 | 2.87 | 2.22 | 1.31 | 0.761 | 0.562 | 0.123 |
| 916 | 10.1 | 7.70 | 6.09 | 3.48 | 2.46 | 1.50 | 0.927 | 0.621 | 0.131 |
| 917 | 3.79 | 4.84 | 5.15 | 3.61 | 2.70 | 1.79 | 0.799 | 0.620 | 0.104 |
| 919 | 10.2 | 8.47 | 6.25 | 4.05 | 3.29 | 1.87 | 1.12 | 0.790 | 0.153 |
| 921 | 7.57 | 5.38 | 3.99 | 3.14 | 2.35 | 1.64 | 0.971 | 0.793 | 0.172 |
| 922 | 10.2 | 8.01 | 5.86 | 3.38 | 2.43 | 1.89 | 0.981 | 0.761 | 0.136 |
| 923 | 8.15 | 6.73 | 4.38 | 3.08 | 2.50 | 1.58 | 0.902 | 1.10 | 0.266 |
| 924 | 7.04 | 6.13 | 4.51 | 3.48 | 2.69 | 1.88 | 1.12 | 0.793 | 0.107 |
| 927 | 11.8 | 9.24 | 6.76 | 4.73 | 2.90 | 1.92 | 1.25 | 0.750 | 0.172 |
| 930 | 13.0 | 10.2 | 4.48 | 5.24 | 3.66 | 2.47 | 1.61 | 0.956 | 0.190 |
| 932 | 8.42 | 5.62 | 4.65 | 3.10 | 2.40 | 1.99 | 1.37 | 0.975 | 0.228 |
| 933 | 12.0 | 8.23 | 6.35 | 4.09 | 3.28 | 2.12 | 1.35 | 0.870 | 0.193 |
| 936 | 6.53 | 5.28 | 3.80 | 2.73 | 1.94 | 1.68 | 0.916 | 0.654 | 0.192 |
| 937 | 11.6 | 7.26 | 6.23 | 4.10 | 2.92 | 1.94 | 1.04 | 0.712 | 0.238 |
| 938 | 6.79 | 5.04 | 4.09 | 2.65 | 1.87 | 1.92 | 1.22 | 0.873 | 0.252 |
| 940 | 12.8 | 9.38 | 7.92 | 4.96 | 3.53 | 2.62 | 1.48 | 1.17 | 0.164 |
| 945 | 7.97 | 6.30 | 4.41 | 2.97 | 2.42 | 1.92 | 1.17 | 0.638 | 0.162 |
| 946 | 10.9 | 7.95 | 5.91 | 4.08 | 3.47 | 2.16 | 1.70 | 1.11 | 0.313 |
| 948 | 6.68 | 8.31 | 6.64 | 4.27 | 3.23 | 2.22 | 1.09 | 0.835 | 0.214 |
| n | 23 | 23 | 23 | 23 | 23 | 23 | 23 | 23 | 23 |
| Mean | 9.04 | 7.27 | 5.53 | 3.76 | 2.78 | 1.97 | 1.16 | 0.827 | 0.192 |
| SD | 2.36 | 1.49 | 1.19 | 0.799 | 0.621 | 0.418 | 0.270 | 0.215 | 0.0749 |
| CV % | 26.1 | 20.5 | 21.6 | 21.2 | 22.4 | 21.2 | 23.3 | 26.0 | 39.0 |
| Min | 3.79 | 4.84 | 3.80 | 2.65 | 1.87 | 1.30 | 0.714 | 0.447 | 0.0855 |
| Median | 8.42 | 7.26 | 5.78 | 3.48 | 2.69 | 1.92 | 1.12 | 0.793 | 0.172 |
| Max | 13.0 | 10.2 | 7.92 | 5.54 | 4.13 | 2.95 | 1.70 | 1.33 | 0.417 |

TABLE 12

Plasma Concentrations (ng/mL) of Nalmefene Following T3 Treatment
(6 mg nalmefene HCl IN dose, two 0.1 mL sprays in one nostril)

| Subject | Time 0.00 | 0.0416 | 0.0833 | 0.125 | 0.166 | 0.250 | 0.333 | 0.500 | 0.750 | 1.00 |
|---|---|---|---|---|---|---|---|---|---|---|
| 901 | 0.00 | 0.435 | 3.62 | 4.88 | 9.12 | 12.8 | 10.7 | 7.67 | 6.69 | 8.38 |
| 903 | 0.00 | . | 10.3 | 29.8 | 33.6 | 32.2 | 27.0 | 11.8 | 10.2 | 10.9 |
| 906 | 0.00 | 1.50 | 28.9 | 33.8 | 32.9 | 21.3 | 17.6 | 7.42 | 6.21 | 6.05 |
| 907 | 0.00 | 0.887 | 1.70 | 3.62 | . | 8.60 | 10.5 | 15.4 | 15.4 | 14.1 |
| 912 | 0.00 | 0.872 | 4.51 | 7.88 | 11.3 | 16.3 | 13.3 | 11.2 | 9.92 | 9.25 |
| 913 | 0.00 | 1.16 | 3.62 | 3.49 | 8.21 | 11.1 | 9.67 | 10.4 | 5.57 | 6.26 |
| 916 | 0.00 | 0.234 | 1.34 | 2.36 | 3.37 | 5.54 | 5.09 | 5.80 | 6.98 | 7.17 |
| 917 | 0.00 | 8.54 | 0.630 | 6.77 | 7.95 | 39.3 | 30.4 | 21.8 | 12.8 | 10.8 |
| 919 | 0.00 | 0.515 | 3.68 | 6.97 | 9.60 | 11.7 | 9.62 | 6.02 | 9.52 | 11.1 |
| 921 | 0.00 | 0.320 | 0.894 | 2.34 | 5.05 | 3.79 | 8.90 | 6.49 | 7.08 | 7.81 |
| 922 | 0.00 | 0.253 | 1.51 | 2.73 | 4.09 | 5.58 | 6.76 | 7.56 | 7.57 | 8.50 |
| 923 | 0.00 | 1.19 | 1.84 | 4.56 | 6.23 | . | 5.96 | 7.88 | 6.78 | 7.20 |
| 924 | 0.00 | 2.19 | 2.78 | 4.49 | 7.43 | 8.55 | 7.77 | 7.41 | 4.33 | 6.27 |
| 927 | 0.00 | 0.228 | 1.41 | 3.84 | 3.74 | 11.3 | 11.7 | 10.5 | 11.1 | 13.3 |
| 930 | 0.00 | 0.746 | 3.99 | 10.2 | 18.3 | 26.1 | 15.1 | 17.3 | 16.3 | 14.3 |
| 932 | 0.00 | 0.708 | 18.9 | 22.1 | 34.5 | 28.5 | 18.2 | 10.1 | 10.1 | 7.29 |
| 933 | 0.00 | 2.60 | 8.20 | 30.0 | 30.5 | 26.2 | 15.8 | 9.41 | 9.86 | 10.4 |
| 936 | 0.00 | 0.102 | 1.41 | 4.92 | 8.55 | 13.0 | 10.5 | 4.72 | 6.57 | 6.45 |
| 937 | 0.00 | 0.453 | 5.28 | 19.2 | 14.7 | 25.9 | 28.5 | 12.8 | 15.5 | 10.7 |
| 938 | 0.00 | 0.242 | 1.86 | 4.15 | 6.65 | 8.21 | 7.92 | 7.14 | 7.47 | 6.52 |
| 940 | 0.00 | 1.16 | . | . | 13.2 | 17.4 | 16.9 | 16.9 | 16.7 | 16.6 |
| 945 | 0.00 | 0.324 | 2.36 | 5.00 | 7.25 | 11.1 | 12.2 | 8.95 | 15.6 | 11.6 |
| 946 | 0.00 | 3.59 | 2.38 | 32.2 | 41.3 | 37.2 | 41.3 | 21.2 | . | 13.6 |
| 948 | 0.00 | 2.88 | . | . | 6.63 | 8.09 | 7.95 | 7.03 | . | 5.55 |
| n | 24 | 23 | 22 | 22 | 23 | 23 | 24 | 24 | 22 | 24 |
| Mean | 0.00 | 1.35 | 5.05 | 11.2 | 14.1 | 16.9 | 14.6 | 10.5 | 9.92 | 9.59 |
| SD | 0.00 | 1.83 | 6.71 | 11.0 | 11.7 | 10.5 | 8.96 | 4.76 | 3.87 | 3.13 |
| CV % | NC | 135 | 133 | 98.6 | 82.9 | 62.1 | 61.6 | 45.2 | 39.0 | 32.7 |
| Min | 0.00 | 0.102 | 0.630 | 2.34 | 3.37 | 3.79 | 5.09 | 4.72 | 4.33 | 5.55 |
| Median | 0.00 | 0.746 | 2.58 | 4.96 | 8.55 | 12.8 | 11.2 | 9.18 | 9.69 | 8.88 |
| Max | 0.00 | 8.54 | 28.9 | 33.8 | 41.3 | 39.3 | 41.3 | 21.8 | 16.7 | 16.6 |

| Subject | Time 2.00 | 3.00 | 4.00 | 6.00 | 8.00 | 12.0 | 18.0 | 24.0 | 48.0 |
|---|---|---|---|---|---|---|---|---|---|
| 901 | 7.13 | 6.24 | 4.52 | 3.03 | 2.28 | 1.28 | 0.718 | 0.455 | 0.0712 |
| 903 | 7.10 | 5.33 | 4.69 | 3.58 | 2.35 | 1.82 | 1.16 | 0.910 | . |
| 906 | 6.19 | 4.83 | 4.10 | 3.38 | 2.71 | 2.24 | 1.29 | 0.853 | 0.254 |
| 907 | 10.3 | 8.78 | 6.17 | 4.05 | 2.67 | 2.18 | 1.27 | 0.665 | 0.0916 |
| 912 | 10.5 | 10.0 | 7.96 | 5.15 | 4.01 | 2.66 | 1.61 | 1.38 | 0.346 |
| 913 | 5.95 | 4.50 | 4.15 | 2.65 | 2.14 | 1.27 | 0.696 | 0.568 | 0.0888 |
| 916 | 7.37 | 4.93 | 3.97 | 3.08 | 2.53 | 1.87 | 0.830 | 0.558 | 0.117 |
| 917 | 15.8 | 5.43 | 4.18 | 3.45 | 2.29 | 1.45 | 0.885 | 0.608 | 0.141 |
| 919 | 11.3 | 9.72 | 7.58 | 4.53 | 3.77 | 2.31 | 1.37 | 0.641 | 0.186 |
| 921 | 8.32 | 6.73 | 3.94 | 3.09 | 2.36 | 1.67 | 1.02 | 0.742 | 0.170 |
| 922 | 10.8 | 7.93 | 5.91 | 4.25 | 3.04 | 1.84 | 0.898 | 0.731 | 0.176 |
| 923 | 7.00 | 5.78 | 4.84 | 3.21 | 2.24 | 1.80 | 1.27 | 0.973 | 0.337 |
| 924 | 5.76 | 4.12 | 3.29 | 2.92 | 2.16 | 1.56 | 0.888 | 0.553 | 0.116 |
| 927 | 11.0 | 11.5 | 6.66 | 4.53 | 3.05 | 1.94 | 0.921 | 0.621 | 0.180 |
| 930 | 11.7 | 8.79 | 8.96 | 5.54 | 3.90 | 2.62 | 1.45 | 0.934 | 0.187 |
| 932 | 6.65 | 4.75 | 5.08 | 2.88 | 1.86 | 1.62 | 1.12 | 0.920 | 0.221 |
| 933 | 8.87 | 7.14 | 5.65 | 3.51 | 2.51 | 1.81 | 1.12 | 0.723 | 0.132 |
| 936 | 5.33 | 3.96 | 3.74 | 2.08 | 1.86 | 1.52 | 0.978 | 0.679 | 0.201 |
| 937 | 11.7 | 9.97 | 6.60 | 3.75 | 2.40 | 1.55 | 1.00 | 0.727 | 0.221 |
| 938 | 6.85 | 5.08 | 3.63 | 3.50 | 2.16 | 1.81 | 1.25 | 0.962 | 0.156 |
| 940 | 12.8 | 9.58 | 7.36 | 5.28 | 3.89 | 2.82 | 1.39 | 1.16 | 0.167 |
| 945 | 9.42 | 6.05 | 4.02 | 2.40 | 2.22 | 1.66 | 1.05 | 0.752 | 0.164 |
| 946 | 9.06 | 8.09 | 6.84 | 4.73 | 3.42 | 2.52 | 1.39 | 1.18 | 0.236 |
| 948 | 5.84 | 6.45 | 4.93 | 4.08 | 2.68 | 2.38 | 1.13 | 0.714 | 0.224 |
| n | 24 | 24 | 24 | 24 | 24 | 24 | 24 | 24 | 23 |
| Mean | 8.86 | 6.90 | 5.37 | 3.69 | 2.69 | 1.93 | 1.11 | 0.792 | 0.182 |
| SD | 2.69 | 2.19 | 1.57 | 0.918 | 0.658 | 0.442 | 0.240 | 0.225 | 0.0699 |
| CV % | 30.4 | 31.7 | 29.3 | 24.9 | 24.5 | 23.0 | 21.5 | 28.4 | 38.4 |
| Min | 5.33 | 3.96 | 3.29 | 2.08 | 1.86 | 1.27 | 0.696 | 0.455 | 0.0712 |
| Median | 8.60 | 6.35 | 4.89 | 3.51 | 2.46 | 1.82 | 1.12 | 0.729 | 0.176 |
| Max | 15.8 | 11.5 | 8.96 | 5.54 | 4.01 | 2.82 | 1.61 | 1.38 | 0.346 |

TABLE 13

Plasma PK Parameters of Nalmefene after IN Administration of 3 mg Nalmefene HCl in One Nostril (Treatment A, T1), 3 mg (6 mg Total Dose) Nalmefene HCl in Each Nostril (Treatment B, T2), and 6 mg Nalmefene HCl in One Nostril (Treatment C, T3)

| Parameter | n | Treatment A (T1): Nalmefene HCl 3.0 mg in One Nostril | | | n | Treatment B (T2): Nalmefene HCl 3 mg in Each Nostril | | |
|---|---|---|---|---|---|---|---|---|
| | | Mean | SD | CV % | | Mean | SD | CV % |
| $T_{max}{}^a$ (h) | 23 | 0.267 (0.167-2.03) | | | 23 | 0.250 (0.117-3.00) | | |
| $C_{max}$ (ng/mL) | 23 | 10.8 | 4.87 | 45.2 | 23 | 22.2 | 13.5 | 60.8 |
| $AUC_{last}$ (h*ng/mL) | 23 | 44.9 | 9.97 | 22.2 | 23 | 86.2 | 16.0 | 18.5 |
| $AUC_{inf}$ (h*ng/mL) | 23 | 46.8 | 10.1 | 21.5 | 23 | 89.5 | 17.0 | 19.0 |
| $AUC_{Extrap}$ (%) | 23 | 4.22 | 2.14 | 50.7 | 23 | 3.61 | 1.61 | 44.7 |
| $t_{1/2}$ (h) | 23 | 11.4 | 2.51 | 22.0 | 23 | 11.3 | 1.87 | 16.6 |
| CL/F (L/h) | 23 | 66.9 | 14.2 | 21.2 | 23 | 69.2 | 12.0 | 17.3 |
| $V_z/F$ (L) | 23 | 1090 | 300 | 27.5 | 23 | 1120 | 228 | 20.3 |
| $AUC_{0-2.5\ min}$ (h*ng/mL) | 23 | 0.00829 | 0.00573 | 69.2 | 23 | 0.0432 | 0.0924 | 214 |
| $AUC_{0-5\ min}$ (h*ng/mL) | 23 | 0.0618 | 0.0568 | 92.0 | 23 | 0.222 | 0.374 | 169 |
| $AUC_{0-7.5\ min}$ (h*ng/mL) | 23 | 0.219 | 0.185 | 84.7 | 23 | 0.638 | 0.854 | 134 |
| $AUC_{0-10\ min}$ (h*ng/mL) | 23 | 0.480 | 0.364 | 75.7 | 23 | 1.21 | 1.28 | 106 |
| $AUC_{0-15\ min}$ (h*ng/mL) | 23 | 1.18 | 0.713 | 60.5 | 23 | 2.67 | 2.03 | 76.0 |
| $AUC_{0-20\ min}$ (h*ng/mL) | 23 | 1.92 | 1.04 | 54.5 | 23 | 4.14 | 2.68 | 64.6 |
| $AUC_{0-30\ min}$ (h*ng/mL) | 23 | 3.19 | 1.57 | 49.4 | 23 | 6.46 | 3.52 | 54.6 |

| Parameter | n | Treatment C (T3): Nalmefene HCl 6 mg in One Nostril | | |
|---|---|---|---|---|
| | | Mean | SD | CV % |
| $T_{max}{}^a$ (h) | 24 | 0.250 (0.117-2.03) | | |
| $C_{max}$ (ng/mL) | 24 | 18.9 | 11.2 | 59.2 |
| $AUC_{last}$ (h*ng/mL) | 24 | 82.1 | 18.3 | 22.3 |
| $AUC_{inf}$ (h*ng/mL) | 24 | 85.7 | 18.7 | 21.9 |
| $AUC_{Extrap}$ (%) | 24 | 4.18 | 3.23 | 77.2 |
| $t_{1/2}$ (h) | 24 | 11.3 | 1.86 | 16.5 |
| CL/F (L/h) | 24 | 73.3 | 15.9 | 21.7 |
| $V_z/F$ (L) | 24 | 1190 | 300 | 25.2 |
| $AUC_{0-2.5\ min}$ (h*ng/mL) | 24 | 0.0273 | 0.0337 | 124 |
| $AUC_{0-5\ min}$ (h*ng/mL) | 24 | 0.146 | 0.122 | 83.5 |
| $AUC_{0-7.5\ min}$ (h*ng/mL) | 24 | 0.482 | 0.432 | 89.7 |
| $AUC_{0-10\ min}$ (h*ng/mL) | 24 | 0.988 | 0.867 | 87.8 |
| $AUC_{0-15\ min}$ (h*ng/mL) | 24 | 2.24 | 1.70 | 75.9 |
| $AUC_{0-20\ min}$ (h*ng/mL) | 24 | 3.53 | 2.40 | 68.2 |
| $AUC_{0-30\ min}$ (h*ng/mL) | 24 | 5.58 | 3.28 | 58.7 |

$^a T_{max}$ presented as median (range)
Treatment A: T1: 3 mg IN nalmefene dose (one 0.1 mL spray of a 30 mg/mL solution in one nostril)
Treatment B: T2: 6 mg IN nalmefene dose (one 0.1 mL spray of a 30 mg/mL solution in each nostril)
Treatment C: T3: 6 mg IN nalmefene dose (two 0.1 mL sprays of a 30 mg/mL solution in one nostril)

TABLE 14

Dose-Normalized Plasma PK Parameters of Nalmefene after IN Administration of 3 mg Nalmefene HCl in One Nostril (Treatment A, T1), 3 mg (6 mg Total Dose) Nalmefene HCl in Each Nostril (Treatment B, T2), and 6 mg Nalmefene HCl in One Nostril (Treatment C, T3)

| Parameter | n | Treatment A (T1): Nalmefene HCl 3.0 mg in One Nostril | | | n | Treatment B (T2): Nalmefene HCl 3 mg in Each Nostril | | |
|---|---|---|---|---|---|---|---|---|
| | | Mean | SD | CV % | | Mean | SD | CV % |
| $C_{max}/D$ (ng/mL/mg) | 23 | 3.59 | 1.62 | 45.2 | 23 | 3.70 | 2.25 | 60.8 |
| $AUC_{last}/D$ (h*ng/mL/mg) | 23 | 15.0 | 3.32 | 22.2 | 23 | 14.4 | 2.66 | 18.5 |
| $AUC_{inf}/D$ (h*ng/mL/mg) | 23 | 15.6 | 3.36 | 21.5 | 23 | 14.9 | 2.83 | 19.0 |
| $AUC_{0-2.5\ min}/D$ (h*ng/mL/mg) | 23 | 0.00276 | 0.00191 | 69.2 | 23 | 0.00720 | 0.0154 | 214 |
| $AUC_{0-5\ min}/D$ (h*ng/mL/mg) | 23 | 0.0206 | 0.0189 | 92.0 | 23 | 0.0369 | 0.0623 | 169 |
| $AUC_{0-7.5\ min}/D$ (h*ng/mL/mg) | 23 | 0.0728 | 0.0617 | 84.7 | 23 | 0.106 | 0.142 | 134 |
| $AUC_{0-10\ min}/D$ (h*ng/mL/mg) | 23 | 0.160 | 0.121 | 75.7 | 23 | 0.202 | 0.213 | 106 |
| $AUC_{0-15\ min}/D$ (h*ng/mL/mg) | 23 | 0.393 | 0.238 | 60.5 | 23 | 0.445 | 0.338 | 76.0 |
| $AUC_{0-20\ min}/D$ (h*ng/mL/mg) | 23 | 0.639 | 0.348 | 54.5 | 23 | 0.691 | 0.446 | 64.6 |
| $AUC_{0-30\ min}/D$ (h*ng/mL/mg) | 23 | 1.06 | 0.525 | 49.4 | 23 | 1.08 | 0.587 | 54.6 |

TABLE 14-continued

Dose-Normalized Plasma PK Parameters of Nalmefene after IN Administration of 3 mg Nalmefene HCl in One Nostril (Treatment A, T1), 3 mg (6 mg Total Dose) Nalmefene HCl in Each Nostril (Treatment B, T2), and 6 mg Nalmefene HCl in One Nostril (Treatment C, T3)

| Parameter | Treatment C (T3): Nalmefene HCl 6 mg in One Nostril | | | |
|---|---|---|---|---|
| | n | Mean | SD | CV % |
| $C_{max}/D$ (ng/mL/mg) | 24 | 3.15 | 1.87 | 59.2 |
| $AUC_{last}/D$ (h*ng/mL/mg) | 24 | 13.7 | 3.06 | 22.3 |
| $AUC_{inf}/D$ (h*ng/mL/mg) | 24 | 14.3 | 3.12 | 21.9 |
| $AUC_{0-2.5\ min}/D$ (h*ng/mL/mg) | 24 | 0.00455 | 0.00562 | 124 |
| $AUC_{0-5\ min}/D$ (h*ng/mL/mg) | 24 | 0.0244 | 0.0203 | 83.5 |
| $AUC_{0-7.5\ min}/D$ (h*ng/mL/mg) | 24 | 0.0803 | 0.0720 | 89.7 |
| $AUC_{0-10\ min}/D$ (h*ng/mL/mg) | 24 | 0.165 | 0.145 | 87.8 |
| $AUC_{0-15\ min}/D$ (h*ng/mL/mg) | 24 | 0.374 | 0.284 | 75.9 |
| $AUC_{0-20\ min}/D$ (h*ng/mL/mg) | 24 | 0.588 | 0.401 | 68.2 |
| $AUC_{0-30\ min}/D$ (h*ng/mL/mg) | 24 | 0.931 | 0.546 | 58.7 |

[a]$T_{max}$ presented as median (range)
Treatment A: T1: 3 mg IN nalmefene dose (one 0.1 mL spray of a 30 mg/mL solution in one nostril)
Treatment B: T2: 6 mg IN nalmefene dose (one 0.1 mL spray of a 30 mg/mL solution in each nostril)
Treatment C: T3: 6 mg IN nalmefene dose (two 0.1 mL sprays of a 30 mg/mL solution in one nostril)

TABLE 15

Statistical Analysis of the Natural Log-Transformed, Dose-Normalized Exposure Parameters of Nalmefene Comparing 6 mg Nalmefene Hydrochloride in One Nostril (Treatment C, T3, Test) and 3 mg Nalmefene Hydrochloride in One Nostril (Treatment A, T1, Reference)

| Dependent Variable | Geometric Mean[a] | | Ratio (%)[b] (Test, C/Ref, A) | 90% CI[c] | | ANOVA | | |
|---|---|---|---|---|---|---|---|---|
| | Test (C) | Ref (A) | | Lower | Upper | Power | p-value[d] | CV % |
| $C_{max}$/Dose | 2.68 | 3.31 | 80.89 | 69.46 | 94.21 | 0.7803 | 0.0241 | 31.44 |
| $AUC_{2.5\ min}$/Dose | 0.00271 | 0.00202 | 134.62 | 86.89 | 208.57 | 0.2146 | 0.2598 | 108.46 |
| $AUC_{5\ min}$/Dose | 0.0172 | 0.0149 | 115.52 | 81.29 | 164.16 | 0.2757 | 0.4937 | 80.65 |
| $AUC_{7.5\ min}$/Dose | 0.0560 | 0.0582 | 96.28 | 75.12 | 123.39 | 0.4344 | 0.7983 | 53.28 |
| $AUC_{10\ min}$/Dose | 0.117 | 0.132 | 88.62 | 71.87 | 109.27 | 0.5440 | 0.3375 | 44.15 |
| $AUC_{15\ min}$/Dose | 0.284 | 0.340 | 83.67 | 69.87 | 100.18 | 0.6551 | 0.1034 | 37.52 |
| $AUC_{20\ min}$/Dose | 0.469 | 0.565 | 83.00 | 70.46 | 97.76 | 0.7277 | 0.0624 | 33.90 |
| $AUC_{30\ min}$/Dose | 0.791 | 0.959 | 82.42 | 71.48 | 95.04 | 0.8270 | 0.0275 | 29.29 |
| $AUC_{last}$/Dose | 13.5 | 14.7 | 91.77 | 87.68 | 96.06 | 1.0000 | 0.0029 | 9.21 |
| $AUC_{inf}$/Dose | 14.0 | 15.3 | 91.19 | 87.19 | 95.38 | 1.0000 | 0.0013 | 9.07 |

Treatment A: T1: 3 mg IN nalmefene dose (one 0.1 mL spray of a 30 mg/mL solution in one nostril) (Ref)
Treatment C: T3: 6 mg IN nalmefene dose (two 0.1 mL sprays of a 30 mg/mL solution in one nostril) (Test)
[a]Geometric Mean for Treatment C, T3 (Test) and Treatment A, T1 (Ref) based on Least Squares Mean of log-transformed parameter values
[b]Ratio(%) = Geometric Mean (Test)/Geometric Mean (Ref)
[c]90% Confidence Interval
[d]pvalue for the difference between treatments; Significant difference defined a priori as p < 0.05

TABLE 16

Statistical Analysis of the Natural Log-Transformed, Dose-Normalized Exposure Parameters of Nalmefene Comparing 3 mg Nalmefene Hydrochloride in Each Nostril (6 mg Total Dose, Treatment B, T2, Test) and 3 mg Nalmefene Hydrochloride in One Nostril (Treatment A, T1, Reference)

| Dependent Variable | Geometric Mean[a] | | Ratio (%)[b] (Test, B/Ref, A) | 90% CI[c] | | ANOVA | | |
|---|---|---|---|---|---|---|---|---|
| | Test (B) | Ref (A) | | Lower | Upper | Power | p-value[d] | CV % |
| $C_{max}$/Dose | 3.25 | 3.31 | 98.15 | 84.27 | 114.31 | 0.7803 | 0.8374 | 31.44 |
| $AUC_{2.5\ min}$/Dose | 0.00280 | 0.00202 | 139.05 | 89.75 | 215.43 | 0.2146 | 0.2123 | 108.46 |
| $AUC_{5\ min}$/Dose | 0.0187 | 0.0149 | 125.35 | 88.21 | 178.13 | 0.2757 | 0.2857 | 80.65 |
| $AUC_{7.5\ min}$/Dose | 0.0666 | 0.0582 | 114.51 | 89.34 | 146.76 | 0.4344 | 0.3637 | 53.28 |
| $AUC_{10\ min}$/Dose | 0.143 | 0.132 | 108.32 | 87.84 | 133.56 | 0.5440 | 0.5248 | 44.15 |
| $AUC_{15\ min}$/Dose | 0.358 | 0.340 | 105.44 | 88.06 | 126.26 | 0.6551 | 0.6233 | 37.52 |
| $AUC_{20\ min}$/Dose | 0.588 | 0.565 | 104.11 | 88.39 | 122.63 | 0.7277 | 0.6809 | 33.90 |
| $AUC_{30\ min}$/Dose | 0.964 | 0.959 | 100.46 | 87.13 | 115.84 | 0.8270 | 0.9568 | 29.29 |

TABLE 16-continued

Statistical Analysis of the Natural Log-Transformed, Dose-Normalized Exposure Parameters of Nalmefene Comparing 3 mg Nalmefene Hydrochloride in Each Nostril (6 mg Total Dose, Treatment B, T2, Test) and 3 mg Nalmefene Hydrochloride in One Nostril (Treatment A, T1, Reference)

| Dependent Variable | Geometric Mean[a] | | Ratio (%)[b] | 90% CI[c] | | ANOVA | | |
|---|---|---|---|---|---|---|---|---|
| | Test (B) | Ref (A) | (Test, B/Ref, A) | Lower | Upper | Power | p-value[d] | CV % |
| $AUC_{last}$/Dose | 14.2 | 14.7 | 96.87 | 92.55 | 101.40 | 1.0000 | 0.2481 | 9.21 |
| $AUC_{inf}$/Dose | 14.8 | 15.3 | 96.23 | 92.00 | 100.65 | 1.0000 | 0.1576 | 9.07 |

Treatment A: T1: 3 mg IN nalmefene dose (one 0.1 mL spray of a 30 mg/mL solution in one nostril)
Treatment B: T2: 6 mg IN nalmefene dose (one 0.1 mL spray of a 30 mg/mL solution in each nostril)
[a]Geometric Mean for Treatment B, T2 (Test) and Treatment A, T1 (Ref) based on Least Squares Mean of log-transformed parameter values
[b]Ratio(%) = Geometric Mean (Test)/Geometric Mean (Ref)
[c]90% Confidence Interval
[d]pvalue for the difference between treatments; Significant difference defined a priori as p < 0.05

TABLE 17

Statistical Analysis of the Natural Log-Transformed, Dose-Normalized Exposure Parameters of Nalmefene Comparing 3 mg Nalmefene Hydrochloride in Each Nostril (6 mg Total Dose, Treatment B, T2, Test) and 6 mg Nalmefene Hydrochloride in One Nostril (Treatment C, T3, Reference)

| Dependent Variable | Geometric Mean[a] | | Ratio (%)[b] | 90% CI[c] | | ANOVA | | |
|---|---|---|---|---|---|---|---|---|
| | Test (B) | Ref (C) | (Test, B/Ref, C) | Lower | Upper | Power | p-value[d] | CV % |
| $C_{max}$/Dose | 3.25 | 2.68 | 121.33 | 104.17 | 141.30 | 0.7803 | 0.0388 | 31.44 |
| $AUC_{2.5\ min}$/Dose | 0.00280 | 0.00271 | 103.29 | 66.67 | 160.02 | 0.2146 | 0.9017 | 108.46 |
| $AUC_{5\ min}$/Dose | 0.0187 | 0.0172 | 108.51 | 76.36 | 154.20 | 0.2757 | 0.6979 | 80.65 |
| $AUC_{7.5\ min}$/Dose | 0.0666 | 0.0560 | 118.94 | 92.80 | 152.44 | 0.4344 | 0.2464 | 53.28 |
| $AUC_{10\ min}$/Dose | 0.143 | 0.117 | 122.23 | 99.13 | 150.71 | 0.5440 | 0.1146 | 44.15 |
| $AUC_{15\ min}$/Dose | 0.358 | 0.284 | 126.03 | 105.25 | 150.91 | 0.6551 | 0.0366 | 37.52 |
| $AUC_{20\ min}$/Dose | 0.588 | 0.469 | 125.44 | 106.50 | 147.76 | 0.7277 | 0.0248 | 33.90 |
| $AUC_{30\ min}$/Dose | 0.964 | 0.791 | 121.89 | 105.71 | 140.56 | 0.8270 | 0.0242 | 29.29 |
| $AUC_{last}$/Dose | 14.2 | 13.5 | 105.56 | 100.85 | 110.49 | 1.0000 | 0.0528 | 9.21 |
| $AUC_{inf}$/Dose | 14.8 | 14.0 | 105.53 | 100.89 | 110.37 | 1.0000 | 0.0504 | 9.07 |

Treatment B: T2: 6 mg IN nalmefene dose (one 0.1 mL spray of a 30 mg/mL solution in each nostril) (Test)
Treatment C: T3: 6 mg IN nalmefene dose (two 0.1 mL sprays of a 30 mg/mL solution in one nostril) (Ref)
[a]Geometric Mean for Treatment B, T2 (Test) and Treatment C, T3 (Ref) based on Least Squares Mean of log-transformed parameter values
[b]Ratio(%) = Geometric Mean (Test)/Geometric Mean (Ref)
[c]90% Confidence Interval
[d]pvalue for the difference between treatments; Significant difference defined a priori as p < 0.05

Safety Results: There were no serious AEs (SAEs) or AEs that led to a subject withdrawal or death.

A total of 68 treatment-emergent AEs (TEAEs) were reported by 22 subjects over the course of the study: 20 AEs were reported by 10 (43.5%) subjects following Treatment A (3 mg), 24 AEs were reported by 14 (60.9%) subjects following Treatment B (6 mg [1 spray in each nostril]), and 24 AEs were reported by 14 (58.3%) subjects following Treatment C (6 mg [2 sprays in 1 nostril]).

No clinically significant abnormalities in ECGs, physical examinations, or nasal examinations were observed. There were clinically significant findings in NRS data. There were no AEs related to clinically significant out-of-range vital signs.

The most frequently reported postdose AEs were:
Nasal congestion (Overall 7 instances; 1 instance reported by 1 subject after Treatment A, 2 instances reported by 1 subject after Treatment B, and 4 instances reported by 4 subjects after Treatment C)
Nasal discomfort (Overall 7 instances; 1 instance reported by 1 subject after Treatment A, 3 instances reported by 3 subjects after Treatment B, and 3 instances reported by 3 subjects after Treatment C)
Nausea (Overall 7 instances; 1 instance reported by 1 subject after Treatment A, 5 instances reported by 5 subjects after Treatment B, and 1 instance reported by 1 subject after Treatment C)

The MedDRA system organ class (SOC) with the greatest frequency of TEAEs was respiratory, thoracic, and mediastinal disorders (29 instances reported by 15 subjects [62.5%] across all treatments).

All TEAEs were mild in severity. Of the 68 reported TEAEs, 37 AEs were judged by the Investigator as probably related to the study treatment, 19 AEs were judged as possibly related to the study treatment, 5 AEs were judged as definitely related to the study treatment, 4 AEs were judged as unlikely related to the study treatment, and 3 AEs were judged as definitely not related to the study treatment.

Of the 22 subjects who experienced AEs during the study, 5 subjects experienced AEs that were judged by the Investigator as definitely related to the study treatment, 1 subject experienced AEs that were judged as unlikely related to the study treatment, 12 subjects experienced AEs that were judged as possibly related to the study treatment, 15 subjects experienced AEs that were judged as probably related to the study treatment, and 3 subjects experienced AEs that were judged as definitely not related to the study treatment.

Conclusions: A total of 24 subjects participated in the study, and 23 of these subjects completed all 3 study periods. Subject 202 withdrew consent after completing Period 1.

Overall, the investigational product was well-tolerated when administered as a 3 mg and 6 mg dose in healthy subjects under fasted conditions.

PK data from 24 subjects (n=23 in Treatment A, n=23 in Treatment B, and n=24 in Treatment C) were included in the PK analysis; data from 23 subjects were included in the statistical analyses.

Peak plasma concentrations of nalmefene were observed at approximately 0.250 h to 0.267 h (15 to 16 mins) postdose for all treatments; median (range) Tmax values for Treatments A (T1), B (T2), and C (T3) were 0.267 h (0.167-2.03 h), 0.250 h (0.117-3.00 h), and 0.250 h (0.117-2.03), respectively.

Mean half-life (t½), clearance (CL/F), and volume of distribution (Vz/F) values were similar across treatments.

Based on dose-normalized parameter values, mean Cmax, AUClast, and AUCinf were similar across treatments. Mean Cmax/D values for Treatments A (T1), B (T2), and C (T3) were 3.59, 3.70, and 3.15 ng/mL/mg, respectively. Dose-normalized systemic exposure based on AUClast and AUCinf were also comparable across treatments. Mean AUClast/D values for Treatments A (T1), B (T2), and C (T3) were 15.0, 14.4, and 13.7 h*ng/ml/mg, respectively. Mean AUCinf/D values for Treatments A (T1), B (T2), and C (T3) were 15.6, 14.9, and 14.3 h*ng/ml/mg, respectively.

Treatment C (T3, 6.0 mg in one nostril) vs. Treatment A (T1, 3.0 mg in one nostril): Based on dose-normalized ANOVA results, nalmefene Cmax was approximately 19% lower after Treatment C (T3) compared to Treatment A (T1); nalmefene AUClast and AUCinf) were similar for both treatments (geometric mean ratios were 91.77% and 91.19%, respectively). Dose-normalized early partial areas (AUCs from 0 h to 2.5 mins and 5 mins, respectively) were approximately 35% and 16% higher after Treatment C (T3) compared to Treatment A (T1); dose-normalized partial areas from 7.5 mins onward were similar for both treatments (geometric mean ratios ranged from 82.42% to 96.28%).

Treatment B (T2, 3.0 mg in each nostril) vs. Treatment A (T1, 3.0 mg in one nostril): Based on dose-normalized ANOVA results, nalmefene Cmax, AUClast, and AUCinf were similar for both treatments; geometric mean ratios were 98.15%, 96.87%, and 96.23%, respectively. Dose-normalized early partial areas (AUCs from 0 h to 2.5 mins, 5 mins, and 7.5 mins, respectively) were approximately 39%, 25%, and 15% higher after Treatment B (T2) compared to Treatment A (T1); dose-normalized partial areas from 10 min onward were similar for both treatments (geometric mean ratios ranged from 100.46% to 108.32%).

Treatment B (T2, 3.0 mg in each nostril) vs. Treatment C (T3, 6.0 mg in one nostril): Based on dose-normalized ANOVA results, nalmefene Cmax was approximately 21% higher after Treatment B (T2) compared to Treatment C (T3); nalmefene AUClast and AUCinf were similar for both treatments (geometric mean ratios were 105.56% and 105.53%, respectively). Dose-normalized partial areas (AUCs from 0 h to 2.5 mins and 5 mins,) were similar after both treatments with geometric mean ratios of 103.29% and 108.51%, respectively. Dose normalized partial areas from 7.5 mins onward were approximately 19% to 26% higher after 3.0 mg administered to each nostril (Treatment B, T2) compared to that after 6.0 mg administered to one nostril (Treatment C, T3).

Example 14: A Two-Part Open-Label Study of the Pharmacodynamic Effects of Intranasal Nalmefene Compared to Intranasal Naloxone in Healthy Volunteers Under Steady-State Opioid Agonism Objectives: The primary objective of Part 1 is to determine the relationship between remifentanil dose and suppression of $CO_2$-induced increases in minute ventilation. The secondary objectives of Part 1 is to determine the effect of brief mask removal on minute ventilation; to determine tolerability of intravenous (IV) remifentanil; to determine effects of intranasal (IN) naloxone on minute ventilation during steady-state remifentanil infusion.

The primary objective of Part 2 is to demonstrate noninferiority of IN nalmefene hydrochloride compared to IN naloxone hydrochloride on minute ventilation during steady-state remifentanil infusion. The secondary objective of Part 2 is to determine tolerability of administration of IN nalmefene hydrochloride during remifentanil infusion.

Design and Treatments: This was a single-center, open-label, 2-part study. Part 1 and Part 1 extension was a pilot study to determine the relationship between remifentanil dose and suppression of $CO_2$-induced increases in minute ventilation in healthy volunteers with prior opioid exposure. Part 2 was a randomized, 2-period, 2-treatment crossover study to evaluate the pharmacodynamic (PD) effects of IN nalmefene hydrochloride compared to IN naloxone hydrochloride to reverse remifentanil-induced suppression of $CO_2$-induced increases in minute ventilation, in healthy volunteers with prior opioid exposure. Part 1, Part 1 extension, and Part 2 of the study consisted of an outpatient Screening Visit, an in-clinic Treatment Phase, and a follow-up phone call.

Part 1: Screening occurred within 28 days before first drug administration. All subjects who provided their written informed consent and who met all of the inclusion and none of the exclusion criteria were enrolled in the study. Eligible subjects were admitted to the clinical research unit (CRU) following eligibility review on Day-1 and remained in the CRU for 7 days to complete the Treatment Phase of Part 1. On Days 1 and 5 prior to dosing and at scheduled time points, respiratory volume of subjects was monitored using the ExSpiron® device. Ventilatory response to hypercapnia (VRH) was also monitored with the subjects breathing through a tightly sealed face mask while lying on a bed at 45° recumbent.

Day 1: On Day 1, 7 subjects fasted for a period of at least 8 hours received pretreatment with 8 mg ondansetron (oral) and 30 mL of sodium citrate (oral) 30 minutes to 1 hour prior to remifentanil infusion. Subjects started receiving a hypercapnic gas mixture (50% $O_2$, 43% $N_2$, 7% $CO_2$) using a VRH face mask at Time 0 minutes, followed by a remifentanil hydrochloride infusion at Time 5 minutes. For the first group of 4 subjects this was at a rate of 0.05 μg/kg/min (estimated to produce a blood concentration of approximately 1.0 ng/ml), using an initial bolus (0.5 μg/kg) to achieve an expected steady-state. Minute ventilation was continuously measured.

To assess the effect of brief mask removal on minute ventilation, the VRH face mask was removed at Time 19 minutes and 50 seconds for approximately 10 seconds. During that time, subjects were asked to hold their breath; then the VRH face mask was reapplied. After the VRH face mask was reapplied, each subject received 4 mg IN naloxone hydrochloride. To administer the IN naloxone hydrochloride, the VRH face mask was removed at Time 24 minutes and 50 seconds for approximately 10 seconds. During that time, subjects were asked to hold their breath and the IN naloxone hydrochloride was administered at Time 25 minutes. After IN administration of naloxone hydrochloride, the VRH face mask was reapplied to continue to assess the effect on respiration, and remifentanil infusion continued for a further 90 minute period up to Time 115 minutes. The VRH face mask was removed at Time 45 minutes (i.e., 20 minutes after IN administration of naloxone hydrochloride). The VRH face mask was then reapplied for 10 minutes at Time 75 minutes and at Time 105 minutes, respectively (i.e., between 50 to 60 minutes and 80 to 90 minutes after IN administration of naloxone hydrochloride).

A decision regarding dose administration for the second group of subjects on Day 1 was made by the Investigator and Opiant based on the results from the first group of subjects. The Investigator and Opiant have taken a decision based on the available data at the time.

For the second group of 3 subjects on Day 1, the remifentanil infusion was at a rate of 0.10 µg/kg/min, using an initial bolus (0.5 µg/kg) to achieve an expected steady state.

There was a 4-day washout period before each of the groups received a second dose.

Remifentanil dose for Day 5: Remifentanil dose for Day 5 was determined based on the data from Day 1 by the Investigator and the Sponsor.

Day 5: On Day 5, 5 subjects fasted for a period of at least 8 hours received pretreatment (30 minutes to 1 hour prior to remifentanil infusion) with ondansetron (8 mg, oral) and sodium citrate (30 mL, oral). Subjects started receiving a hypercapnic gas mixture (50% O2, 43% N2, 7% CO2) using a VRH face mask at Time 0 minutes, followed by a remifentanil hydrochloride infusion at Time 5 minutes; in order to obtain data on 4 subjects, for 1 subject this was at a rate of 0.10 µg/kg/min, using an initial bolus (0.5 µg/kg) to achieve an expected steady state. Minute ventilation was continuously measured. The remifentanil infusion rate was then adjusted based on the % suppression of CO2 induced increases in minute ventilation, and safety and tolerability.

Subjects received 4 mg IN naloxone hydrochloride. To administer the IN naloxone hydrochloride, the VRH face mask was removed at Time 24 minutes and 50 seconds for approximately 10 seconds. During that time, subjects were asked to hold their breath and the IN naloxone hydrochloride was administered at Time 25 minutes. After IN administration of naloxone hydrochloride, the VRH face mask was reapplied to continue to assess the effect on respiration, and remifentanil infusion continued for a further 90 minute period up to Time 115 minutes. The VRH face mask was removed at Time 45 minutes (i.e., 20 minutes after IN administration of naloxone hydrochloride). The VRH face mask was then reapplied for 10 minutes at Time 75 minutes and at Time 105 minutes, respectively (i.e., between 50 to 60 minutes and 80 to 90 minutes after IN administration of naloxone hydrochloride).

A decision regarding dose administration for the second group of subjects on Day 5 was made by the Investigator and Opiant based on the results from the second group of subjects on Day 1. The Investigator and Opiant have taken a decision based on the available data at the time.

For the second group of 4 subjects on Day 5, the remifentanil infusion was at a rate of 0.15 µg/kg/min, using an initial bolus (0.5 µg/kg) to achieve an expected steady state.

Progression to Part 1 extension was based on the data from Part 1 and discussion between Investigator and the Sponsor.

Part 1 (extension): Screening occurred up to 28 days before first drug administration. All subjects who had given their written informed consent and who satisfied all of the relevant inclusion and exclusion criteria were screened for eligibility to participate in the study.

On the day of clinic admission (Day-1), a naloxone challenge test was performed to ensure the subject was not physically dependent on opioids, and eligibility was reviewed confirming all the relevant inclusion criteria and none of the exclusion criteria had been met.

On Day 1 prior to dosing and at scheduled time points specified, respiratory volume of subjects was monitored using the ExSpiron® device. VRH was also monitored with the subjects breathing through a tightly sealed face mask while lying on a bed at about a 45° recumbent position.

Day 1: On Day 1, 8 subjects, fasted for a period of at least 8 hours, received pretreatment (30 minutes to 1 hour prior to remifentanil infusion) with famotidine (20 mg IV), ondansetron (8 mg, oral), and sodium citrate (30 mL, oral). Subjects started receiving a hypercapnic gas mixture (50% O2, 43% N2, 7% CO2) using a VRH face mask at Time 0 minutes, followed by a remifentanil hydrochloride infusion at Time 10 minutes, for the first group of 4 subjects this was at a rate of 0.175 µg/kg/min, using an initial bolus (0.5 µg/kg) to achieve an expected steady state. Minute ventilation was continuously measured. Each subject received 4 mg IN naloxone hydrochloride, to administer the IN naloxone hydrochloride, the VRH face mask was removed at Time 24 minutes and 50 seconds for approximately 10 seconds. During that time, subjects were asked to hold their breath and the IN naloxone hydrochloride was administered at Time 25 minutes. After IN administration of naloxone hydrochloride, the VRH face mask was reapplied to continue to assess the effect on respiration, and remifentanil infusion was continued for a further 121 minutes period up to Time 146 minutes. The VRH face mask was removed at Time 46 minutes (i.e., 21 minutes after IN administration of naloxone hydrochloride). The VRH face mask was then reapplied for 11 minutes at Time 75 minutes, at Time 105 minutes, and at Time 135 minutes, respectively (i.e., between 50 to 61 minutes, 80 to 91 minutes and 110 to 121 minutes after IN administration of naloxone hydrochloride).

The remifentanil infusion rate for the second group of subjects dosed on Day 1 was at 0.175 µg/kg/min.

The decision regarding dose administration for the second group was made by the Investigator and Opiant based on the results from the first group. The Investigator and Opiant have taken a decision based on the available data.

For the second group of 4 subjects on Day 1, the remifentanil infusion was at a rate of 0.175 µg/kg/min, using an initial bolus (0.5 µg/kg) to achieve an expected steady state.

Day 5: Not conducted.

Part 2: Screening occurred up to 28 days before first drug administration. All subjects who had given their written informed consent and who satisfied all of the relevant inclusion and exclusion criteria were screened for eligibility to participate in the study.

Eligible subjects were admitted to the CRU following naloxone challenge test and eligibility review on Day 1 and remained in the CRU for 8 days to complete the Treatment Phase of Part 2. After a naloxone challenge test, eligibility review and completion of admission procedures, each subject was randomized to receive either IN nalmefene hydrochloride or IN naloxone hydrochloride in a 2 period crossover manner.

On the day of clinic admission (Day-1), a naloxone challenge test was performed to ensure the subject was not physically dependent on opioids, and eligibility was reviewed confirming all the relevant inclusion criteria and none of the exclusion criteria had been met.

Prior to dosing on days of study drug administration and at the scheduled time points, the respiratory volume of subjects was monitored using the ExSpiron® device. VRH was also monitored with the subjects breathing through a tightly sealed face mask while lying on a bed at about a 45° recumbent position.

On days of study drug administration (Days 1 and 5), a total of 75 subjects fasted for a period of at least 8 hours received pretreatment (30 minutes to 1 hour prior to remifentanil infusion) with famotidine (20 mg IV), ondansetron (8 mg, oral), and sodium citrate (30 mL, oral). Subjects started receiving a hypercapnic gas mixture (50% O2, 43% N2, 7% CO2) using a VRH face mask at Time 0 minutes, followed by a remifentanil hydrochloride infusion at Time 10 minutes, at a rate of 0.175 µg/kg/min, using an initial bolus (0.5 µg/kg) to achieve an expected steady state. Minute ventilation was continuously measured. A total of 69 subjects received a single dose of either 3 mg IN nalmefene hydrochloride or 4 mg IN naloxone hydrochloride, in a randomized 2 period crossover manner, in accordance with the randomization schedule, with an approximately 4-day washout period between doses, with 52 subjects receiving both treatments.

To administer the IN nalmefene hydrochloride and IN naloxone hydrochloride, the VRH face mask was removed at Time 24 minutes and 50 seconds for approximately 10 seconds. During that time, subjects were asked to hold their breath and IN nalmefene hydrochloride or naloxone hydrochloride was administered at Time 25 minutes. After IN administration of nalmefene hydrochloride or naloxone hydrochloride, the VRH face mask was reapplied to continue to assess the effect on respiration, and remifentanil infusion continued for a further 121 minutes period up to Time 146 minutes. The VRH face mask was removed at Time 46 minutes (i.e., 21 minutes after IN administration of nalmefene hydrochloride or naloxone hydrochloride). The VRH face mask was then reapplied for 11 minutes at Time 75 minutes, at Time 105 minutes and at Time 135 minutes, respectively (i.e., between 50 to 61 minutes, 80 to 91 minutes and 110 to 121 minutes after IN administration of nalmefene hydrochloride or naloxone hydrochloride).

Study Schedule
    Screening: Day-28 and Day-2
    Confinement Period: Part 1-7 days in the clinic from Day-1 (admission) to Day 6
    Part 1 extension-7 days in the clinic from Day-1 (admission) to Day 6
    Part 2-8 days in the clinic from Day-1 (admission) to Day 7
    Follow-Up Phone Call: Part 1-3 to 7 days after discharge from the clinic
    Part 1 extension-3 to 7 days after discharge from the clinic
    Part 2-3 to 7 days after discharge from the clinic Subjects
    Part 1:7 healthy volunteers with prior opioid exposure
    Part 1 Extension: 8 healthy volunteers with prior opioid exposure
    Part 2:69 healthy volunteers with prior opioid exposure Main Criteria for Inclusion
    Age: 18 to 55 years, inclusive, at screening
    Weight: ≥50 kg, inclusive, at screening
    Body mass index (BMI): 18.0 to 32.0 kg/m2, inclusive, at screening
    Subjects: Male or female; female subjects may be of childbearing potential, of nonchildbearing potential, or postmenopausal
    Status: Healthy subjects who are nondependent opioid experienced users. Opioid experience defined as exposure to an opioid on at least 1 occasion prior to screening
    Other: Subjects pass a naloxone challenge test at Day-1 to ensure that they are not opioid dependent (Part 1 extension and Part 2 only).

Study Drug
    Test preparation
        Active substance: Nalmefene hydrochloride
        Activity: Opioid antagonist
        In development for: Emergency treatment of known or suspected opioid overdose, as manifested by respiratory and/or central nervous system depression
        Strength: 3 mg (1 spray in 1 nostril delivers 0.1 mL of 30 mg/mL nalmefene hydrochloride)
        Dosage form: Nasal spray
        Manufacturer: Opiant Pharmaceuticals, Inc.
        Batch number: RNPA2003B
    Reference medication (Narcan®)
        Active substance: Naloxone hydrochloride
        Activity: Opioid antagonist
        Indication: Emergency treatment of known or suspected opioid overdose, as manifested by respiratory and/or central nervous system depression
        Strength: 4 mg (1 spray in 1 nostril delivers 0.1 mL of 40 mg/mL naloxone hydrochloride)
        Dosage form: Nasal spray
        Manufacturer: Adapt Pharma, Inc.; sourced by pharmacy at ICON
        Batch number: 201617, 211853, 211834

Variables
    Pharmacodynamics (PD): PD parameters: minute ventilation (VE), respiratory rate (RR), tidal volume (VT), end-tidal $CO_2$ ($ET_{CO2}$) defined as below.
    Minute ventilation (expired minute volume, VE; L/min): volume of gas exhaled per minute from the lungs)
    Respiratory rate (breaths/min)
    Tidal volume (expired tidal volume, VT; mL): volume of gas displaced between normal inhalation and exhalation when extra effort is not applied
    $ET_{CO2}$ (mm Hg): partial pressure of carbon dioxide at the end of an exhaled breath (VRH device)
    Pharmacokinetics (PK): Plasma concentrations of naloxone and nalmefene
    Plasma PK parameters of naloxone and nalmefene estimated using noncompartmental analysis, as appropriate: Cmax, tmax, AUC0-t, AUC0-inf, and Partial AUCs (AUC0-2.5 min, AUC0-5 min, AUC0 10 min, AUC0 15 min, AUC0-20 min, AUC10 20 min).
    Safety: Adverse events (AEs), clinical laboratory, vital signs, 12-lead electrocardiogram (ECG), continuous cardiac monitoring, physical examination, nasal cavity examination, noninvasive blood pressure, continuous oxygen saturation, Mallampati intubation score, Columbia-suicide severity rating scale (C-SSRS).

Statistical Methods
    Sample size calculation: With the sample size of 46 subjects (in a crossover design), the coverage probability was to be 90% that the upper limit of a 2 sided 95% confidence interval (CI) for the difference between the treatments (reference/naloxone-test/nalmefene) in mean change from nadir for minute ventilation would be less than the noninferiority limit of 0.6 L/min (given alpha =0.025 and a standard deviation of 1.75).

Interim analyses were conducted for sample size estimation. The sample size was reviewed based on data generated in Part 2 after 22 subjects and 50 subjects were dosed.

Based on the need to have 46 subjects complete both treatments at the primary endpoint for the 5 minutes post dose after naloxone hydrochloride or nalmefene hydrochloride administration, up to 68 subjects were planned to be enrolled in Part 2.

PD parameters: The Primary PD assessment was performed on the data generated by the ExSpiron® device. The following PD parameters were derived for each PD measurement, per subject, per treatment condition, per timepoint: VE, RR, VT, ETCO2 (VRH data). Descriptive statistics (n, mean, SD, standard error [SE], coefficient of variation [% CV], median, min, max, as well as quartiles [Q1 and Q3]) were used to summarize the ExSpiron® device measurements for Part 1, Part 1 extension, and Part 2. The primary endpoint of interest was the VE Change at 5 minutes post study drug administration (naloxone hydrochloride or nalmefene hydrochloride) in Part 2. The statistical analyses of noninferiority were performed, from the intent-to-treat (ITT) set, using only subjects who took both treatments and completed the data collection for 5 minutes post dose, in Part 2. The primary endpoint of VE Change at 5 minutes after study drug administration was analyzed using the linear model for a 2 treatment, 2-period crossover study. The model included treatment, period and sequence as fixed effects, and subject nested within sequence as a random effect. The least squares (LS) means and the mean difference (naloxone-nalmefene) of change in minute ventilation and corresponding 2 sided 95% CI were estimated. Noninferiority was demonstrated if the upper limit of the 95% CI was less than 20% of the mean change in minute ventilation for naloxone hydrochloride.

ETCO2 recorded with the VRH device was summarized using descriptive statistics (n, mean, SD, SE, % CV, median, min, max, as well as quartiles [Q1 and Q3]) by the timepoint.

In order to compare the proportion of subjects with extreme responses to the two treatments, the Pearson chi-square test was employed to test the proportion of subjects with a change in minute ventilation on nalmefene hydrochloride that is less than 50% of the change in minute ventilation on naloxone hydrochloride vs the proportion of the subjects with a change in minute ventilation on naloxone hydrochloride that is less than 50% of the change in minute ventilation on nalmefene hydrochloride.

As a sensitivity analysis, the primary analysis was rerun excluding the subjects for which the change in minute ventilation from remifentanil-induced nadir to 5 minutes was more than 1.5 interquartile range (IQR) below first quartile (Q1) or more than 1.5 IQR range above third quartile (Q3).

PK parameters: Plasma PK parameters (Cmax, tmax, AUC0-t, AUC0-inf, AUC0-2.5, AUC0-5, AUC0-10, AUC0-15, AUC0-20, and AUC10-20) for naloxone and nalmefene for Part 2 were estimated using noncompartmental methods with WinNonlin® using best fit regression. The PK parameters were estimated from the concentration-time profiles, and AUCs were calculated using linear up/log down method. In estimating the PK parameters, values below the quantifiable limit were set to 0. Actual sampling times, rather than scheduled sampling times, were used in all computations involving sampling times. If the actual time was missing, the scheduled time was substituted and flagged.

Descriptive statistics (number of subjects, mean, geometric mean, SD, % CV, median, min, and max) were used to summarize the calculated PK parameters by treatment. For tmax, only median, min and max were presented.

All parameters were listed by subject, parameters that met the inclusion criteria were accompanied by an indication that each was criterion was met.

Safety parameters: Statistical methods for the safety analyses were primarily descriptive in nature. Safety data, including AEs, clinical laboratory, vital signs, 12-lead ECG, continuous cardiac monitoring, physical examination, nasal cavity examination, noninvasive blood pressure, continuous oxygen saturation, Mallampati intubation score, and C-SSRS. All safety data were included in the data listings.

Results

Subject Disposition: In Part 1, a total of 7 subjects were enrolled, of which 5 (71.4%) subjects completed and 2 (28.6%) subjects discontinued the study. Both subjects withdrew their consent for personal reasons.

In Part 1 extension, 8 subjects were enrolled, and no subject discontinued the study.

In Part 2 of the study, 68 subjects were planned to be enrolled. In total, 75 subjects were randomized to 1 of 2 treatment sequences. Seven subjects were replacement subjects. Sixty-nine subjects were included in the analysis sets. Of these, 51 (73.9%) subjects completed the study, 50 subjects were included in the analysis for the primary endpoint (49 subjects who completed the study and 1 early termination subject who had data for the primary endpoint), and 18 (26.1%) subjects were discontinued. Six (8.7%) subjects met protocol specified withdrawal criteria, 5 (7.2%) subjects discontinued the study by withdrawing their consent, 4 (5.8%) subjects were discontinued due to AEs, 2 (2.9%) subjects were discontinued by the study physician, and 1 (1.4%) subject was discontinued due to other reasons (Table 18).

TABLE 18

Summary of Subject Disposition

| | Part 1 (N = 7) n (%) | Part 1 Extension (N = 8) n (%) | Part 2 (N = 69) n (%) | Overall (N = 84) n (%) |
|---|---|---|---|---|
| Completed Study | 5 (71.4) | 8 (100.0) | 51 (73.9) | 64 (76.2) |
| Discontinued Study | 2 (28.6) | 0 | 18 (26.1) | 20 (23.8) |
| Reason for Study Discontinuation | | | | |
| Adverse Event | 0 | 0 | 4 (5.8) | 4 (4.8) |
| Protocol Deviation | 0 | 0 | 0 | 0 |
| Lost to Follow-Up | 0 | 0 | 0 | 0 |
| Withdrawal by Subject | 2 (28.6) | 0 | 5 (7.2) | 7 (8.3) |
| Study Terminated by Sponsor | 0 | 0 | 0 | 0 |
| Pregnancy | 0 | 0 | 0 | 0 |
| Death | 0 | 0 | 0 | 0 |
| Physician Decision | 0 | 0 | 2 (2.9) | 2 (2.4) |
| Sponsor Request | 0 | 0 | 0 | 0 |
| Protocol-Specified Withdrawal Criterion Met | 0 | 0 | 6 (8.7) | 6 (7.1) |
| Other | 0 | 0 | 1 (1.4) | 1 (1.2) |

N = number of subjects.
Percentages are based on the number of subjects in the Safety Set.

Overall, 84 subjects who received at least one dose of any study drug were included in the Safety Set. In Part 1 and Part 1 extension, 7 and 8 subjects were included in the Safety Set, respectively. Sixty-nine subjects in Part 2 of the study were included in the Safety Set, ITT Set, and PK Set.

All enrolled subjects met all the inclusion and none of the exclusion criteria, except 1 subject who was deemed not eligible by the Medical Monitor due to history of suicidality. There were no clinically relevant findings in medical history.

Demographics

Overall, subjects were predominantly male (60 [71.4%]), white (69 [82.1%]), with a mean age of 29.1 years (18 to 54 years), and a mean BMI of 25.17 kg/m2 (18.1 to 31.7 kg/m2).

Part 1, Part 1 extension, and Part 2 had comparable subject demographics for sex, race, ethnicity, age, weight, height, and BMI. Subject demographics are summarized in Table 19.

TABLE 19

Summary of Demographic Characteristics

| | Category or Statistics | Part 1 (N = 7) | Part 1 Extension (N = 8) | Part 2 (N = 69) | Overall (N = 84) |
|---|---|---|---|---|---|
| Sex | Female | 1 (14.3) | 2 (25.0) | 21 (30.4) | 24 (28.6) |
| | Male | 6 (85.7) | 6 (75.0) | 48 (69.6) | 60 (71.4) |
| Race | White | 6 (85.7) | 6 (75.0) | 57 (82.6) | 69 (82.1) |
| | Black or African American | 1 (14.3) | 2 (25.0) | 6 (8.7) | 9 (10.7) |
| | Asian | 0 | 0 | 2 (2.9) | 2((2.4) |
| | American Indian or Alaskan Native | 0 | 0 | 3 (4.3) | 3 (3.6) |
| | Native Hawaiian or Other Pacific Islander | 0 | 0 | 1 (1.4) | 1 (1.2) |
| | Not Reported | 0 | 0 | 0 | 0 |
| | Unknown | 0 | 0 | 0 | 0 |
| Ethnicity | Hispanic or Latino | 2 (28.6) | 1 (12.5) | 11 (15.9) | 14 (16.7) |
| | Not Hispanic or Latino | 5 (71.4) | 7 (87.5) | 58 (84.1) | 70 (83.3) |
| | Not Reported | 0 | 0 | 0 | 0 |
| | Unknown | 0 | 0 | 0 | 0 |
| Age (yrs) | n | 7 | 8 | 69 | 84 |
| | Mean | 28.6 | 29.1 | 29.1 | 29.1 |
| | SD | 4.50 | 11.05 | 7.79 | 7.84 |
| | Median | 28.0 | 25.0 | 27.0 | 27.0 |
| | Min, Max | 23, 37 | 21, 54 | 18, 52 | 18, 54 |
| Weight | n | 7 | 8 | 69 | 84 |
| | Mean | 79.13 | 78.65 | 78.30 | 78.40 |
| | SD | 16.616 | 9.735 | 14.120 | 13.833 |
| | Median | 74.70 | 78.90 | 79.10 | 78.10 |
| | Min, Max | 56.1, 99.8 | 66.5, 98.0 | 50.0, 108.5 | 50.0, 108.5 |
| Height | n | 7 | 8 | 69 | 84 |
| | Mean | 178.7 | 179.8 | 175.6 | 176.3 |
| | SD | 9.71 | 9.38 | 10.21 | 10.08 |
| | Median | 184.9 | 181.2 | 176.0 | 178.0 |
| | Min, Max | 167, 188 | 166, 197 | 143, 198 | 143, 198 |
| BMI | n | 7 | 8 | 69 | 84 |
| | Mean | 25.03 | 24.48 | 25.27 | 25.17 |
| | SD | 3.338 | 3.665 | 3.316 | 3.317 |
| | Median | 25.80 | 24.60 | 24.90 | 24.90 |
| | Min, Max | 20.4, 29.8 | 19.8, 29.9 | 18.1, 31.7 | 18.1, 31.7 |

BMI = body mass index;
max = maximum;
min = minimum;
n = number of subjects;
SD = standard deviation;
yrs = years.

Pharmacodynamics

Part 1: Following hypercapnic gas mixture administration, the mean minute volume increased for 5 minutes and results from Day 1 and Day 5 were comparable. The impact of transient mask removal on minute ventilation was minimal.

At the remifentanil infusion rates tested in Part 1, the ventilatory effects (i.e., reductions in minute ventilation from remifentanil baseline) were lower and more variable than expected. Furthermore, the reversal following naloxone hydrochloride administration was generally too high at 5 minutes, which would have restricted the possibility to demonstrate the study endpoints. Based on these findings, a decision regarding dose administration was made by the Investigator and Opiant based on the available data at the time. The highest remifentanil dose (0.15 µg/kg/min) used in Part 1 was considered safe and generally well tolerated. The decision after subjects were dosed at 0.15 µg/kg/min was to increase the remifentanil dose for the next infusions to 0.175 µg/kg/min in the Part 1 extension with the objective of both producing a more consistent remifentanil-induced response (i.e., suppression of minute ventilation) and a more moderate naloxone reversal needed to demonstrate study endpoints.

Furthermore, the decision was made to increase duration of exposure to the hypercapnic gas mixture from 5 to 10 minutes prior to remifentanil dosing to capture any additional increases in minute ventilation that may not be manifested by a shorter (5 minute) exposure. Concomitantly, the duration of remifentanil infusion was reduced by 5 minutes (from 20 to 15 minutes).

Part 1 extension: For the first set of 4 subjects in Part 1 extension of the study, it was noted that at 5 minutes post dose, naloxone hydrochloride produced a reversal of the remifentanil induced respiratory depression in 3 subjects such that the study endpoints could be demonstrated. One subject did not respond to the remifentanil dose.

For further confirmation, the second set of 4 subjects dosed into Part 1 extension received the same remifentanil dose of 0.175 µg/kg/min on Day 1.

For the second set of 4 subjects in Part 1 extension of the study, it was noted that 3 subjects responded to the remifentanil infusion. At 5 minutes post naloxone hydrochloride administration, the remifentanil induced respiratory depression was reversed in 2 subjects such that the study endpoints could be demonstrated. One subject reversed the remifentanil-induced respiratory depression at 15 minutes post naloxone hydrochloride administration. For 1 subject, reversal of the remifentanil-induced respiratory depression was observed only at 2.5 and 15 minutes post naloxone hydrochloride administration, but not at 5 minutes.

Overall, in Part 1 extension, sufficient suppression of the minute ventilation and subsequent reversal following naloxone hydrochloride administration were generally demonstrated, and a decision regarding dose administration was made by the Investigator and Opiant based on the available data at the time. The remifentanil exposure of 15 minutes and a remifentanil infusion rate of 0.175 µg/kg/min were considered sufficient to elicit the pharmacological response needed to demonstrate the study endpoints. The remifentanil dose was considered safe and generally well tolerated. Therefore, these conditions were used during Part 2 of the study.

Part 2: Naloxone hydrochloride: Prior to infusion of remifentanil, the mean minute volume was 17.299 L/min. Following administration of remifentanil at 0.175 μg/kg/min infusion rate, the mean minute ventilation decreased to 10.546 L/min in 15 minutes. Following administration of naloxone hydrochloride, the maximum minute ventilation from the nadir baseline was 16.439 L/min (mean change: 5.927) after 20 minutes relative to remifentanil induced nadir.

Nalmefene hydrochloride: Prior to infusion of remifentanil, the mean minute volume was 16.626 L/min. Following administration of remifentanil at 0.175 μg/kg/min, the mean minute ventilation decreased to 10.633 L/min in 15 minutes. Following administration of nalmefene hydrochloride, the maximum minute ventilation from nadir baseline was 17.750 L/min (mean change: 7.117) after 15 minutes relative to remifentanil induced nadir.

The mean minute ventilation values and mean changes in minute ventilation from nadir baseline after administration of study drug at each time point are presented in Table 20.

TABLE 20

Minute Ventilation and Change in Minute Ventilation from Nadir Baseline after Study Drug Administration-Part 2

| Minutes in Relation to Study Drug Administration | Naloxone hydrochloride: Minute Ventilation (MV) & Mean Change in MV from Nadir Baseline | | Nalmefene hydrochloride Minute Ventilation (MV) & Mean Change in MV from Nadir Baseline | |
|---|---|---|---|---|
| | Mean MV (L/min) | Mean Change (L/min) | Mean MV (L/min) | Mean Change (L/min) |
| -15 (Remifentanil baseline) | 17.299 | — | 16.626 | — |
| 0 (Nadir baseline) | 10.546 | — | 10.633 | — |
| 2.5 | 12.251 | 1.705 | 13.238 | 2.547 |
| 5 | 13.978 | 3.432 | 16.435 | 5.744 |
| 7.5 | 14.558 | 4.012 | 17.009 | 6.376 |
| 10 | 15.506 | 4.960 | 17.213 | 6.580 |
| 15 | 16.047 | 5.549 | 17.750 | 7.117 |
| 20 | 16.439 | 5.927 | 17.463 | 6.786 |
| 60 | 12.988 | 2.517 | 13.601 | 2.924 |
| 90 | 12.669 | 2.143 | 13.424 | 2.711 |
| 120 | 12.490 | 2.016 | 13.590 | 2.877 |

MV = minute ventilation
Mean change of minute ventilation for each timepoint after the study drug is presented.

The summary of the PD parameters related to the time to maximum effect and maximum effect of study drug administration is presented in Table 21.

TABLE 21

Summary of ExSpiron ® Device Minute Ventilation PD Parameters-Part 2

| PD Parameter | Statistic | Hypercapnic Gas Mixture + Remifentanil + Naloxone | Hypercapnic Gas Mixture + Remifentanil + Nalmefene |
|---|---|---|---|
| $TE_{max}$ (min) | n | 59 | 61 |
| | Median | 40.0 | 40.0 |
| | Min, Max | 28, 145 | 28, 120 |
| VE $E_{max}$ | n | 59 | 61 |
| | Mean | 7.237 | 9.307 |
| | SD | 5.3971 | 5.4774 |
| | SE | 0.703 | 0.701 |
| | % CV | 74.6 | 58.9 |
| | Median | 6.550 | 9.300 |

TABLE 21-continued

Summary of ExSpiron ® Device Minute Ventilation PD Parameters-Part 2

| PD Parameter | Statistic | Hypercapnic Gas Mixture + Remifentanil + Naloxone | Hypercapnic Gas Mixture + Remifentanil + Nalmefene |
|---|---|---|---|
| | Min, Max | -1.76, 28.73 | -1.04, 24.74 |
| | Q1, Q3 | 3.490, 9.330 | 5.590, 12.170 |

CV = coefficient of variation;
Min = minimum;
Max = maximum;
n = number of subjects;
Q1 = first quartile;
Q3 = third quartile;
SE = standard error;
$TE_{max}$ = time to maximum effect Emax relative to start of hypercapnic gas mixture administration;
VE $E_{max}$ = maximum effect after study drug administration.
The maximum effect was defined as the maximum change from remifentanil-induced nadir after study drug administration (naloxone or nalmefene). The maximum change can be a negative change or a positive change as the maximum value among all post dose changes in minute ventilation were captured for each subject and set as VE $E_{max}$.

The time to maximum effect (Table 21) has been presented as the time relative to start of hypercapnic gas mixture administration, which represents 15 minutes after administration of nalmefene and naloxone. However, it is noted that following administration of nalmefene, the mean minute ventilation returned to 98.9% of pre remifentanil levels after 5 minutes post dose, compared to 95.0% of pre remifentanil levels after 20 minutes for naloxone (Table 20).

Noninferiority of IN nalmefene hydrochloride compared to IN naloxone hydrochloride was demonstrated at 5 minutes post administration on minute ventilation during steady-state remifentanil infusion. From the ITT set, only subjects who took both treatments and completed the data collection for 5 minutes post dose were included in the analysis. The upper limit of the 95% CI (-1.175) was less than 20% of the Least Squares (LS) mean change in minute ventilation for naloxone (0.6022), demonstrating noninferiority of IN nalmefene hydrochloride compared to IN naloxone hydrochloride. Results are presented in Table 22.

TABLE 22

Statistical Analysis of Noninferiority Analysis of Nalmefene Versus Naloxone at 5 minutes post dose - Part 2

| | LS Mean | | | | | | |
|---|---|---|---|---|---|---|---|
| | Hypercapnic Gas Mixture + Remifentanil + Naloxone (Ref) | | Hypercapnic Gas Mixture + Remifentanil + Nalmefene (Test) | | LS Mean Difference (Ref − Test) | | 20%*LS Mean |
| Parameter | n | Result | n | Result | Estimate | 95% CI | Naloxone |
| VE Change(L/min) | 50 | 3.011 | 50 | 5.745 | −2.73 | (−4.293, −1.175) | 0.6022 |

CI = confidence interval; LS = least squares; n = number of subjects; Ref = reference; VE Change = post dose change in minute ventilation from nadir baseline at 5 minutes post dose.

Analysis was performed using a linear mixed effects model with treatment, period, and sequence as fixed effects and subject nested within sequence as a random effect.

From the ITT set, only subjects who took both treatments and completed the data collection for 5 minutes post dose were included in the analysis.

The results were further confirmed by the sensitivity analyses performed, which also demonstrated noninferiority. As a sensitivity analysis, the primary analysis was rerun excluding the subjects for which the change in minute ventilation from nadir baseline to 5 minutes was more than 1.5 interquartile range below the first quartile (Q1) or more than 1.5 interquartile range above the third quartile (Q3). Only subjects who took both treatments and completed the data collection for 5 minutes post dose were included in the analysis. Results are presented in Table 23.

The analysis was performed using a chi-square test for the proportion of the subjects with a change in minute ventilation after nalmefene that was less than 50% of the change in minute ventilation after naloxone vs the proportion of the subjects with a change in minute ventilation after naloxone that was less than 50% of the change in minute ventilation after nalmefene.

In Part 1, 4 subjects received remifentanil at a rate of 0.05 μg/kg/min on Day 1, 3 subjects received remifentanil at a rate of 0.10 μg/kg/min on Day 1, 1 subject received remifentanil at a rate of 0.10 μg/kg/min on Day 5, and 4 subjects received remifentanil at a rate of 0.15 μg/kg/min on Day 5. Naloxone hydrochloride (4 mg) was administered to 7

TABLE 23

Sensitivity Analysis: Statistical Analysis of Noninferiority Analysis of Nalmefene Versus Naloxone - Part 2

| | LS Mean | | | | | | |
|---|---|---|---|---|---|---|---|
| | Hypercapnic Gas Mixture + Remifentanil + Naloxone (Ref) | | Hypercapnic Gas Mixture + Remifentanil + Nalmefene (Test) | | LS Mean Difference (Ref − Test) | | 20%*LS Mean |
| Parameter | n | Result | n | Result | Estimate | 95% CI | Naloxone |
| VE Change(L/min) | 48 | 2.546 | 48 | 5.052 | −2.51 | (−3.729, −1.283) | 0.5092 |

CI = confidence interval; LS = least squares; n = number of subjects; Ref = reference; VE Change = post dose change in minute ventilation from nadir baseline at 5 minutes post dose.

An exploratory analysis showed an unequal proportion of subjects with extreme responses. The results are shown in Table 24.

TABLE 24

Statistical Analysis Comparing the Proportions of Subjects with Extreme Responses

| Parameter | Change on Nalmefene < 50% Change on Naloxone n (%) | Change on Naloxone < 50% Change on Nalmefene n (%) | P-value |
|---|---|---|---|
| VE Change (L/min) (5 Minutes Post Naloxone or Nalmefene) | 8 (16.0) | 25 (50.0) | 0.0003 | n = number of subjects;
VE Change = post dose change in minute ventilation from nadir baseline at 5 minutes after naloxone or nalmefene administration.

subjects on Day 1 and 5 subjects on Day 5. ExSpiron® Device PD measurements (VE, RR, and VT) over time are displayed in FIG. 12.

Hypercapnic Gas Mixture:

Hypercapnic Gas mixture-Day 1: At gas baseline the mean minute volume was 9.763 L/min. Following hypercapnic gas mixture administration, the mean minute volume increased and reached 14.037 L/min in 5 minutes.

Hypercapnic Gas mixture-Day 5: At gas baseline the mean minute volume was 8.062 L/min. Following hypercapnic gas mixture administration, the mean minute volume increased and reached 14.032 L/min in 5 minutes. Results from Day 1 and Day 5 were comparable.

VRH Mask Removal: On Day 1, the mask was removed for approximately 10 seconds at timepoint 19 minutes and 50 seconds. A 1.726 L/min mean change in minute ventilation from removed mask baseline was observed 1 minute after mask removal (12.503 L/min versus 10.777 L/min). After 2 minutes the minute ventilation increased to 12.755 L/min (0.757 change), and 4 minutes after mask removal, the change in minute ventilation was closer to removed mask baseline values with only a mean change values of 0.246 from mask removal (12.749 L/min of the mean after 4 minutes vs 12.503 of the mean for removed mask baseline). Overall, the impact of transient mask removal on minute ventilation was minimal.

Remifentanil at a rate of 0.05 µg/kg/min-Day 1: Prior to infusion of remifentanil, the mean minute volume was 12.175 L/min. Following administration of remifentanil at 0.05 µg/kg/min infusion rate, the mean minute ventilation decreased to 10.338 L/min in 15 minutes (−1.838 change).

Data from 4 subjects on Day 1 showed a nadir baseline minute ventilation of 10.900 L/min. Following administration of naloxone hydrochloride, the maximum minute ventilation value from nadir baseline was 13.093 L/min (mean change: 2.193) after 10 minutes.

The mean changes in minute ventilation from nadir baseline to 5 and 120 minutes after naloxone hydrochloride administration were 1.542 (12.443 L/min) and 3.683 (7.218 L/min), respectively.

Due to the variability in both remifentanil induced response and naloxone response from nadir baseline to 5 minutes after naloxone hydrochloride administration, a decision regarding dose administration was made by the Investigator and Opiant based on the available data at the time. The reversal following naloxone hydrochloride administration was too high at 5 minutes, which would have restricted the possibility to demonstrate the study endpoints, and there was a nonresponder. The remifentanil dose was considered safe and well tolerated. The decision after subjects were dosed at 0.05 µg/kg/min was to increase the remifentanil dose for the next infusions to 0.10 µg/kg/min.

Remifentanil at a rate of 0.10 µg/kg/min Day 1 and Day 5

Day 1: On Day 1, prior to infusion of remifentanil, the mean minute volume was 16.087 L/min. Following administration of remifentanil at 0.10 µg/kg/min infusion rate, the mean minute ventilation decreased to 11.363 L/min in 15 minutes (−4.723 change).

Data from 3 subjects on Day 1 showed a nadir baseline in minute ventilation of 15.063 L/min. Following administration of naloxone hydrochloride, the maximum positive change in minute ventilation from nadir baseline was 3.980 (19.043 L/min) after 15 minutes.

The mean changes in minute ventilation from nadir baseline to 5 and 120 minutes after naloxone hydrochloride administration were 0.910 (15.973 L/min) and −5.513 (9.550 L/min) respectively.

Day 5: On Day 5, prior to infusion of remifentanil, the mean minute volume was 7.830 L/min for 1 subject. Following administration of remifentanil at 0.10 µg/kg/min infusion rate, the mean minute ventilation decreased to 5.200 L/min in 15 minutes (−2.630 change).

Data from 1 subject on Day 5 showed a nadir baseline in minute ventilation of 6.180 L/min. Following administration of naloxone hydrochloride, the maximum minute ventilation from nadir baseline was 7.740 L/min (mean change: 1.560) after 15 minutes.

The changes in minute ventilation from nadir baseline to 5 and 120 minutes after naloxone hydrochloride administration were 0.790 (6.970 L/min) and −1.730 (4.450 L/min) respectively.

Due to the variability in both remifentanil induced responses and naloxone responses from nadir baseline to 5 minutes after naloxone hydrochloride administration between subjects and inconsistencies in the data, a decision regarding dose administration was made by the Investigator and Opiant based on the available data at the time. Three of the four subjects either did not achieve a sufficient remifentanil-induced suppression of minute ventilation, or the reversal following naloxone hydrochloride administration was too high at 5 minutes, which would have restricted the possibility to demonstrate the study endpoints. The remifentanil dose was considered safe and well tolerated. The decision after subjects were dosed at 0.10 µg/kg/min was to increase the remifentanil dose for the next infusions to 0.15 µg/kg/min.

Remifentanil at a Rate of 0.15 µg/Kg/Min—Day 5

Prior to infusion of remifentanil, the mean minute volume was 14.690 L/min. Following administration of remifentanil at 0.15 µg/kg/min infusion rate, the mean minute ventilation decreased to 8.965 L/min in 15 minutes (−5.725 change).

Data from 4 subjects on Day 5 showed a nadir baseline minute ventilation of 9.455 L/min. Following administration of naloxone hydrochloride, the maximum minute ventilation value from nadir baseline was 16.870 L/min (mean change: 7.415) after 15 minutes.

The changes in minute ventilation from nadir baseline to 5 and 120 minutes after naloxone hydrochloride administration were 5.292 (14.748 L/min) and 0.710 (8.745 L/min) respectively.

Due to the between subject variability in both remifentanil induced responses and naloxone responses from nadir baseline to 5 minutes after naloxone hydrochloride administration and resulting inconsistencies in the data, a decision regarding dose administration was made by the Investigator and Opiant based on the available data at the time. The reversal following naloxone hydrochloride administration was considered too high at 5 minutes, which would have restricted the possibility to demonstrate the study endpoints. The remifentanil dose was considered safe and generally well tolerated. The decision after subjects were dosed at 0.15 µg/kg/min was to increase the remifentanil dose for the next infusions to 0.175 µg/kg/min in the Part 1 extension with the objective of both producing a more consistent remifentanil-induced response (i.e., suppression of minute ventilation) and a naloxone reversal sufficient to demonstrate study endpoints.

Furthermore, the decision was made to increase duration of exposure to the hypercapnic gas mixture from 5 to 10 minutes prior to remifentanil dosing to capture any additional increases in minute ventilation that may not be manifested by a shorter (5 minute) exposure. Concomitantly, the duration of remifentanil infusion was reduced by 5 minutes (from 20 to 15 minutes). A bolus dose followed by infusion of remifentanil has been demonstrated to result in steady-state blood concentrations within 15 minutes.

Pharmacodynamic Parameters

The summary of PD Parameters is presented in Table 25. Mean (SD) $E_{max}$ values for naloxone hydrochloride increased with remifentanil infusion rate: 3.080 (SD: 2.2608) L/min when administration of remifentanil was carried out at 0.05 µg/kg/min infusion rate (Day 1); 4.577 (SD: 2.0854) L/min when administration of remifentanil was carried out at 0.10 µg/kg/min infusion rate (Day 1); and 8.090 (SD: 2.5218) L/min when administration of remifentanil was carried out at 0.15 µg/kg/min infusion rate (Day 5). The time to maximum change in minute ventilation after naloxone hydrochloride administration ranged from 37.5 to 42.5 minutes relative to start of hypercapnic gas mixture administration.

TABLE 25

Summary of ExSpiron® Minute Ventilation PD Parameter-Part 1

| PD Parameter | Statistic | Hypercapnic Gas Mixture + Remifentanil + Naloxone | | | |
|---|---|---|---|---|---|
| | | 0.05 (μg/kg/min) Day 1 | 0.10 (μg/kg/min) Day 1 | 0.10 (μg/kg/min) Day 5 | 0.15 (μg/kg/min) Day 5 |
| $TE_{max}$ (min) | n | 4 | 3 | 1 | 4 |
| | Median | 37.5 | 40.0 | 40.0 | 42.5 |
| | Min, Max | 33, 85 | 40, 45 | 40, 40 | 35, 45 |
| VE $E_{max}$ | n | 4 | 3 | 1 | 4 |
| | Mean | 3.080 | 4.577 | 1.560 | 8.090 |
| | SD | 2.2608 | 2.0854 | | 2.5218 |
| | SE | 1.130 | 1.204 | | 1.261 |
| | % CV | 73.4 | 45.6 | | 31.2 |
| | Median | 2.355 | 4.750 | 1.560 | 8.705 |
| | Min, Max | 1.39, 6.22 | 2.41, 6.57 | 1.56, 1.56 | 4.52, 10.43 |
| | Q1, Q3 | 1.430, 4.730 | 2.410, 6.570 | 1.560, 1.560 | 6.500, 9.680 |

CV = coefficient of variation;
Min = minimum; Max = maximum;
n = number of subjects;
Q1 = first quartile;
Q3 = third quartile;
SE = standard error;
$TE_{max}$ = time to maximum effect $E_{max}$;
VE $E_{max}$ = maximum effect after study drug administration.
The maximum effect was defined as the maximum change from remifentanil-induced nadir after study drug administration (naloxone or nalmefene). The maximum change can be negative change or positive change as the maximum value among all post dose changes in minute ventilation were captured and set as VE $E_{max}$.

PD Measurements—ETCO2

IN naloxone hydrochloride decreased ETCO2 relative to the nadir baseline. An ETCO2 decrease from 42.33 (SD: 1.686) mm Hg to 39.84 (SD: 4.033) mm Hg was observed 2.5 minutes after naloxone hydrochloride administration at a remifentanil infusion rate of 0.05 μg/kg/min (Day 1); a decrease from 47.90 (SD: 0.712) mm Hg to 46.98 (SD: 0.945) mm Hg was observed 2.5 minutes after naloxone hydrochloride administration at a remifentanil infusion rate of 0.10 μg/kg/min (Day 1); a decrease from 41.75 mm Hg to 41.00 mm Hg was observed 2.5 minutes after naloxone hydrochloride administration at a remifentanil infusion rate of 0.10 μg/kg/min (Day 5); a decrease from 49.08 (SD: 7.208) mm Hg to 48.01 (SD: 5.506) mm Hg was observed 2.5 minutes after naloxone hydrochloride administration at a remifentanil infusion rate of 0.15 μg/kg/min (Day 5).

Mean ETCO2 values at 20 minutes after naloxone administration were as follows: 39.58 (SD: 2.922) mm Hg at a remifentanil infusion rate of 0.05 μg/kg/min (Day 1); 44.31 (SD: 2.485) mm Hg at a remifentanil infusion rate of 0.10 μg/kg/min (Day 1); 40.00 mm Hg at a remifentanil infusion rate of 0.10 μg/kg/min (Day 5) and 41.92 (SD: 3.414) mm Hg at a remifentanil infusion rate of 0.15 μg/kg/min (Day 5). The VRH ETCO2 results over time are shown in FIG. 13.

Pharmacodynamic Results—Part 1 Extension

In Part 1 extension, 8 subjects received remifentanil at a rate of 0.175 μg/kg/min on Day 1. Naloxone hydrochloride (4 mg) was administered to 7 subjects on Day 1 only. Day 5 was not conducted. ExSpiron® Device PD measurements (VE, RR, and VT) over time are displayed in FIG. 14.

Remifentanil at a Rate of 0.175 μg/kg/min

At gas baseline the mean minute volume was 10.915 L/min. Following hypercapnic gas mixture administration, the mean minute volume increased and reached 17.093 L/min at 10 minutes.

Prior to infusion of remifentanil, the mean minute volume was 16.729 L/min. Following administration of remifentanil the mean minute ventilation decreased to 11.899 L/min in 15 minutes relative to the start of remifentanil infusion.

Following administration of naloxone hydrochloride, the maximum minute ventilation value from nadir baseline was 15.489 L/min (mean change: 3.590) after 15 minutes.

The mean changes in minute ventilation from nadir baseline to 5 and 120 minutes after naloxone hydrochloride administration were −0.777 (11.121 L/min) and 0.855 (12.754 L/min) respectively.

For the first set of 4 subjects in Part 1 extension of the study, it was noted that at 5 minutes post dose, naloxone hydrochloride reversed the remifentanil induced respiratory depression in 3 subjects such that the study endpoints could be demonstrated. One subject did not respond to the remifentanil dose.

For further confirmation, the second set of 4 subjects dosed into Part 1 extension received the same remifentanil dose of 0.175 μg/kg/min on Day 1.

For the second set of 4 subjects in Part 1 extension of the study, it was noted that 3 subjects responded to the remifentanil infusion. At 5 minutes post naloxone hydrochloride administration, the remifentanil induced respiratory depression was reversed in 2 subjects such that the study endpoints could be demonstrated. One subject exhibited a reversal of the remifentanil-induced respiratory depression at 15 minutes post naloxone hydrochloride administration. For 1 subject, reversal of the remifentanil-induced respiratory depression was observed at 2.5 and 15 minutes post naloxone hydrochloride administration, but not at 5 minutes.

Overall, in Part 1 extension, sufficient suppression of the minute ventilation and subsequent reversal following naloxone hydrochloride administration were generally demonstrated, and a decision regarding dose administration was made by the Investigator and Opiant based on the available data at the time. The remifentanil exposure of 15 minutes and a remifentanil infusion rate of 0.175 μg/kg/min were considered sufficient to elicit the pharmacological response needed to demonstrate the study endpoints. The remifentanil dose was considered safe and generally well tolerated. Therefore, these conditions were used during Part 2 of the study.

Pharmacodynamic Parameters

The summary of PD parameters is presented in Table 26. Mean (SD) Emax value for naloxone hydrochloride was 4.715 (SD: 4.0480) L/min when remifentanil was delivered at an infusion rate of 0.175 μg/kg/min. The median time to maximum change in minute ventilation after naloxone hydrochloride administration was 42.5 minutes relative to start of the hypercapnic gas mixture administration, which represents 17.5 minutes after administration of naloxone hydrochloride.

TABLE 26

Summary of ExSpiron ® Minute Ventilation PD Parameter-Part 1 Extension

| PD Parameter | Statistic | Hypercapnic Gas Mixture + Remifentanil + Naloxone |
|---|---|---|
| $TE_{max}$ (min) | n | 8 |
| | Median | 42.5 |
| | Min, Max | 33, 145 |
| VE $E_{max}$ | n | 8 |
| | Mean | 4.715 |
| | SD | 4.0480 |

TABLE 26-continued

Summary of ExSpiron ® Minute Ventilation PD Parameter-Part 1 Extension

| PD Parameter | Statistic | Hypercapnic Gas Mixture + Remifentanil + Naloxone |
|---|---|---|
| | SE | 1.431 |
| | % CV | 85.9 |
| | Median | 4.280 |
| | Min, Max | −3.26, 10.02 |
| | Q1, Q3 | 3.620, 7.580 |

CV = coefficient of variation;
Min = minimum;
Max = maximum;
n = number of subjects;
Q1 = first quartile;
Q3 = third quartile;
SE = standard error;
$TE_{max}$ = time to maximum effect $E_{max}$;
$VE\ E_{max}$ = maximum effect after study drug administration.
The maximum effect was defined as the maximum change from remifentanil-induced nadir after study drug administration (naloxone or nalmefene). The maximum change can be negative change or positive change as the maximum value among all post dose changes in minute ventilation were captured and set as $VE\ E_{max}$.

PD Measurements—ETCO2

IN naloxone hydrochloride decreased ETCO2 relative to the nadir baseline. An ETCO2 decrease from 46.72 (SD: 6.963) mm Hg to 45.89 (SD: 6.067) mm Hg was observed 2.5 minutes after naloxone hydrochloride administration at a remifentanil infusion rate of 0.175 µg/kg/min. The mean ETCO2 value at 20 minutes after naloxone hydrochloride administration was 44.87 (SD: 5.674) mm Hg. The VRH ETCO2 results over time are shown in FIG. 15.

Pharmacodynamic Results Part 2

In Part 2, 69 subjects received remifentanil at a rate of 0.175 µg/kg/min. Naloxone hydrochloride (4 mg) was administered to 60 subjects and nalmefene hydrochloride (3 mg) was administered to 61 subjects. ExSpiron® Device PD measurements (VE, RR, and VT) over time are displayed in FIG. 16.

Naloxone hydrochloride: At gas baseline the mean minute volume was 10.152 L/min. Following hypercapnic gas mixture administration, the mean minute volume increased and reached 17.355 L/min in 10 minutes.

Prior to infusion of remifentanil (remifentanil baseline), the mean minute volume was 17.299 L/min. Following administration of remifentanil at 0.175 µg/kg/min infusion rate, the mean minute ventilation decreased to 10.546 L/min in 15 minutes (nadir baseline).

Following administration of naloxone hydrochloride, the maximum minute ventilation value from nadir baseline was 16.439 L/min (mean change: 5.927) after 20 minutes of naloxone hydrochloride administration. The mean minute ventilation and mean change in minute ventilation from nadir baseline after naloxone hydrochloride administration at different timepoints are described in the table below.

TABLE 27

Minute Ventilation and Change in Minute Ventilation from Nadir Baseline after Naloxone Hydrochloride Administration

| Minutes in Relation to Study Drug Administration | Minute Ventilation (MV) & Mean Change in MV from Nadir Baseline | |
|---|---|---|
| | Mean MV (L/min) | Mean Change (L/min) |
| −15 (Remifentanil baseline) | 17.299 | — |
| 0 (Nadir baseline) | 10.546 | — |
| 2.5 | 12.251 | 1.705 |
| 5 | 13.978 | 3.432 |
| 7.5 | 14.558 | 4.012 |
| 10 | 15.506 | 4.960 |
| 15 | 16.047 | 5.549 |
| 20 | 16.439 | 5.927 |
| 60 | 12.988 | 2.517 |
| 90 | 12.669 | 2.143 |
| 120 | 12.490 | 2.016 |

MV = minute ventilation
Mean change of MV for each timepoint after the study drug is presented.

Nalmefene hydrochloride: At gas baseline the mean minute volume was 10.117 L/min. Following hypercapnic gas mixture administration, the mean minute volume increased and reached 17.185 L/min in 10 minutes.

Prior to infusion of remifentanil (remifentanil baseline), the mean minute volume was 16.626 L/min. Following administration of remifentanil at 0.175 µg/kg/min, the mean minute ventilation decreased to 10.633 L/min in 15 minutes (nadir baseline).

Following administration of nalmefene hydrochloride, the maximum minute ventilation value from nadir baseline to was 17.750 L/min. (mean change: 7.117) after 15 minutes of nalmefene hydrochloride administration. The mean minute ventilation and mean change in minute ventilation from nadir baseline after nalmefene hydrochloride administration at different timepoints are described in the table below.

TABLE 28

Minute Ventilation and Change in Minute Ventilation from Nadir Baseline after Nalmefene Hydrochloride Administration

| Minutes in Relation to Study Drug Administration | Minute Ventilation (MV) & Mean Change in MV from Nadir Baseline | |
|---|---|---|
| | Mean MV (L/min) | Mean Change (L/min) |
| −15 (Remifentanil baseline) | 16.626 | — |
| 0 (Nadir baseline) | 10.633 | — |
| 2.5 | 13.238 | 2.547 |
| 5 | 16.435 | 5.744 |
| 7.5 | 17.009 | 6.376 |
| 10 | 17.213 | 6.580 |
| 15 | 17.750 | 7.117 |
| 20 | 17.463 | 6.786 |
| 60 | 13.601 | 2.924 |
| 90 | 13.424 | 2.711 |
| 120 | 13.590 | 2.877 |

MV = minute ventilation
Mean changes in MV for each timepoint after the study drug are presented.

Pharmacodynamic Parameters

The summary of PD parameters is presented in Table 29. Mean (SD) Emax values for the 2 treatments were as follows: naloxone hydrochloride, 7.237 (SD: 5.3971) L/min; and nalmefene hydrochloride, 9.307 (5.4774) L/min. These results indicate that nalmefene hydrochloride increased VE to a greater extent when compared to naloxone hydrochloride. The time to maximum change in minute ventilation after study drug administration was 40 minutes for both naloxone and nalmefene treatments, relative to start of hypercapnic gas mixture administration, i.e. 15 minutes in relation to administration of naloxone hydrochloride and nalmefene hydrochloride.

However, it is noted that following administration of nalmefene hydrochloride, the mean minute ventilation returned to pre remifentanil levels after 5 minutes post dose, compared to 20 minutes for naloxone hydrochloride (Table 27 and Table 28).

TABLE 29

Summary of ExSpiron ® Device Minute Ventilation PD Parameter-Part 2

| PD Parameter | Statistic | Hypercapnic Gas Mixture + Remifentanil + Naloxone | Hypercapnic Gas Mixture + Remifentanil + Nalmefene |
|---|---|---|---|
| $TE_{max}$ (min) | n | 59 | 61 |
| | Median | 40.0 | 40.0 |
| | Min, Max | 28, 145 | 28, 120 |
| VE $E_{max}$ | n | 59 | 61 |
| | Mean | 7.237 | 9.307 |
| | SD | 5.3971 | 5.4774 |
| | SE | 0.703 | 0.701 |
| | % CV | 74.6 | 58.9 |
| | Median | 6.550 | 9.300 |
| | Min, Max | −1.76, 28.73 | −1.04, 24.74 |
| | Q1, Q3 | 3.490, 9.330 | 5.590, 12.170 |

CV = coefficient of variation;
Min = minimum;
Max = maximum;
Q1 = first quartile;
Q3 = third quartile;
SE = standard error;
$TE_{max}$ = time to maximum effect $E_{max}$;
VE $E_{max}$ = maximum effect after study drug administration.
The maximum effect was defined as the maximum change from nadir baseline after study drug administration (naloxone or nalmefene). The maximum change can be a negative change or a positive change as the maximum value among all post dose changes in minute ventilation were captured and set as VE $E_{max}$.

The summary of the change in minute ventilation from the maximum change in minute ventilation from nadir baseline to 120 minutes after study drug administration is presented in Table 30. Mean (SD) VE Change values for the 2 treatments were as follows: naloxone hydrochloride, −2.32 (6.165); and nalmefene hydrochloride, 2.61 (4.262).

However, it is noted that following administration of nalmefene hydrochloride, the mean change in minute ventilation from the nadir baseline after 120 minutes post dose, is 2.877 L/min, compared to 2.016 L/min for naloxone hydrochloride (Table 27 and Table 28). Nonetheless, mean changes in minute ventilation were lower than expected based on plasma concentrations of study drugs.

TABLE 30

Summary of ExSpiron ® Device Minute Ventilation Change from Emax-Part 2

| Timepoint | Statistic | Hypercapnic Gas Mixture + Remifentanil + Naloxone (N = 60) Result | Hypercapnic Gas Mixture + Remifentanil + Nalmefene (N = 61) Result |
|---|---|---|---|
| Baseline ($E_{max}$) | N | 59 | 61 |
| | Mean | 7.237 | 9.307 |
| | SD | 5.3971 | 5.4774 |
| | SE | 0.703 | 0.701 |
| | % CV | 74.6 | 58.9 |
| | Median | 6.550 | 9.300 |
| | Min, Max | −1.76, 28.73 | −1.04, 24.74 |
| | Q1, Q3 | 3.490, 9.330 | 5.590, 12.170 |
| VE Change (120 Minutes from nadir baseline) | N | 56 | 59 |
| | Mean | −2.32 | −2.61 |
| | SD | 6.165 | 4.262 |
| | SE | 0.824 | 0.555 |
| | % CV | −265.6 | −163.4 |
| | Median | −2.70 | −2.03 |
| | Min, Max | −18.5, 27.0 | −12.6, 4.9 |
| | Q1, Q3 | −5.62, −0.26 | −6.23, 0.44 |

CV = coefficient of variation;
Min = minimum;
Max = maximum;
Q1 = first quartile;
Q3 = third quartile;
SE = standard error;
VE Change = post dose change in minute ventilation from nadir baseline at selected timepoints.
Baseline ($E_{max}$) was defined as the maximum change from nadir baseline after study drug administration (naloxone hydrochloride or nalmefene hydrochloride).
VE Change (120 Minutes from nadir baseline) was defined as the change in minute ventilation at 120 minutes relative to nadir baseline minus the $E_{max}$.

PD Measurements—ETCO2: IN naloxone hydrochloride and IN nalmefene hydrochloride increased ETCO2 relative to baseline. The maximum ETCO2 increase was observed 2.5 minutes after naloxone hydrochloride administration (51.90 mm Hg) and after nalmefene hydrochloride administration (49.52 mm Hg). From study drug administration to 20 minutes after, mean ETCO2 decreased from 47.78 mm Hg to 45.63 mm Hg for IN naloxone hydrochloride and from 48.61 to 44.07 mm Hg for IN nalmefene hydrochloride. The VRH ETCO2 results over time are shown in FIG. 17.

Statistical Analysis:

Noninferiority Analysis: The primary objective was to demonstrate noninferiority of IN nalmefene hydrochloride compared to IN naloxone hydrochloride on minute ventilation during steady-state remifentanil infusion. The statistical analysis of noninferiority was performed using the ITT set for Part 2 with ExSpiron® Device. From the ITT set, only subjects who took both treatments and completed the data collection for 5 minutes post dose, were included in the analysis. The upper limit of the 95% CI (−1.175) was less than 20% of the Least Squares (LS) mean change in minute ventilation for naloxone (0.6022), demonstrating noninferiority of IN nalmefene hydrochloride compared to IN naloxone hydrochloride. Results are presented in Table 31.

TABLE 31

Statistical Analysis of Noninferiority Analysis of Nalmefene Versus Naloxone at 5 minute post dose - Part 2

| | LS Mean | | | | | | |
|---|---|---|---|---|---|---|---|
| | Hypercapnic Gas Mixture + Remifentanil + Naloxone (Ref) | | Hypercapnic Gas Mixture + Remifentanil + Nalmefene (Test) | | LS Mean Difference (Ref − Test) | | 20%*LS Mean |
| Parameter | n | Result | n | Result | Estimate | 95% CI | Naloxone |
| VE Change(L/min) | 50 | 3.011 | 50 | 5.745 | −2.73 | (−4.293, −1.175) | 0.6022 |

CI = confidence interval; LS = least squares; VE Change = post dose change in minute ventilation from nadir baseline at selected timepoints.

Analysis was performed using a linear mixed effects model with treatment, period, and sequence as fixed effects and subject nested within sequence as a random effect.

Exploratory Analysis:

The exploratory analysis was conducted in order to compare the proportion of subjects with the extreme responses to the two treatments. From the ITT set, only subjects who took both treatments and completed the data collection for 5 minutes post dose, were included in the analysis.

The small p-value for the test (p<0.05) indicates that the null hypothesis of equal proportions can be rejected and that the proportions are unequal, i.e. the proportion of the subjects with a change in minute ventilation on nalmefene hydrochloride that is less than 50% of the change in minute ventilation on naloxone hydrochloride is not equal to the proportion of the subjects with a change in minute ventilation on naloxone hydrochloride that is less than 50% of the change in minute ventilation on nalmefene hydrochloride (Table 32).

TABLE 32

Statistical Analysis Comparing the Proportions of Subjects with Extreme Responses

| Parameter | Change on Nalmefene < 50% Change on Naloxone n (%) | Change on Naloxone < 50% Change on Nalmefene n (%) | P-value |
|---|---|---|---|
| VE Change (L/min) (5 Minutes Post Naloxone or Nalmefene) | 8 (16.0) | 25 (50.0) | 0.0003 |

VE Change = post dose change in minute ventilation from nadir baseline at timepoint 5 minutes after naloxone or nalmefene administration..

The analysis was performed using a chi-square test for the proportion of the subjects with a change in minute ventilation on nalmefene that was less than 50% of the change in minute ventilation after naloxone vs the proportion of the subjects with a change in minute ventilation after naloxone that was less than 50% of the change in minute ventilation after nalmefene.

Sensitivity Analysis: As a sensitivity analysis, the primary analysis was rerun excluding the subjects for which the change in minute ventilation from remifentanil-induced nadir to 5 minutes was more than 1.5 interquartile range below first quartile (Q1) or more than 1.5 interquartile range above third quartile (Q3). Only subjects who took both treatments and completed the data collection for 5 minutes post dose, were included in the analysis.

The upper limit of the 95% CI (−1.283) was less than 20% of the LS mean change in minute ventilation for naloxone (0.5092), demonstrating noninferiority of IN nalmefene hydrochloride compared to IN naloxone hydrochloride. Results are presented in Table 33.

TABLE 33

Sensitivity Analysis: Statistical Analysis of Noninferiority Analysis of Nalmefene Versus Naloxone - Part 2

| | LS Mean | | | | | | |
|---|---|---|---|---|---|---|---|
| | Hypercapnic Gas Mixture + Remifentanil + Naloxone (Ref) | | Hypercapnic Gas Mixture + Remifentanil + Nalmefene (Test) | | LS Mean Difference (Ref − Test) | | 20%*LS Mean |
| Parameter | n | Result | n | Result | Estimate | 95% CI | Naloxone |
| VE Change(L/min) | 48 | 2.546 | 48 | 5.052 | −2.51 | (−3.729, −1.283) | 0.5092 |

CI = confidence interval; LS = least squares; VE Change = post dose change in minute ventilation from nadir baseline at selected timepoints.

Pharmacokinetics:

Mean peak plasma concentrations of naloxone were observed at 45 minutes (tmax) post dose. The geometric mean peak concentration (Cmax) was 5.21 ng/ml. After the maximum concentration was reached in this study, naloxone plasma concentrations declined in a bi-phasic manner over a 2-hour period.

Mean peak plasma concentrations of nalmefene were observed at 30 minutes post dose. The geometric mean peak concentration (Cmax) was 6.3 ng/ml. After the maximum concentration was reached, nalmefene plasma concentrations declined in a bi-phasic manner over a 2-hour period.

Following single-dose IN administration of 4 mg naloxone hydrochloride and 3 mg nalmefene hydrochloride during steady-state remifentanil infusion, naloxone and nalmefene geometric mean Cmax values were 5.21 and 6.30 ng/mL, respectively. Geometric mean naloxone and nalmefene AUC0-t were 5.88 and 7.51 h*ng/mL, respectively. Geometric mean naloxone and nalmefene AUC0-inf were 11.3 and 22.3 h*ng/ml, respectively.

Naloxone Plasma Concentration: Plots of mean (±SD) naloxone plasma concentrations versus time on linear and semi-logarithmic scales are presented in FIG. 18 and FIG. 19, respectively.

As shown in the figures following single-dose IN administration of 4 mg naloxone hydrochloride during steady-state remifentanil infusion, naloxone plasma concentrations were first quantifiable in 84.7% of subjects by 2.5 minutes post dose and remained quantifiable until 2 hours post dose in all subjects.

Mean peak plasma concentrations of naloxone were achieved at 45 minutes post dose. The geometric mean peak concentration ($C_{max}$) was 5.21 ng/ml. This value is similar to another reported study in which naloxone hydrochloride nasal spray resulted in measurable concentrations for 6 hours.30 After the maximum concentration was reached in this study, plasma concentrations declined in a bi-phasic manner over a 2-hour period.

Nalmefene Plasma Concentration: Plots of mean (±SD) nalmefene plasma concentrations versus time on linear and semi-logarithmic scales are presented in FIG. 20 and FIG. 19, respectively.

As shown in the figures following single-dose intranasal (IN) administration of 3 mg nalmefene hydrochloride during steady-state remifentanil infusion, nalmefene plasma concentrations were first quantifiable in 98.4% of subjects by 2.5 minutes post dose and remained quantifiable until 2 hours post dose in all subjects.

Mean peak plasma concentrations of nalmefene were observed at 30 minutes post dose. Nalmefene geometric mean peak concentration (Cmax) was 6.3 ng/mL. After maximum concentration was reached, nalmefene plasma concentrations declined in a bi-phasic manner over a 2-hour period.

Pharmacokinetic Parameters of Naloxone and Nalmefene in Plasma (Part 2)

Summary statistics of PK parameters for naloxone and nalmefene in plasma are presented in Table 34. Following single-dose IN administration of 4 mg naloxone hydrochloride and 3 mg nalmefene hydrochloride during steady-state remifentanil infusion, naloxone and nalmefene geometric mean $C_{max}$ values were 5.21 and 6.30 ng/mL, respectively. Geometric mean naloxone and nalmefene $AUC_{0-t}$ were 5.88 and 7.51 h*ng/mL, respectively. Geometric mean naloxone and nalmefene $AUC_{0-inf}$ were 11.3 and 22.3 h*ng/ml, respectively.

TABLE 34

Summary of Pharmacokinetic Parameters for Naloxone and Nalmefene in Plasma

| Parameter | Statistics | Treatment Naloxone (N = 69) | Nalmefene (N = 69) |
|---|---|---|---|
| $C_{max}$ (ng/mL) | n | 60 | 61 |
| | Mean | 5.81 | 6.78 |
| | SD | 3.04 | 2.71 |
| | % CV | 49.1 | 40.0 |
| | Median | 5.08 | 6.48 |
| | Min, Max | 1.72, 17.9 | 2.72, 13.8 |
| | Geo Mean | 5.21 | 6.30 |
| $t_{max}$ (h) | n | 60 | 61 |
| | Median | 0.75 | 0.50 |
| | Min, Max | 0.13, 2.00 | 0.04, 2.00 |
| $AUC_{0-t}$ (h*ng/mL) | n | 60 | 61 |
| | Mean | 6.55 | 8.63 |
| | SD | 2.61 | 3.07 |
| | % CV | 62.4 | 86.7 |
| | Median | 6.06 | 8.78 |
| | Min, Max | 0.211, 14.3 | 0.134, 14.3 |
| | Geo Mean | 5.88 | 7.51 |
| $AUC_{0-inf}$ (h*ng/mL) | n | 51 | 43 |
| | Mean | 13.4 | 24.5 |
| | SD | 11.2 | 12.7 |
| | % CV | 54.9 | 44.3 |
| | Median | 10.4 | 23.6 |
| | Min, Max | 4.56, 78.6 | 8.72, 89.3 |
| | Geo Mean | 11.3 | 22.3 |
| $AUC_{0-2.5}$ (h*ng/mL) | n | 60 | 60 |
| | Mean | 0.0147 | 0.0282 |
| | SD | 0.0218 | 0.0355 |
| | % CV | 501534.9 | 1346.4 |
| | Median | 0.00434 | 0.0123 |
| | Min, Max | 0.000000, 0.115 | 0.000000, 0.128 |
| | Geo Mean | 0.00131 | 0.00791 |
| $AUC_{0-5}$ (h*ng/mL) | n | 60 | 60 |
| | Mean | 0.0632 | 0.109 |
| | SD | 0.0752 | 0.105 |
| | % CV | 358.6 | 199.1 |
| | Median | 0.0304 | 0.0728 |
| | Min, Max | 0.000685, 0.343 | 0.00375, 0.384 |
| | Geo Mean | 0.0248 | 0.0596 |
| $AUC_{0-10}$ (h*ng/mL) | n | 59 | 59 |
| | Mean | 0.250 | 0.404 |
| | SD | 0.241 | 0.292 |
| | % CV | 187.3 | 98.8 |
| | Median | 0.150 | 0.328 |
| | Min, Max | 0.00742, 0.939 | 0.0443, 1.36 |
| | Geo Mean | 0.140 | 0.303 |
| $AUC_{0-15}$ (h*ng/mL) | n | 59 | 59 |
| | Mean | 0.482 | 0.761 |
| | SD | 0.417 | 0.467 |
| | % CV | 132.3 | 71.1 |
| | Median | 0.339 | 0.624 |
| | Min, Max | 0.0385, 1.84 | 0.137, 2.18 |
| | Geo Mean | 0.317 | 0.631 |
| $AUC_{0-20}$ (h*ng/mL) | n | 59 | 59 |
| | Mean | 0.765 | 1.18 |
| | SD | 0.605 | 0.643 |
| | % CV | 103.9 | 59.3 |
| | Median | 0.555 | 1.03 |
| | Min, Max | 0.103, 3.03 | 0.271, 2.75 |
| | Geo Mean | 0.554 | 1.02 |
| $AUC_{10-20}$ (h*ng/mL) | n | 59 | 59 |
| | Mean | 0.515 | 0.772 |
| | SD | 0.386 | 0.411 |
| | % CV | 88.6 | 53.6 |
| | Median | 0.387 | 0.677 |
| | Min, Max | 0.0852, 2.09 | 0.226, 2.00 |
| | Geo Mean | 0.394 | 0.680 |

% CV = coefficient of variation;
Min = minimum;
Max = maximum;
SD = standard deviation.

Safety

Part 1, Brief Summary of Adverse Events: On Day 1, a total of 6 TEAEs were reported by 4 (57.1%) subjects receiving naloxone hydrochloride. On Day 5, a total of 2 TEAEs were reported by 2 (28.6%) subjects receiving naloxone hydrochloride. There were no AEs leading to discontinuation of the study treatment.

Drug-related Adverse Events: On Day 1, 5 TEAEs (4 events of headache and 1 event of epistaxis) were likely to be related to naloxone hydrochloride and 1 (nasal obstruction) was not related to the study drug. On Day 5, 1 TEAE of headache was considered definitely related to the study drug, while no relationship to naloxone hydrochloride was found for erythema.

Adverse Events by Severity: On Day 1, 3 Grade 2 TEAEs of headache and 3 Grade 1 TEAEs (headache, epistaxis and nasal obstruction) were reported by 4 (57.1%) subjects. On Day 5, both TEAEs of headache and erythema were of Grade 1 severity and were reported by 2 (28.6%) subjects.

Adverse Events by Frequency: On Day 1, the most frequently reported AEs were headache, 4 events likely related to study drug reported by 4 (57.1%) subjects, 3 with outcome recovered/resolved and 1 with outcome unknown; epistaxis, 1 event likely related to study drug, with outcome unknown, reported by 1 (14.3%) subject and nasal obstruction (1 recovered/resolved event, not related to study drug, reported by 1 [14.3%] subject). On Day 5, headache (definitely related to study drug) and erythema (not related to study drug) were reported by 1 (14.3%) subject each, with both outcomes recovered/resolved.

Part 1 Extension

Brief Summary of Adverse Events: A total of 10 TEAEs were reported by 4 (50.0%) subjects. There were no AEs leading to discontinuation of the study treatment.

Drug-related Adverse Events: Among the 10 TEAEs reported, 6 (3 events of nausea and 3 events of headache) were considered likely to be related to study drug, 3 (feeling cold, muscle twitching and dizziness) possibly related to study drug and 1 event of upper abdominal pain unlikely to be related to naloxone hydrochloride.

Adverse Events by Severity: All 10 TEAEs were of Grade 1 severity.

Adverse Events by Frequency: The most frequently reported TEAEs were nausea and headache (3 events likely related to study drug reported by 3 subjects, 1 each, all with outcome recovered/resolved).

Part 2

Brief Summary of Adverse Events: A total of 131 TEAEs were reported by 52 (86.7%) subjects after administration of naloxone hydrochloride, and 172 TEAEs were reported by 56 (91.8%) subjects after administration of nalmefene hydrochloride. Overall, a total of 9 (13.0%) subjects receiving either naloxone hydrochloride or nalmefene hydrochloride, discontinued the study drug due to an AE. Among them, 5 (8.3%) subjects receiving naloxone hydrochloride reported 4 TEAEs of hypercapnia and 1 TEAE of hypoxia, while 4 (6.6%) subjects receiving nalmefene hydrochloride reported 2 TEAEs of headache and 2 TEAEs of hypercapnia, all with outcome recovered/resolved.

Drug-related Adverse Events: Overall, the most common TEAEs were headache (reported by 48 [69.6%] subjects receiving either naloxone hydrochloride or nalmefene hydrochloride), nausea (39 [56.5%] subjects receiving either naloxone hydrochloride or nalmefene hydrochloride), and dizziness (21 [30.4%] subjects receiving either naloxone hydrochloride or nalmefene hydrochloride).

Adverse Events by Severity: The majority of the subjects reported Grade 1 and Grade 2 severity TEAEs, reported by 49 (71.0%) and 18 (26.1%) subjects overall, respectively. Among the subjects receiving naloxone hydrochloride, 44 (73.3%) and 8 (13.3%) reported Grade 1 and 2 severity TEAEs, respectively. Forty-two (68.9%) and 14 (23.0%) subjects receiving nalmefene hydrochloride reported Grade 1 and 2 severity TEAEs, respectively.

Adverse Events by Frequency: Overall, nervous system and gastrointestinal disorders were most frequently reported among subjects receiving naloxone hydrochloride and nalmefene hydrochloride, reported by 55 (79.7%) and 46 (66.7%) subjects, respectively. All events had outcome recovered/resolved.

Conclusions:

Overall, the primary study endpoint of noninferiority was met indicating that IN nalmefene hydrochloride performed as well as naloxone hydrochloride. The results were further confirmed by the sensitivity analyses performed. PD, PK, and safety conclusions are summarized below.

Pharmacodynamics: From the data in Part 1 and Part 1 extension, remifentanil infusion for 15 minutes and at an infusion rate of 0.175 µg/kg/min was considered sufficient to elicit the pharmacological response needed to demonstrate the study endpoints in Part 2.

In Part 1, it was demonstrated that the overall impact of brief mask removal on minute ventilation, necessary to administer the nasal spray, was minimal.

In Part 2, the change in minute ventilation at 5 minutes during steady-state remifentanil infusion was greater for nalmefene hydrochloride (LS mean 5.745 L/min) compared to naloxone hydrochloride (LS mean 3.011 L/min).

In Part 2, the maximum increase in minute ventilation was greater for nalmefene hydrochloride when compared with naloxone hydrochloride.

In Part 2, following administration of nalmefene, the mean minute ventilation returned to 98.9% of pre remifentanil levels after 5 minutes post dose, compared to 95.0% of pre-remifentanil levels after 20 minutes for naloxone.

In Part 2, the sensitivity analysis also demonstrated that the change in minute ventilation at 5 minutes during steady-state remifentanil infusion was greater for nalmefene hydrochloride (LS mean 5.052 L/min) compared to naloxone hydrochloride (LS mean 2.546 L/min).

At the primary endpoint (5 minutes post administration of IN naloxone hydrochloride or IN nalmefene hydrochloride), the noninferiority of IN nalmefene hydrochloride compared to IN naloxone hydrochloride on minute ventilation during steady-state remifentanil infusion was demonstrated in both the noninferiority and sensitivity analyses.

At 5 minutes post administration, the proportion of subjects administered naloxone hydrochloride with a change in minute ventilation that was less than 50% of the change in minute ventilation following nalmefene hydrochloride was significantly greater (p=0.0003) than the proportion of the subjects administered nalmefene hydrochloride with a change in minute ventilation that was less than 50% of the change in minute ventilation following naloxone hydrochloride.

From the data in Part 1 and Part 1 extension, remifentanil infusion for 15 minutes at an infusion rate of 0.175 µg/kg/min was considered sufficient to elicit the pharmacological response needed to demonstrate the study endpoints in Part 2.

In Part 1, it was demonstrated that the overall impact of brief mask removal on minute ventilation, necessary to administer the nasal spray, was minimal.

In Part 2, the change in minute ventilation at 5 minutes during steady-state remifentanil infusion was greater for nalmefene (LS mean 5.745 L/min) compared to naloxone (LS mean 3.011 L/min).

In Part 2, the maximum increase in minute ventilation was greater for nalmefene hydrochloride when compared with naloxone hydrochloride.

In Part 2, following administration of nalmefene, the mean minute ventilation returned to 98.9% of pre-remifentanil levels after 5 minutes post dose, compared to 95.0% of pre-remifentanil levels after 20 minutes for naloxone.

In Part 2, the sensitivity analysis also demonstrated that the change in minute ventilation at 5 minutes during steady-state remifentanil infusion was greater for nalmefene (LS mean 5.052 L/min) compared to naloxone (LS mean 2.546 L/min).

At the primary endpoint (5 minutes post administration of IN naloxone hydrochloride or IN nalmefene hydrochloride), the noninferiority of IN nalmefene hydrochloride compared to IN naloxone hydrochloride on minute ventilation during steady-state remifentanil infusion was demonstrated in both the noninferiority and sensitivity analyses.

At 5 minutes post administration, the proportion of subjects administered naloxone hydrochloride with a change in minute ventilation that was less than 50% of the change in minute ventilation following nalmefene hydrochloride was significantly greater (p=0.0003) than the proportion of the subjects administered nalmefene hydrochloride with a change in minute ventilation that was less than 50% of the change in minute ventilation following naloxone hydrochloride.

Pharmacokinetics: Nalmefene absorption was faster compared to naloxone: tmax values were 30 and 45 minutes, respectively.

Exposure of nalmefene was higher compared to naloxone: AUC0-inf and Cmax of nalmefene were 2.0 and 1.2-fold higher, respectively, compared to naloxone AUC0-inf and Cmax.

Nalmefene absorption was faster compared to naloxone: tmax values were 30 and 45 minutes, respectively.

Geometric mean Cmax was 5.21 and 6.30 ng/ml for naloxone and nalmefene, respectively.

Geometric mean AUC0-t and AUC0-inf was 5.88 and 11.3 h*ng/ml for naloxone, respectively.

Geometric mean AUC0-t and AUC0-inf was 7.51 and 22.3 h*ng/ml for nalmefene, respectively.

Safety

Treatment with naloxone hydrochloride and nalmefene hydrochloride was safe and well tolerated.

The frequency of reported TEAEs was similar between subjects receiving naloxone hydrochloride and nalmefene hydrochloride.

The most frequently reported TEAEs were headache, reported by 35 (58.3%) and 36 (59.0%) subjects receiving naloxone and nalmefene hydrochloride, respectively, and nausea, reported by 25 (41.7%) and 24 (39.3%) subjects receiving naloxone and nalmefene hydrochloride, respectively.

The safety profiles of naloxone hydrochloride and nalmefene hydrochloride were similar.

There were no deaths or serious AEs reported during this study, and all AEs leading to withdrawals in Part 2 of the study were recovered/resolved.

There were no findings of clinical relevance with respect to clinical laboratory, ECGs, vital signs, or physical examination.

Discussions and Overall Conclusions

The efficacy of nalmefene hydrochloride in treating opioid overdose has been established. Both the high affinity of nalmefene hydrochloride at u opiate receptors and its long half-life led to the development of an IN formulation as a rescue medication that could be especially useful in treating opioid overdose without the use of needles.

The primary objective of this study was to assess the PD effects of IN nalmefene hydrochloride compared to IN naloxone hydrochloride (the current FDA approved treatment for opioid overdose) in healthy volunteers with prior opioid exposure, under steady-state opioid agonism.

Under normal circumstances, hypercapnia triggers a reflex that increases breathing and access to oxygen. Opioids are, however, known to reduce the responsiveness of the respiratory centers to carbon dioxide, with decreased slopes of the hypercapnic ventilatory response. Part 1 and the Part 1 extension of the study determined the remifentanil dose required to achieve an approximate 40% or more suppression of $CO_2$ induced increases in minute ventilation.

Part 2 was a randomized, 2-period, 2-treatment, crossover study. The selected dose for IN naloxone hydrochloride (4 mg) administered in this study was the standard unit dose (Narcan® Nasal Spray 4 mg) generally available to first responders during opioid overdose emergencies. The dose for IN nalmefene hydrochloride (3 mg) was selected based on PK data obtained in a pilot clinical study, and the FDA guidance on parenteral dosing of nalmefene that produces a maximum reversal of a suspected opioid overdose. The key PD, PK and safety findings are summarized below.

Pharmacodynamics: Part 1 was exploratory in nature and the primary objective of this study part was to determine the relationship between remifentanil dose and suppression of $CO_2$ induced increases in minute ventilation in order to select a suitable dose to be used in Part 2 of the study. In Part 1, remifentanil was administered for 20 minutes prior to naloxone administration at infusion rates ranging from 0.05 to 0.15 µg/kg/min, using an initial bolus (0.5 µg/kg) to achieve an expected steady state. These experimental conditions were supported by the literature. However, at the remifentanil infusion rates tested in this study, the ventilatory effects were lower and more variable than expected and the reversal following naloxone hydrochloride administration was generally too high at 5 minutes which would have restricted the possibility to demonstrate the study endpoints. For these reasons, in the Part 1 extension, the duration of exposure to a hypercapnic gas mixture was increased from 5 to 10 minutes and the duration of remifentanil-infusion was reduced to 15 minutes prior to naloxone administration at an infusion rate of 0.175 µg/kg/min, using an initial bolus (0.5 µg/kg) to achieve an expected steady state. These conditions produced a more consistent remifentanil induced response and also a more consistent naloxone reversal of the remifentanil induced respiratory depression. Results from Part 1 extension of the study showed that a remifentanil dose of 0.175 µg/kg/min was sufficient to elicit the pharmacological response needed to demonstrate study endpoints in Part 2. Therefore, the same remifentanil dosing conditions were used in Part 2. Part 1 also demonstrated that the overall impact of brief mask removal on minute ventilation, necessary to administer the nasal spray, was minimal.

The primary objective of Part 2 was to demonstrate noninferiority of IN nalmefene hydrochloride compared to IN naloxone hydrochloride on minute ventilation during steady state remifentanil infusion.

For the primary endpoint, the change in minute ventilation at 5 minutes during steady state remifentanil infusion was greater for nalmefene hydrochloride (LS mean 5.745 L/min) compared to naloxone hydrochloride (LS mean 3.011 L/min). Overall, the primary study endpoint of noninferiority was met indicating that IN nalmefene hydrochloride performed as well as naloxone hydrochloride.

The results were further confirmed by the sensitivity analyses performed, which also demonstrated noninferiority. For the primary endpoint, the change in minute ventilation at 5 minutes during steady-state remifentanil infusion was greater for nalmefene hydrochloride. Overall, the primary study endpoint of noninferiority was met indicating that IN nalmefene hydrochloride performed as well as naloxone hydrochloride (LS mean 5.052 L/min compared to LS mean 2.546 L/min, respectively).

The VE Emax values for nalmefene hydrochloride were higher than those for naloxone hydrochloride. The time to maximum effect (TEmax) was 15 minutes after administration of nalmefene and naloxone.

However, it is noted that following administration of nalmefene, the mean minute ventilation returned to 98.9% of pre remifentanil levels after 5 minutes post dose, compared to 95.0% of pre remifentanil levels after 20 minutes for naloxone.

The change in minute ventilation from the maximum change in minute ventilation from remifentanil-induced nadir to 120 minutes after study drug administration was similar for nalmefene and naloxone (Mean −2.62 L/min compared to −2.31 L/min, respectively).

The mean changes in minute ventilation at 60-, 90- and 120-minutes post study drug administration were greater following nalmefene compared to naloxone. Nonetheless, mean changes in minute ventilation were lower than expected based on plasma concentrations of study drugs. For example, plasma concentrations of nalmefene at 60-, 90-, and 120-minutes post-administration were comparable to or greater than plasma concentrations at 7.5-, 10- and 15-minutes post-administration, when a complete reversal of remifentanil-induced respiratory depression was observed. Similarly, plasma concentrations of naloxone at 60 minutes post-administration were equal to or greater than the values obtained at 20 minutes, when a full reversal of remifentanil-induced depression of minute ventilation was achieved. It is noted that three mask removal 'holidays' of 30, 20, and 20 minutes duration were introduced at 46, 86, and 116 minutes of the study protocol, respectively. Mask holidays were intended to reduce study dropouts due to the discomfort produced by wearing a tight-fitting mask for an extended period. However, the data indicate that the introduction of mask holidays appears to reduce the ability of subjects to increase minute ventilation in response to a hypercapnic challenge that is readily demonstrated following continuous administration of the hypercapnic gas mixture, in both the absence (study times 0-10 minutes) and presence of remifentanil and an opioid antagonist (study times 25-45 minutes), prior to the first mask removal.

The exploratory analysis showed an unequal proportion of subjects with extreme responses. The proportion of the subjects with a change in minute ventilation on naloxone that was less than 50% of the change in minute ventilation on nalmefene (n=25, 50%) was significantly greater (p=0.0003) than the proportion of the subjects with a change in minute ventilation on nalmefene that was less than 50% of the change in minute ventilation on naloxone (n=8, 16%).

The performance reliability of the nalmefene hydrochloride nasal spray has been demonstrated with no issues reported during the course of the study (n=61).

From the data in Part 1 and Part 1 extension, remifentanil infusion for 15 minutes at an infusion rate of 0.175 μg/kg/min was considered sufficient to elicit the pharmacological response needed to demonstrate the study endpoints in Part 2.

In Part 1, it was demonstrated that the overall impact of brief mask removal on minute ventilation, necessary to administer the nasal spray, was minimal.

In Part 2, the change in minute ventilation at 5 minutes during steady-state remifentanil infusion was greater for nalmefene hydrochloride (LS mean 5.745 L/min) compared to naloxone hydrochloride (LS mean 3.011 L/min).

In Part 2, the maximum increase in minute ventilation was greater for nalmefene hydrochloride when compared with naloxone hydrochloride.

In Part 2, following administration of nalmefene, the mean minute ventilation returned to 98.9% of pre-remifentanil levels after 5 minutes post dose, compared to 95.0% of pre-remifentanil levels after 20 minutes for naloxone.

In Part 2, the sensitivity analysis also demonstrated that the change in minute ventilation at 5 minutes during steady-state remifentanil infusion was greater for nalmefene hydrochloride (LS mean 5.052 L/min) compared to naloxone hydrochloride (LS mean 2.546 L/min).

At the primary endpoint (5 minutes post administration of IN naloxone hydrochloride or IN nalmefene hydrochloride), the noninferiority of IN nalmefene hydrochloride compared to IN naloxone hydrochloride on minute ventilation during steady-state remifentanil infusion was demonstrated in both the noninferiority and sensitivity analyses.

At 5 minutes post administration, the proportion of subjects administered naloxone hydrochloride with a change in minute ventilation that was less than 50% of the change in minute ventilation following nalmefene hydrochloride was significantly greater (p=0.0003) than the proportion of the subjects administered nalmefene hydrochloride with a change in minute ventilation that was less than 50% of the change in minute ventilation following naloxone hydrochloride.

FIG. 22 shows a comparison of pharmacokinetic data between the nalmefene nasal spray (OPNT003) and the NARCAN nasal spray.

FIG. 23 illustrates the results of the non-inferiority study comparing nasal nalmefene and nasal naloxone in reversing the respiratory depression produced by remifentanil, using the change in minute ventilation, with a primary endpoint at 5 minutes.

FIG. 24A shows the change in minute ventilation from the time nasal nalmefene or nasal naloxone is given until 5 minutes later. The increase in minute ventilation was 5.7 L/min for nasal nalmefene and 3.0 L/min for nasal naloxone, a difference that clearly favored nalmefene.

FIG. 24B represents the FDA criteria that were established to demonstrate non-inferiority. The filled circle represents the difference in MV between nasal nalmefene and nasal naloxone (the lines to either side of the filled circle represent the 95% confidence interval). The dotted line at "0" represents no difference in MV between the two treatments. The dotted line to the right of "0" is the point that was proposed by Opiant to represent non-inferiority between nasal nalmefene and nasal naloxone, where nasal nalmefene could be no more than 20% lower than nasal naloxone. This graph shows that the trial clearly met the primary endpoint.

FIG. 24C shows the first 20 minutes post dose of nasal nalmefene or nasal naloxone. By 5 minutes, treatment with nasal nalmefene results in MV returning to "pre-remifentanil" levels, while it takes 20 minutes for the MV of those treated with nasal naloxone to return to "pre-remifentanil" levels.

The findings from this study support the use of IN nalmefene for treatment of opioid overdose.

Pharmacokinetics: An objective of this study was to compare the PK profiles of naloxone and nalmefene following a single 4 mg and 3 mg IN dose of naloxone and nalmefene respectively, during steady-state remifentanil infusion in healthy subjects.

Following single-dose IN administration of 4 mg and 3 mg naloxone and nalmefene respectively, to healthy subjects, the median time to peak plasma concentrations (tmax) was 45 minutes after naloxone administration and 30 minutes after nalmefene administration, respectively. The extent of systemic exposure ($AUC_{0-inf}$) and $C_{max}$ of nalmefene (geometric means) were increased 2.0 and 1.2 times following nalmefene administration, respectively, compared to naloxone administration.

Nalmefene absorption was faster compared to naloxone: tmax values were 30 and 45 minutes, respectively Exposure of nalmefene was higher compared to naloxone: AUC0-inf and $C_{max}$ of nalmefene were 2.0 and 1.2-fold higher, respectively, compared to naloxone AUC0 inf and $C_{max}$.

Safety: The safety objective was to determine tolerability of administration of IN nalmefene hydrochloride during remifentanil infusion. The results of this study showed that treatment with naloxone hydrochloride and nalmefene hydrochloride was safe and well tolerated. The safety profiles of naloxone hydrochloride and nalmefene hydrochloride were similar. The most common TEAEs were headache, nausea, and dizziness for both treatments. The AEs observed in this study are generally consistent with the safety and tolerability profiles of naloxone hydrochloride and nalmefene hydrochloride and no new safety concerns were raised.

Treatment with naloxone hydrochloride and nalmefene hydrochloride was safe and well tolerated.

The frequency of reported TEAEs was similar between subjects receiving naloxone hydrochloride and nalmefene hydrochloride.

The most frequently reported TEAEs were headache, reported by 35 (58.3%) and 36 (59.0%) subjects receiving naloxone and nalmefene hydrochloride, respectively, and nausea, reported by 25 (41.7%) and 24 (39.3%) subjects receiving naloxone and nalmefene hydrochloride, respectively.

The safety profiles of naloxone hydrochloride and nalmefene hydrochloride were similar.

There were no deaths or SAEs reported during this study, and all AEs leading to withdrawals in Part 2 of the study were recovered/resolved.

There were no findings of clinical relevance with respect to clinical laboratory, ECGs, vital signs, or physical examination.

The embodiments described herein are intended to be merely exemplary. Persons of ordinary skill in the art will understand that variations and modifications may be made without departing from the scope of the invention encompassed by the claims below.

What is claimed is:

1. A method of emergency treatment of a known or suspected opioid overdose or a symptom thereof caused by natural or synthetic opioids in an adult human subject in need thereof, comprising nasally administering to the subject a pharmaceutical formulation in an aqueous solution of about 100 μL, comprising:
   about 3 mg of nalmefene hydrochloride;
   about 0.87 mg NaCl;
   about 0.25 mg dodecyl maltoside;
   about 0.04 mg benzalkonium chloride (50% solution);
   about 0.2 mg disodium edetate; and
   water in an amount sufficient to achieve a volume of about 100 μL;
   wherein said formulation has a pH of 4.1 to 4.9;
   further wherein upon intranasal administration of said formulation to said adult human subject, median $T_{max}$ is less and the $C_{max}$ geometric mean is higher than each would have been for intramuscular administration of 1 mg nalmefene hydrochloride;
   further wherein upon intranasal administration of said formulation to said adult human subject, the time to onset of reversal in said adult human subject of a remifentanil-induced respiratory depression ranges from 2.5 to 5 minutes after said administration in a ventilatory-response to hypercapnia model, and the time to full reversal of remifentanil-induced depression of minute ventilation in said adult human subject ranges from 5 and 15 minutes after said administration in the model;
   further wherein the plasma concentration versus time curve of the nalmefene in said adult human subject has a $T_{max}$ of between 12 and 18 minutes; and wherein the $C_{max}$ geometric mean is between 89 ng/ml and 12 ng/ml;
   thereby treating the opioid overdose or a symptom thereof in the adult human subject.

2. A method of treating a remifentanil-induced respiratory depression in an adult human subject in need thereof, comprising nasally administering to the subject a pharmaceutical formulation in an aqueous solution of about 100 μL, comprising:
   about 3 mg of nalmefene hydrochloride;
   about 0.87 mg NaCl;
   about 0.25 mg dodecyl maltoside;
   about 0.04 mg benzalkonium chloride (50% solution);
   about 0.2 mg disodium edetate; and
   water in an amount sufficient to achieve a volume of about 100 μL;
   wherein said formulation has a pH of 4.1 to 4.9;
   further wherein upon intranasal administration of said formulation to said adult human subject, median $T_{max}$ is less and the $C_{max}$ geometric mean is higher than each would have been for intramuscular administration of 1 mg nalmefene hydrochloride;
   further wherein upon intranasal administration of said formulation to said adult human subject, the time to onset of reversal in said adult human subject of respiratory depression ranges from 2.5 to 5 minutes after said administration in a ventilatory-response to hypercapnia model, and the time to full reversal of remifentanil-induced depression of minute ventilation in said adult human subject ranges from 5 and 15 minutes after said administration in the model;
   further wherein the plasma concentration versus time curve of the nalmefene in said adult human subject has a $T_{max}$ of between 12 and 18 minutes; and wherein the $C_{max}$ geometric mean is between 8 ng/ml and 12 ng/ml;
   thereby treating the remifentanil-induced respiratory depression in the adult human subject and wherein the remifentanil-induced respiratory depression is created by an initial bolus of 0.5 micrograms/kg dose of remifentanil followed by an infusion of remifentanil for about 15 minutes at an infusion rate of about 0.175 micrograms/kg/min.

\* \* \* \* \*

UNITED STATES PATENT AND TRADEMARK OFFICE
CERTIFICATE OF CORRECTION

PATENT NO. : 12,290,596 B2
APPLICATION NO. : 17/881306
DATED : May 6, 2025
INVENTOR(S) : Phil Skolnick et al.

Page 1 of 1

It is certified that error appears in the above-identified patent and that said Letters Patent is hereby corrected as shown below:

In the Specification

Column 6, Line 66, please delete "graphical".

Signed and Sealed this
Twenty-fourth Day of June, 2025

Coke Morgan Stewart
*Acting Director of the United States Patent and Trademark Office*